US010138499B2

(12) United States Patent
Gutierrez et al.

(10) Patent No.: US 10,138,499 B2
(45) Date of Patent: Nov. 27, 2018

(54) METHODS FOR IMPROVING THE EFFICIENCY OF SIMULTANEOUS SACCHARIFICATION AND FERMENTATION REACTIONS

(75) Inventors: Christina Gutierrez, San Mateo, CA (US); Colin Mitchinson, Half Moon Bay, CA (US); Tom T. Huang, Fremont, CA (US); Bruce A. Diner, Chadds Fort, PA (US); Paul Joseph Fagan, Wilmington, DE (US); William D. Hitz, Wilmington, DE (US)

(73) Assignee: DANISCO US INC., Palo Alto, CA (US)

( * ) Notice: Subject to any disclaimer, the term of this patent is extended or adjusted under 35 U.S.C. 154(b) by 0 days.

(21) Appl. No.: 13/516,610

(22) PCT Filed: Dec. 17, 2010

(86) PCT No.: PCT/US2010/061082
§ 371 (c)(1),
(2), (4) Date: Feb. 22, 2013

(87) PCT Pub. No.: WO2011/079048
PCT Pub. Date: Jun. 30, 2011

(65) Prior Publication Data
US 2013/0143277 A1 Jun. 6, 2013

Related U.S. Application Data

(60) Provisional application No. 61/289,917, filed on Dec. 23, 2009.

(51) Int. Cl.
| | | |
|---|---|---|
| *C12P 7/06* | (2006.01) | |
| *C12N 1/22* | (2006.01) | |
| *C12N 9/42* | (2006.01) | |
| *C12N 9/24* | (2006.01) | |
| *C12P 7/04* | (2006.01) | |
| *C12P 7/10* | (2006.01) | |
| *C12P 7/16* | (2006.01) | |
| *C12P 19/44* | (2006.01) | |
| *C12N 15/80* | (2006.01) | |
| *C12P 7/18* | (2006.01) | |
| *C12P 19/02* | (2006.01) | |

(52) U.S. Cl.
CPC ............... *C12P 7/06* (2013.01); *C12N 1/22* (2013.01); *C12N 9/248* (2013.01); *C12N 9/2434* (2013.01); *C12N 9/2477* (2013.01); *C12N 15/80* (2013.01); *C12P 7/04* (2013.01); *C12P 7/10* (2013.01); *C12P 7/16* (2013.01); *C12P 7/18* (2013.01); *C12P 19/02* (2013.01); *C12P 19/44* (2013.01); *C12Y 302/01037* (2013.01); *Y02E 50/10* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | |
|---|---|---|
| 4,797,361 A | 1/1989 | Montenencourt |
| 5,405,769 A | 4/1995 | Campbell et al. |
| 5,426,043 A | 6/1995 | De Graaff et al. |
| 5,437,992 A | 8/1995 | Bodie et al. |
| 5,536,325 A | 7/1996 | Brink |
| 5,681,732 A | 10/1997 | De Graaff et al. |
| 5,705,369 A | 1/1998 | Torget et al. |
| 5,817,499 A | 10/1998 | Dalboge et al. |
| 5,830,734 A | 11/1998 | Christgau et al. |
| 5,997,913 A | 12/1999 | Fowler et al. |
| 6,022,725 A | 2/2000 | Fowler et al. |
| 6,132,727 A | 10/2000 | Rohde, Jr. et al. |
| 6,409,841 B1 | 6/2002 | Lombard |
| 6,423,145 B1 | 7/2002 | Nguyen et al. |
| 6,509,171 B1 | 1/2003 | Berka et al. |
| 6,555,335 B1 | 4/2003 | Saloheimo et al. |
| 6,573,086 B1 | 6/2003 | Emalfarb et al. |
| 6,660,506 B2 | 12/2003 | Nguyen et al. |
| 6,768,001 B2 | 7/2004 | Saloheimo et al. |
| 6,982,159 B2 | 1/2006 | Dunn-Coleman et al. |
| 7,005,289 B2 | 2/2006 | Dunn-Coleman et al. |
| 7,045,332 B2 | 5/2006 | Dunn-Coleman et al. |
| 7,314,743 B2 | 1/2008 | Clarkson et al. |
| 7,459,299 B2 | 12/2008 | Goedegebuur et al. |
| 7,960,146 B2 | 6/2011 | Dunn-Coleman et al. |
| 7,960,147 B2 | 6/2011 | Danenberg et al. |
| 8,288,148 B2 | 10/2012 | Cervin et al. |
| 8,476,048 B2 | 7/2013 | Caimi et al. |
| 8,518,684 B2 | 8/2013 | Brown et al. |
| 8,647,850 B2 | 2/2014 | Hitz et al. |
| 8,673,618 B2 | 3/2014 | Gusakov et al. |
| 8,721,794 B2 | 5/2014 | Hennessey et al. |
| 8,906,235 B2 | 12/2014 | Hennessey et al. |
| 9,175,275 B2 | 11/2015 | Gray et al. |
| 9,279,112 B2 | 3/2016 | Scott et al. |
| 9,447,400 B2 | 9/2016 | Bott et al. |
| 2002/0084046 A1 | 7/2002 | Hsu et al. |
| 2003/0113732 A1 | 6/2003 | Dunn-Coleman et al. |
| 2003/0113734 A1 | 6/2003 | Dunn-Coleman et al. |
| 2003/0113735 A1 | 6/2003 | Dunn-Coleman et al. |
| 2003/0114330 A1 | 6/2003 | Dunn-Coleman et al. |
| 2004/0102619 A1 | 5/2004 | Dunn-Coleman et al. |

(Continued)

FOREIGN PATENT DOCUMENTS

| | | |
|---|---|---|
| DE | 10043662 | 2/2001 |
| EP | 2397491 | 12/2011 |

(Continued)

OTHER PUBLICATIONS

Zhang et al., Formation of ethyl β-xylopyranoside during simultaneous saccharification and co-fermentation of paper sludge, Enz. Microbial Tech., Apr. 2009, 44, 196-202.*

(Continued)

*Primary Examiner* — Robert B Mondesi
*Assistant Examiner* — Todd Matthew Epstein

(57) ABSTRACT

The present disclosure is directed, in a first aspect, to the use of inverting beta-xylosidase enzymes to reduce byproduct formation and increase the yield of fermentation products, as well as, in a second aspect, to the use of retaining beta-xylosidase enzymes to improve production of alkyl-beta-xylopyranoside compounds, in a simultaneous saccharification and fermentation reactions.

39 Claims, 39 Drawing Sheets

Figures 1, 1A:
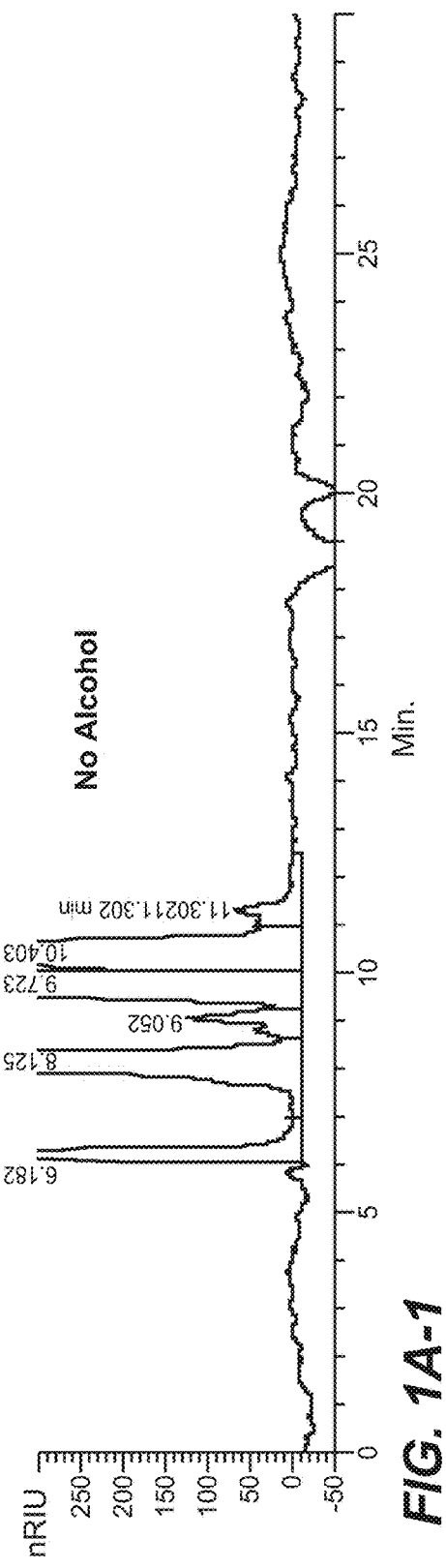

Specification includes a Sequence Listing.

(56) References Cited

U.S. PATENT DOCUMENTS

| | | |
|---|---|---|
| 2005/0191736 A1 | 9/2005 | Brown et al. |
| 2006/0003408 A1 | 1/2006 | Dunn-Coleman et al. |
| 2006/0075522 A1 | 4/2006 | Cleveland et al. |
| 2006/0258554 A1 | 11/2006 | Dunn-Coleman et al. |
| 2007/0031918 A1 | 2/2007 | Dunson et al. |
| 2007/0031919 A1 | 2/2007 | Dunson et al. |
| 2007/0031953 A1 | 2/2007 | Dunson et al. |
| 2007/0037259 A1 | 2/2007 | Hennessey et al. |
| 2007/0077630 A1 | 4/2007 | Harris et al. |
| 2008/0076159 A1 | 3/2008 | Baez-Vasquez et al. |
| 2008/0293109 A1* | 11/2008 | Berka et al. .................. 435/107 |
| 2008/0299613 A1 | 12/2008 | Merino et al. |
| 2009/0050134 A1 | 2/2009 | Friend et al. |
| 2009/0099079 A1 | 4/2009 | Emalfarb et al. |
| 2009/0280541 A1* | 11/2009 | Jordan et al. .................. 435/105 |
| 2010/0124769 A1 | 5/2010 | Brown et al. |
| 2011/0039320 A1 | 2/2011 | Li et al. |
| 2011/0086408 A1 | 4/2011 | Power et al. |
| 2011/0136182 A1* | 6/2011 | Huang et al. .................. 435/99 |
| 2011/0212505 A1 | 9/2011 | Dunn-Coleman et al. |
| 2011/0318803 A1 | 12/2011 | Hitz et al. |
| 2012/0135499 A1 | 5/2012 | Bower et al. |
| 2013/0143277 A1 | 6/2013 | Gutierrez et al. |
| 2013/0143301 A1 | 6/2013 | Bott et al. |
| 2013/0177947 A1 | 7/2013 | Bower et al. |
| 2013/0337508 A1 | 12/2013 | Fujdala et al. |
| 2014/0073017 A1 | 3/2014 | Kaper et al. |
| 2014/0106408 A1 | 4/2014 | Mitchinson et al. |
| 2014/0134677 A1 | 5/2014 | Mitchinson et al. |
| 2014/0295475 A1 | 10/2014 | England et al. |
| 2015/0010981 A1 | 1/2015 | Yang et al. |
| 2016/0060665 A1 | 3/2016 | Power et al. |
| 2016/0177279 A1 | 6/2016 | Bower et al. |
| 2016/0272956 A1 | 9/2016 | Garcia et al. |
| 2017/0096651 A1 | 4/2017 | Mitchinson et al. |

FOREIGN PATENT DOCUMENTS

| | | |
|---|---|---|
| WO | 97/00964 | 1/1997 |
| WO | 9815633 | 4/1998 |
| WO | 9902693 | 1/1999 |
| WO | 0149859 | 7/2001 |
| WO | 02095014 | 11/2002 |
| WO | 03027306 | 4/2003 |
| WO | 03052118 | 6/2003 |
| WO | 03093420 A2 | 11/2003 |
| WO | 2004016760 | 2/2004 |
| WO | 2004033646 | 4/2004 |
| WO | 2004043980 | 5/2004 |
| WO | 2004078919 | 9/2004 |
| WO | 2004081185 | 9/2004 |
| WO | 2005001036 | 1/2005 |
| WO | 2005001065 | 1/2005 |
| WO | 2005028636 | 3/2005 |
| WO | 2005074647 A2 | 8/2005 |
| WO | 2005074656 A2 | 8/2005 |
| WO | 2005093050 | 10/2005 |
| WO | 2005093073 | 10/2005 |
| WO | 2005118769 A1 | 12/2005 |
| WO | 2006074005 | 7/2006 |
| WO | 2006110901 | 10/2006 |
| WO | 2006110902 A1 | 10/2006 |
| WO | 2006114095 A1 | 11/2006 |
| WO | 2007071818 A1 | 6/2007 |
| WO | 2007/094852 | 8/2007 |
| WO | 2007089290 A2 | 8/2007 |
| WO | 2008025165 A1 | 3/2008 |
| WO | 2008039370 | 4/2008 |
| WO | WO 2008045977 A2 * | 4/2008 |
| WO | 2008140749 A2 | 11/2008 |
| WO | 2008147396 | 12/2008 |
| WO | 2008151079 | 12/2008 |
| WO | 2008153712 | 12/2008 |
| WO | 2008153903 | 12/2008 |
| WO | 2009003167 | 12/2008 |
| WO | 2009009142 A2 | 1/2009 |
| WO | 2009033071 A2 | 3/2009 |
| WO | 2009035537 | 3/2009 |
| WO | 2009045627 A2 | 4/2009 |
| WO | 2009074685 | 6/2009 |
| WO | 2009076676 | 6/2009 |
| WO | 2009085859 A2 | 7/2009 |
| WO | 2009/108941 | 9/2009 |
| WO | 2009117689 A1 | 9/2009 |
| WO | 2009132008 A2 | 10/2009 |
| WO | 2009149202 | 12/2009 |
| WO | 2010096673 | 8/2010 |
| WO | 2010138754 A1 | 12/2010 |
| WO | 2010141779 | 12/2010 |
| WO | 2010148148 A2 | 12/2010 |
| WO | 2011/038019 | 3/2011 |
| WO | 2011063308 | 5/2011 |
| WO | 2011079048 A2 | 6/2011 |
| WO | 2011137150 | 11/2011 |
| WO | 2011153276 | 12/2011 |
| WO | 2011161063 | 12/2011 |
| WO | 2012030845 | 3/2012 |
| WO | 2012125925 A2 | 9/2012 |
| WO | 2012125937 A2 | 9/2012 |
| WO | 2012125951 | 9/2012 |
| WO | 2012154735 | 11/2012 |
| WO | 2013090053 | 6/2013 |
| WO | 2014070837 | 5/2014 |
| WO | 2014070841 | 5/2014 |
| WO | 2014093275 | 6/2014 |
| WO | 2015/004254 A1 | 2/2015 |
| WO | 2015/017255 A1 | 2/2015 |
| WO | 2015/017256 A1 | 2/2015 |
| WO | 2015084596 | 6/2015 |

OTHER PUBLICATIONS

Drouet et al., Enzymatic synthesis of alkyl β-D-xylosides by transylosylation and reverse hydrolysis, Biotech. Bioeng., 1994, 43, 1075-80.*

Smaali et al., Expression in *Escherichaia coli* and characterization of β-xylosidase GH39 and GH-43 from Bacillus halodurans C-125, Appl. Microbiol. Biotechnol., 2006, 73, 582-90.*

Margolles-Clark et al., Cloning of genes encoding α-L-arabinofuranosidase and β-xylosidase from Trichoderma reesei by expression in *Saccharomyces cerevisiae*, Appl. Environ. Microbiol., 1996, 62, 3840-46.*

Mamma et al., Fungal multienzyme production on industrial by-products of the citrus-processing industry, Bioresource Tech., Jun. 2007, 99, 2373-83.*

UniProt, Accession No. N1S321, 2013, www.uniprot.org.*

Megazyme, 1,4-β-D-xylohexaose (Lot 121206), 2013.*

Nagendran et al., Reduced genomic potential for secreted plant cell-wall-degrading enzymes in the ectomycorrhizal fungus Amanita bisporigera, based on the secretome of Trichoderma reesei, Fungal Genetics Biol., 2009, 46, 427-35.*

Knob et al., β-xylosidases from filamentous fungi, World J. Microbiol. Biotechnol., Oct. 2009, 26, 389-407.*

Brux et al., The Structure of an Inverting GH43 β-Xylosidase from Geobacillus stearothermophilus with its Substrate Reveals the Role of the Three Catalytic Residues, J. Mol. Biol., 2006, 359, 97-109.*

Saha, Purification and characterization of an extracellular β-xylosidase from a newly isolated Fusarium verticillioides, J. Indust. Microbiol. Biotechnol., 2001, 27, 241-45.*

U.S. Appl. No. 61/245,273, filed Sep. 23, 2009.*

Shallom et al., Biochemical Characterization and Identification of the Catalytic Residues of a Family 43 beta-D-Xylosidase from Geobacillus stearothermophilus T-6, Biochemistry, 2005, 44, 287-97.*

GenBank, Accession No. AY690618.1, 2004, www.ncbi.nlm.nih.gov.*

Olofsson et al., A short review on SSF—an interesting process option for ethanol production from lignocellulosic feedstocks, Biotech. Biofuels, 2008, 1, 7.*

(56) References Cited

OTHER PUBLICATIONS

Akel, et al., "Molecular Regulation of Arabinan and L-Arabinose Metabolism in Hypocrea jecorina (Trichoderma reesei)," Eukaryotic Cell, vol. 8, No. 12, Dec. 1, 2009, pp. 1837-1844.
Brown, et al., "Comparative Analysis of 87,000 Expressed Sequence Tags from the Fumonisin-producingfungus *Fusarium verticillioides*," Fungal Genetics and Biology, CA, US, San Diego, vol. 42, No. 10, Oct. 1, 2005, pp. 848-861.
Database EMBL [Online], Database Accession No. DR631218 sequence, Jul. 12, 2005, "EST1021346 Fvl Gibberella moniliformis cDNA clone FVIE185, mRNA sequence," retrieved from EBI Accession No. EMBL: DR631218.
Database EMBL [Online], Database Accession No. DR628222 sequence, Jul. 12, 2005, "EST1018350 Fvl Gibberella moniliformis cDNA clone FVICQ42, mRNA sequence," retrieved from EBI Accession No. EM EST: DR628222.
Database EMBL [Online] Database Accession No. DR630608 sequence, Jul. 12, 2005, "EST1020736 Fvl Gibberella moniliformis cDNA clone FVIDS84, mRNA sequence," retrieved from EBI Accession No. EM EST: DR630608.
Database UniProt [Online], Database Accession No. Q09LXO sequence, Oct. 17, 2006, "SubName: Full=Beta-xylosidase", retrieved from EBI Accession No. UniProt: Q09LXO.
Database UniProt [Online], Database Accession No. A4UVM8 Sequence, May 15, 2007, retrieved from EBI Accession No. UniProt: A4UVM8.
Database Geneseq [Online] Database Accession No. AXR37961 sequence, Nov. 26, 2009, "Plant biomass degradation related protein Seq ID No. 107," retrieved from EBI Accession No. GSP: AXR37961 xp002672566.
Database Geneseq [Online], Database Accession No. AXR38055 sequence, Nov. 26, 2009, "Plant biomass degradation related Seq 1D No. 199," retrieved from EBI Accession No. GSP: AXR38055.
Database Geneseq [Online], Accession No. AXR38027, Nov. 26, 2009, "Plant biomass degradation related Seq 1D No. I72," retrieved from EBI Accession No. GSP: AXR38027.
Database Geneseq [Online], Database Accession No. AXR38047 sequence, Nov. 26, 2009, "Plant biomass degradation related Seq 1D No. 192," retrieved from EBI Accession No. GSP: AXR38047.
Kitamoto, et al., "Sequence Analysis, Overexpression, and Antisense Inhibition of a b-Xylosidase Gene, xylA,from ASpergillus orvzae KBN616," Applied and Environmenta Microbiology, Jan. 1999, pp. 20-24.
Zhang, et al., "Formation of Ethyl Beta-xylopyranoside During Simultaneous Saccharification and Co-fermentation of Paper Sludge," Enzyme and Microbial Technology, Stoneham, MA, US, vol. 44, No. 4, Apr. 6, 2009, pp. 196-202.
International Search Report mailed on May 7, 2012, for PCT Patent Application No. PCT/US2010/061082, filed on Dec. 17, 2010.
Akel, Eda, "Molecular Regulation of Arabinan and I-Arabinose Metabolism in Hypocrea jecornia (Trichoderma reesei)," Eukaryotic Cell, Dec. 1, 2009, vol. 8, No. 12, pp. 1837-1844.
Brüx, Christian, et al., "Crystallization and preliminary crystallographic analysis of a family 43 β-D-xylosidase from Geobacillus stearothermophilus T-6," Acta Crystallographica, Section F., Nov. 12, 2005, pp. 1054-1057.
Dogaris, Ioannis, et al. Induction of Cellulases and hemicellulases from Neurospora crassa under solid-state cultivated for bioconversion of sorghum bagasse into alcohol, Industrial Crops and Products, Mar. 2009, vol. 29, No. 2-3, pp. 401-411.
Drouet, Philippe, et al., "Production of Nkyl P-D-Xylosides with the Trichoderma reesei β- Xylosidase," Annals of the New York Academy of Sciences, Mar. 1, 1995, vol. 750, pp. 306-311.
Gargouri, Mohammed, et al., "Fungus β-glycosidases: immobilization and use in alkyl-β-glycoside synthesis," Journal of Molecular Catalysis B: Enzymatic, Jun. 1, 2004, vol. 29, No. 1-6, pp. 89-94.
Geneseq Accession No. AXR37961 (Plant biomass degradation related protein; Seq ID No. 107 from WO2009108941-A2, published Sep. 3, 2009), printed Mar. 29, 2012.

GenBank Accession No. EGU86020 (hypothetical protein FOXB_03424 [Fusarium oxysporum Fo5176]): last modification date Aug. 5, 2011; printed on Mar. 9, 2016, pp. 1-2.
GenBank Accession No. CAK96229 (unnamed protein product [Aspergillus niger]) last modification date Mar. 14, 2015); printed on Mar. 9, 2016, pp. 1-2.
GenBank Accession No. AAD13106 (beta-xylosidase [Aspergillus niger]]): last modification date Dec. 4, 2001; printed on Mar. 9, 2016, pp. 1-2.
Zhang, et al., "Formation of Ethyl β-xylopyranoside during simultaneous saccharification and co-fermentation of papers sludge," Enyzme and Microbial Technology, Apr. 2009, vol. 44, No. 4, pp. 196-202.
Matsuo, M., et al., "Four Types of β-Xylosidases fom Penicillium wortmanni IFO 7237," Agricultural and Biological Chemistry, 1987, vol. 51, No. 9, pp. 2367-2380.
Saha, B.C., "Xylanase from a newly isolated Fusarium verticillioides capable of utilizing corn fiber xylan," Applied Microbiol and Biotechnol. Sep. 1, 2001, vol. 56, No. 5-6, pp. 762-766.
Shinoyama, Hirofumi, et al., "Enzymatic Synthesis of Alkyl β-Xylosides from Xylobiose by Application of the Transxylosyl Reaction of Aspergillus niger β-Xylosidase," Agricultural and Biological Chemistry, Jan. 1, 1988, vol. 52, No. 9, pp. 2197-2202.
Smaali, Issam, et al., "Biocatalytic conversion of wheat bran hydrolysate using an immobilized GH43 beta-xylosidase", Bioresource Technology, Jan. 1, 2009, vol. 100, No. 1, pp. 338-344.
Sorensen, HR, et al., "Enzymatic hydrolysis of water-soluble wheat arabinoxylan. 1. Synergy between α-L-arabinofuranosidases, endo-1,4-β-xylanases, and β-xylosidase activities," Biotechnology and Bioengineering, Mar. 20, 2003, vol. 81, No. 6, pp. 726-731.
Sorensen, HR, et al., "Enzymatic Hydrolysis of Wheat Arabinoxylan by a Recombinant "Minimal" Enzyme Cocktail Containing β-Xylosidase and Novel endo-1,4-β-Xylanase and α-L-Arabinofuranosidase Activities," Biotechnology Progress, Jan. 1, 2007, vol. 23, No. 1, pp. 100-107.
UniProtKB/Swiss-Prot: Accession No. Q4X0K2 (Xylosidase : arabinofuranosidase): last modification date Oct. 31, 2006; printed on Mar. 10, 2016, pp. 1-2.
UniProtKB/Swiss-Prot: Accession No. P45702 (RecName: Full= Beta-xylosidase; AltName: Full=1,4-beta-D-xylan xylohydrolase; AltName: Full=Xylan 1,4-beta-xylosidase; Flags: Precursor): last modification date Jan. 7, 2015, printed Mar. 10, 2016, pp. 1-2.
UniProtKB/Swiss-Prot: Accession No. P36906 (RecName: Full= Beta-xylosidase; AltName: Full=1,4-beta-D-xylan xylohydrolase; AltName: Full=Xylan 1,4-beta-xylosidase): last modification date Oct. 14, 2015, printed Mar. 10, 2016, pp. 1-7.
UniProtKB/Swiss-Prot: Accession No. P48792 (RecName: Full= Arabinofuranosidase/B-xylosidase: Includes: RecName: Full=Alpha-L-arabinofuranosidase; Short=Arabinosidase; Includes: RecName: Full=Beta-xylosidase; AltName: Full=1,4-beta-D-xylan xylohydrolase; AltName: Full=Xylan 1,4-beta-xylosidase; Flags: Prescursor): last modification date Dec. 9, 2015, printed Mar. 10, 2016, pp. 1-2.
Wakiyama, M. et al, "Purification and Properties of an Extracellular β-Xylosidase from Aspergillus japonicus and Sequence Analysis of the Encoding Gene," Journal of Bioscience and Bioengineering, Oct. 1, 2008, vol. 106, No. 4, pp. 398-404.
Ma et al., Comparative genomics reveals mobile pathogenicity chromosomes in *Fusarium*, Nature, Mar. 18, 2010, pp. 367-373, vol. 464.
Supplementary Information, Figures S1-S20, from Ma et al. Comparative genomics reveals mobile pathogenicity chromosomes in *Fusarium*, Nature, 2010, pp. 367-373, vol. 464, No. 18.
Supplementary Information, pp. 1-31, from Ma et al. Comparative genomics reveals mobile pathogenicity chromosomes in *Fusarium*, Nature, 2010, pp. 367-373, vol. 464, No. 18.
Supplementary Information, Tables S1-S25, from Ma et al. Comparative genomics reveals mobile pathogenicity chromosomes in *Fusarium*, Nature, 2010, pp. 367-373, vol. 464, No. 18.
Fusarium Comparative Genome Project, Broad Institute, pp. 1-6; www.broadinstitute.org/scientific-community/science/projects/fungal-genome-initiative/fusarium-comparative-genome-project; printed Mar. 3, 2017.

(56) References Cited

OTHER PUBLICATIONS

Genbank Accession No. XP018761619, alpha-N-arabinofuranosidase [Fusarium verticilloides 7600], last modification date Oct. 27, 2016.
Genbank Accession No. XM_018902798, Fusarium verticillioides 7600 alpha-N-arabinofuranosidase partial mRNA, last modification date Oct. 27, 2016.
Cuomo et al. The Fusarium Graminearum Genome Reveals a Link Between Localized Polymorphism and Pathogen Specialization, Science, 2007, vol. 317, No. 5843, pp. 1400-2.
Genbank Accession No. XM_018379765, *Fusarium Oxysporum F.* sp. *Lycopersici* 4287 Beta-Glucosidase, mRNA, last modification date Sep. 26, 2016; printed on Feb. 28, 2017, pp. 1-2.
Genbank Accession No. XP_018235878, Beta-Glucosidase [*Fusarium Oxysporum F.* sp. *Lycopersici* 4287]), last modification date Sep. 26, 2016; printed on Feb. 28, 2017, pp. 1-2.
*Fusarium Oxysporum F.* sp. *Lycopersici* Genome, *Fusarium Oxysporum f.* sp. *Lycopersici* Ensembl Genomes 34, pp. 1-2; fungi.ensembl.org/Fusarium_oxysporum/Info/Annotation/; printed Mar. 3, 2017.
Pending U.S. Appl. No. 15/440,341, filed Feb. 23, 2017.
PCT International Search Report issued for PCT/US2012/029498 dated May 8, 2012.
PCT Written Opinion issued for PCT/US2012/029498 dated May 8, 2012.
Knowles et al., 'Cellulase families and their genes,' Trends in Biotechnology, 1987, vol. 5, No. 9, pp. 255-261.
Kosecki et al., 'Mutational analysis of N-glycosylation recognition sites on the biochemical properties of Aspergillus kawachii α-L-arabinofuranosidase 54,' Biochim. Biophys. Acta, 2006, vol. 1760, pp. 1458-1464.
Kotake et al., 'An α-L-arabinofuranosidase/β-D-xylosidase from immature seeds of radish (*Raphanus sativus* L),' J. Exp. Botany, 2006, vol. 57, pp. 2353-2362.
Kurakake et al., 'Characteristics of transxylosylation by β-xylosidase from Aspergillus awamori K4,' Biochim. Biophys. Acta, 2005, vol. 1726, pp. 272-279.
Lee et al., 'Bifunctional family of 3 glycoside hydrolases from barley with α-L-arabinofuranosidase and β-D-xylosidase activity. Characterization, primary structures and COOH-terminal processing,' J. Biol. Chem., 2003, vol. 278, pp. 5377-5387.
Li et al., 'Catalytic mechanism of a family 3 β-glucosidase and mutagenesis study on residue Asp-24,' Biochem. J., 2001, vol. 355, pp. 835-840.
Luthi et al., 'Xylanase from the extremely thermophilic bacterium "*Caldocellum saccharolyticum*": overexpression of the gene in *Escherichia coli* and characterization of the gene product,' Appl. Environ. Microbiol., 1990, vol. 56, No. 9, pp. 2677-2683.
Machida et al., 'Nucelotide sequences of saccharomycopsis fibuligera genes for extracellular β-glucosidases as expressed in *saccharomyces cerevisiae*,' Appl. Environ. Microbiol., 1988, vol. 54, pp. 3147-3155.
Margolles et al., 'Purificationa nd functional characterization of a novel α-l-arabinofuranosidase from bifidobacterium longum B66,' Appl. Environ. Microbiol., 2003, vol. 69, pp. 5096-5103.
Miyazaki et al., 'Hyperthermophilic α-L-arabinofuranosidase from thermotoga maritima MSB8: molecular cloning, gene expression, and characterization of the recombinant protein,' Extremophiles, 2005, vol. 9, pp. 399-406.
Morosoli et al., 'Purification and properties of a xylanase from Streptomyces lividans,' Biochem. J., 1986, vol. 239, pp. 587-592.
Numan et al., 'α-L-arabinofuranosidases: the potential applications in biotechnology,' J. Ind. Microbiol. Biotechnol., 2006, vol. 33, pp. 247-260.
Nuyens et al., Heterologous expression of the bacillus pumilus endo-β-xylanase (xynA) gene in the yeast *saccharomyces cerevisiae*,' Applied Microbiology and Biotechnology, 2001, vol. 56, pp. 431-434.
Oguntimein et al., 'Properties of soluble and immobilized Aspergillus niger β-xylosidase,' Biotechnol. Bioeng., 1980, vol. 22, pp. 1143-1154.
Olsson et al., 'Fermentation of lignocellulosic hydrolysates for ethanol production,' Enzyme Microb Technol., 1996, vol. 18, pp. 312-331.
Oshima et al., 'Purification and characterization of an Exo-1, 5-alpha-L-arabinanase from Aspergillus sojae,' Journal of Applied Glycoscience, 2005, vol. 52, pp. 261-265.
Pace et al., 'How to measure and predict the molar absorption coefficient of a protein,' Protein Science, 1995, vol. 4, pp. 2411-2423.
Panagiotou et al., 'Induction, purification and characterization of two extracellular-L-arabinofuranosidases from Fusarium oxysporum,' Can. J. Microbial., 2003, vol. 49, pp. 639-644.
Pentilla et al., 'A versatile transformation system for the cellulolytic filamentous fungus *Trichoderma reesei*,' Gene, 1987, vol. 61, pp. 155-164.
Pinphanichakarn et al., 'Purification and characterization of β-xylosidase from *streptomyces* sp. CH7 and its gene sequence analysis,' World J. Microbial. Biotechnol., 2004, vol. 20, pp. 727-733.
Pozzo et al., 'Structural and functional analysis of β-glucosidase 3B from thermotoga neapolitana: a thermostable three-domain representative of glycoside hydrolase 3,' J. Mol. Biol., 2010, vol. 397, pp. 724-739.
Rahman et al., 'A role of xylanase,-L-arabinofuranosidase and xylosidase in xylan degradation,' Can. J. Microbiol., 2003, vol. 49, pp. 58-64.
Rahman et al., 'Substrate specificity of the α-L-arabinofuranosidase from Rhizomucor pusillus HHT-1,' Carbohydrate Research, 2003, vol. 338, pp. 1469-1476.
Reen et al., 'Molecular characterization and expression analysis of the first hemicellulase gene (bxl1) encoding β-xylosidase from the thermophilic fungus *Talaromyces emersonii*,' Biochem. Biophys. Res. Commun., 2003, vol. 305, No. 3, pp. 579-585.
Rose et al., 'Crystallization and preliminary x-ray diffraction study of a xylanase from trichoderma harzianum,' J. Mol. Biol., 1987, vol. 194, No. 4, pp. 755-756.
Sader et al., 'Application of Kjeldahl and Dumas combustion methods for nitrogen analysis,' Archives of Veterinary Science, 2004, vol. 9, No. 2, pp. 73-79.
Sakamoto et al., 'Purification and properties of two type-B α-L-arabinofuranosidases produced by Penicillium chrysogenum,' Biochimic et Biophys. Acta, 2003, vol. 1621, pp. 204-210.
Schmidt et al., 'Xylanases and β-xylosidase of trichoderma lignorum,' Methods in Enzymology, 1988, vol. 160, pp. 662-671.
Schulein et al., 'Cellulases of trichoderma reesei,' Methods in Enzymology, 1988, vol. 160, pp. 234-242.
Shallom et al., 'Detailed kinetic analysis and identification of the nucleophile in α-L-arabinofuranosidase from Geobacillus stearothermophilus T-6, a family 51 glycoside hydrolase,' J. Biol. Chem., 2002, vol. 277, pp. 43667-43673.
Shareck et al., 'Sequences of three genes specifying xylanases in Streptomyces lividans,' Gene, 1991, vol. 107, pp. 75-82.
Shin et al., 'Purification and characterization of α-L-arabinopyranosidase and α-L-arabinofuranosidase from bifidobacterium breve K-110, a human intestinal anaerobic bacterium metabolizing ginsenoside Rb2 and Rc,' Appl. Environ. Microbiol., 2003, vol. 69, pp. 7116-7123.
Simpson et al., 'An extremely thermostable xylanase from the thermophilic eubacterium thermotoga,' Biochem. J., 1991, vol. 277, pp. 413-417.
Sluiter et al., 'Determination of structural carbohydrates and lignin in biomass,' National Renewable Energy Laboratory, 2008, Golden, CO, pp. 1-15.
Taylor et al., 'Structural insight into the ligand specificity of a thermostable family 51 arabinofuranosidase, Araf51, from Clostridium thermocellum,' Biochem. J., 2006, vol. 395, pp. 31-37.
Teixeira et al., 'Alkaline and peracetic acid pretreatments of biomass for ethanol production,' Appl. Biochem and Biotech., 1999, vol. 77, pp. 19-34.
Teymouri et al., 'Ammonia fiber explosion treatment of corn stover,' Applied Biochemistry and Biotechnology, 2004, vol. 113-116, pp. 951-963.

(56) References Cited

OTHER PUBLICATIONS

Tuncer et al., 'Purification and partial characterization of α-L-arabinofuranosidase produced by thermonospora fusca,' Folia Microbiol., 2008, vol. 48, No. 2, pp. 168-172.
Walseth et al., 'Occurrence of cellulases in enzyme preparations from microorganisms,' TAPPI, May 1952, vol. 35, No. 5, pp. 228-233.
Weichselbaum et al., 'An accurate and rapid method for the determination of proteins in small amounts of blood serum and plasma,' American Journal of Clinical Pathology, Mar. 1946, pp. 40-49.
Winterhalter et al., 'Two extremely thermostable xylanases of the hyperthermophilic bacterium thermotoga maritima MSB8,' Appl. Environ. Microbiol., 1995, vol. 61, No. 5, pp. 1810-1815.
Wong et al., 'The cloning, expression and characterization of a cellobiase gene encoding a secretory enzyme from cellulomonas biazotea,' Gene, 1998, vol. 207, pp. 79-86.
Wood et al., 'The genome sequence of Schizosaccharomyces Pombe,' Nature, 2002, vol. 415, pp. 871-880.
Wood et al., 'The cellulase of fusarium solani,' Biochem. J. 1971, vol. 121, pp. 353-362.
Xue et al., 'Expression and characterization of a thermostable β-xylosidase from the hyperthermophile, thermotoga maritima,' Biotechnol. Lett., 2004, vol. 26, pp. 1511-1515.
Yang et al., 'Nucleotide sequence of a bacillus circulans xylanese gene,' Nucleic Acids Res., 1988, vol. 16, No. 14, p. 7187.
Zaldivar et al., 'Fuel ethanol production from lignocellulose: a challenge for metabolic engineering and process integration,' Appl. Microbiol. Biotechnol., 2001, vol. 56, pp. 17-34.
Zanoelo et al., 'Purification and biochemical properties of a thermostable xylose-tolerant β-D-xylosidase from Scytalidium thermophilum,' J. Ind. Microbiol. Biotechnol., 2004, vol. 31, pp. 170-176.
Zappe et al., 'Nucleotide sequence of a clostridium acetobutylicum P262 xylanase gene (xynB),' Nucleic Acids Res., 1990, vol. 18, No. 8, p. 2179.
UniProt Accession No. Q9ZFM2, (Recname: Full=Beta-Xylosidase; Altname: Full=1,4-Beta-D-Xylan Xylohydrolase; Altname: Full=Xylan 1, 4-Beta-Xylosidase), last modification date Nov. 2, 2016; printed on Feb. 28, 2017, pp. 1-2.
Andrade et al., 'Effect of carbon source on the biochemical properties of β-xylosidases produced by Aspergillus versicolor,' Process Biochem., 2004, vol. 39, pp. 1931-1938.
Barnett et al., 'Cloning and amplification of the gene encoding an extracellular β-glucosidase from Trichoderma reesei: evidence for improved rates of saccharification of cellulosic substrates,' Biotechnology, 1991, vol. 9, No. 6, pp. 562-567.
Bernier et al., 'Molecular cloning of a Bacillus subtilis xylanase gene in *Escherichia coli.*' Gene, 1983, vol. 26, No. 1, pp. 59-65.
Campbell et al., 'Improved transformation efficiency of Aspergillus niger using the homologous niaD gene for nitrate reductase,' Current Genetics, 1989, vol. 16, pp. 53-56.
Canals et al., 'Structure of xylanase Xys1 from Steptomyces halstedii,' Acta Crystalogr. Section D Biological Chrystallography, 2003, vol. 59, pp. 1447-1453.
Cantarel et al., 'The carbohydrate-active enzymes database (CAZy): an expert resource for Glycogenomics,' Nucleic Acids Res., 2009, vol. 37, pp. D233-38.
Chacon-Martinez et al., 'Identification and characterization of the α-L-arabinofuranosidase B of Fusarium oxysporum f. sp. Dianthi,' Physiol. Mol. Plant Pathol., 2004, vol. 64, pp. 201-208.
Chen et al., 'Potential of agricultural residues and hay for bioethanol production,' Appl Biochem Biotechnol., Sep. 2007, vol. 142(3), pp. 276-290.
Chen et al., 'Purification and characterization of two extracellular β-glucosidases from Trichoderma reesei,' Biochimica et Biophysica Acta, 1992, vol. 1121, pp. 54-60.
Clarke et al., 'A modular xylanase from mesophilic Cellulomonas fimi contains the same cellulose-binding and thermostabilizing domains as xylanases from thermophilic bacteria,' Fems Microbiology Letters, 1996, vol. 139, pp. 27-35.
Coutinho et al., 'The modular structure of cellulases and other carbohydrate-active enzymes: an integrated database approach,' Genetics, Biochemistry, and Ecology of Cellulse Degradation, UNI Publishers Co., 1999, pp. 15-23.
Database Geneseq ID: AXR39051 )Plant biomass degrading enzyme encoding DNA #271): Seq ID No. 2785 from International Patent Application Publication No. WO2009108941-A2, published Sep. 3, 2009, printed Mar. 18, 2016, pp. 1-2.
Database EMBL, Database Accession No. GY256384, 'Sequence 1 from U.S. Pat. No. 7,960,146,' Jun. 21, 2011.
Debeche et al., 'Probing the catalytically residues of the α-L-arabinofuranosidase from Thermobacillus kylanilyticus,' Protein Engineering, 2002, vol. 15, No. 1, pp. 21-28.
Deog et al., 'Construction and characterization of novel chimeric beta-glucosidases with Cellvibrio gilvus (CG) and thermotoga maritima TM by overlapping PCR,' Biotechnology and Bioprocess Engineering, Jun. 1, 2009, vol. 14, No. 3, pp. 266-273.
Dominguez et al., 'A common protein fold and similar active site in two distinct families of β-glycanases,' Nature Structural Biology, Jul. 1995, vol. 2, No. 7, pp. 569-576.
Emsley et al., 'Features and development of Coot,' Acta Cryst., 2010, vol. D66, pp. 486-501.
Foreman et al., 'Transcirptional regulation of biomass-degrading enzymes in the filamentous fungus trichoderma reesei,' Journal of Biological Chemistry, Aug. 22, 2003, vol. 278, No. 34, pp. 31988-31997.
Galbe et al., 'A review of the production of ethanol from softwood,' Appl. Microbiol. Biotechnol., 2002, vol. 59, pp. 618-628.
GenBank Accession No. KNA97832, Beta-glucosidase, Fusarium Oxysporum F. Sp. Lycopersici 4287), last modification date Jul. 23, 2015; printed on Mar. 3, 2017, pp. 1-2.
GenbankAccession No. XM_018379766, Fusarium Oxysporum F. Sp. Lycopersici 4287 beta glucosidase mRNA, last modification date Sep. 26, 2016; printed on Mar. 3, 2017, pp. 1-2.
Genbank Accession No. XM_018893759, Fusarium Verticilloides 7600 beta-glucosidase mRNA, last modification date Oct. 27, 2016; printed on Mar. 3, 2017, pp. 1-2.
Genbank Accession No. XP_018235880, Beta glucosidase fusarium oxysporum f. sp. Lycopersici 4287, last modification date Sep. 26, 2016; printed on Mar. 3, 2017; pp. 1-2.
Genbank Accession No. XP_018750667, Beta-glucosidase fusarium verticilloides 7600, last modification date Oct. 27, 2016; printed on Mar. 3, 2017; pp. 1-2.
Genbank Accession No. XM_018379764, Fusarium oxysporum f. sp. Lycopersici 4287 beta glucosidase mRNA, last modification date Sep. 26, 2016; printed on Mar. 3, 2017, pp. 1-2.
Genbank Accession No. AY281374.1, Trichoderma reesei strain QM6a Cel3b (cel3b) mRNA, Last modification date Mar. 25, 2015; printed on Mar. 17, 2016; pp. 1-2.
Genbank Accession No. XM_006965219, Trichoderma reesei QM6a glycosidase hydolase family 3 (TRIREDRAFT_121735), Mma, Last modification date Mar. 15, 2014; printed on Mar. 18, 2016; pp. 1-3.
Genbank Accession No. XP_386781, Hypothetical protein FG06605.1, [*Fusarium graminearum* PH-1], Last modification date Oct. 19, 2010; printed Mar. 18, 2016, p. 1.
Genbank Accession No. XP_001912683, Hypothetical protein [*Podospora anserina* S mat+], last modification date May 5, 2010; printed on Nov. 24, 2015, pp. 1-2.
Genbank Accession No. XP_003045443, Hypothetical protein NECHADRAFT_39290 [Nectria haematococca mpVI77-13-4], last modification date Aug. 14, 2010; printed on Nov. 24, 2015, pp. 1-2.
Genbank Accession No. CAK48740, beta-glucosidase bgl1-Aspergillus niger, last modification date Mar. 14, 2015; printed on Nov. 24, 2015, pp. 1-2.
Genbank Accession No. AAL69548, beta-glucosidase [*Rasamsonia emersonii*], last modification date Jul. 10, 2003; printed on Nov. 25, 2015; pp. 1-2.
Genbank Accession No. AAP57755, Cel3b [*Trichoderma reese*]), last modification date Mar. 26, 2003; printed on Nov. 25, 2015; pp. 1-2.

(56) References Cited

OTHER PUBLICATIONS

Genbank Accession No. AAA18473, beta-D-glucoside glucohydrolase [*Trichoderma reesei*], last modification date May 26, 1994; printed on Nov. 25, 2015; pp. 1-2.

Genbank Accession No. Q0GC07, Beta-glucosidase) last modification date Nov. 28, 2006; printed on Nov. 25, 2015, pp. 1-2.

Genbank Accession No. Q7Z9M5, Cel3b, last modification date Oct. 31, 2006; printed on Nov. 25, 2015, pp. 1-2.

Ghose, 'International union of pure and applied chemistry,' Pure and Applied Chemistry, 1987, vol. 59, No. 2, pp. 257-268.

Gilbert et al., 'Molecular cloning of multiple xylanase genes from *pseudomonas fluorescens* subsp. *Cellulosa*,' Journal of General Microbiology, 1988, vol. 134, pp. 3239-3247.

Gornall et al., 'Determination of serum proteins by means of the biuret reaction,' J. Biol. Chem., 1949, vol. 177, pp. 752-766.

Gould et al., 'Alkaline peroxide delignification of agricultural residues to enhance enzymatic saccharification,' Biotech and Bioeng., 1984, vol. 26, pp. 46-52.

Goyal et al., 'Enhancement of transglycosylation activity by construction by chimeras between mesophilic and thermophilic beta-glucosidase,' Archives of Biochemistry and Biophysics, Nov. 1, 2002, vol. 407, No. 1, pp. 125-134.

Henrissat et al., 'A scheme for designating enzymes that hydrolyse the polysaccharides in the cell walls of plants,' Febs Letters, 1998, vol. 425, No. 2, pp. 352-354.

Iwashita et al., 'The bglA gene of Aspergillus kawachii encodes both extracellular and cell wall-bound β-glucosidases,' Appl. Environ. Microbiol., 1999, vol. 65, pp. 5546-5553.

Jung et al., 'Purification and characterization of α-L-arabinosidase from Trichoderma sp. SY,' Agric. Chem. Biotechnol., 2005, vol. 48, pp. 7-10.

Karlsson et al., 'Homologous expression and characterization of Cel61A (EG IV) reesei,' Eur. J. Biochem., 2001, vol. 268, pp. 6498-6507.

Kawaguchi et al., 'Cloning and sequencing of the cDNA encoding β-glucosidase 1 from Aspergillus aculeatus,' Gene, 1996, vol. 173, pp. 287-288.

Kim et al., 'Characterization of the arfA gene from Bacillus stearothermophilus No. 236 and its protein product, α-L-arabinofuranosidase,' J. Microbiol. Biotechnol., 2004, vol. 14, pp. 474-482.

Kim et al., 'Purification and characterization of β-xylosidase from *Trichoderma* sp. SY,' J. Microbiol. Biotechnol., 2004, vol. 14, pp. 643-645.

Kinoshita et al., 'Cloning of the xynNB gene encoding xylanase B from Aspergillus niger and its expression in Aspergillus kawachii,' Journal of Fermentation and Bioengineering, 1995, vol. 79, No. 5, pp. 422-428.

Kluepfel et al., 'Purification and characterization of a new xylanase (xylanase B) produced by Streptomyces lividans 66,' Biochem J., 1990, vol. 287, pp. 45-50.

Abdelkader et al., 'In-vitro studies on wood degradation in soil by soft-rot fungi: *Aspergillus niger* and *Penicillium chrysogenum*,' International Biodeterioration & Biodegradation, 2013, vol. 78, pp. 98-108.

Altschul et al., 'Blast Manual,' J. Mol. Biol., 1990, vol. 215, pp. 403-410.

Altschul et al., 'Gapped Blast and Psi-Blast: a new generation of protein database search programs,' Nucleic Acids Research, 1997, vol. 25:17, pp. 3389-3402.

Ausubel et al., (eds.) 'Current Protocols in Molecular Biology,' 1987, Supplement 30, Section 7.7.18 (copy not Provided as book is commonly available).

Berka et al., 'Molecular cloning and deletion of the gene encoding aspergillopepsin A from Aspergillus awamori,' Gene, 1990, vol. 86, pp. 153-162.

Biely et al., 'Proceedings of the second Tricel symposium on Trichoderma reesei Cellulases and other Hydrolases,' Espoo, Finland 1993, Souminen, P. and Reinikainen, R. (eds.), "Foundation for Biotechnical and Industrial Fermentation Research," 1993, vol. 8, pp. 125-135.

Harris et al., 'Stimulation of lignocellulosic biomass hydrolysis by proteins of glycoside hydrolase family 61: structure and function of a large, enigmatic family,' Biochemistry, American Chemical Society, Us, vol. 49, No. 15, Apr. 1, 2010, pp. 3305-3316, XP002608645, Issn: 0006-2960, Doi: 10.1021/Bi100009p [Retrieved on Mar. 15, 2010].

Herpoel-Gimbert et al., 'Comparative secretome analysis of two Trichoderma reesei RUT-C30 and CL847 hypersecretory strains,' Biotechnology for Biofuels, 2008, 1:18 doi:10.1186/1754-6834-1-18.

Juturu et al., 'Insight into microbial hemicellulases other than xylanases: a review,' J Chem Technol Biotechnol, 2013, vol. 88, pp. 353-363.

Mach-Aigner et al., 'Transcriptional regulation of xryl, encoding the main regulator of the xylanolytic and cellulolytic enzyme system in Hypocrea jecorina,' Applied and Environmental Microbiology, Nov. 2008, vol. 74, pp. 3554-6562.

Mandels, Cellulases Annu. Rep. Ferment. Process., 1982, 5, 35.

Margolles-Clark, 'Expression patterns of ten hemicellulase genes of the filamentous fungus Trichoderma reesei on various carbon sources' Journal of Biotechnology, Sep. 16, 1997, vol. 57, pp. 167-179.

Ogasawara et al., 'Cloning, Functional Expression and Promoter Analysis of Xylanase III Gene from Trichoderma reesei,' Applied Microbiology and Biotechnology,' 2006, vol. 72:5, pp. 995-1003.

Pearson et al., 'Improved tools for biological sequence comparison,' Proc. Natl. Acad. Sci. USA, 1988, 85, pp. 244-2448.

Persson et al., 'Fungal cellulolytic enzyme production: a review,' Process Biochemistry, 1991, vol. 26, pp. 65-74.

Pollet et al., 'Structural determinants of the substrate specificities of xylanases from different glycoside hydrolase families,' Critical Reviews in Biotechnology, 2010, vol. 30:3, pp. 176-191.

Prior et al., 'Hydrolysis of Ammonia-pretreated Sugar Cane Bagasse with Cellulase, β-Glucosidase and Hemicellulase Preparations,' Applied Biochemistry and Biotechnology, Mar. 2008, vol. 146, Issue 1-3, pp. 151-164.

Saha et al., 'a-L-Arabinofuranosidases: biochemistry, molecular biology and application in biotechnology,' Biotechnology Advances, 2000, vol. 18, pp. 403-423.

Schulte et al., UniProt, Accession No. Q9P3R7, version 15, Apr. 14, 2009.

Shallom et al., 'Microbial Hemicellulases,' Current Opinion in Microbiology, 2003, vol. 6:3, pp. 219-228.

Sheir-Neiss et al., 'Characterization of the secreted cellulases of Trichoderma reesei wild type and mutants during controlled fermentations,' Appl. Microbiol. Biotechnology, 1984, vol. 20, pp. 46-53.

Shirkot et al., 'Effect of Dithiocarbamates on Cellulase Activity in Culture Filtrates of Trichoderma reesei,' Biotechnology and Bioengineering, 1982, vol. XXIV, pp. 1233-1240.

Sorensen et al., 'Enzymatic hydrolysis of water-soluble wheat arabinoxylan. 1.Synergy between alpha-L-arabinofuranosidases, endo-1,4-beta-xylanases, and beta-xlyosidase activities,' Biotechnology and Bioengineering, 2003, 81:6, pp. 726-731.

Tabka et al., 'Enzymatic Saccharification of wheat straw for bioethanol production by a combined cellulase xylanase and feruloyl esterase treatment,' Enzyme and Microbial Technology,' 2006, vol. 39, pp. 897-902.

Tangnu et al., 'Enhanced production of cellulase, hemicellulase, and P-Glucosidase by Trichoderma reesei (Rut C-30),' Biotechnology and Bioengineering, 1981, vol. XXIII, pp. 1837-1849.

Tenkanen et al., 'Two major xylaneses of trichoderma reesei,' Enzyme Microb. Technol., 1992, 14:566-574.

Thygesen et al., 'Production of cellulose and hemicellulose-degrading enzymes by filamentous fungi cultivated on wet-oxidised wheat straw,' Enzyme and Microbial Technology, 2003, 32:5, pp. 606-615.

(56) References Cited

OTHER PUBLICATIONS

Torronen et al., 'The two major xylanases from trichoderma reesei: characterization of both enzymes and gens,' Biotechnology, 1992, vol. 10, pp. 1461-1465.
Xu et al., 'A third xylanase from trichoderma reesei PC-3-7,' Appl. Microbiol. Biotechnol. 1998, 49:718-724.
UniProt Acc# Q9P973 from Ogasawara et al., Appl Microbiol Biotechnol, 2006, 72: 995-1003, Alignment with Seq ID No. 2.
UniProt Acc# Q92458 from Margolles-Clark et al., Appl. Environ. Microbiol., vol. 62, No. 10 Oct. 1996, pp. 3840-3846, Alignment with Seq ID No. 17.
UniProt Acc# Q92455 from Margolles-Clark et al., Appl. Environ. Microbiol., vol. 62, No. 10 Oct. 1996, pp. 3840-3846, Alignment with Seq ID No. 3.
Database EMBL, Database Accession No. AB093564, 'Penicillium herquei mRNA for xylosidase, complete cds', Apr. 15, 2003, XP002633644.
Database EMBL, Database Accession No. EF490448, 'Penicillium purpurogenum alpha-L-arabinofuranosidase 2 (abf2) gene, complete cds.', Apr. 19, 2007, XP002633645.
Database REFSEQ, Database Accession No. XP_383785, NCBI reference sequence collection 'Hypothetical protein FG03609 [Giberella zeae PH-1], Apr. 9, 2008, XP002660306.
Database REFSEQ, Database Accession No. XP 386639.1, NCBI reference sequence collection 'Hypothetical protein FG06463.1 [Giberella zeae PH-1], Apr. 9, 2008, XP002660307.
Database EMBL, Database Accession No. FJ040192, 'Trichoderma sp. SSL endoglucanase IV mRNA, complete Cds.', Sep. 22, 2008, XP002683383.
PCT International Search Report issued for PCT/US2009/037853, dated Jul. 16, 2009.
PCT Written Opinion issued for PCT/US2009/037853, dated Jul. 16, 2009.
PCT International Search Report issued for PCT/US2010/049849, dated Sep. 30, 2011.
PCT Written Opinion issued for PCT/US2010/049849, dated Sep. 30, 2011.
PCT Written Opinion issued for PCT/US2010/061082, dated May 7, 2012.
PCT International Search Report issued for PCT/US2012/029445 dated Oct. 22, 2012.
PCT Written Opinon issued for PCT/US2012/029445 dated Oct. 22, 2012.
PCT International Search Report issued for PCT/US2012/029470, dated Sep. 14, 2012.
PCT Written Opinion issued for PCT/US2012/029470, dated Sep. 14, 2012.
Pending U.S. Appl. No. 15/647,775, filed Jul. 12, 2017.

\* cited by examiner

| | | | | | |
|---|---|---|---|---|---|
| exp2 Proton | | | SPECIAL | | |
| | | | temp | | 25.0 |
| | SAMPLE | | gain | | not used |
| date | | June 5 2009 | spin | | not used |
| solvent | | 020 | hst | | 0.008 |
| file | | exp | pw90 | | 14.500 |
| | ACQUISITION | | alfa | | 6.600 |
| sw | | 8012.8 | | FLAGS | |
| at | | 2.049 | il | | n |
| np | | 32830 | in | | n |
| fb | | 4000 | dp | | y |
| bs | | 32 | hs | | nn |
| ss | | 2 | | PROCESSING | |
| d1 | | 0.100 | lb | | 0.50 |
| nt | | 64 | fn | | 65536 |
| ct | | 64 | | DISPLAY | |
| | TRANSMITTER | | sp | | 370.1 |
| tn | | H1 | wp | | 2314.5 |
| sfrq | | 499.750 | rfl | | 1007.9 |
| tof | | 499.7 | rfp | | 0 |
| tpwr | | 57 | rp | | -118.6 |
| pw | | 7.250 | lp | | -34.5 |
| | DECOUPLER | | | PLOT | |
| dn | | C13 | wc | | 240 |
| dof | | 0 | sc | | 0 |
| dm | | nnn | vs | | 2491 |
| dmm | | c | th | | 12 |
| dpwr | | 36 | al cdc ph | | |
| dmf | | 32258 | | | |

*FIG. 3A*

| FIG. 3A | FIG. 3B |
|---|---|

*FIG. 3*

SEQ ID NO:1
Nucleotide sequence for Fv43D, GH43D family enzyme from *Fusarium verticillioides* atgcagctcaagtttctgtcttcagcattgttgctgtctttgaccggcaattgcgctgcgcaagacac
taatgatatccctcctctgatcaccgacctctggtctgcggatccctcggctcatgttttcgagggca
aactctgggtttacccatctcacgacatcgaagccaatgtcgtcaacggcaccggaggcgctcagtac
gccatgagagattatcacacctattccatgaagaccatctatggaaaagatccgttatcgaccatgg
cgtcgctctgtcagtcgatgatgtcccatgggccaagcagcaaatgtgggctcctgacgcagcttaca
agaacggcaaatattatctctacttccccgccaaggataaagatgagatcttcagaattggagttgct
gtctccaacaagcccagcggtccttttcaaggccgacaagagctggatccccggtacttacagtatcga
tcctgctagctatgtcgacactaatggcgaggcatacctcatctggggcggtatctggggcggccagc
ttcaggcctggcaggatcacaagacctttaatgagtcgtggctcggcgacaaagctgctcccaacggc
accaacgccctatctcctcagatcgccaagctaagcaaggacatgcacaagatcaccgagacaccccg
cgatctcgtcatcctggcccccgagacaggcaagccccttcaagcagaggacaataagcgacgatttt
tcgagggccctgggttcacaagcgcggcaagctgtactacctcatgtactctaccggcgacacgcac
ttcctcgtctacgcgacttccaagaacatctacggtccttatacctatcagggcaagattctcgaccc
tgttgatgggtggactacgcatggaagtattgttgagtacaagggacagtggtggttgttctttgcgg
atgcgcatacttctggaaaggattatctgagacaggttaaggcgaggaagatctggtatgacaaggat
ggcaagattttgcttactcgtcctaagatttag

*FIG. 19A*

SEQ ID NO:2
Protein sequence of Fv43D

<u>mqlkflssalllsltgncaa</u>qdtndippliitdlwsadpsahvfegklwvypshdieanvvngtggaqy
amrdyhtysmktiygkdpvidhgvalsvddvpwakqqm**wapdaaykngkyylyfpakdkdeifrigva
vsnkpsgpfkadkswipgtysidpasyvdtngeayliwggiwggqlqawqdhktfneswlgdkaapng
tnalspqiaklskdmhkitetprdlvilapetgkplqaednkrrffegpwvhkrgklyylmystgdth
flvyatskniygpytyqgkildpvdgwtthgsiveykgqwwlffadahtsgkdylrqvkarkiwydkd
g**killtrpki

*FIG. 19B*

SEQ ID NO:3
Nucleotide sequence of Bxl1, a GH3 family β-xylosidase from *Trichoderma reesei*

```
atggtgaata acgcagctct tctcgccgcc ctgtcggctc tcctgcccac ggccctggcg    60
cagaacaatc aaacatacgc caactactct gctcagggcc agcctgatct ctaccccgag   120
acacttgcca cgctcacact ctcgttcccc gactgcgaac atggcccct caagaacaat    180
ctcgtctgtg actcatcggc cggctatgta gagcgagccc aggccctcat ctcgctcttc   240
accctcgagg agctcattct caacacgcaa aactcgggcc ccggcgtgcc tcgcctgggt   300
cttccgaact accaagtctg gaatgaggct ctgacggct tggaccgcgc caacttcgcc    360
accaaggcg gccagttcga atgggcgacc tcgttcccca tgcccatcct cactacggcg    420
gccctcaacc gcacattgat ccaccagatt gccgacatca tctcgaccca agctcgagca   480
ttcagcaaca gcggccgtta cggtctcgac gtctatgcgc caaacgtcaa tggcttccga   540
agcccctct ggggccgtgg ccaggagacg cccggcgaag acgcctttt cctcagctcc    600
gcctatactt acgagtacat cacgggcatc cagggtggcg tcgaccctga gcacctcaag   660
gttgccgcca cggtgaagca ctttgccgga tacgacctcg agaactggaa caaccagtcc   720
cgtctcggtt tcgacgccat cataactcag caggacctct ccgaatacta cactcccag    780
ttcctcgctg cggcccgtta tgcaaagtca cgcagcttga tgtgcgcata caactccgtc   840
aacggcgtgc ccagctgtgc caacagcttc ttcctgcaga cgcttttgcg cgagagctgg   900
ggcttccccg aatggggata cgtctcgtcc gattgcgatg ccgtctacaa cgttttcaac   960
cctcatgact acgccagcaa ccagtcgtca gccgccgcca gctcactgcg agccggcacc  1020
gatatcgact gcggtcagac ttacccgtgg cacctcaacg agtcctttgt ggccggcgaa  1080
gtctcccgcg gcgagatcga gcggtccgtc accgtctgt acgccaacct cgtccgtctc  1140
ggatacttcg acaagaagaa ccagtaccgc tcgctcggtt ggaaggatgt cgtcaagact  1200
gatgcctgga acatctcgta cgaggctgct gttgagggca tcgtcctgct caagaacgat  1260
ggcactctcc ctctgtccaa gaaggtgcgc agcattgctc tgatcggacc atgggccaat  1320
gccacaaccc aaatgcaagg caactactat ggccctgccc atacctcat cagccctctg   1380
gaagctgcta agaaggccgg ctatcacgtc aactttgaac tcggcacaga gatcgccggc  1440
aacagcacca ctggcttttc caaggccatt gctgccgcca agaagtcgga tgccatcatc  1500
tacctcggtg gaattgacaa caccattgaa caggagggcg ctgaccgcac ggacattgct  1560
tggcccgta atcagctgga tctcatcaag cagctcagcg aggtcggcaa accccttgtc  1620
gtcctgcaaa tgggcggtgg tcaggtagac tcatcctcgc tcaagagcaa caagaaggtc  1680
aactccctcg tctggggcgg atatcccggc cagtcgggag cgttgccct cttcgacatt  1740
ctctctggca gcgtgctcc tgccggccga ctggtcacca ctcagtaccc ggctgagtat  1800
gttcaccaat tcccccagaa tgacatgaac ctccgacccg atggaaagtc aaaccctgga  1860
cagacttaca tctggtacac cggcaaaccc gtctacgagt ttggcagtgg tctcttctac  1920
accaccttca aggagactct cgccagccac cccaagagcc tcaagttcaa cacctcatcg  1980
atcctctctg ctcctcaccc cggatacact tacagcgagc agattcccgt cttcaccttc  2040
gaggccaaca tcaagaactc gggcaagacg gagtccccat atacggccat gctgtttgtt  2100
cgcacaagca acgctggccc agcccgtac ccgaacaagt ggctcgtcgg attcgaccga  2160
cttgccgaca tcaagcctgg tcactcttcc aagctcagca tcccatccc tgtcagtgct  2220
ctcgcccgtg ttgattctca cggaaaccgg attgtatacc ccggcaagta tgagctagcc  2280
ttgaacaccg acgagtctgt gaagcttgag tttgagttgg tgggagaaga ggtaacgatt  2340
gagaactggc cgttggagga gcaacagatc aaggatgcta cacctgacgc ataa         2394
```

*FIG. 20A*

SEQ ID NO: 4
Protein sequence of Bxl1, a GH3 family β-xylosidase from *Trichoderma reesei*

<u>mvnnaallaalsallptala</u>qnnqtyanysaqgqpdlypetiatltlsfpdcehgplknnlvcdssag
yveraqalislftleeliintqnsgpgvprlglpnyqvwnealhgldranfatkggqfewatsfpmpi
lttaalnrtlihqiadiistqarafsnsgrygldvyapnvngfrsplwgrgqetpgedafflssayty
eyitgiqggvdpehlkvaatvkhfagydlenwnnqsrlgfdaiitqqdlseyytpqflaaaryaksrs
lmcaynsvngvpscansfflqtllreswgfpewgyvssdcdavynvfnphdyasnqssaaasslragt
didcgqtypwhlnesfvagevsrgeiersvtrlyanlvrlgyfdkknqyrslgwkdvvktdawnisye
aavegivllkndgtlplskkvrsialigpwanattqmqgnyygpapylispleaakkagyhvnfelgt
eiagnsttgfakaiaaakksdaiiylggidntieqegadrtdiawpgnqldlikqlsevgkplvvlqm
gggqvdssslksnkkvnslvwggypgqsggvalfdilsgkrapagrlvttqypaeyvhqfpqndmnlr
pdgksnpgqtyiwytgkpvyefgsglfyttfketlashpkslkfntssilsaphpqytyseqipvftf
eaniknsgktespytamlfvrtsnagpapypnkwlvgfdrladikpghssklsipipvsalarvdshg
nrivypgkyelalntdesvklefelvgeevtienwpleeqqikdatpda

*FIG. 20B*

SEQ ID NO:5
**Nucleotide sequence for Fv3A, a GH3 family enzyme from *Fusarium verticillioides*** atgctgctcaatcttcaggtcgctgccagcgctttgtcgctttctcttttaggtggattggctgaggc
tgctacgccatataccct tccggactgtaccaaaggacctttgagcaagaatggaatctgcgatactt
cgttatctccagctaaaagagcggctgctctagttgctgctctgacgcccgaagagaaggtgggcaat
ctggtcaggtaaaatataccccccccataatcactattcggagattggagctgacttaacgcagcaa
tgcaactggtgcaccaagaatcggacttccaaggtacaactggtggaacgaagcccttcatggcctcg
ctggatctccaggtggtcgctttgccgacactcctccctacgacgcggccacatcatttcccatgcct
cttctcatggccgctgctttcgacgatgatctgatccacgatatcggcaacgtcgtcggcaccgaagc
gcgtgcgttcactaacggcggttggcgcggagtcgacttctggacacccaacgtcaacccttttaaag
atcctcgctggggtcgtggctccgaaactccaggtgaagatgcccttcatgtcagccggtatgctcgc
tatatcgtcaggggtctcgaaggcgataaggagcaacgacgtattgttgctacctgcaagcactatgc
tggaaacgactttgaggactggggaggcttcacgcgtcacgactttgatgccaagattactcctcagg
acttggctgagtactacgtcaggcctttccaggagtgcacccgtgatgcaaaggttggttccatcatg
tgcgcctacaatgccgtgaacggcattcccgcatgcgcaaactcgtatctgcaggagacgatcctcag
agggcactggaactggacgcgcgataacaactggatcactagtgattgtggcgccatgcaggatatct
ggcagaatcacaagtatgtcaagaccaacgctgaaggtgcccaggtagcttttgagaacggcatggat
tctagctgcgagtatactactaccagcgatgtctccgattcgtacaagcaaggcctcttgactgagaa
gctcatggatcgttcgttgaagcgccttttcgaagggcttgttcatactggtttctttgacggtgcca
aagcgcaatggaactcgctcagttttgcggatgtcaacaccaaggaagctcaggatcttgcactcaga
tctgctgtggagggtgctgttcttcttaagaatgacggcactttgcctctgaagctcaagaagaagga
tagtgttgcaatgatcggattctgggccaacgatacttccaagctgcagggtggttacagtggacgtg
ctccgttcctccacagcccgctttatgcagctgagaagcttggtcttgacaccaacgtggcttggggt
ccgacactgcagaacagctcatctcatgataactggaccaccaatgctgttgctgcggcgaagaagtc
tgattacattctctactttggtggtcttgacgcctctgctgctggcgaggacagagatcgtgagaacc
ttgactggcctgagagccagctgacccttcttcagaagctctctagtctcggcaagccactggttgtt
atccagcttggtgatcaagtcgatgacaccgctcttttgaagaacaagaagattaacagtattctttg
ggtcaattaccctggtcaggatggcggcactgcagtcatggacctgctcactggacgaaagagtcctg
ctggccgactacccgtcacgcaatatcccagtaaatacactgagcagattggcatgactgacatggac
ctcagacctaccaagtcgttgccagggagaacttatcgctggtactcaactccagttcttccctacgg
ctttggcctccactacaccaagttccaagccaagttcaagtccaacaagttgacgtttgacatccaga
agcttctcaagggctgcagtgctcaatactccgatacttgcgcgctgcccccatccaagttagtgtc
aagaacaccggccgcattacctccgactttgtctctctggtctttatcaagagtgaagttggacctaa
gccttaccctctcaagacccttgcggcttatggtcgcttgcatgatgtcgcgccttcatcgacgaagg
atatctcactggagtggacgttggataacattgcgcgacggggagagaatggtgatttggttgtttat
cctgggacttacactctgttgctggatgagcctacgcaagccaagatccaggttacgctgactggaaa
gaaggctattttggataagtggcctcaagaccccaagtctgcgtaa

*FIG. 21A*

SEQ ID NO:6
Protein sequence of Fv3A mllnlqvaasaislsllgglaeaatpytlpdctkgplskngicdtslspakraaalvaaltpeekvqn
lvsnATGAPRIGLPRYNWWNEALHGLAGSPGGRFADTPPYDAATSFPMPLLMAAAFDDDLIHDIGNVV
GTEARAFTNGGWRGVDFWTPNVNPFKDPRWGRGSETPGEDALHVSRYARYIVRGLEGDKEQRRIVATC
KHYAGNDFEDWGGFTRHDFDAKITPQDLAEYYVRPFQECTRDAKVGSIMCAYNAVNGIPACANSYLQE
TILRGHWNWTRDNNWITSDCGAMQDIWQNHKYVKTNAEGAQVAFENGMDssceytttsdvsdsykqgl
lteklmdrslkrlfeglvhtgffdgakaqwnslsfadvntkeaqdlalrsavegAVLLKNDGTLPLKL
KKKDSVAMIGFWANDTSKLQGGYSGRAPFLHSPLYAAEKLGLDTNVAWGPTLQNSSSHDNWTTNAVAA
AKKSDYILYFGGLDASAAGEDRDRENLDWPESQLTLLQKLSSLGKPLVVIQLGDQVDDTALLKNKKIN
SILWVNYPGQDGGTAVMDLLTGRKSPAGRLPVTQYPSKYTEQIGMTDMDLRPTKSLPGRTYRWYSTPV
LPYGFGLHYTkfqakfksnkltfdiqkllkgcsaqysdtcalppiqvsvkntgritsdfvslvfikse
vgpkpyplktlaaygrlhdvapsstkdislewtldniarrgengdlvvypgtytillideptqakiqvt
ltgkkaildkwpqdpksa

FIG. 21B

SEQ ID NO:7
**Nucleotide sequence for Pf43A, a GH43 family enzyme from *Penicillium funiculosum*** atgcttcagcgatttgcttatattttaccactggctctattgagtgttggagtgaaagccgacaaccc
ctttgtgcagagcatctacaccgctgatccggcaccgatggtatacaatgaccgcgtttatgtcttca
tggaccatgacaacaccggagctacctactacaacatgacagactggcatctgttctcgtcagcagat
atggcgaattggcaagatcatggcattccaatgagcctggccaatttcacctgggccaacgcgaatgc
gtgggccccgcaagtcatccctcgcaacggccaattctactttatgctcctgtccgacacaacgatg
gttctatggctatcggtgtgggagtgagcagcaccatcacaggtccataccatgatgctatcggcaaa
ccgctagtagagaacaacgagattgatccaccgtgttcatcgacgatgacggtcaggcatacctgta
ctggggaaatccagacctgtggtacgtcaaattgaaccaagatatgatatcgtacagcgggagccta
ctcagattccactcaccacggctggatttggtactcgaacgggcaatgctcaacggccgaccactttt
gaagaagctccatggtatacaaacgcaacggcatctactatcgcctatgcagccgattgttgttc
tgaggatattcgctactccacgggaaccagtgccactggtccgtggacttatcgaggcgtcatcatgc
cgacccaaggtagcagcttcaccaatcacgagggtattatcgacttccagaacaactcctactttttc
tatcacaacggcgctcttccggcggaggcggctaccaacgatctgtatgtgtggagcaattcaaata
caatgcagatggaaccattccgacgatcgaaatgaccaccgccggtccagctcaaattgggactctca
acccttacgtgcgacaggaagccgaaacggcggcatggtcttcaggcatcactacggaggtttgtagc
gaaggcggaattgacgtcgggtttatcaacaatggcgattacatcaaagttaaaggcgtagctttcgg
ttcaggagcccattctttctcagcgcgggttgcttctgcaaatagcggcggcactattgcaatacacc
tcggaagcacaactggtacgctcgtgggcacttgtactgtcccagcactggcggttggcagacttgg
actaccgttacctgttctgtcagtggcgcatctgggacccaggatgtgtatttgttttcggtggtag
cggaacaggatacctgttcaactttgattattggcagttcgcataa

FIG. 22A

SEQ ID NO:8
Protein sequence of Pf43A

*mlqrfayilplallsvqvka*dnpfvqsiytadpapmvyndrvyvfmdhdntgatyynmtdwhlfssad
manwqdhgipmslanftwananawapqviprngqfyfyapvrhndgsmaigvgvsstitgpyhdaigk
plvenneidptvfidddgqaylywgnpdlwyvklnqdmisysgsptqiplttagfgtrtgnaqrpttf
eeapwvykrngiyyiayaadccsedirystgtsatgpwtyrgvimptqgssftnhegiidfqnnsyff
yhngalpggggyqrsvcveqfkynadgti*ptiemttagpaqigtlnpyvrq*EAETAAWSSGITTEVCS
EGGIDVGFINNGDYIKVKGVAFGSGAHSFSARVASANSGGTIAIHLGSTTGTLVGTCTVPSTGGWQTW
TTVTCSVSGASGTQDVYFVFGGSGTGYLFNFDYWQFa

FIG. 22B

SEQ ID NO:9
Nucleotide sequence for Fv43E, a GH43 family enzyme from *Fusarium verticillioides*

```
atgaaggtatactggctcgtggcgtgggccacttctttgacgccggcactggctggcttgattggaca
ccgtcgcgccaccaccttcaacaatcctatcatctactcagactttccagataacgatgtattcctcg
gtccagataactactactacttctctgcttccaacttccacttcagccaggagcaccgttttgaag
tctaaagatctgctaaactgggatctcatcggccattcaattccccgcctgaactttggcgacggcta
tgatcttcctcctggctcacgttattaccgtggaggtacttgggcatcatccctcagatacagaaaga
gcaatggacagtggtactggatcggctgcatcaacttctggcagacctgggtatacactgcctcatcg
ccggaaggtccatggtacaacaagggaaacttcggtgataacaattgctactacgacaatggcatact
gatcgatgacgatgataccatgtatgtcgtatacggttccggtgaggtcaaagtatctcaactatctc
aggacggattcagccaggtcaaatctcaggtagttttcaagaacactgatattggggtccaagacttg
gagggtaaccgcatgtacaagatcaacgggctctactatatcctaaacgatagcccaagtggcagtca
gacctggatttggaagtcgaaatcaccctggggcccttatgagtctaaggtcctcgccgacaaagtca
ccccgcctatctctggtggtaactcgccgcatcagggtagtctcataaagactcccaatggtggctgg
tacttcatgtcattcacttgggcctatcctgccggccgtcttccggttcttgcaccgattacgtgggg
tagcgatggtttccccattcttgtcaagggtgctaatggcggatggggatcatcttacccaacacttc
ctggcacggatggtgtgacaagaattggacaaggactgataccttcgcggaacctcacttgctccg
tcctgggagtggaaccataatccggacgtcaactccttcactgtcaacaacggcctgactctcgcac
tgctagcattacgaaggatatttaccaggcgaggaacacgctatctcaccgaactcatggtgatcatc
caacaggaatagtgaagattgatttctctccgatgaaggacggcgaccgggccgggctttcagcgttt
cgagaccaaagtgcatacatcggtattcatcgagataacggaaagttcacaatcgctacgaagcatgg
gatgaatatggatgagtggaacggaacaacaacagacctgggacaaataaaagccacagctaatgtgc
cttctggaaggaccaagatctggctgagacttcaacttgataccaacccagcaggaactggcaacact
atctttcttacagttgggatggagtcaagtatgaaacactgggtcccaacttcaaactgtacaatgg
ttgggcattctttattgcttaccgattcggcatcttcaacttcgccgagacggctttaggaggctcga
tcaaggttgagtctttcacagctgcatag
```

FIG. 23A

SEQ ID NO:10
Protein sequence of Fv43E mkvywlvawatsltpalaglighrrattfnnpiiysdfpdndvflgpdnyyyfsasnfhfspgapvlk
skdllnwdlighsiprlnfgdgydlppgsryyrggtwasslryrksngqwywigcinfwqtwvytass
pegpwynkgnfgdnncyydngilidddtmyvvygsgevkvsqlsqdgfsqvksqvvfkntdigvqdl
egnrmykinglyyilndspsgsqtwiwkskspwgpyeskvladkvtppisggnsphqgsliktpnggw
yfmsftwaypagrlpvlapitwgsdgfpilvkganggwgssyptlpgtdgvtknwtrtdtfrgtslap
swewnhnpdvnsftvnngltlrtasitkdiyqarntlshrthgdhptgivkidfspmkdgdraglsaf
rdqsayigihrdngkftiatkhgmnmdewngtttdlgqikatanvpsgrtkiwlrlqldtnpagtgnt
ifsyswdgvkyetlgpnfklyngwaffiayrfgifnfaetalggsikvesftaa

FIG. 23B

SEQ ID NO:11
**Nucleotide sequence for Fv43B, a GH43 family enzyme from *Fusarium verticillioides*** atgcgcttctcttggctattgtgccccttctagcgatgggaagtgctcttcctgaaacgaagacgga
tgtttcgacatacaccaaccctgtccttccaggatggcactcggatccatcgtgtatccagaaagatg
gcctctttctctgcgtcacttcaacattcatctccttccaggtcttcccgtctatgctcaagggat
ctagtcaactggcgtctcatcagccatgtctggaaccgcgagaaacagttgcctggcattagctggaa
gacggcaggacagcaacagggaatgtatgcaccaaccattcgataccacaagggaacatactacgtca
tctgcgaatacctggcgttggagatattattggtgtcatcttcaagaccaccaatccgtgggacgag
agtagctggagtgaccctgttaccttcaagccaaatcacatcgacccgatctgttctggatgatga
cggaaaggtttattgtgctacccatggcatcactctgcaggagattgatttggaaactggagagctta
gcccggagcttaatatctggaacggcacaggaggtgtatggcctgagggtccccatatctacaagcgc
gacggttactactatctcatgattgccgagggtggaactgccgaagaccacgctatcacaatcgctcg
ggcccgcaagatcaccggcccctatgaagcctacaataacaacccaatcttgaccaaccgcgggacat
ctgagtacttccagactgtcggtcacggtgatctgttccaagataccaagggcaactggtgggggtctt
tgtcttgctactcgcatcacagcacagggagtttcacccatgggccgtgaagctgttttgttcaatgg
cacatggaacaagggcgaatggcccaagttgcaaccagtacgaggtcgcatgcctggaaacctcctcc
caaagccgacgcgaaacgttccgggagatgggcccttcaacgctgacccagacaactacaacttgaag
aagactaagaagatccctcctcactttgtgcaccatagagtcccaagagacggtgccttctctttgtc
ttccaagggtctgcacatcgtgcctagtcgaaacaacgttaccggtagtgtgttgccaggagatgaga
ttgagctatcaggacagcgaggtctagctttcatcggacgcgccaaactcacactctgttcaaatat
agtgttgatatcgacttcaagcccaagtccgatgatcaggaagctggaatcaccgttttccgcacgca
gttcgaccatatcgatcttggcattgttcgtcttctacaaaccaaggcagcaacaagaaatctaagc
ttgccttccgattccgggccacaggagctcagaatgttcctgcaccgaaggtagtaccggtccccgat
ggctggagaagggcgtaatcagtctacatatcgaggcagccaacgcgacgcactacaaccttggagc
ttcgagccacagaggcaagactctcgacatcgcgacagcatcagcaagtcttgtgagtggaggcacgg
gttcatttgttggtagtttgcttggaccttatgctacctgcaacggcaaaggatctggagtggaatgt
cccaagggaggtgatgtctatgtgacccaatggacttataagcccgtggcacaagagattgatcatgg
tgtttttgtgaaatcagaattgtag

FIG. 24A

SEQ ID NO:12
Protein sequence of Fv43B

<u>mrfswllcpllamqsa</u>lpetktdvstytnpvlpgwhsdpsciqkdglflcvtstfisfpglpvyasrd
lvnwrlishvwnrekqlpgiswktagqqqgmyaptiryhkgtyyviceylgvgdiigvifkttnpwde
sswsdpvtfkpnhidpdlfwdddgkvycathgitlqeidletgelspelniwngtggvwpegphiykr
dgyyylmiaeggtaedhaitiararkitgpyeaynnnpiltnrgtseyfqtvghgdlfqdtkgnwwgl
clatritaqgvspmgreavlfngtwnkgewpklqpvrgrmpgnllpkptrnvpgdgpfnadpdnynlk
ktkkipphfvhhrvprdgafslsskglhivpsrnnvtgsvlpgdeielsgqrglafigrrqthtlfky
svdidfkpksddqeagitvfrtqfdhidlgivrlptnqgsnkksklafrfratgaqnvpapkvvpvpd
gwekqvislhieaanathynlgasshrgktldiatasaslvsggtgsfvgsllgpyatcngkgsgvec
pkggdvyvtqwtykpvaqeidhgvfvksel

*FIG. 24B*

SEQ ID NO:13
**Nucleotide sequence for Af43A, a GH43 family enzyme from *Aspergillus fumigatus*** atggcagctccaagtttatcctaccccacaggtatccaatcgtataccaatcctctcttccctggttg
gcactccgatccagctgtgcctacgtagcggagcaagacaccttttctgcgtgacgtccactttca
ttgccttccccggtcttcctctttatgcaagccgagatctgcagaactggaaactggcaagcaatatt
ttcaatcggcccagccagatccctgatcttcgcgtcacggatggacagcagtcgggtatctatgcgcc
cactctgcgctatcatgagggccagttctacttgatcgtttcgtacctggcccgcagactaagggct
tgctgttcacctcgtctgatccgtacgacgatgccgcgtggagcgatccgctcgaattcgcggtacat
ggcatcgacccggatatcttctggatcacgacgggacggtctatgtcacgtccgccgaggaccagat
gattaagcagtacacactcgatctgaagacggggcgattggcccggttgactacctctggaacggca
ccggaggagtctggcccgagggccgcacatttacaagagagacggatactactacctcatgatcgca
gagggaggtaccgagctcggccactcggagaccatggcgcgatctagaaccccggacaggtccctggga
gccataccgcacaatccgctcttgtcgaacaagggcacctcggagtacttccagactgtgggccatg
cggacttgttccaggatgggaacggcaactggtgggccgtggcgttgagcaccgatcagggcctgca
tgaagaactatccatgggtcggagacggtgctcgccccgccgcttgggagaagggtgagtggcc
tgtcattcagcctgtgagaggccaaatgcaggggccgtttccaccaccaaataagcgagttcctcgcg
gcgagggcggatggatcaagcaacccgacaaagtggatttcaggcccggatcgaagataccggcgcac
ttccagtactggcgatatcccaagacagaggattttaccgtctcccctcgggggccacccgaatactct
tcggctcacaccctccttttacaacctcaccggaactgcggacttcaagccggatgatggcctgtcgc
ttgttatgcgcaaacagaccgacaccttgttcacgtacactgtggacgtgtcttttgaccccaaggtt
gccgatgaagaggcgggtgtgactgtttttccttacccagcagcagcacatcgatcttggtattgtcct
tctccagacaaccgaggggctgtcgttgtccttccggttccgcgtggaaggccgcggtaactacgaag
gtcctcttccagaagccaccgtgcctgttcccaaggaatggtgtggacagaccatccggcttgagatt
caggccgtgagtgacaccgagtatgtctttgcggctgccccggctcggcaccctgcacagaggcaaat
catcagccgcgccaactcgttgattgtcagtggtgatacgggacggtttactggctcgcttgttggcg
tgtatgccacgtcgaacgggggtgccggatccacgccgcatatatcagcagatggagatacgaagga
cggggccagatgattgattttggtcgagtggtcccgagctactga

*FIG. 25A*

SEQ ID NO:14
Protein sequence of Af43A maapslsyptgiqsytnplfpgwhsdpscayvaeqdtffcvtstfiafpglplyasrdlqnwklasni
fnrpsqipdlrvtdgqqsgiyaptlryhegqfylivsylgpqtkqllftssdpyddaawsdplefavh
gidpdifwdhdgtvyvtsaedqmikqytldlktgaigpvdylwngtggvwpegphiykrdgyyylmia
eggtelghsetmarsrtrtgpwepyphnpllsnkgtseyfqtvghadlfqdgngnwwavalstrsgpa
wknypmgretvlapaawekgewpviqpvrgqmqgpfpppnkrvprgeggwikqpdkvdfrpgskipah
fqywrypktedftvsprghpntlrltpsfynltgtadfkpddglslvmrkqtdtlftytvdvsfdpkv
adeeagvtvfltqqqhidlgivllqtteglslsfrfrvegrgnyegplpeatvpvpkewcgqtirlei
qavsdteyvfaaaparhpaqrqiisranslivsgdtgrftgslvgvyatsnggagstpayisrwryeg
rgqmidfgrvvpsy

*FIG. 25B*

SEQ ID NO:15
**Nucleotide sequence of Fv51A, a GH51 family enzyme from *Fusarium verticillioides*** atggttcgcttcagttcaatcctagcggctgcggcttgcttcgtggctgttgagtcagtcaacatcaa
ggtcgacagcaagggcggaaacgctactagcggtcaccaatatggcttccttcacgaggttggtattg
acacaccactggcgatgattgggatgctaacttggagctaggatatcaacaattccggtgatggtggc
atctacgctgagctcatccgcaatcgtgctttccagtacagcaagaaataccctgtttctctatctgg
ctggagacccatcaacgatgctaagctctccctcaacgtctcgacactcctctctcgacgctctcc
ccgtttccatgaacgtgaagcctggaaagggcaaggccaaggagattggtttcctcaacgagggttac
tggggaatggatgtcaagaagcaaaagtacactggctctttctgggttaaggcgcttacaagggcca
ctttacagcttctttgcgatctaaccttaccgacgatgtctttggcagcgtcaaggtcaagtccaagg
ccaacaagaagcagtgggttgagcatgagtttgtgcttactcctaacaagaatgcccctaacagcaac
aacacttttgctatcacctacgatcccaaggtgagtaacaatcaaaactgggacgtgatgtatactga
caatttgtagggcgctgatggagctcttgacttcaacctcattagcttgttccctcccacctacaagg
gccgcaagaacggtcttcgagttgatcttgccgaggctctcgaaggtctccacccgtaaggtttacc
gtctcacgtgtatcgtgaacagtcgctgacttgtagaaaagagcctgctgcgcttccccggtggtaac
atgctcgagggcaacaccaacaagacctggtgggactggaaggataccctcggacctctccgcaaccg
tcctggtttcgagggtgtctggaactaccagcagacccatggtcttggaatcttggagtacctccagt
gggctgaggacatgaaccttgaaatcagtaggttctataaaattcagtgacggttatgtgcatgctaa
cagatttcagttgtcggtgtctacgctggcctctccctcgacggctccgtcaccccaaggaccaact
ccagcccctcatcgacgacgcgctcgacgagatcgaattcatccgaggtcccgtcacttcaaagtggg
gaaagaagcgcgctgagctcggccaccccaagcctttcagactctcctacgttgaagtcggaaacgag
gactggctcgctggttatcccactggctggaactcttacaaggagtaccgcttccccatgttcctcga
ggctatcaagaaagctcacccgatctcaccgtcatctcctctggtgcttctattgacccgttggta
agaaggatgctggtttcgatattcctgctcctggaatcggtgactaccaccttaccgcgagcctgat
gttcttgttgaggagttcaacctgtttgataacaataagtatggtcacatcattggtgaggttgcttc
tacccaccccaacggtggaactggctggagtggtaaccttatgccttaccctggtggatctctggtg
ttggcgaggccgtcgctctctgcggttatgagcgcaacgccgatcgtattcccggaacattctacgct
cctatcctcaagaacgagaaccgttggcagtgggctatcaccatgatccaattcgccgccgactccgc
catgaccacccgctccaccagctggtatgtctggtcactcttcgcaggccaccccatgacccatactc
tccccaccaccgccgacttcgacccctctactacgtcgctggtaagaacgaggacaagggaactctt
atctggaagggtgctgcgtataacaccaccaaggggtgctgacgttccgtgtctctgtccttcaaggg
tgtcaagcccggtgctcaagctgagcttactcttctgaccaacaaggagaaggatccttttgcgttca
atgatcctcacaagggcaacaatgttgttgatactaagaagactgttctcaaggccgatggaaagggt
gctttcaacttcaagcttcctaacctgagcgtcgctgttcttgagaccctcaagaagggaaagcctta
ctctagctag

*FIG. 26A*

SEQ ID NO:16
Protein sequence of Fv51A mvrfssilaaaacfvavesvnikvdskggnatsghqygflhedinnsgdggiyaelirnrafqyskky
pvslsqwrpindaklslnrldtplsdalpvsmnvkpgkgkakeigflnegywgmdvkkqkytgsfwvk
gaykghftaslrsnltddvfgsvkvkskankkqwvehefvltpnknapnsnntfaitydpkgadgald
fnlislfpptykgrknglrvdlaealeglhpsllrfpggnmlegntnktwwdwkdtlgplrnrpgfeg
vwnyqqthglqileylqwaedmnleiivgvyaglsldgsvtpkdqlqpliddaldeiefirgpvtskw
gkkraelghpkpfrlsyvevgnedwlagyptgwnsykeyrfpmfleaikkahpdltvissgasidpvg
kkdagfdipapgigdyhpyrepdvlveefnlfdnnkyghii**gevasthpnggtgwsgnlmpypwwisg
vgeavalcgyernadripgtfyapilknenrwqwaitmiqfaadsamttrstswyvwslfaghpmtht
lpttadfdplyyvagknedkgtliwkgaaynttkgadvpvslsfkgvkpgaqaeltlltnkekdpfaf
ndphkgnnvvdtkktvlkadgkgafnfklpnls**vavletlkkgkpyss

*FIG. 26B*

SEQ ID NO:17
Nucleotide sequence for Xyn3, a GH10 xylanase from *Trichoderma reesei* atgaaagcaaacgtcatcttgtgcctcctggccccgctggtcgccgctctcccaccgaaaccatcca
cctcgaccccgagctcgccgctctccgcgccaacctcaccgagcgaacagccgacctctgggaccgcc
aagcctctcaaagcatcgaccagctcatcaagagaaaaggcaagctctactttggcaccgccaccgac
cgcggcctcctccaacgggaaaagaacgcggccatcatccaggcagacctcggccaggtgacgccgga
gaacagcatgaagtggcagtcgctcgagaacaaccaaggccagctgaactggggagacgccgactatc
tcgtcaactttgcccagcaaaacggcaagtcgatacgcggccacactctgatctggcactcgcagctg
cctgcgtgggtgaacaatatcaacaacgcggatactctgcggcaagtcatccgcacccatgtctctac
tgtggttgggcggtacaagggcaagattcgtgcttgggtgagttttgaacaccacatgcccttttct
tagtccgctcctcctcctcttggaacttctcacagttatagccgtatacaacattcgacaggaaattt
aggatgacaactactgactgacttgtgtgtgtgatggcgataggacgtggtcaatgaaatcttcaacg
aggatggaacgctgcgctcttcagtcttttccaggctcctcggcgaggagtttgtctcgattgccttt
cgtgctgctcgagatgctgaccttctgccgtctttacatcaacgactacaatctcgaccgcgccaa
ctatggcaaggtcaacgggttgaagacttacgtctccaagtggatctctcaaggagttcccattgacg
gtattggtgagccacgaccctaaatgcccccattagagtctctttctagagccaaggcttgaagcc
attcagggactgacacgagagccttctctacaggaagccagtcccatctcagcggcggcggaggctct
ggtacgctgggtgcgctccagcagctggcaacggtacccgtcacgagctggccattaccgagctgga
cattcaggggggcaccgacgacggattacacccaagttgttcaagcatgcctgagcgtctccaagtgcg
tcggcatcaccgtgtgggggcatcagtgacaaggtaagttgcttcccctgtctgtgcttatcaactgta
agcagcaacaactgatgctgtctgtctttacctaggactcgtggcgtgccagcaccaaccctcttctg
tttgacgcaaacttcaaccccaagccggcatataacagcattgttggcatcttacaatag

*FIG. 27A*

SEQ ID NO:18
Protein sequence for Xyn3 mkanvilcllaplvaalptetihldpelaalranltertadlwdrqasq**sidqlikrkgklyfgtatd
rgllqreknaaiiqadlgqvtpensmkwqslennqgqlnwgdadylvnfaqqngksirghtliwhsql
pawvnninnadtlrqvirthvstvvgrykgkirawdvvneifnedgtlrssvfsrllgeefvsiafra
ardadpsarlyindynldranygkvnglktyvskwisqgvpidgigsqshlsggggsgtlgalqqlat
vpvtelaiteldiqgapttdytqvvqaclsvskcvgitvwgisdkdswrastnpllfdanfnpkpayn
sivgilq**

*FIG. 27B*

SEQ ID NO:19
Nucleotide sequence xlnA, a xylanase from *Aspergillus tubingensis*

```
aacgtctgca gtccgtact gtttaccaaa atgccaggcc actggtggat atacaactt     60
gtaatacgtt gccggagtca gcccctactc cctgatgggt tcccactccc tagttacttc   120
ctactgggta gtaggctcct agagtggggt aaagtttgcc aagggtttag cccagtctt    180
gtttatgctt ggctaggcag gacctgggta agttgatggc tcctgcattc ctacctgagt   240
atttccagct ataagcgaga tttgccatac tcttcagcga gtccggatgg tccgcgccga   300
ggttgaccct gccttcatca cctacacaaa gaactcctcg gccaactccc ggtggcctcc   360
gagctccaaa gtaccttcgc gacctttggc cagtgtttct cgcagcgttt actgagccta   420
aggcttgcta caataaataa agagacataa ccttgcagta catcgtctt gtatgagcga    480
ggaactgtgt tcagtagtag atcagtgggt acataatcat gaacatgact tctgagccag   540
aaaaccttct gcagggaacc ggtgaagaaa ccccacttcc ccgcctccac taactgcagc   600
ccctttatcc gcctgccgtc catttagcca aatgtagtcc atttagccaa gtgcggtcca   660
tttagccaag tccagtgctt aggttggtgg ctacacagga acggccatg aatgtagaca    720
caactataga actgtccta gaaataggct cgaggttgtt agagcgttta aggtgatgcg    780
gcaaaatgca tatgactgag ttgcttcaac gtgcagggga aagggataaa tagtcttttt   840
cgcagaatat aaatagaggt agagcgggct cgcagcaata ttgaccagga cagggcttct   900
tttccagttg catacatcca ttcacagcat tcagctttct tcaatcatca tgaaggtcac    960
tgcggctttt gcaggtcttt tggtcacggc attcgccgct cctgcccag aacctgatct   1020
ggtgtcgcga agtgccgta tcaactacgt gcaaaactac aacggcaacc ttggtgattt   1080
cacctacgac gagagtgccg gaacatttc catgtactgg aagatggag tgagctccga    1140
ctttgtcgtt ggtctgggct ggaccactgg ttcttctaag tgagtgactg tattctttaa   1200
ccaaggtcta ggatctaacg tcttccagcg ctatcaccta ctctgccgaa tacagcgctt   1260
ctggctccgc ttcctacctc gctgtgtacg gctgggtcaa ctatcctcaa gctgagtact   1320
acatcgtcga ggattacggt gattataacc cttgcagttc ggccacaagc cttggtaccg   1380
tgtactctga tggaagcacc taccaagtct gcaccgacac tcgaacaaac gaaccgtcca   1440
tcacgggaac aagcacgttc acgcagtact ctccgttcg agagagcacg cgcacatctg   1500
gaacggtgac tgttgccaac catttcaact tctgggcgca ccatgggttc ggcaatagcg   1560
acttcaatta tcaggtcgtg gcggtggaag catggagcgg tgctggcagc gctagtgtca   1620
caatctcttc ttgagagatt agtgcctag tagtcggaag atatcaacgc ggcagtttgc    1680
tctcaggtgg tgtgatgatc ggatccggtc tctggggtta cattgaggct gtataagttg   1740
ttgtggggcc gagctgtcag cggctgcgtt ttcagcttgc acagataatc aactctcgtt   1800
ttctatctct tgcgtttcct cgctgcttat cctatccata gataattatt ttgcccacta   1860
ccacaacttg ttcggtcgca gtagtcactc cgagcaaggc attgggaaat ggggatgcg    1920
gggtgctgcg tacctctaa cctagggcat tttaaaggat atttaccctc cagatattct   1980
atagatacag acttcttagg actgcgggta atatagagag cgaaatttct acagttcgat   2040
gcagttcaat gcga                                                    2054
```

*FIG. 28A*

SEQ ID NO:20
Protein sequence for xlnA

<u>MKVTAAFAGLLVTAFAAPAPEPDLVSR</u>SAGINYVQNYNGNLGDFTYDESAGTFSMYWEDGVSSDFVVGLG
WTTGSSNAITYSAEYSASGSASYLAVYGWVNYPQAEYYIVEDYGDYNPCSSATSLGTVYSDGSTYQVCTD
TRTNEPSITGTSTFTQYFSVRESTRTSGTVTVANHFNFWAHHGFGNSDFNYQVVAVEAWSGAGSASVTIS
S

*FIG. 28B*

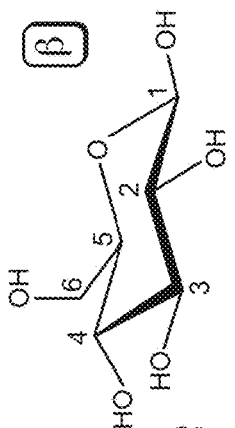

FIG. 29A

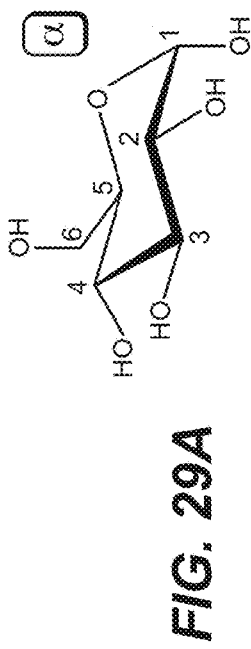

FIG. 29B

FIG. 30A

SEQ ID NO:21
**Nucleotide sequence for Gz43A, a GH43 family enzyme from *Gibberella zeae*** atgaagtccaagttgttattcccactcctctctttcgttggtcaaagtcttgccaccaacgacgactgtcctctcatcactag
tagatggactgcggatccttcggctcatgtctttaacgacaccttgtggctctacccgtctcatgacatcgatgctggatttg
agaatgatcctgatggaggccagtacgccatgagagattaccatgtctactctatcgacaagatctacggttccctgccggtc
gatcacggtacggccctgtcagtggaggatgtcccctgggcctctcgacagatgtgggctcctgacgctgcccacaagaacgg
caaatactacctatacttccctgccaaagacaaggatgatatcttcagaatcggcgttgctgtctcaccaacccccggcggac
cattcgtccccgacaagagttggatccctcacactttcagcatcgaccccgccagtttcgtcgatgatgatgacagagcctac
ttggcatggggtggtatcatgggtggccagcttcaacgatggcaggataagaacaagtacaacgaatctggcactgagccagg
aaacggcaccgctgccttgagccctcagattgccaagctgagcaaggacatgcacactctggcagagaagcctcgcgacatgc
tcattcttgaccccaagactggcaagccgctcctttctgaggatgaagaccgacgcttcttcgaaggaccctggattcacaag
cgcaacaagatttactacctcacctactctactggcacaacccactatcttgtctatgcgacttcaaagacccccctatggtcc
ttacacctaccagggcagaattctggagccagttgatggctggactactcactctagtatcgtcaagtaccagggtcagtggt
ggctattttatcacgatgccaagacatctggcaaggactatcttcgccaggtaaaggctaagaagatttggtacgatagcaaa
ggaaagatcttgacaaagaagccttga

FIG. 30B

SEQ ID NO:22
Protein sequence of Gz43A mkskllfpllsfvgqslatnddcplitsrwtadpsahvfndtlwlypshdidagfendpdggqyamrdyh
vysidkiygslpvdhgtalsvedvpwasrqmwapdaahkngkyylyfpakdkddifrigvavsptpggpf
vpdkswiphtfsidpasfvddddraylawggimggqlqrwqdknkynesgtepgngtaalspqiaklskd
mhtlaekprdmlildpktgkpllsededrrffegpwihkrnkiyyltystgtthylvyatsktpygpyty
qgrilepvdgwtthssivkyqgqwwlfyhdaktsgkdylrqvkakkiwydskgkiltkkp

SEQ ID NO:23
Nucleotide sequence for Fo43A, a GH43 family enzyme from *Fusarium oxysporum* atgcagctcaagtttctgtcttcagcattgctgttctctctgaccagcaaatgcgctgcgcaagacac
taatgacattcctcccctgatcaccgacctctggtccgcagatccctcggctcatgttttcgaaggca
agctctgggtttacccatctcacgacatcgaagccaatgttgtcaacggcacaggaggcgctcaatac
gccatgagggattaccatacctactccatgaagagcatctatggtaaagatcccgttgtcgaccacgg
cgtcgctctctcagtcgatgacgttccctgggcgaagcagcaaatgtgggctcctgacgcagctcata
agaacggcaaatattatctgtacttccccgccaaggacaaggatgagatcttcagaattggagttgct
gtctccaacaagcccagcggtcctttcaaggccgacaagagctggatccctggcacgtacagtatcga
tcctgctagctacgtcgacactgataacgaggcctacctcatctggggcggtatctggggcggccagc
tccaagcctggcaggataaaaagaactttaacgagtcgtggattggagacaaggctgctcctaacggc
accaatgccctatctcctcagatcgccaagctaagcaaggacatgcacaagatcaccgaaacaccccg
cgatctcgtcattctcgcccccgagacaggcaagcctcttcaggctgaggacaacaagcgacgattct
tcgagggccttggatccacaagcgcggcaagctttactacctcatgtactccaccggtgatacccac
ttccttgtctacgctacttccaagaacatctacggtccttatacctaccggggcaagattcttgatcc
tgttgatgggtggactactcatggaagtattgttgagtataagggacagtggtggcttttctttgctg
atgcgcatacgtctggtaaggattaccttcgacaggtgaaggcgaggaagatctggtatgacaagaac
ggcaagatcttgcttcaccgtccttag

FIG. 31A

SEQ ID NO:24
Protein sequence of Fo43A

Mqlkflssallfsltskcaaqdtndippliitdlwsadpsahvfegklwvypshdieanvvngtggaqy
amrdyhtysmksiygkdpvvdhgvalsvddvpwakqqm**wapdaahkngkyylyfpakdkdeifrigva
vsnkpsgpfkadkswipgtysidpasyvdtdneayliwggiwggqlqawqdkknfneswigdkaapng
tnalspqiaklskdmhkitetprdlvilapetgkplqaednkrrffegpwihkrgklyylmystgdth
flvyatskniygpytyrgkildpvdgwtthgsiveykgqwwlffadahtsgkdylrqvkarkiwydkn
g**killhrp

FIG. 31B

```
Fv43D  ---MQLKFLSSALLLSLTGNCAAQDTNDIPPLITDLWSADPSAHVFEGKLWVYPSHDIEA
Fo43A  ---MQLKFLSSALLFSLTSKCAAQDTNDIPPLITDLWSADPSAHVFEGKLWVYPSHDIEA
Gz43A  ---MKSKLLFP--LLSFVG--QSLATNDDCPLITSRWTADPSAHVFNDTLWLYPSHDIDA
Pf43A  --MLQRFAYILPLALLSVG--VKADN----PFVQSIYTADPAPMVYNDRVYVFMDHDNTG
Fv43A  -MWLTSPLLFASTLLGLTGVALADN-----PIVQDIYTADPAPMVYNGRVYLFTGHDNDG
Fv43B  ---MRFSWLLCPLLAMGSALPETKTDVSTYTNPVLPGWHSDPSC-IQKDGLFLCVTSTFIS
Af43A  --------------MAAPSLSYPTGIQSYTNPLFPGWHSDPSCAYVAEQDTFFCVTSTFI
Pf43B  ----MSRSILPYASVFALLGGAIAEP-----FLVLNSDFPDPSLIETSSGYYAFGTTGNGV
Fv43E  MKVYWLVAWATSLTPALAGLIGHRRATTFNNPIIYSDFPDNDVFLGPDNYYYFSASNFHF

Fv43D  NVVNGTGGAQYAMRDYHTYSMKTIYGKDPVIDHGVALSVDDVPWAKQQMWAPDAAYK---N
Fo43A  NVVNGTGGAQYAMRDYHTYSMKSIYGKDPVVDHGVALSVDDVPWAKQQMWAPDAAHK---N
Gz43A  GFENDPDGGQYAMRDYHVYSIDKIYGSLP-VDHGTALSVEDVPWASRQMWAPDAAHK---N
Pf43A  -------ATYYNMTDWHLFSSADMANWQD---HGIPMSLANFTWANANAWAPQVIPR--N
Fv43A  -------STDFNMTDWRLFSSADMVNWQH---HGVPMSLKTFSWANSRAWAGQVVAR--N
Fv43B  FP-----GLPVYASRDLVNWRLISHVWNRE---KQLPGISWKTAGGQQGMYAPTIRYH--K
Af43A  AFP---GLPLYASRDLQNWKLASNIFNRP---SQIPDLR-VTDGQQSGIYAPTLRYH--E
Pf43B  N-------AQVASSPDFNTWTLLSGT------DALPGPFPSWVASSPQIWAPDVLVKA-D
Fv43E  SP----GAPVLKSKDLLNWDLIGHSIPRLNFGDGYDLPPGSRYYRG-GTWASSLRYRKSN

Fv43D  GKYYLYFPAK-DK-DEIFRIGVAVSNKPSGPFK----ADK-SWIPGTYSIDPASYVDTNGE
Fo43A  GKYYLYFPAK-DK-DEIFRIGVAVSNKPSGPFK----ADK-SWIPGTYSIDPASYVDTDNE
Gz43A  GKYYLYFPAK-DK-DDIFRIGVAVSPTPGGPFV----PDK-SWIPHTFSIDPASFVDDDDR
Pf43A  GQFYFYAPVR-HN-DGSMAIGVGVSSTITGPYH----DAIGKPLVENNEIDPTVFIDDDGQ
Fv43A  GKFYFYVPVRNAK-TGGMAIGVGVSTNILGPYT----DALGKPLVENNEIDPTVYIDTDGQ
Fv43B  GTYYVICEYLGVG-DIIGVIFKTTNPWDESSWS----DPV----TFKPNHIDPDLFWDDDGK
Af43A  GQFYLIVSYLGP--QTKGLLFTSSDPYDDAAWS---DPL----EFAVHGIDPDIFWDHDGT
Pf43B  GTYVMYFSASAASDSGKHCVGAATATSPEGPYTPVDSAVACPLDQGGAIDANGFIDTDGT
Fv43E  GQWYWIGCIN------FWQTWVYTASSPEGPWY----NKGNFGDNNCYYDNGILIDDDDT

Fv43D  AYLIWGGI-WGGQLQAWQDHKTFNESWLGDKAAPNGTNALSPQIAKLSKDMHKITETPRD
Fo43A  AYLIWGGI-WGGQLQAWQDKKNFNESWIGDKAAPNGTNALSPQIAKLSKDMHKITETPRD
Gz43A  AYLAWGGI-MGGQLQRWQDKNKYNES--GTEPG-NGTAALSPQIAKLSKDMHTLAEKPRD
Pf43A  AYLYWG---------------------------NPDLWYVKLNQDMISYSGSPTQ
Fv43A  AYLYWG---------------------------NPGLYYVKLNQDMLSYSGSINK
Fv43B  VYCATHG----ITLQEIDLETGELSPELNIWNGTGGVWPEGPHIYKRDGYYYLMIAEGGT
Af43A  VYVTSAED-QMIKQYTLDLKTGAIGPVDYLWNGTGGVWPEGPHIYKRDGYYYLMIAEGGT
Pf43B  IYVVYKID---------------------------GNSLDGDTTHPTPIMLQQMEADGT
Fv43E  MYVVYGSGEVKVSQLSQDGFSQVKSQVVFKNTDIGVQDLEGNRMYKING--------LYYI

Fv43D  LVILAPETGKPLQAEDNKRRFFEGP-----WVHKRGKLYYLMYSTG-----------
Fo43A  LVILAPETGKPLQAEDNKRRFFEGP-----WIHKRGKLYYLMYSTG-----------
Gz43A  MLILDPKTGKPLLSEDEDRRFFEGP-----WIHKRNKIYYLTYSTG-----------
Pf43A  IPLTTAGFGTRTGNAQRPTTFEEAP-----WVYKRNGIYYIAYAAD-----------
Fv43A  VSLTTAGFGSRPNNAQRPTTFEEGP-----WLYKRGNLYYMIYAAN-----------
Fv43B  ----AEDHAITIARARKITGPYEAYNNNPILTNRGTSEYFQTVGHGDLFQDTKGNWWGLC
Af43A  ----ELGHSETMARSRTRTGPWEPYPHNPLLSNKGTSEYFQTVGHADLFQDGNGNWWAVA
Pf43B  --TPTGSPIQLIDRSDLDGPLIEAP-----SLLLSNGIYYLSFSSN-----------
Fv43E  LNDSPSGSQTWIWKSKSPWGPYESRVLADKVTPPISGGNSPHQGSLIKTPNGGWY-----

Fv43D  -DTHFLVYATSKN---IYGPYT----------YQGKILDPVDG--------WTTHG
Fo43A  -DTHFLVYATSKN---IYGPYT----------YRGKILDPVDG--------WTTHG
Gz43A  -TTHYLVYATSKT---PYGPYT----------YQGRILEPVDG--------WTTHS
Pf43A  CCSEDIRYSTGTS---ATGPWT----------YRGVIMPTQGSS-------FTNHE
```

FIG. 32-1

```
Fv43A  CCSEDIRYSTGPS---ATGPWT-------------YRGVVMNKAGRS--------FTNHP
Fv43B  LATRITAQGVSPMGREAVLFNGTWNKGEWPKLQPVRGRMPGNLLPKPTRN------VPGD
Af43A  LSTRSGPAWKNYPMGRETVLAPAAWEKGEWPVIQPVRGQMQG-PFPPPNKR----VPRGE
Pf43B  YYNTNYYDTSYAYASSITGPWT-----------KQSAPYAPLLVTGT--------ETSND
Fv43E  FMSFTWAYPAGRLPVLAPITWG--------------SDGFPILVKGANGGWGSSYPTLPGT

Fv43D  SIVEYKGQWWLFFAD-AHTSGKDYLRQVKARKIWYDKDG-----KILLTRPKI--------
Fo43A  SIVEYKGQWWLFFAD-AHTSGKDYLRQVKARKIWYDKNG------KILLHRP---------
Gz43A  SIVKYQGQWWLFYHD-AKTSGKDYLRQVKAKKIWYDSKG-----KILTKKP----------
Pf43A  GIIDFQNNSYFFYHNGALPGGGGYQRSVCVEQFKYNADG-------TIPTIEMTTAG-----
Fv43A  GIIDFENNSYFFYHNGALDGGSGYTRSVAVESFKYGSDG-----LIPEIKMTTQG------
Fv43B  GPFNADPDNYNLKKTKKIPPHFVHHRVPRDGAFSLSSKG-----LHIVPSRNNVTGSVLPG
Af43A  GGWIKQPDKVDFRPGSKIPAHFQYWRYPKTEDFTVSPRGHPNTLRLTPSFYNLTG------
Pf43B  GALSAPGGADFSVDGTKMLFHANLNGQDISGGRALFAAS-------ITEASDVVTLQ----
Fv43E  DGVTKNWTRTDTFRGTSLAPSWEWNHNPDVNSFTVNNGLTLRTASITKDIYQARN-----

Fv43D  ------------------------------------------------------------
Fo43A  ------------------------------------------------------------
Gz43A  ------------------------------------------------------------
Pf43A  -----------------PAQIGTLNPYVRQEAETAAWSSGITTEVCSEGGIDVGFINNG
Fv43A  -----------------PAQLKSLNPYVKQEAETIAWSEGIETEVCSEGGLNVAFIDNG
Fv43B  DEIELSGQRGLAFIGRRQTHTLFKYSVDIDFKPKSDDQEAGITVFRTQFDHIDLGIVRLP
Af43A  -TADFKPDDGLSLVMRKQTDTLFTYTVDVSFDPKVADEEAGVTVFLTQQQHIDLGIVLLQ
Pf43B  ------------------------------------------------------------
Fv43E  -------------TLSHRTHGDHPTGIVKIDFSPMKDGDRAGLSAFRDQSAYIGIHRDNGK

Fv43D  ------------------------------------------------------------
Fo43A  ------------------------------------------------------------
Gz43A  ------------------------------------------------------------
Pf43A  DYIK-----------VKGVAFGS-GAHSFSARVASANSGGTIAIHLGSTTGTLVGTCTV
Fv43A  DYIK-----------VKGVDFGSTGAKTFSARVASNSSGGKIELRLGSKTGKLVGTCTV
Fv43B  TNQGSNKKSKLAFRFRATGAQNVPAPK---VVPVPDGWEKGVISLHIEAANATHYNLGAS
Af43A  TTEG-----LSLSFRFRVEGRGNYEGPLPEATVPVPKEWCGQTIRLEIQAVSDTEYVFAAA
Pf43B  ------------------------------------------------------------
Fv43E  FTIAT-----KHGMNMDEWNGTTTDLGQIKATANVPSGRTKIWLRLQLDTNPAGTGNTIFS

Fv43D  ------------------------------------------------------------
Fo43A  ------------------------------------------------------------
Gz43A  ------------------------------------------------------------
Pf43A  PSTGGWQTWTTVTCSVSGASGTQ---------DVYFVFGGSGTGYLFN------FDYWQFA
Fv43A  TTTGNWQTYKTVDCPVSGATGTS---------DLFFVFTGSGSGSLFN------FNWWQFS
Fv43B  --SHRGKTLDIATASASLVSGGTGSFVGSLLGPYATCNGKGSGVECPKGGDVYVTQWTYK
Af43A  PARHPAQRQIISRANSLIVSGDTGRFTGSLVGVYATSNG-GAGSTP------AYISRWRYE
Pf43B  ------------------------------------------------------------
Fv43E  YSWDGVKYETLGPNFKLYNG----------WAFFIAYRFGIFNFAETALGGSIKVESFT

Fv43D  -----------------
Fo43A  -----------------
Gz43A  -----------------
Pf43A  -----------------
Fv43A  -----------------
Fv43B  PVAQEIDHGVFVKSEL
Af43A  GRGQMIDFGRVVPSY-
Pf43B  -----------------
Fv43E  AA---------------
```

*FIG. 32-2*

SEQ ID NO: 25
**Protein sequence of XynB3, a GH43 family enzyme from *Geobacillus stearothermophilus***

MSKIKNPILTGFHPDPSICRVGDDYYIAVSTFEWFPGVRIYHSKDLKNWRLVARPLNRLSQLNMIGNPDS
GGVWAPHLSYSDGKFWLIYTDVKVVEGQWKDGHNYLVTCDTIDGAWSDPIYLNSSGFDPSLFHDEDGRKY
LVNMYWDHRVDHHPFYGIVLQEYSVEQKKLVGEPKIIFKGTDLRITEGPHLYKINGYYYLLTAEGGTRYN
HAATIARSTSLYGPYEVHPDNPLLTSWPYPRNPLQKAGHASIVHTHTDEWFLVHLTGRPLPREGQPLLEH
RGYCPLGRETAIQRLEWKDGWPYVVGGNGPSLEIDGPSVEEVSWEKDYDEKDDFDGDTLNHHFQTLRIPL
GEDIATLKARPGHLRLYGRESLTSRFTQAFVARRWQHFHFVAETKVSFRPTTFQQSAGLVNYYNTQNWTT
LQITWHEEKGRILELMTCDHLVVDQPLRGREIVVPDDIEYVYLRVTVQATTYKYSYSFDGMNWIDLPVTF
ESYKLSDDYIKSRAAFTGAFVGMHCRDGSGQNNYADFDYFLYKEL

*FIG. 33*

SEQ ID NO:26
**Protein sequence of Bgl1, a GH3 family β-glucosidase from *Trichoderma reesei*** mryrtaaalalatqpfaradshstsgasaeavvppagtpwgtaydkakaalakinlqdkvgivsgvgw
nggpcvgntspaskisypslclqdgplgvrystgstaftpgvqaastwdvnlirergqfigeevkasg
ihvilgpvagplgktpqggrnwegfgvdpyltgiamgqtingiqsvgvqatakhyilneqelnretis
snpddrtlhelytwpfadavqanvasvmcsynkvnttwacedqytlqtvlkdqlgfpgyvmtdwnaqh
ttvqsansgldmsmpgtdfngnnrlwgpaltnavnsnqvptsrvddmvtrilaawyltgqdqagypsf
nisrnvqgnhktnvraiardgivllkndanilplkkpasiavvgsaaiignharnspscndkgcddga
lgmgwgsgavnypyfvapydaintrassqgtqvtlsntdntssgasaargkdvaivfitadsgegyit
vegnagdrnnldpwhngnalvqavagansnvivvvhsvgaiileqilalpqvkavvwaglpsqesgna
lvdvlwgdvspsgklvytiakspndyntrivsggsdsfseglfidykhfddanitpryefgyglsytk
fnysrlsvlstaksgpatgavvpggpsdlfqnvatvtvdiansgqvtgaevaqlyitypssaprtppk
qlrgfaklnltpgqsgtatfnirrrdlsywdtasqkwvvpsgsfgisvgassrdirltstlsva

*FIG. 34*

SEQ ID NO:39
Nucleotide sequence of XlnD, a GH3 enzyme from *Aspergillus japonicus*

ATGGCTGTGGCGGCTCTTGCTCTGCTGGCTCTACTGCCTCAAGCTCTGGGGCAACATAACAGCAGCTACG
TGGATTACAACGTCGAAGCCAATCCGGACTTGTTTCCACAATGTCTAGACACAATCTCCCTGTCCTTCCC
CGACTGCCAGAGCGGTCCTCTGAGCAAGAACCTCGTCTGCGACTCGACTGCCTCGCCCTATGACCGCGCC
GCGGCTCTGGTCTCCCTCTTCACCCTCGAGGAACTTATCGCCAACACTGGTAACACCAGCCCGGGTGTCC
CTCGTCTGGGTCTGCCTCCATACCAGGTCTGGAGTGAGGCCCTGCATGGCCTGGCTCGCGCCAACTTCAC
CGACAACGGGGCTTACAGCTGGGCGACGTCCTTCCCCTCACCCATTCTCTCCGCAGCGGCCTTCAATCGC
ACCCTGATCAACCAGATCGCCTCCATTATTTCGACTCAGGGCCGTGCCTTCAACAACGCCGGCCGCTTTG
GCCTCGACGTCTACTCGCCAAACATCAATACCTTCCGCCATCCAGTCTGGGGTCGTGGACAGGAAACTCC
TGGCGAGGATGCGTACACTCTTACGGCCGCCTACGCCTACGAATACATCACGGGTATCCAGGGTGGTGTG
AACCCAGAGCATCTGAAGCTCGCCGCGACAGCCAAGCACTTTGCCGGCTACGACATCGAGAACTGGGACA
ACCACTCCCGGCTGGGGAACGATGTCAACATTACGCAGCAAGACCTGGCCGAGTACTACACGCCGCAGTT
CCTCGTCGCCGCGCGCGACGCCCACGTCCACAGCTTCATGTGCTCCTACAACGCCGTTAACGGAGTGCCC
AGCTGCTCCAACACCTTCTTTCTGCAGACCCTCCTGCGCGACACCTTCTCCTTCGTCGACCACGGCTACG
TCTCCGGCGACTGCGGCGCCGTCTACGGCGTCTTCAACCCCCACGGCTACGCGGCCAACGAGCCCAGCGC
CGCCGCCGATGCCATCCTCGCCGGCACTGACATTGACTGCGGCACCTCCTATCAATATCACTTCAACGAG
TCCATCACCACCGGGGCTGTCGCCCGCGACGACATCGAGCGTGGTTTCATCCGGCTGTACGCCAACCTCG
TCGAGCTGGGCTACTTCGACGGCAACAGCAGCAGCAGCAACCCGTACCGCAGCCTGGGCTGGCCCGACGT
CCAGAAGACAGACGCATGGAACATTTCCTACGAGGCGGCAGTCGAAGGCATCGTCCTCCTGAAGAACGAC
GGCACCCTCCCTCTTGCCTCCCCTCCGAGGGCAAGAACAAATCCATCGCCCTCATCGGCCCCTGGGCCA
ACGCCACCACCCAGCTCCAGGGTAACTACTACGGCGACGCGCCATACCTCATCAGCCCGGTCGACGCCTT
CACGGCCGCCGGGTACACAGTACACTACGCCCCCGGCACGGAGATCTCGACGAACTCGACGGCGAACTTC
AGCGCCGCGCTCTCCGCGGCGCGCGCCGCCGACACCATCGTATTCTTGGGGGGCATCGATAACACCATCG
AAGCCGAAGCCCAAGACCGCAGCTCGATCGCCTGGCCCGGCAACCAACTCGAGCTGATCTCGCAACTCGC
GGCGCAGAAATCCGACGACCAGCCCCTGGTGGTGTACCAGATGGGCGGCGGCCAGGTCGACTCCTCCGCC
CTCAAATCCAACGCGAAGGTCAACGCCCTCCTCTGGGGCGGCTACCCGGGCCAATCCGGCGGCCTCGCCC
TGCGCGACATCCTCACGGGCGCGCGCGCCCCCGCCGGCCGCCTCACCACGACCCAGTACCCGGCCGCCTA
CGCCGAGAGCTTCTCGGCCCTCGACATGAACCTGCGGCCGAATGAGACTACACAGAACCCGGGCCAGACC
TACATGTGGTACACCGGCGAGCCCGTCTACGCCTTCGGCCACGGCCTGTTCTACACCACCTTCAACGCTT
CCTCAGCCCAAGCAGCGAAGACGAAGTATACCTTCAACATCACCGACCTCACCTCCGCCGCACACCCAGA
CACCACGACCGTCGGCCAACGCACCCTCTTCAACTTCACAGCCTCCATCACGAACTCCGGACAGAGGGAT
TCCGATTACACCGCCCTGGTGTACGCCAACACCTCGACTGCGGGCCCCTCCCCGTACCCGAATAAATGGC
TCGTCGGGTTCGACCGGCTCGCCGCCGTGGCGAAGGAGGGCGGCACGGCCGAGTTGAATGTGCCGGTGGC
GGTGGATCGGTTGGCGAGGGTGGATGAAGCGGGTAACACCGTGCTGTTTCCGGGGCGGTATGAGGTGGCC
CTGAATAATGAGCGCGAGGTCGTGGTCGAGGTGGAGTTGGTGGGTGAGCAGGTTGTGCTGTTGAAGTGGC
CGGAGGAGGTGCAGGGGGTGGCGGGGATGAGTAG

*FIG. 35A*

SEQ ID NO:40
Protein sequence of XlnD

```
mavaalalla llpqalgqhn ssyvdynvea npdlfpqcld tislsfpdcq sgplsknlvc
dstaspydra aalvslftie eliantgnts pgvprlgipp yqvwsealhg laranftdng
ayswatsfps pilsaaafnr tlinqiasii stqgrafnna grfgldvysp nintfrhpvw
grgqetpged aytltaayay eyitgiqggv npehlklaat akhfagydie nwdnhsrlgn
dvnitqqdla eyytpqflva ardahvhsfm csynavngvp scsntfflqt llrdtfsfvd
hgyvsgdcga vygvfnphgy aanepsaaad ailagtdidc gtsyqyhfne sittgavard
diergfirly anlvelgyfd gnssssnpyr slgwpdvqkt dawnisyeaa vegivllknd
gtlplaspse gknksialig pwanattqlq gnyygdapyl ispvdaftaa gytvhyapgt
eistnstanf saalsaaraa dtivflggid ntieaeaqdr ssiawpgnql elisqlaaqk
sddqplvvyq mgggqvdssa lksnakvnal lwggypgqsg glalrdiltg arapagrltt
tqypaayaes fsaldmnlrp nettqnpgqt ymwytgepvy afghglfytt fnassaqaak
tkytfnitdl tsaahpdttt vgqrtlfnft asitnsgqrd sdytalvyan tstagpspyp
nkwlvgfdrl aavakeggta elnvpvavdr larvdeagnt vlfpgryeva lnnerevvve
velvgeqvvl lkwpeevqgv agde
```

*FIG. 35B*

SEQ ID NO:41
**Nucleotide sequence of Fv30A, a GH30 enzyme from *Fusarium verticillioides***

```
atgctcttctcgctcgttcttcctacccttgcctttcaagccagcctggcgctcggcgatacatcgt
tactgtcgacaccagccagaaactccaggtcatcgatggctttggtgtctcagaagcctacggccacg
ccaaacaattccaaaacctcggtcctggaccacagaaagagggcctcgatcttctcttcaacactaca
accggcgcaggcttatccatcatccgaaacaagatcggctgcgacgcctccaactccatcaccagcac
caacaccgacaacccagataagcaggctgtttaccattttgacggcgatgatgatggtcaggtatggt
ttagcaaacaggccatgagctatggtgtagatactatctacgctaatgcttggtctgcgcctgtatac
atgaagtcagcccagagtatgggccgtctctgcggtacacctggtgtgtcgtgctcctctggagattg
gagacatcgttacgttgagatgatagctgagtacctctcctactacaagcaggctggcatcccagtgt
cgcacgttggattcctcaatgagggtgacggctcggactttatgctctcaactgccgaacaggctgca
gatgtcattcctcttctacacagcgctttgcagtccaagggccttggcgatatcaagatgacgtgctg
tgataacatcggttggaagtcacagatggactataccgccaagctggctgagcttgaggtggagaagt
atctatctgtcatcacatcccacgagtactccagcagccccaaccagcctatgaacactacattgcca
acctggatgtccgagggagctgccaatgaccaggcatttgccacagcgtggtacgtcaacggcggttc
caacgaaggtttcacatgggcagtcaagatcgcacaaggcatcgtcaatgccgacctctcagcgtata
tctactgggagggcgttgagaccaacaacaaggggtctctatctcacgtcatcgacacggacggtacc
aagtttaccatatcctcgattctctggccattgctcactggtcgcgccatattcgccctggtgcgca
tagactttcgacttcaggtgttgtgcaagatacgattgttggtgcgtttgagaacgttgatggcagtg
tcgtcatggtgctcaccaactctggcactgctgctcagactgtggacctgggtgtttcgggaagtagc
ttctcaacagctcaggctttcacttcggatgctgaggcgcagatggtcgataccaaggtgactctgtc
cgacggtcgtgtcaaggttacggtcccggtgcacggtgtcgtcactgtgaagctcacaacagcaaaaa
gctccaaaccggtctcaactgctgtttctgcgcaatctgccccactccaactagtgttaagcacacc
ttgactcaccagaagacttcttcaacaacactctcgaccgccaaggccccaacctccactcagactac
ctctgtagttgagtcagccaaggcggtgaaataccctgtccccctgtagcatccaagggatcctcga
agagtgctcccaagaagggtaccaagaagaccactacgaagaagggctcccaccaatcgcacaaggcg
catagtgctactcatcgtcgatgccgccatggaagttaccgtcgtggccactgcaccaactaa
```

*FIG. 36A*

SEQ ID NO:42
Protein sequence of Fv30A mlfslviptlafgaslalgdtsvtvdtsqklqvidgfgvseayghakqfqnlgpgpqkegldllfntt
tgaglsiirnkigcdasnsitstntdnpdkqavyhfdgdddgqsaqsmgrlcgtpgvscssgdwrhry
vemiaeylsyykqagipvshvgflnegdgsdfmlstaeqaadviplihsalqskglgdikmtccdnig
wksqmdytaklaelevekylsvitsheyssspnqpmnttlptwmseqaandqafatawyvnggsnegf
twavkiaqgivnadlsayiywegvetnnkgslshvidtdgtkftissilwaiahwsrhirpgahrlst
sgvvqdtivgafenvdgsvvmvltnsgtaaqtvdlgvsgssfstaqaftsdaeaqmvdtkvtlsdgrv
kvtvpvhgvvtvklttaksskpvstavsaqsaptptsvkhtlthqktssttlstakaptstqttsvve
sakavkypvppvaskgssksapkkgtkktttkkgshqshkahsathrrcrhgsyrrghctn

*FIG. 36B*

SEQ ID NO:43
**Nucleotide sequence of Fv30B, a GH30 enzyme from *Fusarium verticillioides*** atgaatcctttatctctcggccttgccgccttgagccttctgggctacgtgggtgtcaactttgttgc
agccttccccacggattcaaactcaggctccgaagtcttgatttctgtcaatggccacgttaaacacc
aagagcttgacggatttggtgcttcacaagcattccaacgggccgaagacattcttggaaaagacggt
ctgtccaagaagggactcagcatgtactggacttgctgttcagcaaggatatcggtgcgggcttctc
tatcctgcgtaatggcattggctcaagcaacagttctgacaagaacttcatgaattcaatcgagccat
tctcgccaggctcacccggagcaaagccacactacgtctgggatggctatgatagcggacaactcacc
gtcgctcaagaagcattcaagagaggattgaagttcctctatggcgatgcttggtccgctcctggtta
catgaagacaaaccacgatgagaataacgggggtatttgtgtggtgttacaggtgctgcctgcgctt
ctggcgactggaagcaggcttacgcagactacttgctgcagtgggttgagttctaccgcaagtcaggc
gtcaaggtcaccaacctaggattccttaacgagcctcagttcgccgctccctacgcggcatgctgtc
taacggcacacaggctgccgacttcatacgtgtactgggcaagacaatcagaaaacgaggtatccacg
accttacaatcgcctgctgtgatggcgagggctggatctccaagaagatatgatggctggtttgact
gctggacctgatccggcaatcaactacctcagtgtcgttactgggcacggctacgttcaccaccgaa
ccatccgctttcaacaacaaagaagacgtggctcaccgagtgggctgatctcacaggccagttcacgc
cctacacgttctacaacaatagcggtcaggggggaaggtatgacctgggctggccgtatccagacggcg
cttgtagatgccaatgtcagcggctttctctattggatcggagccgagaactcgaccaccaacagtgc
tctgatcaacatgatcggcgacaaggtcatccctttccaagaggttctgggcctttgcatccttcagtc
ggtttgctagacctggtgctcgtcgcattgaagccacgagctccgttcctctggtcacagtcagttca
tttctgaataccgacggtactgtcgcgacgcaggtgctgaacaacgacacggttgctcacagtgtgca
actcgttgtctctggcacaggtcgaaatcctcatagcttgaagccgttttgaccgataattctaatg
atttgactgccttgaagcatttgaaggctactggaaagggttcatttcagactacgattcctcctcga
tctcttgttagctttgttacagatttctaacaaagacaatattacttgaagaagacgactatgagggc
tgctttgatcaagttgactatgtctagtatgttggtgtaaatctcctaacaatcttgttgggctgctt
atttcggcttagttacgcaacgtcatgttcagtgtgccgaaagccgaaccacgaaaatagctcacaag
accattctggattttgacacgataagatcctgccttttttttcatacttgttcctctctttcacttgg
cgaaatatgctgtttacgtatccatgctctccc

*FIG. 37A*

SEQ ID NO:44
Protein sequence of Fv30B mnplslqiaaalsllqyvqvnfvaafptdsnsgsevlisvnghvkhqeldgfgasqafqraedilgkdg
lskegtqhvldllfskdigagfsilrngigssnssdknfmnsiepfspgspqakphyvwdgydsgqlt
vaqeafkrglkflygdawsapgymktnhdennggylcgvtgaacasgdwkqayadyllqwvefyrksg
vkvtnlgflnepqfaapyagmlsngtqaadfirvlgktirkrgihdltiaccdgegwdlqedmmaglt
agpdpainylsvvtghgyvsppnhplsttkktwltewaditgqftpytfynnsgqgegmtwagriqta
lvdanvsgflywigaensttnsalinmigdkvipskrfwafasfsrfarpgarrieatssvplvtvss
flntdgtvatqvlnnndtvahsvqlvvsgtgrnphslkpfltdnsndltalkhlkatgkgsfqttippr
slvsfvtdf*

FIG. 37B

SEQ ID NO:45
**Nucleotide sequence of Fv39A, a GH39 enzyme from *Fusarium verticillioides*** atgcactacgctaccctcaccactttggtgctggctctgaccaccaacgtcgctgcacagcaaggcac
agcaactgtcgacctctccaaaaatcatggaccggcgaaggcccttggttcaggcttcatatacggct
ggcctgacaacggaacaagcgtcgacacctccataccagatttcttggtaactgacatcaaattcaac
tcaaaccgcggcggtggcgcccaaatcccatcactgggttgggccagaggtggctatgaaggatacct
cggccgcttcaactcaaccttatccaactatcgcaccacgcgcaagtataacgctgactttatcttgt
tgcctcatgacctctggggtgcggatggcgggcagggttcaaactccccgtttcctggcgacaatggc
aattggactgagatggagttattctggaatcagcttgtgtctgacttgaaggctcataatatgctgga
aggtcttgtgattgatgtttggaatgagcctgatattgatatcttttgggatcgcccgtggtcgcagt
ttcttgagtattacaatcgcgcgaccaaactacttcggtgagtctactactgatccatacgtatttac
agtgagctgactggtcgaattagaaaaacacttcccaaaactcttctcagtggcccagccatggcaca
ttctccattctgtccgatgataaatggcatacctggcttcaatcagtagcgggtaacaagacagtcc
ctgatatttactcctggcatcagattggcgcttggaacgtgagccggacagcactatccccgacttt
accaccttgcgggcgcaatatggcgttcccgagaagccaattgacgtcaatgagtacgctgcacgcga
tgagcaaaatccagccaactccgtctactacctctctcaactagagcgtcataaccttagaggtcttc
gcgcaaactggggtagcggatctgacctccacaactggatgggcaacttgatttacagcactaccggt
acctcggaggggacttactaccctaatggtgaatggcaggcttacaagtactatgcggccatggcagg
gcagagacttgtgaccaaagcatcgtcggacttgaagtttgatgtctttgccactaagcaaggccgta
agattaagattatagccggcacgaggaccgttcaagcaaagtataacatcaaaatcagcggtttggaa
gtagcaggacttcctaagatgggtacgtaaaggtccggacttatcggttcgactgggctgggccgaa
tggaaaggttgacgggcctgttgatttggggggagaagaagtatacttattcggccaatacggtgagca
gccctctacttga

FIG. 38A

SEQ ID NO:46
Protein sequence of Fv39A

<u>mhyatltttlvlalttnvaa</u>qqgtatvdlsknhgpakalgsgfiygwpdngtsvdtsipdflvtdikfn
snrgggaqipslgwarggyegylgrfnstisnyrttrkynadfillphdlwgadggqgsnspfpgdng
nwtemel**fwnqlvsdlkahnmleglvidvwnepdidifwdrpwsqfleyynratkllrktlpktllsg
pamahspilsddkwhtwlqsvagnktvpdiyswhqigawerepdstipdfttlraqygvpekpidvne
yaardeqnpansvyylsql**erhnlrglranwgsgsdlhnwmgnliysttgtsegtyypngewqaykyy
aamagqrlvtkassdlkfdvfatkqgrkikiiagtrtvqakynikisglevaglpkmgtvkvrtyrfd
waqpngkvdgpvdlgekkytysantvsspst

FIG. 38B

SEQ ID NO:47
**Nucleotide sequence of Fv39B, a GH39 enzyme from *Fusarium verticillioides*** atgtggttaatcaaggcctgttccgtcctcgccgctctctccactgtagctgctgacagccccggtcc
caccatcgacttctcctccaacactggagagcctcagcatctcgctgctggtatcctgtacggtatac
ccgacgatgggaaccagatcccagatgatcttctctctggctttggcttcaactactatcgcggtgca
ggtgcccaagtctctcatggatggagttatgacgaggctggcttccagcagcgttttgaaagcgcgca
taacaactacatcgtcacgcgtcgtcacaacggcggctttgtcttgttgctgaatgacctctggggct
ttgattgttcttctaacaacgatacctcacctggtccaggcgataatggcgattggtcgtcctatgac
aagttcgttcaggcgattattgccaatgtcaagaagtacaacatgcaggaaggcttggtcattgatat
ctggaacgagccagagggggctgtttctggggccgtagcattgaccaatggcttcagatgtgggggtc
gcggctggcatcaattcaagtaagtactagataccctctgaggacggatgggacaagaactgactgtct
attcagtgatgccttcggggacagcgtgttgacatccggaccaactcttgcaggcgagccgggaacaa
acgatgactggtggacccaatgggcccaattcgtcaagaacaacgactccatcccgaccaatacgca
tggcacgaggaaggaggctcaggttccaacttcgagaacagctacggcgtcctgcaacaaattctcac
taaatacggtcttccccaacgccaatcaacatcaacgaatacgctacgttcaatgaacaagtccccg
ccggttctgccttctggatctcccagttcgagcgccgtaatgctatcggtcttcgcggcaattggcta
ggaggcactcaacttcacgatctggccgctagtcttctgtccaagcctgaccctcggactacgcttc
cacgggatactttgccaatggagactggtgggtgtataactactactctcacaacatgacgggacagc
gcgtttcgacttcggtgtcttccgatggaaggctggatgcttatgcaacggtggatactacggcgcg
acggctagagtattgcttggctgccatccgcctacgactggtacttatgatgtgacattctctggtct
gacaaagttgggtctgccatcttctggaacacttcaggttaggacttggaagtttgctgtgggcagtg
atgtgcattacagccaggtgggttctcctcaggatctgggtaactatggtcacactattagcaacggt
caggttaccttgccgttctatcagactgatgatgtgactacatacgcatgggagttcaaattctag

FIG. 39A

SEQ ID NO:48
Protein sequence of Fv39B

<u>mwlikacsvlaalstvaa</u>dspgptidfssntgepqhlaagilygipddgnqipddllsgfgfnyyrga
gaqvshgwsydeagfqqrfesahnnyivtrrhnggfvllllndlwgfdcssnndtspgpgdngdwssyd
kfvqaiianvkkynmqeglvidiwnepeggcfwgrsidqwlqmwgrgwhqfndafgdsvltsgptlag
epgtnddwwtqwaqfvknndsipdqyawheeggsgsnfensygvlqqiltkyglpqrqinineyatfn
eqvpagsafwisqferrnaiglrgnwlggtqlhdlaaslskpdpsdyastgyfangdwwvynyyshn
mtgqrvstsvssdgrldayatvdttartarvllgchppttgtydvtfsgltklglpssgtlqvrtwkf
avgsdvhysqvgspqdlgnyghtisngqvtlpfyqtddvttyawefkf*

FIG. 39B

SEQ ID NO:49
Nucleotide sequence of XynB, a GH39 enzyme from *Thermoanaerobacter saccharolyticum*

```
atggtaaaaa taaagatacc aaaaaattct gatggcaaaa aattcaccag tagatggaga
tattgtgtag gtacaggaag gttgggactt gcgctgcaaa aagagtacat ggatacttta
aaatttgtga aagaaaatat agacttcaag tatataagag gacatggcct tttgtgcgac
gatgtaggta tttaccgtga ggacgtagta ggcaacgatg taaggccatt ttacaatttc
acgtatatag atagaatctt tgattcattt ttggaattag ggataaggcc atttgttgaa
gtcggattta tgcctaaaag attagcatct ggtacacaga cagtatttta ttgggaggga
aatgtcaccc ctcccaaaga ttatgaaaaa tggagcaacc ttataaaagc tgttgtttca
catttttatat caaggtatgg catagatgaa gtcgtaaaat ggccatttga aatatggaat
gagccaaacc taaaagagtt ttggaaagat gctgatgaga aagaatactt caagctgtac
aaggttactg caaaggcgat taaagaagta aatgagaatt tgcaggtagg aggacctgct
atatgtggtg gtgctgacta ctggatagaa gattttttga atttctgcta tgaagaaaat
gttcctgttg attttgtatc gcgacacgca tatacgtcta agcaaggtga atatacgcca
catctcatat accaggagat tatgccatct gaatacatgc taaacgaatt caaaacagtg
agagagatca taaaaaactc acattttccg aaccttccgt ttcatataac ggagtacaat
acatcttaca gtccattaaa tcctgtacat gatacgcctt ttaatgcggc gtatcttgcg
aggattttaa gtgaaggcgg agattatgtt gattcatttt cctattggac gtttagcgat
gtgtttgaag aaagagatgt gccaagatcg cagtttcatg gaggatttgg actagttgca
ttgaataaga taccaaagcc gacttttcac atgtttaaat ttttcaatgc tatgggagaa
gaggtgcttt acagagataa ccatatgctt ataactagaa gggatgatgg gtcgattgca
tgattgctt ggaatgagat aatggagaaa acagaaaatc cagataagga atatgaactg
gaaatacctg taggattcaa agatgtcttt ataaagaaac agatgataga tgaggatcac
ggcaatcctt ggggtacgtg gatacacatg ggaaggccga gattcccaag taaagaacaa
attaagactt taagggatat tgcaaagcct aaaatcaaaa caggtagagc cacatcaaat
gatggctatg taaatttgaa atttagattg gggaaaaatg ctgtggtatt gtttgaattg
actgaagtaa tggatgaatc aaacacttat ataggacttg atgatagcaa gataaacgga
tattga
```

FIG. 40A

SEQ ID NO:50
Protein sequence of XynB

```
MIKVRVPDFS DKKFSDRWRY CVGTGRLGLA LQKEYIETLK YVKENIDFKY IRGHGLLCDD
VGIYREDVVG DEVKPFYNFT YIDRIFDSFL EIGIRPFVEI GFMPKKLASG TQTVFYWEGN
VTPPKDYEKW SDLVKAVLHH FISRYGIEEV LKWPFEIWNE PNLKEFWKDA DEKEYFKLYK
VTAKAIKEVN ENLKVGGPAI CGGADYWIED FLNFCYEENV PVDFVSRHAT TSKQGEYTPH
LIYQEIMPSE YMLNEFKTVR EIIKNSHFPN LPFHITEYNT SYSPQNPVHD TPFNAAYIAR
ILSEGGDYVD SFSYWTFSDV FEERDVPRSQ FHGGFGLVAL NMIPKPTFYT FKFFNAMGEE
MLYRDEHMLV TRRDDGSVAL IAWNEVMDKT ENPDEDYEVE IPVRFRDVFI KRQLIDEEHG
NPWGTWIHMG RPRYPSKEQV NTLREVAKPE IMTSQPVAND GYLNLKFKLG KNAVVLYELT
ERIDESSTYI GLDDSKINGY
```

FIG. 40B

SEQ ID NO:51
Nucleotide sequence of XylA, A GH52 enzyme from *Geobacillus stearothermophilus*

```
atgccaacca atgtatttt caacgcccat cactcgccgg ttggggcgtt tgccagcttt
acgctagggt ttccgggaaa aagcggagga ctggacttgg aactcgcccg accgccacgg
caaaatgtct ttattggcgt tgagtcgccc catgagccgg ggctgtatca tatccttcca
ttcgcggaaa cagcaggcga ggatgaaagc aaacgatatg acattgaaaa tcctgatccg
aatccgcaaa aaccaaacat tctcatcccg tttgcgaaag aggagatcaa gcgcgaattc
tgtgtggcaa cggatacatg gaaagctggg gatttaacgt ttacgattta ttcgccggta
aaggcggtgc ctgatcccga acagcggcc gaggaagaac tcaagttggc gttggtccca
gctgtcattg tcgagatgac gatcgataac acgaacggaa caagaacacg acgggcgttt
ttcggattcg aaggcaccga cccgtatacc tcgatgcggg ggatcgatga tacatgcccg
cagctgcgcg gggtcggtca agggcggatt ttgggcattg tatccaagga tgagggtgtt
cgctcagcgc tgcattttag catggaggat atcttaacgg cgactctcga agaaaactgg
acgtttgggc ttgggaaagt cggtgcgtta atcgttgatg tgccggcggg agaaaagaaa
acgtatcaat ttgctgtttg tttttaccgc ggtggttatg ttaccgcagg aatggatgcc
tcttatttt acacccgttt cttccataat atcgaagaag tcggtcttta tgcgttagag
caggccgagg tgttaaagga gcaggcgttc cgttcgaatg aactcattga aaagaatgg
ctctccgatg atcaaaagtt tatgatggcg cacgcgatcc gcagctacta tggcaataca
caactgcttg agcatgaagg aaagccgatt tgggtcgtta tgaaggcga gtaccggatg
atgaatacgt ttgatctcac cgtcgaccag ctcttttttg agttgaaaat gaatccgtgg
acggtgaaaa atgtgcttga cttctatgtc gagcgctaca gctatgagga tcgtgtccgt
ttcccaggag atgagacgga atatcccggc ggcatcagct tcactcatga tatgggagtc
gctaacacgt tctcgcgtcc gcattactcg tcatatgagc tatacggaat cagcggctgc
ttttcgcata tgacgcacga acagctcgtc aactgggtgc tttgcgcggc ggtatacatc
gaacaaacga aagactgggc atggcgcgac cggcggctta cgatcttgga acaatgtctc
gaaagcatgg tgcgtcgtga tcatccggat ccagaaaagc ggaacggcgt gatgggggctt
gacagcaccc gcaccatggg tggagcggaa atcacaacgt atgatagttt ggatgttttcc
ctcggccagg cgcgcaacaa tttatatttg gcaggaaaat gttgggctgc ctatgtggcg
ctcgaaaagt tgttccgcga tgtcggcaaa gaagaactgg ctgcattggc aagggagcag
gcggaaaaat gcgccgcgac gattgtcagt cacgtgacgg aggacgggta tatcccagcc
gtgatgggag aaggaaatga ctcgaaaatc attccggcta ttgagggggct tgtgtttcct
tactttacga actgccatga ggcgttaaga gaagacggac gttttggaga ctatattcgt
gcactgcgac aacatttgca atatgtgttg cgggaaggaa tttgcctatt cccggacggg
ggatggaaaa tttcctcgac aagcaacaac tcgtggttga gcaaaatta cttatgccag
tttattgccc gccgcatttt agggtgggaa tgggatgaac aaggaaaacg agctgatgcg
gctcatgttg cgtggctcac gcatccgacg ctctccattt ggagttggag cgaccaaatt
atcgctggcg aaatcagcgg cagcaaatac tacccgcgcg gcgtgacgag catttatgg
ttggaggagg gggaatga
```

*FIG. 41A*

SEQ ID NO:52
Protein sequence of XylA

<u>mptnlffnah hspvgafasf</u> tlgfpgksgg ldlelarppr qnvligvesl hesglyhvlp
fletaeedes krydienpdp npqkpnilip fakeeiqref hvatdtwkag dltftiyspv
kavpnpetad eeelklalvp avivemtidn tngtrarraf fgfegtdpyt smrriddtcp
qlrgvgqgri lsivskdegv rsalhfsmed iltaqleenw tfglgkvgal ivdvpagekk
tyqfavcfyr ggyvtagmda syfytrffqn ieevglyale qaevlkeqsf rsnkliekew
lsddqtfmma hairsyygnt qllehegkpi wvvnegeyrm mntfdltvdq lffelklnpw
tvknvldlyv erysyedrvr fpgeeteyps gisfthdmgv antfsrphys syelygisgc
fshmtheqlv nwvlcaavyi eqtkdwawrd krlaileqcl esmvrrdhpd peqrngvmgl
dstrtmggae ittydsldvs lgqarnnlyl agkcwaayva leklfrdvgk eelaalageq
aekcaativs hvtddgyipa imgegndski ipaieglvfp yftncheald engrfgayiq
alrnhlqyvl regiclfpdg gwkisstsnn swlskiylcq fiarhilgwe wdeqgkrada
ahvawlthpt lsiwswsdqi iageitgsky yprqvtsilw leege

*FIG. 41B*

SEQ ID NO:53
**Nucleotide sequence of Xyl1, a GH54 enzyme from *Trichoderma koningii* (*Hypocrea koningii*)**

ATGCTCTCCAACGCTCGTATCATCGCAGCGGGCTGTATTGCTGCAGGCTCTCTCGTTGCT
GCTGGGCCTTGTGACATCTACTCCTCGGGCGGAACGCCTTGCGTTGCCGCCCACAGCACC
ACTCGAGCTCTGTTCAGCGCTTATACCGGCCCGTTATACCAGGTAAAGCGCGGCTCCGAT
GGTGCCACAACCGCCATATCGCCCCTCTCAAGTGGTGTGGCCAACGCTGCCGCTCAAGAT
GCTTTCTGTGCGGGAACTACATGCCTCATTACCATCATATACGACCAGTCGGGTCGCGGC
AACCATCTCAGGGAGGCCCCGCCGGGCGGCTTCAGCGGCCCGGAATCCAACGGCTATGAC
AACCTGGCTAGTGCAATTGGGGCGCCGGTAACACTCAACGGCCAGAAGGCGTATGGAGTT
TTCGTGTCTCCAGGAACGGGGTATCGGAATAACGCTGCCAGCGGCACAGCCAAAGGAGAT
GCCGCGGAGGGCATGTATGCGGTTCTCGATGGTACACACTACAACGGCGCCTGCTGCTTT
GACTATGGCAACGCCGAGACCAACAGCCGCGATACAGGCAACGGTCATATGGAGGCCATC
TATTTTGGCGACAGCACTGTCTGGGGTACTGGCTCAGGCAAGGGTCCGTGGATCATGGCT
GATCTCGAGAACGGCTTGTTCTCAGGCTCCAGTCCCGGCAACAATGCCGGTGATCCGTCC
ATCTCGTACCGGTTCGTCACTGCAGCGATCAAGGGGCAGCCAAACCAATGGGCAATCCGT
GGCGGCAATGCTGCGTCTGGCTCGCTGTCAACTTTCTACAGCGGCGCTCGCCCACAAGTC
TCCGGATACAATCCGATGAGCAAAGAGGGCGCCATCATTCTCGGCATTGGCGGCGACAAC
AGCAACGGCGGCCAGGGCACATTCTATGAGGGCGTCATGACCTCTGGATATCCTTCCGAT
GCAACAGAGAATTCAGTGCAAGCCAACATCGTAGCTGCCA

*FIG. 42A*

SEQ ID NO:54
Protein sequence of Xyl1

<u>MLSNARIIAA GCIAAGSLVA</u> AGPCDIYSSG GTPCVAAHST TRALFSAYTG PLYQVKRGSD
GATTAISPLS SGVANAAAQD AFCAGTTCLI TIIYDQSGRG NHLREAPPGG FSGPESNGYD
NLASAIGAPV TLNGQKAYGV FVSPGTGYRN NAASGTAKGD AAEGMYAVLD GTHYNGACCF
DYGNAETNSR DTGNGHMEAI YFGDSTVWGT GSGKGPWIMA DLENGLFSGS SPGNNAGDPS
ISYRFVTAAI KGQPNQWAIR GGNAASGSLS TFYSGARPQV SGYNPMSKEG AIILGIGGDN
SNGGQGTFYE GVMTSGYPSD ATENSVQANI VAARYAVAPL TSGPALTVGS SISLRATTAC
CTTRYIAHSG STVNTQVVSS SSATALKQQA SWTVRAGLAN NACFSFESQD TSGSYIRHSN
FGLVLNANDG SKLFAEDATF CTQAGINGQG SSIRSWSYPT RYFRHYNNTL YIASNGGVHV
FDATAAFNDD VSFVVSGGFA

*FIG. 42B*

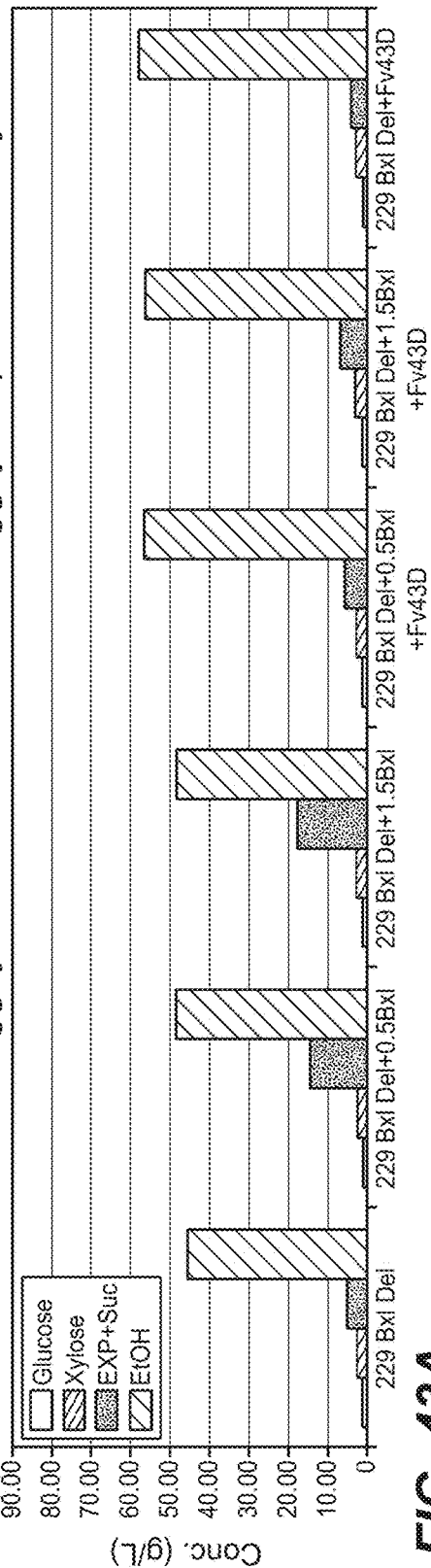
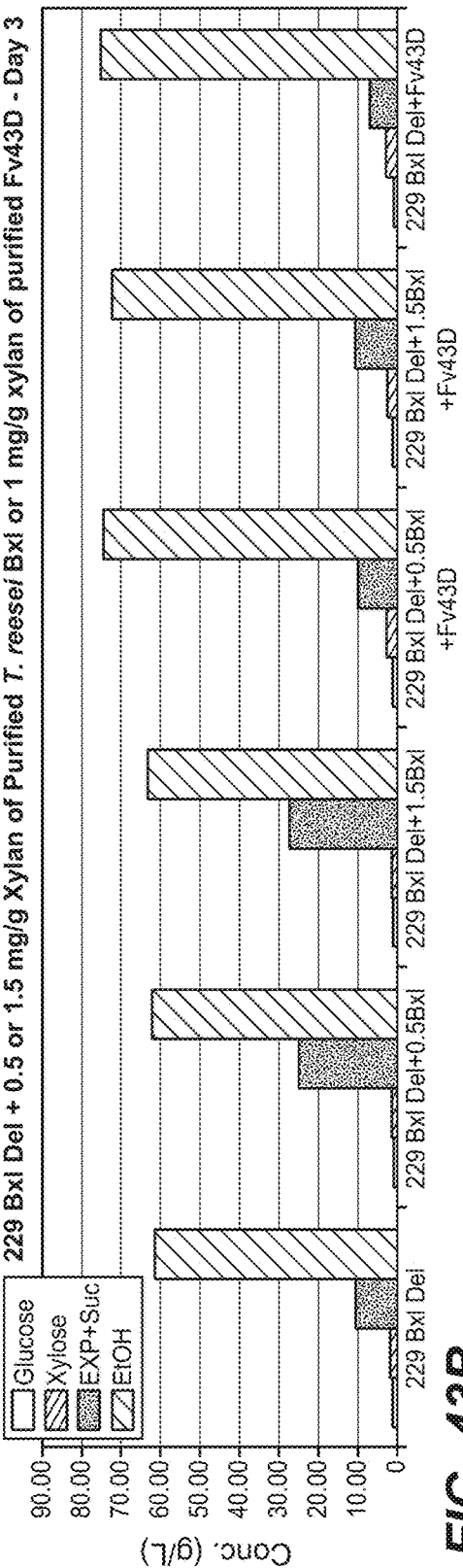
FIG. 43A
FIG. 43B

SEQUENCE LISTING

<160> NUMBER OF SEQ ID NOS: 56

<210> SEQ ID NO 1
<211> LENGTH: 1053
<212> TYPE: DNA
<213> ORGANISM: Fusarium verticillioides

<400> SEQUENCE: 1

```
atgcagctca agtttctgtc ttcagcattg ttgctgtctt tgaccggcaa ttgcgctgcg     60
caagacacta atgatatccc tcctctgatc accgacctct ggtctgcgga tccctcggct    120
catgttttcg agggcaaact ctgggtttac ccatctcacg acatcgaagc caatgtcgtc    180
aacggcaccg gaggcgctca gtacgccatg agagattatc acacctattc catgaagacc    240
atctatggaa agatcccgt tatcgaccat ggcgtcgctc tgtcagtcga tgatgtccca    300
tgggccaagc agcaaatgtg ggctcctgac gcagcttaca gaacggcaa atattatctc    360 tacttccccg ccaaggataa agatgagatc ttcagaattg gagttgctgt ctccaacaag    420
cccagcggtc ctttcaaggc cgacaagagc tggatccccg gtacttacag tatcgatcct    480
gctagctatg tcgacactaa tggcgaggca tacctcatct ggggcggtat ctggggcggc    540
cagcttcagg cctggcagga tcacaagacc tttaatgagt cgtggctcgg cgacaaagct    600
gctcccaacg gcaccaacgc cctatctcct cagatcgcca agctaagcaa ggacatgcac    660
aagatcaccg agacaccccg cgatctcgtc atcctggccc ccgagacagg caagcccctt    720
caagcagagg acaataagcg acgattttc gaggggccct gggttcacaa gcgcggcaag    780
ctgtactacc tcatgtactc taccggcgac acgcacttcc tcgtctacgc gacttccaag    840
aacatctacg tccttatac ctatcagggc aagattctcg accctgttga tgggtggact    900
acgcatggaa gtattgttga gtacaaggga cagtggtggt tgttctttgc ggatgcgcat    960
acttctggaa aggattatct gagacaggtt aaggcgagga agatctggta tgacaaggat   1020
ggcaagattt tgcttactcg tcctaagatt tag                                1053
```

<210> SEQ ID NO 2
<211> LENGTH: 350
<212> TYPE: PRT
<213> ORGANISM: Fusarium verticillioides

<400> SEQUENCE: 2

```
Met Gln Leu Lys Phe Leu Ser Ser Ala Leu Leu Leu Ser Leu Thr Gly
1               5                   10                  15

Asn Cys Ala Ala Gln Asp Thr Asn Asp Ile Pro Pro Leu Ile Thr Asp
            20                  25                  30

Leu Trp Ser Ala Asp Pro Ser Ala His Val Phe Glu Gly Lys Leu Trp
        35                  40                  45

Val Tyr Pro Ser His Asp Ile Glu Ala Asn Val Val Asn Gly Thr Gly
    50                  55                  60

Gly Ala Gln Tyr Ala Met Arg Asp Tyr His Thr Tyr Ser Met Lys Thr
65                  70                  75                  80

Ile Tyr Gly Lys Asp Pro Val Ile Asp His Gly Val Ala Leu Ser Val
                85                  90                  95

Asp Asp Val Pro Trp Ala Lys Gln Gln Met Trp Ala Pro Asp Ala Ala
            100                 105                 110

Tyr Lys Asn Gly Lys Tyr Tyr Leu Tyr Phe Pro Ala Lys Asp Lys Asp
        115                 120                 125
```

```
Glu Ile Phe Arg Ile Gly Val Ala Val Ser Asn Lys Pro Ser Gly Pro
                130                 135                 140

Phe Lys Ala Asp Lys Ser Trp Ile Pro Gly Thr Tyr Ser Ile Asp Pro
145                 150                 155                 160

Ala Ser Tyr Val Asp Thr Asn Gly Glu Ala Tyr Leu Ile Trp Gly Gly
                165                 170                 175

Ile Trp Gly Gly Gln Leu Gln Ala Trp Gln Asp His Lys Thr Phe Asn
                180                 185                 190

Glu Ser Trp Leu Gly Asp Lys Ala Pro Asn Gly Thr Asn Ala Leu
                195                 200                 205

Ser Pro Gln Ile Ala Lys Leu Ser Lys Asp Met His Lys Ile Thr Glu
210                 215                 220

Thr Pro Arg Asp Leu Val Ile Leu Ala Pro Glu Thr Gly Lys Pro Leu
225                 230                 235                 240

Gln Ala Glu Asp Asn Lys Arg Arg Phe Phe Glu Gly Pro Trp Val His
                245                 250                 255

Lys Arg Gly Lys Leu Tyr Tyr Leu Met Tyr Ser Thr Gly Asp Thr His
                260                 265                 270

Phe Leu Val Tyr Ala Thr Ser Lys Asn Ile Tyr Gly Pro Tyr Thr Tyr
                275                 280                 285

Gln Gly Lys Ile Leu Asp Pro Val Asp Gly Trp Thr Thr His Gly Ser
290                 295                 300

Ile Val Glu Tyr Lys Gly Gln Trp Trp Leu Phe Ala Asp Ala His
305                 310                 315                 320

Thr Ser Gly Lys Asp Tyr Leu Arg Gln Val Lys Ala Arg Lys Ile Trp
                325                 330                 335

Tyr Asp Lys Asp Gly Lys Ile Leu Leu Thr Arg Pro Lys Ile
                340                 345                 350

<210> SEQ ID NO 3
<211> LENGTH: 2394
<212> TYPE: DNA
<213> ORGANISM: Trichoderma reesei

<400> SEQUENCE: 3
atggtgaata acgcagctct tctcgccgcc ctgtcggctc tcctgcccac ggccctggcg      60
cagaacaatc aaacatacgc caactactct gctcagggcc agcctgatct ctaccccgag     120
acacttgcca cgctcacact ctcgttcccc gactgcgaac atggcccccct caagaacaat    180 ctcgtctgtg actcatcggc cggctatgta gagcgagccc aggccctcat ctcgctcttc     240
accctcgagg agctcattct caacacgcaa aactcgggcc ccggcgtgcc tcgcctgggt     300
cttccgaact accaagtctg gaatgaggct ctgcacggct ggaccgcgc caacttcgcc      360 accaagggcg ccagttcga atgggcgacc tcgttcccca tgccatcct cactacggcg      420 gccctcaacc gcacattgat ccaccagatt gccgacatca tctcgaccca agctcgagca     480
ttcagcaaca gcggccgtta cggtctcgac gtctatgcgc aaacgtcaa tggcttccga     540 agcccctct ggggccgtgg ccaggagacg cccggcgaag acgccttttt cctcagctcc     600
gcctatactt acgagtacat cacgggcatc caggtggcg tcgaccctga gcacctcaag     660
gttgccgcca cggtgaagca ctttgccgga tacgacctcg agaactggaa caaccagtcc     720
cgtctcggtt tcgacgccat cataactcag caggacctct ccgaatacta cactccccag     780
ttcctcgctg cggcccgtta tgcaaagtca cgcagcttga tgtgcgcata caactccgtc     840
aacggcgtgc ccagctgtgc caacagcttc ttcctgcaga cgcttttgcg cgagagctgg     900
```

```
ggcttccccg aatggggata cgtctcgtcc gattgcgatg ccgtctacaa cgttttcaac    960
cctcatgact acgccagcaa ccagtcgtca gccgccgcca gctcactgcg agccggcacc   1020
gatatcgact gcggtcagac ttacccgtgg cacctcaacg agtcctttgt ggccggcgaa   1080
gtctcccgcg gcgagatcga gcggtccgtc acccgtctgt acgccaacct cgtccgtctc   1140
ggatacttcg acaagaagaa ccagtaccgc tcgctcggtt ggaaggatgt cgtcaagact   1200
gatgcctgga acatctcgta cgaggctgct gttgagggca tcgtcctgct caagaacgat   1260
ggcactctcc ctctgtccaa gaaggtgcgc agcattgctc tgatcggacc atgggccaat   1320
gccacaaccc aaatgcaagg caactactat ggccctgccc catacctcat cagccctctg   1380
gaagctgcta agaaggccgg ctatcacgtc aactttgaac tcggcacaga gatcgccggc   1440
aacagcacca ctggctttgc caaggccatt gctgccgcca agaagtcgga tgccatcatc   1500
tacctcggtg gaattgacaa caccattgaa caggagggcg ctgaccgcac ggacattgct   1560
tggcccggta atcagctgga tctcatcaag cagctcagcg aggtcggcaa acccttgtc    1620
gtcctgcaaa tgggcggtgg tcaggtagac tcatcctcgc tcaagagcaa caagaaggtc   1680
aactccctcg tctggggcgg atatcccggc cagtcgggag gcgttgccct cttcgacatt   1740
ctctctggca agcgtgctcc tgccggccga ctggtcacca ctcagtaccc ggctgagtat   1800
gttcaccaat tccccagaa tgacatgaac ctccgacccg atggaaagtc aaaccctgga   1860
cagacttaca tctggtacac cggcaaaccc gtctacgagt ttggcagtgg tctcttctac   1920
accaccttca aggagactct cgccagccac cccaagagcc tcaagttcaa cacctcatcg   1980
atcctctctg ctcctcaccc cggatacact tacagcgagc agattcccgt cttcaccttc   2040
gaggccaaca tcaagaactc gggcaagacg gagtcccat atacggccat gctgtttgtt    2100
cgcacaagca acgctggccc agccccgtac ccgaacaagt ggctcgtcgg attcgaccga   2160
cttgccgaca tcaagcctgg tcactcttcc aagctcagca tccccatccc tgtcagtgct   2220
ctcgcccgtg ttgattctca cggaaaccgg attgtatacc ccggcaagta tgagctagcc   2280
ttgaacaccg acgagtctgt gaagcttgag tttgagttgg tgggagaaga ggtaacgatt   2340
gagaactggc cgttggagga gcaacagatc aaggatgcta cacctgacgc ataa         2394
```

<210> SEQ ID NO 4
<211> LENGTH: 797
<212> TYPE: PRT
<213> ORGANISM: Trichoderma reesei

<400> SEQUENCE: 4

```
Met Val Asn Asn Ala Ala Leu Leu Ala Ala Leu Ser Ala Leu Leu Pro
1               5                   10                  15

Thr Ala Leu Ala Gln Asn Asn Gln Thr Tyr Ala Asn Tyr Ser Ala Gln
            20                  25                  30

Gly Gln Pro Asp Leu Tyr Pro Glu Thr Leu Ala Thr Leu Thr Leu Ser
        35                  40                  45

Phe Pro Asp Cys Glu His Gly Pro Leu Lys Asn Asn Leu Val Cys Asp
    50                  55                  60

Ser Ser Ala Gly Tyr Val Glu Arg Ala Gln Ala Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110
```

```
Gly Leu Asp Arg Ala Asn Phe Ala Thr Lys Gly Gln Phe Glu Trp
            115                 120                 125
Ala Thr Ser Phe Pro Met Pro Ile Leu Thr Thr Ala Ala Leu Asn Arg
130                 135                 140
Thr Leu Ile His Gln Ile Ala Asp Ile Ile Ser Thr Gln Ala Arg Ala
145                 150                 155                 160
Phe Ser Asn Ser Gly Arg Tyr Gly Leu Asp Val Tyr Ala Pro Asn Val
                165                 170                 175
Asn Gly Phe Arg Ser Pro Leu Trp Gly Arg Gly Gln Glu Thr Pro Gly
            180                 185                 190
Glu Asp Ala Phe Phe Leu Ser Ser Ala Tyr Thr Tyr Glu Tyr Ile Thr
            195                 200                 205
Gly Ile Gln Gly Gly Val Asp Pro Glu His Leu Lys Val Ala Ala Thr
            210                 215                 220
Val Lys His Phe Ala Gly Tyr Asp Leu Glu Asn Trp Asn Asn Gln Ser
225                 230                 235                 240
Arg Leu Gly Phe Asp Ala Ile Ile Thr Gln Gln Asp Leu Ser Glu Tyr
                245                 250                 255
Tyr Thr Pro Gln Phe Leu Ala Ala Ala Arg Tyr Ala Lys Ser Arg Ser
            260                 265                 270
Leu Met Cys Ala Tyr Asn Ser Val Asn Gly Val Pro Ser Cys Ala Asn
            275                 280                 285
Ser Phe Phe Leu Gln Thr Leu Leu Arg Glu Ser Trp Gly Phe Pro Glu
            290                 295                 300
Trp Gly Tyr Val Ser Ser Asp Cys Asp Ala Val Tyr Asn Val Phe Asn
305                 310                 315                 320
Pro His Asp Tyr Ala Ser Asn Gln Ser Ser Ala Ala Ser Ser Leu
                325                 330                 335
Arg Ala Gly Thr Asp Ile Asp Cys Gly Gln Thr Tyr Pro Trp His Leu
            340                 345                 350
Asn Glu Ser Phe Val Ala Gly Glu Val Ser Arg Gly Glu Ile Glu Arg
            355                 360                 365
Ser Val Thr Arg Leu Tyr Ala Asn Leu Val Arg Leu Gly Tyr Phe Asp
            370                 375                 380
Lys Lys Asn Gln Tyr Arg Ser Leu Gly Trp Lys Asp Val Val Lys Thr
385                 390                 395                 400
Asp Ala Trp Asn Ile Ser Tyr Glu Ala Val Glu Gly Ile Val Leu
                405                 410                 415
Leu Lys Asn Asp Gly Thr Leu Pro Leu Ser Lys Lys Val Arg Ser Ile
            420                 425                 430
Ala Leu Ile Gly Pro Trp Ala Asn Ala Thr Thr Gln Met Gln Gly Asn
            435                 440                 445
Tyr Tyr Gly Pro Ala Pro Tyr Leu Ile Ser Pro Leu Glu Ala Ala Lys
            450                 455                 460
Lys Ala Gly Tyr His Val Asn Phe Glu Leu Gly Thr Glu Ile Ala Gly
465                 470                 475                 480
Asn Ser Thr Thr Gly Phe Ala Lys Ala Ile Ala Ala Lys Lys Ser
                485                 490                 495
Asp Ala Ile Ile Tyr Leu Gly Gly Ile Asp Asn Thr Ile Glu Gln Glu
            500                 505                 510
Gly Ala Asp Arg Thr Asp Ile Ala Trp Pro Gly Asn Gln Leu Asp Leu
            515                 520                 525
```

```
Ile Lys Gln Leu Ser Glu Val Gly Lys Pro Leu Val Leu Gln Met
530                 535                 540

Gly Gly Gly Gln Val Asp Ser Ser Leu Lys Ser Asn Lys Val
545                 550                 555                 560

Asn Ser Leu Val Trp Gly Gly Tyr Pro Gly Gln Ser Gly Gly Val Ala
                565                 570                 575

Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
        595                 600                 605

Met Asn Leu Arg Pro Asp Gly Lys Ser Asn Pro Gly Gln Thr Tyr Ile
610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
            645                 650                 655

Asn Thr Ser Ser Ile Leu Ser Ala Pro His Pro Gly Tyr Thr Tyr Ser
                660                 665                 670

Glu Gln Ile Pro Val Phe Thr Phe Glu Ala Asn Ile Lys Asn Ser Gly
            675                 680                 685

Lys Thr Glu Ser Pro Tyr Thr Ala Met Leu Phe Val Arg Thr Ser Asn
690                 695                 700

Ala Gly Pro Ala Pro Tyr Pro Asn Lys Trp Leu Val Gly Phe Asp Arg
705                 710                 715                 720

Leu Ala Asp Ile Lys Pro Gly His Ser Ser Lys Leu Ser Ile Pro Ile
            725                 730                 735

Pro Val Ser Ala Leu Ala Arg Val Asp Ser His Gly Asn Arg Ile Val
                740                 745                 750

Tyr Pro Gly Lys Tyr Glu Leu Ala Leu Asn Thr Asp Glu Ser Val Lys
            755                 760                 765

Leu Glu Phe Glu Leu Val Gly Glu Val Thr Ile Glu Asn Trp Pro
770                 775                 780

Leu Glu Glu Gln Gln Ile Lys Asp Ala Thr Pro Asp Ala
785                 790                 795

<210> SEQ ID NO 5
<211> LENGTH: 2358
<212> TYPE: DNA
<213> ORGANISM: Fusarium verticillioides

<400> SEQUENCE: 5
atgctgctca atcttcaggt cgctgccagc gctttgtcgc tttctctttt aggtggattg      60
gctgaggctg ctacgccata taccttccg gactgtacca aaggaccttt gagcaagaat     120
ggaatctgcg atacttcgtt atctccagct aaaagagcgg ctgctctagt tgctgctctg    180
acgcccgaag agaaggtggg caatctggtc aggtaaaata tacccccccc cataatcact    240
attcggagat tggagctgac ttaacgcagc aatgcaactg gtgcaccaag aatcggactt    300
ccaaggtaca actggtggaa cgaagccctt catggcctcg ctggatctcc aggtggtcgc    360
tttgccgaca ctcctcccta cgacgcggcc acatcatttc ccatgcctct tctcatggcc    420
gctgctttcg acgatgatct gatccacgat atcggcaacg tcgtcggcac cgaagcgcgt    480
gcgttcacta acggcggttg gcgcggagtc gacttctgga cacccaacgt caacccttt     540 aaagatcctc gctggggtcg tggctccgaa actccaggtg aagatgccct tcatgtcagc    600
```

```
cggtatgctc gctatatcgt caggggtctc gaaggcgata aggagcaacg acgtattgtt    660
gctacctgca agcactatgc tggaaacgac tttgaggact ggggaggctt cacgcgtcac    720
gactttgatg ccaagattac tcctcaggac ttggctgagt actacgtcag gccttccag    780
gagtgcaccc gtgatgcaaa ggttggttcc atcatgtgcg cctacaatgc cgtgaacggc    840
attcccgcat gcgcaaactc gtatctgcag gagacgatcc tcagagggca ctggaactgg    900
acgcgcgata caactggat cactagtgat tgtggcgcca tgcaggatat ctggcagaat    960
cacaagtatg tcaagaccaa cgctgaaggt gcccaggtag cttttgagaa cggcatggat   1020
tctagctgcg agtatactac taccagcgat gtctccgatt cgtacaagca aggcctcttg   1080
actgagaagc tcatggatcg ttcgttgaag cgccttttcg aagggcttgt tcatactggt   1140
ttctttgacg gtgccaaagc gcaatggaac tcgctcagtt ttgcggatgt caacaccaag   1200
gaagctcagg atcttgcact cagatctgct gtggagggtg ctgttcttct taagaatgac   1260
ggcactttgc ctctgaagct caagaagaag gatagtgttg caatgatcgg attctgggcc   1320
aacgatactt ccaagctgca gggtggttac agtggacgtg ctccgttcct ccacagcccg   1380
ctttatgcag ctgagaagct tggtcttgac accaacgtgg cttggggtcc gacactgcag   1440
aacagctcat ctcatgataa ctggaccacc aatgctgttg ctgcggcgaa gaagtctgat   1500
tacattctct actttggtgg tcttgacgcc tctgctgctg gcgaggacag agatcgtgag   1560
aaccttgact ggcctgagag ccagctgacc cttcttcaga agctctctag tctcggcaag   1620
ccactggttg ttatccagct tggtgatcaa gtcgatgaca ccgctctttt gaagaacaag   1680
aagattaaca gtattctttg ggtcaattac cctggtcagg atggcggcac tgcagtcatg   1740
gacctgctca ctggacgaaa gagtcctgct ggccgactac ccgtcacgca atatcccagt   1800
aaatacactg agcagattgg catgactgac atggacctca gacctaccaa gtcgttgcca   1860
gggagaactt atcgctggta ctcaactcca gttcttccct acggctttgg cctccactac   1920
accaagttcc aagccaagtt caagtccaac aagttgacgt ttgacatcca gaagcttctc   1980
aagggctgca gtgctcaata ctccgatact tgcgcgctgc ccccatcca gttagtgtc    2040
aagaacaccg gccgcattac ctccgacttt gtctctctgg tctttatcaa gagtgaagtt   2100
ggacctaagc cttaccctct caagaccctt gcggcttatg gtcgcttgca tgatgtcgcg   2160
ccttcatcga cgaaggatat ctcactggag tggacgttgg ataacattgc gcgacgggga   2220
gagaatggtg atttggttgt ttatcctggg acttacactc tgttgctgga tgagcctacg   2280
caagccaaga tccaggttac gctgactgga agaaggcta ttttggataa gtggcctcaa   2340
gaccccaagt ctgcgtaa                                                2358

<210> SEQ ID NO 6
<211> LENGTH: 766
<212> TYPE: PRT
<213> ORGANISM: Fusarium verticillioides

<400> SEQUENCE: 6

Met Leu Leu Asn Leu Gln Val Ala Ala Ser Ala Leu Ser Leu Ser Leu
1               5                   10                  15

Leu Gly Leu Ala Glu Ala Ala Thr Pro Tyr Thr Leu Pro Asp Cys
            20                  25                  30

Thr Lys Gly Pro Leu Ser Lys Asn Gly Ile Cys Asp Thr Ser Leu Ser
        35                  40                  45

Pro Ala Lys Arg Ala Ala Ala Leu Val Ala Ala Leu Thr Pro Glu Glu
    50                  55                  60
```

-continued

```
Lys Val Gly Asn Leu Val Ser Asn Ala Thr Gly Ala Pro Arg Ile Gly
 65                  70                  75                  80

Leu Pro Arg Tyr Asn Trp Trp Asn Glu Ala Leu His Gly Leu Ala Gly
                 85                  90                  95

Ser Pro Gly Gly Arg Phe Ala Asp Thr Pro Pro Tyr Asp Ala Ala Thr
            100                 105                 110

Ser Phe Pro Met Pro Leu Leu Met Ala Ala Ala Phe Asp Asp Asp Leu
        115                 120                 125

Ile His Asp Ile Gly Asn Val Val Gly Thr Glu Ala Arg Ala Phe Thr
    130                 135                 140

Asn Gly Gly Trp Arg Gly Val Asp Phe Trp Thr Pro Asn Val Asn Pro
145                 150                 155                 160

Phe Lys Asp Pro Arg Trp Gly Arg Gly Ser Glu Thr Pro Gly Glu Asp
                165                 170                 175

Ala Leu His Val Ser Arg Tyr Ala Arg Tyr Ile Val Arg Gly Leu Glu
            180                 185                 190

Gly Asp Lys Glu Gln Arg Arg Ile Val Ala Thr Cys Lys His Tyr Ala
        195                 200                 205

Gly Asn Asp Phe Glu Asp Trp Gly Gly Phe Thr Arg His Asp Phe Asp
    210                 215                 220

Ala Lys Ile Thr Pro Gln Asp Leu Ala Glu Tyr Tyr Val Arg Pro Phe
225                 230                 235                 240

Gln Glu Cys Thr Arg Asp Ala Lys Val Gly Ser Ile Met Cys Ala Tyr
                245                 250                 255

Asn Ala Val Asn Gly Ile Pro Ala Cys Ala Asn Ser Tyr Leu Gln Glu
            260                 265                 270

Thr Ile Leu Arg Gly His Trp Asn Trp Thr Arg Asp Asn Asn Trp Ile
        275                 280                 285

Thr Ser Asp Cys Gly Ala Met Gln Asp Ile Trp Gln Asn His Lys Tyr
    290                 295                 300

Val Lys Thr Asn Ala Glu Gly Ala Gln Val Ala Phe Glu Asn Gly Met
305                 310                 315                 320

Asp Ser Ser Cys Glu Tyr Thr Thr Thr Ser Asp Val Ser Asp Ser Tyr
                325                 330                 335

Lys Gln Gly Leu Leu Thr Glu Lys Leu Met Asp Arg Ser Leu Lys Arg
            340                 345                 350

Leu Phe Glu Gly Leu Val His Thr Gly Phe Phe Asp Gly Ala Lys Ala
        355                 360                 365

Gln Trp Asn Ser Leu Ser Phe Ala Asp Val Asn Thr Lys Glu Ala Gln
    370                 375                 380

Asp Leu Ala Leu Arg Ser Ala Val Glu Gly Ala Val Leu Leu Lys Asn
385                 390                 395                 400

Asp Gly Thr Leu Pro Leu Lys Leu Lys Lys Asp Ser Val Ala Met
                405                 410                 415

Ile Gly Phe Trp Ala Asn Asp Thr Ser Lys Leu Gln Gly Gly Tyr Ser
        420                 425                 430

Gly Arg Ala Pro Phe Leu His Ser Pro Leu Tyr Ala Ala Glu Lys Leu
    435                 440                 445

Gly Leu Asp Thr Asn Val Ala Trp Gly Pro Leu Gln Asn Ser Ser
450                 455                 460

Ser His Asp Asn Trp Thr Thr Asn Ala Val Ala Ala Lys Lys Ser
465                 470                 475                 480
```

```
Asp Tyr Ile Leu Tyr Phe Gly Gly Leu Asp Ala Ser Ala Ala Gly Glu
                485                 490                 495

Asp Arg Asp Arg Glu Asn Leu Asp Trp Pro Glu Ser Gln Leu Thr Leu
            500                 505                 510

Leu Gln Lys Leu Ser Ser Leu Gly Lys Pro Leu Val Val Ile Gln Leu
        515                 520                 525

Gly Asp Gln Val Asp Asp Thr Ala Leu Leu Lys Asn Lys Lys Ile Asn
    530                 535                 540

Ser Ile Leu Trp Val Asn Tyr Pro Gly Gln Asp Gly Thr Ala Val
545                 550                 555                 560

Met Asp Leu Leu Thr Gly Arg Lys Ser Pro Ala Gly Arg Leu Pro Val
                565                 570                 575

Thr Gln Tyr Pro Ser Lys Tyr Thr Glu Gln Ile Gly Met Thr Asp Met
            580                 585                 590

Asp Leu Arg Pro Thr Lys Ser Leu Pro Gly Arg Thr Tyr Arg Trp Tyr
        595                 600                 605

Ser Thr Pro Val Leu Pro Tyr Gly Phe Gly Leu His Tyr Thr Lys Phe
    610                 615                 620

Gln Ala Lys Phe Lys Ser Asn Lys Leu Thr Phe Asp Ile Gln Lys Leu
625                 630                 635                 640

Leu Lys Gly Cys Ser Ala Gln Tyr Ser Asp Thr Cys Ala Leu Pro Pro
                645                 650                 655

Ile Gln Val Ser Val Lys Asn Thr Gly Arg Ile Thr Ser Asp Phe Val
            660                 665                 670

Ser Leu Val Phe Ile Lys Ser Glu Val Gly Pro Lys Pro Tyr Pro Leu
        675                 680                 685

Lys Thr Leu Ala Ala Tyr Gly Arg Leu His Asp Val Ala Pro Ser Ser
    690                 695                 700

Thr Lys Asp Ile Ser Leu Glu Trp Thr Leu Asp Asn Ile Ala Arg Arg
705                 710                 715                 720

Gly Glu Asn Gly Asp Leu Val Val Tyr Pro Gly Thr Tyr Thr Leu Leu
                725                 730                 735

Leu Asp Glu Pro Thr Gln Ala Lys Ile Gln Val Thr Leu Thr Gly Lys
            740                 745                 750

Lys Ala Ile Leu Asp Lys Trp Pro Gln Asp Pro Lys Ser Ala
    755                 760                 765

<210> SEQ ID NO 7
<211> LENGTH: 1338
<212> TYPE: DNA
<213> ORGANISM: Penicillium funiculosum

<400> SEQUENCE: 7
atgcttcagc gatttgctta tattttacca ctggctctat tgagtgttgg agtgaaagcc     60
gacaacccct tgtgcagag catctacacc gctgatccgg caccgatggt atacaatgac    120
cgcgtttatg tcttcatgga ccatgacaac accggagcta cctactacaa catgacagac    180
tggcatctgt tctcgtcagc agatatggcg aattggcaag tcatggcat tccaatgagc    240 ctggccaatt tcacctgggc caacgcgaat gcgtgggccc cgcaagtcat ccctcgcaac    300
ggccaattct acttttatgc tcctgtccga cacaacgatg ttctatggc tatcggtgtg    360 ggagtgagca gcaccatcac aggtccatac catgatgcta tcggcaaacc gctagtagag    420
aacaacgaga ttgatcccac cgtgttcatc gacgatgacg tcaggcata cctgtactgg    480 ggaaatccag acctgtggta cgtcaaattg aaccaagata tgatatcgta cagcgggagc    540
```

```
cctactcaga ttccactcac cacggctgga tttggtactc gaacgggcaa tgctcaacgg    600
ccgaccactt tgaagaagc tccatgggta tacaaacgca acggcatcta ctatatcgcc     660
tatgcagccg attgttgttc tgaggatatt cgctactcca cgggaaccag tgccactggt    720
ccgtggactt atcgaggcgt catcatgccg acccaaggta gcagcttcac caatcacgag    780
ggtattatcg acttccagaa caactcctac tttttctatc acaacggcgc tcttcccggc    840
ggaggcggct accaacgatc tgtatgtgtg gagcaattca aatacaatgc agatggaacc    900
attccgacga tcgaaatgac caccgccggt ccagctcaaa ttgggactct caacccttac    960
gtgcgacagg aagccgaaac ggcggcatgg tcttcaggca tcactacgga ggtttgtagc   1020
gaaggcggaa ttgacgtcgg gtttatcaac aatggcgatt acatcaaagt taaaggcgta   1080
gctttcggtt caggagccca ttctttctca gcgcgggttg cttctgcaaa tagcggcggc   1140
actattgcaa tacacctcgg aagcacaact ggtacgctcg tgggcacttg tactgtcccc   1200
agcactggcg gttggcagac ttggactacc gttacctgtt ctgtcagtgg cgcatctggg   1260
acccaggatg tgtattttgt tttcggtggt agcggaacag gatacctgtt caactttgat   1320
tattggcagt tcgcataa                                                  1338
```

<210> SEQ ID NO 8
<211> LENGTH: 445
<212> TYPE: PRT
<213> ORGANISM: Penicillium funiculosum

<400> SEQUENCE: 8

```
Met Leu Gln Arg Phe Ala Tyr Ile Leu Pro Leu Ala Leu Leu Ser Val
1               5                   10                  15

Gly Val Lys Ala Asp Asn Pro Phe Val Gln Ser Ile Tyr Thr Ala Asp
            20                  25                  30

Pro Ala Pro Met Val Tyr Asn Asp Arg Val Tyr Val Phe Met Asp His
        35                  40                  45

Asp Asn Thr Gly Ala Thr Tyr Tyr Asn Met Thr Asp Trp His Leu Phe
    50                  55                  60

Ser Ser Ala Asp Met Ala Asn Trp Gln Asp His Gly Ile Pro Met Ser
65                  70                  75                  80

Leu Ala Asn Phe Thr Trp Ala Asn Ala Asn Trp Ala Pro Gln Val
                85                  90                  95

Ile Pro Arg Asn Gly Gln Phe Tyr Phe Tyr Ala Pro Val Arg His Asn
            100                 105                 110

Asp Gly Ser Met Ala Ile Gly Val Gly Val Ser Ser Thr Ile Thr Gly
        115                 120                 125

Pro Tyr His Asp Ala Ile Gly Lys Pro Leu Val Glu Asn Asn Glu Ile
    130                 135                 140

Asp Pro Thr Val Phe Ile Asp Asp Gly Gln Ala Tyr Leu Tyr Trp
145                 150                 155                 160

Gly Asn Pro Asp Leu Trp Tyr Val Lys Leu Asn Gln Asp Met Ile Ser
                165                 170                 175

Tyr Ser Gly Ser Pro Thr Gln Ile Pro Leu Thr Thr Ala Gly Phe Gly
            180                 185                 190

Thr Arg Thr Gly Asn Ala Gln Arg Pro Thr Thr Phe Glu Glu Ala Pro
        195                 200                 205

Trp Val Tyr Lys Arg Asn Gly Ile Tyr Tyr Ile Ala Tyr Ala Ala Asp
    210                 215                 220
```

```
Cys Cys Ser Glu Asp Ile Arg Tyr Ser Thr Gly Thr Ser Ala Thr Gly
225                 230                 235                 240

Pro Trp Thr Tyr Arg Gly Val Ile Met Pro Thr Gln Gly Ser Ser Phe
                245                 250                 255

Thr Asn His Glu Gly Ile Ile Asp Phe Gln Asn Asn Ser Tyr Phe Phe
            260                 265                 270

Tyr His Asn Gly Ala Leu Pro Gly Gly Gly Tyr Gln Arg Ser Val
        275                 280                 285

Cys Val Glu Gln Phe Lys Tyr Asn Ala Asp Gly Thr Ile Pro Thr Ile
    290                 295                 300

Glu Met Thr Thr Ala Gly Pro Ala Gln Ile Gly Thr Leu Asn Pro Tyr
305                 310                 315                 320

Val Arg Gln Glu Ala Glu Thr Ala Ala Trp Ser Ser Gly Ile Thr Thr
                325                 330                 335

Glu Val Cys Ser Glu Gly Gly Ile Asp Val Gly Phe Ile Asn Asn Gly
            340                 345                 350

Asp Tyr Ile Lys Val Lys Gly Val Ala Phe Gly Ser Gly Ala His Ser
        355                 360                 365

Phe Ser Ala Arg Val Ala Ser Ala Asn Ser Gly Thr Ile Ala Ile
370                 375                 380

His Leu Gly Ser Thr Thr Gly Thr Leu Val Gly Thr Cys Thr Val Pro
385                 390                 395                 400

Ser Thr Gly Gly Trp Gln Thr Trp Thr Val Thr Cys Ser Val Ser
                405                 410                 415

Gly Ala Ser Gly Thr Gln Asp Val Tyr Phe Val Phe Gly Gly Ser Gly
            420                 425                 430

Thr Gly Tyr Leu Phe Asn Phe Asp Tyr Trp Gln Phe Ala
        435                 440                 445

<210> SEQ ID NO 9
<211> LENGTH: 1593
<212> TYPE: DNA
<213> ORGANISM: Fusarium verticillioides

<400> SEQUENCE: 9
atgaaggtat actggctcgt ggcgtgggcc acttctttga cgccggcact ggctggcttg      60
attggacacc gtcgcgccac caccttcaac aatcctatca tctactcaga ctttccagat     120
aacgatgtat tcctcggtcc agataactac tactacttct ctgcttccaa cttccacttc     180
agcccaggag cacccgtttt gaagtctaaa gatctgctaa actgggatct catcggccat     240
tcaattcccc gcctgaactt tggcgacggc tatgatcttc ctcctggctc acgttattac     300
cgtggaggta cttgggcatc atccctcaga tacagaaaga gcaatggaca gtggtactgg     360
atcggctgca tcaacttctg gcagacctgg gtatacactg cctcatcgcc ggaaggtcca     420
tggtacaaca agggaaactt cggtgataac aattgctact acgacaatgg catactgatc     480
gatgacgatg ataccatgta tgtcgtatac ggttccggtg aggtcaaagt atctcaacta     540
tctcaggacg gattcagcca ggtcaaatct caggtagttt tcaagaacac tgatattggg     600
gtccaagact tggagggtaa ccgcatgtac aagatcaacg gctctactac atcctaaac      660 gatagcccaa gtggcagtca gacctggatt tggaagtcga aatcaccctg ggcccttat      720 gagtctaagg tcctcgccga caaagtcacc ccgcctatct ctggtggtaa ctcgccgcat     780
cagggtagtc tcataaagac tcccaatggt ggctggtact tcatgtcatt cacttgggcc     840
tatcctgccg gccgtcttcc ggttcttgca ccgattacgt ggggtagcga tggtttcccc     900
```

```
attcttgtca agggtgctaa tgcggatgg ggatcatctt acccaacact tcctggcacg   960
gatggtgtga caaagaattg gacaaggact gatacctttcc gcggaacctc acttgctccg  1020
tcctgggagt ggaaccataa tccggacgtc aactccttca ctgtcaacaa cggcctgact  1080
ctccgcactg ctagcattac gaaggatatt taccaggcga ggaacacgct atctcaccga  1140
actcatggtg atcatccaac aggaatagtg aagattgatt tctctccgat gaaggacggc  1200
gaccgggccg ggctttcagc gtttcgagac caaagtgcat acatcggtat tcatcgagat  1260
aacggaaagt tcacaatcgc tacgaagcat gggatgaata tggatgagtg aacggaaca   1320 acaacagacc tgggacaaat aaaagccaca gctaatgtgc cttctggaag gaccaagatc  1380
tggctgagac ttcaacttga taccaaccca gcaggaactg gcaacactat cttttcttac  1440
agttgggatg gagtcaagta tgaaacactg gtcccaact tcaaactgta caatggttgg   1500
gcattcttta ttgcttaccg attcggcatc ttcaacttcg ccgagacggc tttaggaggc  1560
tcgatcaagg ttgagtcttt cacagctgca tag                               1593
```

<210> SEQ ID NO 10
<211> LENGTH: 530
<212> TYPE: PRT
<213> ORGANISM: Fusarium verticillioides

<400> SEQUENCE: 10

```
Met Lys Val Tyr Trp Leu Val Ala Trp Ala Thr Ser Leu Thr Pro Ala
1               5                   10                  15

Leu Ala Gly Leu Ile Gly His Arg Arg Ala Thr Thr Phe Asn Asn Pro
            20                  25                  30

Ile Ile Tyr Ser Asp Phe Pro Asp Asn Asp Val Phe Leu Gly Pro Asp
        35                  40                  45

Asn Tyr Tyr Tyr Phe Ser Ala Ser Asn Phe His Phe Ser Pro Gly Ala
    50                  55                  60

Pro Val Leu Lys Ser Lys Asp Leu Leu Asn Trp Asp Leu Ile Gly His
65                  70                  75                  80

Ser Ile Pro Arg Leu Asn Phe Gly Asp Gly Tyr Asp Leu Pro Pro Gly
                85                  90                  95

Ser Arg Tyr Tyr Arg Gly Gly Thr Trp Ala Ser Ser Leu Arg Tyr Arg
            100                 105                 110

Lys Ser Asn Gly Gln Trp Tyr Trp Ile Gly Cys Ile Asn Phe Trp Gln
        115                 120                 125

Thr Trp Val Tyr Thr Ala Ser Ser Pro Glu Gly Pro Trp Tyr Asn Lys
    130                 135                 140

Gly Asn Phe Gly Asp Asn Asn Cys Tyr Tyr Asp Asn Gly Ile Leu Ile
145                 150                 155                 160

Asp Asp Asp Asp Thr Met Tyr Val Val Tyr Gly Ser Gly Glu Val Lys
                165                 170                 175

Val Ser Gln Leu Ser Gln Asp Gly Phe Ser Gln Val Lys Ser Gln Val
            180                 185                 190

Val Phe Lys Asn Thr Asp Ile Gly Val Gln Asp Leu Glu Gly Asn Arg
        195                 200                 205

Met Tyr Lys Ile Asn Gly Leu Tyr Tyr Ile Leu Asn Asp Ser Pro Ser
    210                 215                 220

Gly Ser Gln Thr Trp Ile Trp Lys Ser Lys Ser Pro Trp Gly Pro Tyr
225                 230                 235                 240

Glu Ser Lys Val Leu Ala Asp Lys Val Thr Pro Pro Ile Ser Gly Gly
                245                 250                 255
```

Asn Ser Pro His Gln Gly Ser Leu Ile Lys Thr Pro Asn Gly Gly Trp
            260                 265                 270

Tyr Phe Met Ser Phe Thr Trp Ala Tyr Pro Ala Gly Arg Leu Pro Val
        275                 280                 285

Leu Ala Pro Ile Thr Trp Gly Ser Asp Gly Phe Pro Ile Leu Val Lys
290                 295                 300

Gly Ala Asn Gly Gly Trp Gly Ser Ser Tyr Pro Thr Leu Pro Gly Thr
305                 310                 315                 320

Asp Gly Val Thr Lys Asn Trp Thr Arg Thr Asp Thr Phe Arg Gly Thr
                325                 330                 335

Ser Leu Ala Pro Ser Trp Glu Trp Asn His Asn Pro Asp Val Asn Ser
        340                 345                 350

Phe Thr Val Asn Asn Gly Leu Thr Leu Arg Thr Ala Ser Ile Thr Lys
            355                 360                 365

Asp Ile Tyr Gln Ala Arg Asn Thr Leu Ser His Arg Thr His Gly Asp
370                 375                 380

His Pro Thr Gly Ile Val Lys Ile Asp Phe Ser Pro Met Lys Asp Gly
385                 390                 395                 400

Asp Arg Ala Gly Leu Ser Ala Phe Arg Asp Gln Ser Ala Tyr Ile Gly
                405                 410                 415

Ile His Arg Asp Asn Gly Lys Phe Thr Ile Ala Thr Lys His Gly Met
        420                 425                 430

Asn Met Asp Glu Trp Asn Gly Thr Thr Thr Asp Leu Gly Gln Ile Lys
            435                 440                 445

Ala Thr Ala Asn Val Pro Ser Gly Arg Thr Lys Ile Trp Leu Arg Leu
450                 455                 460

Gln Leu Asp Thr Asn Pro Ala Gly Thr Gly Asn Thr Ile Phe Ser Tyr
465                 470                 475                 480

Ser Trp Asp Gly Val Lys Tyr Glu Thr Leu Gly Pro Asn Phe Lys Leu
                485                 490                 495

Tyr Asn Gly Trp Ala Phe Phe Ile Ala Tyr Arg Phe Gly Ile Phe Asn
        500                 505                 510

Phe Ala Glu Thr Ala Leu Gly Gly Ser Ile Lys Val Glu Ser Phe Thr
            515                 520                 525

Ala Ala
    530

<210> SEQ ID NO 11
<211> LENGTH: 1725
<212> TYPE: DNA
<213> ORGANISM: Fusarium verticillioides

<400> SEQUENCE: 11
atgcgcttct cttggctatt gtgccccctt ctagcgatgg gaagtgctct tcctgaaacg      60
aagacggatg tttcgacata caccaaccct gtccttccag gatggcactc ggatccatcg     120
tgtatccaga aagatggcct cttttctctgc gtcacttcaa cattcatctc cttcccaggt    180
cttcccgtct atgcctcaag ggatctagtc aactggcgtc tcatcagcca tgtctggaac    240
cgcgagaaac agttgcctgg cattagctgg aagacggcag acagcaaca gggaatgtat     300 gcaccaacca ttcgatacca aagggaaca tactacgtca tctgcgaata cctgggcgtt     360
ggagatatta ttggtgtcat cttcaagacc accaatccgt gggacgagag tagctggagt    420
gaccctgtta ccttcaagcc aaatcacatc gaccccgatc tgttctggga tgatgacgga    480
aaggtttatt gtgctaccca tggcatcact ctgcaggaga ttgatttgga aactggagag    540

-continued

```
cttagcccgg agcttaatat ctggaacggc acaggaggtg tatggcctga gggtccccat      600
atctacaagc gcgacggtta ctactatctc atgattgccg agggtggaac tgccgaagac      660
cacgctatca caatcgctcg ggcccgcaag atcaccggcc cctatgaagc ctacaataac      720
aacccaatct tgaccaaccg cgggacatct gagtacttcc agactgtcgg tcacggtgat      780
ctgttccaag ataccaaggg caactggtgg ggtctttgtc ttgctactcg catcacagca      840
cagggagttt cacccatggg ccgtgaagct gttttgttca atggcacatg gaacaagggc      900
gaatggccca agttgcaacc agtacgaggt cgcatgcctg gaaacctcct cccaaagccg      960
acgcgaaacg ttcccggaga tgggcccttc aacgctgacc cagacaacta caacttgaag     1020
aagactaaga agatccctcc tcactttgtg caccatagag tcccaagaga cggtgccttc     1080
tctttgtctt ccaagggtct gcacatcgtg cctagtcgaa acaacgttac cggtagtgtg     1140
ttgccaggag atgagattga gctatcagga cagcgaggtc tagctttcat cggacgccgc     1200
caaactcaca ctctgttcaa atatagtgtt gatatcgact tcaagcccaa gtccgatgat     1260
caggaagctg gaatcaccgt tttccgcacg cagttcgacc atatcgatct tggcattgtt     1320
cgtcttccta caaaccaagg cagcaacaag aaatctaagc ttgccttccg attccgggcc     1380
acaggagctc agaatgttcc tgcaccgaag gtagtaccgg tccccgatgg ctgggagaag     1440
ggcgtaatca gtctacatat cgaggcagcc aacgcgacgc actacaacct tggagcttcg     1500
agccacagag gcaagactct cgacatcgcg acagcatcag caagtcttgt gagtggaggc     1560
acgggttcat tgttggtag tttgcttgga cccttatgcta cctgcaacgg caaaggatct     1620
ggagtggaat gtcccaaggg aggtgatgtc tatgtgaccc aatggactta taagcccgtg     1680
gcacaagaga ttgatcatgg tgttttttgtg aaatcagaat tgtag                    1725
```

<210> SEQ ID NO 12
<211> LENGTH: 574
<212> TYPE: PRT
<213> ORGANISM: Fusarium verticillioides

<400> SEQUENCE: 12

```
Met Arg Phe Ser Trp Leu Leu Cys Pro Leu Leu Ala Met Gly Ser Ala
1               5                   10                  15

Leu Pro Glu Thr Lys Thr Asp Val Ser Thr Tyr Thr Asn Pro Val Leu
            20                  25                  30

Pro Gly Trp His Ser Asp Pro Ser Cys Ile Gln Lys Asp Gly Leu Phe
        35                  40                  45

Leu Cys Val Thr Ser Thr Phe Ile Ser Phe Pro Gly Leu Pro Val Tyr
    50                  55                  60

Ala Ser Arg Asp Leu Val Asn Trp Arg Leu Ile Ser His Val Trp Asn
65                  70                  75                  80

Arg Glu Lys Gln Leu Pro Gly Ile Ser Trp Lys Thr Ala Gly Gln Gln
                85                  90                  95

Gln Gly Met Tyr Ala Pro Thr Ile Arg Tyr His Lys Gly Thr Tyr Tyr
            100                 105                 110

Val Ile Cys Glu Tyr Leu Gly Val Gly Asp Ile Gly Val Ile Phe
        115                 120                 125

Lys Thr Thr Asn Pro Trp Asp Glu Ser Ser Trp Ser Asp Pro Val Thr
    130                 135                 140

Phe Lys Pro Asn His Ile Asp Pro Asp Leu Phe Trp Asp Asp Asp Gly
145                 150                 155                 160
```

-continued

```
Lys Val Tyr Cys Ala Thr His Gly Ile Thr Leu Gln Glu Ile Asp Leu
                165                 170                 175
Glu Thr Gly Glu Leu Ser Pro Glu Leu Asn Ile Trp Asn Gly Thr Gly
            180                 185                 190
Gly Val Trp Pro Glu Gly Pro His Ile Tyr Lys Arg Asp Gly Tyr Tyr
        195                 200                 205
Tyr Leu Met Ile Ala Glu Gly Thr Ala Glu Asp His Ala Ile Thr
    210                 215                 220
Ile Ala Arg Ala Arg Lys Ile Thr Gly Pro Tyr Glu Ala Tyr Asn Asn
225                 230                 235                 240
Asn Pro Ile Leu Thr Asn Arg Gly Thr Ser Glu Tyr Phe Gln Thr Val
                245                 250                 255
Gly His Gly Asp Leu Phe Gln Asp Thr Lys Gly Asn Trp Trp Gly Leu
            260                 265                 270
Cys Leu Ala Thr Arg Ile Thr Ala Gln Gly Val Ser Pro Met Gly Arg
        275                 280                 285
Glu Ala Val Leu Phe Asn Gly Thr Trp Asn Lys Gly Glu Trp Pro Lys
    290                 295                 300
Leu Gln Pro Val Arg Gly Arg Met Pro Gly Asn Leu Leu Pro Lys Pro
305                 310                 315                 320
Thr Arg Asn Val Pro Gly Asp Gly Pro Phe Asn Ala Asp Pro Asp Asn
                325                 330                 335
Tyr Asn Leu Lys Lys Thr Lys Lys Ile Pro Pro His Phe Val His His
            340                 345                 350
Arg Val Pro Arg Asp Gly Ala Phe Ser Leu Ser Ser Lys Gly Leu His
        355                 360                 365
Ile Val Pro Ser Arg Asn Asn Val Thr Gly Ser Val Leu Pro Gly Asp
    370                 375                 380
Glu Ile Glu Leu Ser Gly Gln Arg Gly Leu Ala Phe Ile Gly Arg Arg
385                 390                 395                 400
Gln Thr His Thr Leu Phe Lys Tyr Ser Val Asp Ile Asp Phe Lys Pro
                405                 410                 415
Lys Ser Asp Asp Gln Glu Ala Gly Ile Thr Val Phe Arg Thr Gln Phe
            420                 425                 430
Asp His Ile Asp Leu Gly Ile Val Arg Leu Pro Thr Asn Gln Gly Ser
        435                 440                 445
Asn Lys Lys Ser Lys Leu Ala Phe Arg Phe Arg Ala Thr Gly Ala Gln
450                 455                 460
Asn Val Pro Ala Pro Lys Val Val Pro Val Pro Asp Gly Trp Glu Lys
465                 470                 475                 480
Gly Val Ile Ser Leu His Ile Glu Ala Ala Asn Ala Thr His Tyr Asn
                485                 490                 495
Leu Gly Ala Ser Ser His Arg Gly Lys Thr Leu Asp Ile Ala Thr Ala
            500                 505                 510
Ser Ala Ser Leu Val Ser Gly Gly Thr Gly Ser Phe Val Gly Ser Leu
        515                 520                 525
Leu Gly Pro Tyr Ala Thr Cys Asn Gly Lys Gly Ser Gly Val Glu Cys
    530                 535                 540
Pro Lys Gly Gly Asp Val Tyr Val Thr Gln Trp Thr Tyr Lys Pro Val
545                 550                 555                 560
Ala Gln Glu Ile Asp His Gly Val Phe Val Lys Ser Glu Leu
                565                 570
```

<210> SEQ ID NO 13
<211> LENGTH: 1677
<212> TYPE: DNA
<213> ORGANISM: Aspergillus fumigatus

<400> SEQUENCE: 13

```
atggcagctc caagtttatc ctaccccaca ggtatccaat cgtataccaa tcctctcttc    60
cctggttggc actccgatcc cagctgtgcc tacgtagcgg agcaagacac cttttctgc    120
gtgacgtcca ctttcattgc cttccccggt cttcctcttt atgcaagccg agatctgcag    180
aactggaaac tggcaagcaa tattttcaat cggcccagcc agatccctga tcttcgcgtc    240
acggatggac agcagtcggg tatctatgcg cccactctgc gctatcatga gggccagttc    300
tacttgatcg tttcgtacct gggcccgcag actaagggct gctgttcac ctcgtctgat    360
ccgtacgacg atgccgcgtg gagcgatccg ctcgaattcg cggtacatgg catcgacccg    420
gatatcttct gggatcacga cgggacggtc tatgtcacgt ccgccgagga ccagatgatt    480
aagcagtaca cactcgatct gaagacgggg gcgattggcc cggttgacta cctctggaac    540
ggcaccggag gagtctggcc cgagggcccg cacatttaca agagagacgg atactactac    600
ctcatgatcg cagaggggagg taccgagctc ggccactcgg agaccatggc gcgatctaga    660
acccggacag gtccctggga gccatacccg cacaatccgc tcttgtcgaa caagggcacc    720
tcggagtact ccagactgt gggccatgcg gacttgttcc aggatgggaa cggcaactgg    780
tgggccgtgg cgttgagcac ccgatcaggg cctgcatgga agaactatcc catgggtcgg    840
gagacggtgc tcgcccccgc cgcttgggag aagggtgagt ggcctgtcat tcagcctgtg    900
agaggccaaa tgcaggggcc gtttccacca ccaaataagc gagttcctcg cggcgagggc    960
ggatggatca gcaacccga caaagtggat tcaggcccg gatcgaagat accggcgcac    1020
ttccagtact ggcgatatcc caagacagag gattttaccg tctcccctcg gggccacccg    1080
aatactcttc ggctcacacc ctccttttac aacctcaccg gaactgcgga cttcaagccg    1140
gatgatggcc tgtcgcttgt tatgcgcaaa cagaccgaca ccttgttcac gtacactgtg    1200
gacgtgtctt ttgaccccaa ggttgccgat gaagaggcgg gtgtgactgt tttccttacc    1260
cagcagcagc acatcgatct tggtattgtc cttctccaga caaccgaggg gctgtcgttg    1320
tccttccggt ccgcgtgga aggccgcggt aactacgaag gtcctcttcc agaagccacc    1380
gtgcctgttc caaggaatg gtgtggacag accatccggc ttgagattca ggccgtgagt    1440
gacaccgagt atgtctttgc ggctgccccg gctcggcacc ctgcacagag gcaaatcatc    1500
agccgcgcca actcgttgat tgtcagtggt gatacgggag ggtttactgg ctcgcttgtt    1560
ggcgtgtatg ccacgtcgaa cgggggtgcc ggatccacgc cgcatatat cagcagatgg    1620
agatacgaag gacggggcca gatgattgat tttggtcgag tggtcccgag ctactga    1677
```

<210> SEQ ID NO 14
<211> LENGTH: 558
<212> TYPE: PRT
<213> ORGANISM: Aspergillus fumigatus

<400> SEQUENCE: 14

```
Met Ala Ala Pro Ser Leu Ser Tyr Pro Thr Gly Ile Gln Ser Tyr Thr
 1               5                  10                  15

Asn Pro Leu Phe Pro Gly Trp His Ser Asp Pro Ser Cys Ala Tyr Val
             20                  25                  30

Ala Glu Gln Asp Thr Phe Phe Cys Val Thr Ser Thr Phe Ile Ala Phe
         35                  40                  45
```

```
Pro Gly Leu Pro Leu Tyr Ala Ser Arg Asp Leu Gln Asn Trp Lys Leu
     50              55                  60

Ala Ser Asn Ile Phe Asn Arg Pro Ser Gln Ile Pro Asp Leu Arg Val
 65              70              75                          80

Thr Asp Gly Gln Gln Ser Gly Ile Tyr Ala Pro Thr Leu Arg Tyr His
                 85              90                      95

Glu Gly Gln Phe Tyr Leu Ile Val Ser Tyr Leu Gly Pro Gln Thr Lys
                100             105             110

Gly Leu Leu Phe Thr Ser Ser Asp Pro Tyr Asp Ala Ala Trp Ser
                115             120             125

Asp Pro Leu Glu Phe Ala Val His Gly Ile Asp Pro Asp Ile Phe Trp
    130             135             140

Asp His Asp Gly Thr Val Tyr Val Thr Ser Ala Glu Asp Gln Met Ile
145             150             155                         160

Lys Gln Tyr Thr Leu Asp Leu Lys Thr Gly Ala Ile Gly Pro Val Asp
                165             170             175

Tyr Leu Trp Asn Gly Thr Gly Val Trp Pro Glu Gly Pro His Ile
                180             185             190

Tyr Lys Arg Asp Gly Tyr Tyr Leu Met Ile Ala Glu Gly Gly Thr
                195             200             205

Glu Leu Gly His Ser Glu Thr Met Ala Arg Ser Arg Thr Arg Thr Gly
    210             215             220

Pro Trp Glu Pro Tyr Pro His Asn Pro Leu Leu Ser Asn Lys Gly Thr
225             230             235                         240

Ser Glu Tyr Phe Gln Thr Val Gly His Ala Asp Leu Phe Gln Asp Gly
                245             250             255

Asn Gly Asn Trp Trp Ala Val Ala Leu Ser Thr Arg Ser Gly Pro Ala
                260             265             270

Trp Lys Asn Tyr Pro Met Gly Arg Glu Thr Val Leu Ala Pro Ala Ala
                275             280             285

Trp Glu Lys Gly Glu Trp Pro Val Ile Gln Pro Val Arg Gly Gln Met
    290             295             300

Gln Gly Pro Phe Pro Pro Asn Lys Arg Val Pro Arg Gly Glu Gly
305             310             315                         320

Gly Trp Ile Lys Gln Pro Asp Lys Val Asp Phe Arg Pro Gly Ser Lys
                325             330             335

Ile Pro Ala His Phe Gln Tyr Trp Arg Tyr Pro Lys Thr Glu Asp Phe
                340             345             350

Thr Val Ser Pro Arg Gly His Pro Asn Thr Leu Arg Leu Thr Pro Ser
                355             360             365

Phe Tyr Asn Leu Thr Gly Thr Ala Asp Phe Lys Pro Asp Gly Leu
    370             375             380

Ser Leu Val Met Arg Lys Gln Thr Asp Thr Leu Phe Thr Tyr Thr Val
385             390             395                         400

Asp Val Ser Phe Asp Pro Lys Val Ala Asp Glu Ala Gly Val Thr
                405             410             415

Val Phe Leu Thr Gln Gln Gln His Ile Asp Leu Gly Ile Val Leu Leu
                420             425             430

Gln Thr Thr Glu Gly Leu Ser Leu Ser Phe Arg Phe Arg Val Glu Gly
        435             440             445

Arg Gly Asn Tyr Glu Gly Pro Leu Pro Glu Ala Thr Val Pro Val Pro
450             455             460
```

```
Lys Glu Trp Cys Gly Gln Thr Ile Arg Leu Glu Ile Gln Ala Val Ser
465                 470                 475                 480

Asp Thr Glu Tyr Val Phe Ala Ala Ala Pro Ala Arg His Pro Ala Gln
                485                 490                 495

Arg Gln Ile Ile Ser Arg Ala Asn Ser Leu Ile Val Ser Gly Asp Thr
            500                 505                 510

Gly Arg Phe Thr Gly Ser Leu Val Gly Val Tyr Ala Thr Ser Asn Gly
        515                 520                 525

Gly Ala Gly Ser Thr Pro Ala Tyr Ile Ser Arg Trp Arg Tyr Glu Gly
    530                 535                 540

Arg Gly Gln Met Ile Asp Phe Gly Arg Val Val Pro Ser Tyr
545                 550                 555

<210> SEQ ID NO 15
<211> LENGTH: 2186
<212> TYPE: DNA
<213> ORGANISM: Fusarium verticillioides

<400> SEQUENCE: 15
```

| | | | | | |
|---|---|---|---|---|---|
| atggttcgct | tcagttcaat | cctagcggct | gcggcttgct | tcgtggctgt | tgagtcagtc | 60 |
| aacatcaagg | tcgacagcaa | gggcggaaac | gctactagcg | gtcaccaata | tggcttcctt | 120 |
| cacgaggttg | gtattgacac | accactggcg | atgattggga | tgctaacttg | agctaggat | 180 |
| atcaacaatt | ccggtgatgg | tggcatctac | gctgagctca | tccgcaatcg | tgctttccag | 240 |
| tacagcaaga | aataccctgt | ttctctatct | ggctggagac | ccatcaacga | tgctaagctc | 300 |
| tccctcaacc | gtctcgacac | tcctctctcc | gacgctctcc | ccgtttccat | gaacgtgaag | 360 |
| cctggaaagg | gcaaggccaa | ggagattggt | ttcctcaacg | agggttactg | gggaatggat | 420 |
| gtcaagaagc | aaaagtacac | tggctctttc | tgggttaagg | gcgcttacaa | gggccacttt | 480 |
| acagcttctt | tgcgatctaa | ccttaccgac | gatgtctttg | gcagcgtcaa | ggtcaagtcc | 540 |
| aaggccaaca | agaagcagtg | ggttgagcat | gagtttgtgc | ttactcctaa | caagaatgcc | 600 |
| cctaacagca | acaacacttt | tgctatcacc | tacgatccca | aggtgagtaa | caatcaaaac | 660 |
| tgggacgtga | tgtatactga | caatttgtag | ggcgctgatg | gagctcttga | cttcaacctc | 720 |
| attagcttgt | tccctcccac | ctacaagggc | cgcaagaacg | tcttcgagt | tgatcttgcc | 780 |
| gaggctctcg | aaggtctcca | ccccgtaagg | tttaccgtct | cacgtgtatc | gtgaacagtc | 840 |
| gctgacttgt | agaaaagagc | ctgctgcgct | tccccggtgg | taacatgctc | gagggcaaca | 900 |
| ccaacaagac | ctggtgggac | tggaaggata | ccctcggacc | tctccgcaac | cgtcctggtt | 960 |
| tcgagggtgt | ctggaactac | cagcagaccc | atggtcttgg | aatcttggag | tacctccagt | 1020 |
| gggctgagga | catgaacctt | gaaatcagta | ggttctataa | aattcagtga | cggttatgtg | 1080 |
| catgctaaca | gatttcagtt | gtcggtgtct | acgctggcct | ctccctcgac | ggctccgtca | 1140 |
| cccccaagga | ccaactccag | cccctcatcg | acgacgcgct | cgacgagatc | gaattcatcc | 1200 |
| gaggtcccgt | cacttcaaag | tggggaaaga | agcgcgctga | gctcggccac | cccaagcctt | 1260 |
| tcagactctc | ctacgttgaa | gtcggaaacg | aggactggct | cgctggttat | cccactggct | 1320 |
| ggaactctta | caaggagtac | cgcttcccca | tgttcctcga | ggctatcaag | aaagctcacc | 1380 |
| ccgatctcac | cgtcatctcc | tctggtgctt | ctattgaccc | cgttggtaag | aaggatgctg | 1440 |
| gtttcgatat | tcctgctcct | ggaatcggtg | actaccaccc | ttaccgcgag | cctgatgttc | 1500 |
| ttgttgagga | gttcaacctg | tttgataaca | ataagtatgg | tcacatcatt | ggtgaggttg | 1560 |
| cttctaccca | ccccaacggt | ggaactggct | ggagtggtaa | ccttatgcct | taccctggt | 1620 |

-continued

```
ggatctctgg tgttggcgag gccgtcgctc tctgcggtta tgagcgcaac gccgatcgta    1680
ttcccggaac attctacgct cctatcctca agaacgagaa ccgttggcag tgggctatca    1740
ccatgatcca attcgccgcc gactccgcca tgaccacccg ctccaccagc tggtatgtct    1800
ggtcactctt cgcaggccac cccatgaccc atactctccc caccaccgcc gacttcgacc    1860
ccctctacta cgtcgctggt aagaacgagg acaagggaac tcttatctgg aagggtgctg    1920
cgtataacac caccaagggt gctgacgttc ccgtgtctct gtccttcaag ggtgtcaagc    1980
ccggtgctca agctgagctt actcttctga ccaacaagga gaaggatcct tttgcgttca    2040
atgatcctca aagggcaac aatgttgttg atactaagaa gactgttctc aaggccgatg    2100
gaaagggtgc tttcaacttc aagcttccta acctgagcgt cgctgttctt gagaccctca    2160
agaagggaaa gccttactct agctag                                         2186
```

<210> SEQ ID NO 16
<211> LENGTH: 660
<212> TYPE: PRT
<213> ORGANISM: Fusarium verticillioides

<400> SEQUENCE: 16

```
Met Val Arg Phe Ser Ser Ile Leu Ala Ala Ala Cys Phe Val Ala
1               5                   10                  15

Val Glu Ser Val Asn Ile Lys Val Asp Ser Lys Gly Gly Asn Ala Thr
            20                  25                  30

Ser Gly His Gln Tyr Gly Phe Leu His Glu Asp Ile Asn Asn Ser Gly
        35                  40                  45

Asp Gly Gly Ile Tyr Ala Glu Leu Ile Arg Asn Arg Ala Phe Gln Tyr
    50                  55                  60

Ser Lys Lys Tyr Pro Val Ser Leu Ser Gly Trp Arg Pro Ile Asn Asp
65                  70                  75                  80

Ala Lys Leu Ser Leu Asn Arg Leu Asp Thr Pro Leu Ser Asp Ala Leu
                85                  90                  95

Pro Val Ser Met Asn Val Lys Pro Gly Lys Gly Lys Ala Lys Glu Ile
            100                 105                 110

Gly Phe Leu Asn Glu Gly Tyr Trp Gly Met Asp Val Lys Lys Gln Lys
        115                 120                 125

Tyr Thr Gly Ser Phe Trp Val Lys Gly Ala Tyr Lys Gly His Phe Thr
    130                 135                 140

Ala Ser Leu Arg Ser Asn Leu Thr Asp Asp Val Phe Gly Ser Val Lys
145                 150                 155                 160

Val Lys Ser Lys Ala Asn Lys Lys Gln Trp Val Glu His Glu Phe Val
                165                 170                 175

Leu Thr Pro Asn Lys Asn Ala Pro Asn Ser Asn Asn Thr Phe Ala Ile
            180                 185                 190

Thr Tyr Asp Pro Lys Gly Ala Asp Gly Ala Leu Asp Phe Asn Leu Ile
        195                 200                 205

Ser Leu Phe Pro Pro Thr Tyr Lys Gly Arg Lys Asn Gly Leu Arg Val
    210                 215                 220

Asp Leu Ala Glu Ala Leu Glu Gly Leu His Pro Ser Leu Leu Arg Phe
225                 230                 235                 240

Pro Gly Gly Asn Met Leu Glu Gly Asn Thr Asn Lys Thr Trp Trp Asp
                245                 250                 255

Trp Lys Asp Thr Leu Gly Pro Leu Arg Asn Arg Pro Gly Phe Glu Gly
            260                 265                 270
```

-continued

```
Val Trp Asn Tyr Gln Gln Thr His Gly Leu Gly Ile Leu Glu Tyr Leu
        275                 280                 285

Gln Trp Ala Glu Asp Met Asn Leu Glu Ile Ile Val Gly Val Tyr Ala
        290                 295                 300

Gly Leu Ser Leu Asp Gly Ser Val Thr Pro Lys Asp Gln Leu Gln Pro
305                 310                 315                 320

Leu Ile Asp Asp Ala Leu Asp Glu Ile Glu Phe Ile Arg Gly Pro Val
                325                 330                 335

Thr Ser Lys Trp Gly Lys Lys Arg Ala Glu Leu Gly His Pro Lys Pro
                340                 345                 350

Phe Arg Leu Ser Tyr Val Glu Val Gly Asn Glu Asp Trp Leu Ala Gly
                355                 360                 365

Tyr Pro Thr Gly Trp Asn Ser Tyr Lys Glu Tyr Arg Phe Pro Met Phe
        370                 375                 380

Leu Glu Ala Ile Lys Lys Ala His Pro Asp Leu Thr Val Ile Ser Ser
385                 390                 395                 400

Gly Ala Ser Ile Asp Pro Val Gly Lys Lys Asp Ala Gly Phe Asp Ile
                405                 410                 415

Pro Ala Pro Gly Ile Gly Asp Tyr His Pro Tyr Arg Glu Pro Asp Val
                420                 425                 430

Leu Val Glu Glu Phe Asn Leu Phe Asp Asn Asn Lys Tyr Gly His Ile
                435                 440                 445

Ile Gly Glu Val Ala Ser Thr His Pro Asn Gly Gly Thr Gly Trp Ser
        450                 455                 460

Gly Asn Leu Met Pro Tyr Pro Trp Trp Ile Ser Gly Val Gly Glu Ala
465                 470                 475                 480

Val Ala Leu Cys Gly Tyr Glu Arg Asn Ala Asp Arg Ile Pro Gly Thr
                485                 490                 495

Phe Tyr Ala Pro Ile Leu Lys Asn Glu Asn Arg Trp Gln Trp Ala Ile
                500                 505                 510

Thr Met Ile Gln Phe Ala Ala Asp Ser Ala Met Thr Thr Arg Ser Thr
        515                 520                 525

Ser Trp Tyr Val Trp Ser Leu Phe Ala Gly His Pro Met Thr His Thr
        530                 535                 540

Leu Pro Thr Thr Ala Asp Phe Asp Pro Leu Tyr Tyr Val Ala Gly Lys
545                 550                 555                 560

Asn Glu Asp Lys Gly Thr Leu Ile Trp Lys Gly Ala Ala Tyr Asn Thr
                565                 570                 575

Thr Lys Gly Ala Asp Val Pro Val Ser Leu Ser Phe Lys Gly Val Lys
                580                 585                 590

Pro Gly Ala Gln Ala Glu Leu Thr Leu Leu Thr Asn Lys Glu Lys Asp
                595                 600                 605

Pro Phe Ala Phe Asn Asp Pro His Lys Gly Asn Asn Val Val Asp Thr
        610                 615                 620

Lys Lys Thr Val Leu Lys Ala Asp Gly Lys Gly Ala Phe Asn Phe Lys
625                 630                 635                 640

Leu Pro Asn Leu Ser Val Ala Val Leu Glu Thr Leu Lys Lys Gly Lys
                645                 650                 655

Pro Tyr Ser Ser
        660
```

```
<210> SEQ ID NO 17
<211> LENGTH: 1352
<212> TYPE: DNA
<213> ORGANISM: Trichoderma reesei

<400> SEQUENCE: 17
atgaaagcaa acgtcatctt gtgcctcctg gcccccctgg tcgccgctct ccccaccgaa    60
accatccacc tcgaccccga gctcgccgct ctccgcgcca acctcaccga gcgaacagcc   120
gacctctggg accgccaagc tctcaaagc atcgaccagc tcatcaagag aaaaggcaag    180
ctctactttg gcaccgccac cgaccgcggc ctcctccaac gggaaaagaa cgcggccatc   240
atccaggcag acctcggcca ggtgacgccg gagaacagca tgaagtggca gtcgctcgag   300
aacaaccaag gccagctgaa ctggggagac gccgactatc tcgtcaactt gcccagcaa    360
aacggcaagt cgatacgcgg ccacactctg atctggcact cgcagctgcc tgcgtgggtg   420
aacaatatca caacgcgga tactctgcgg caagtcatcc gcacccatgt ctctactgtg    480
gttgggcggt acaagggcaa gattcgtgct tgggtgagtt ttgaacacca catgcccctt   540
ttcttagtcc gctcctcctc ctcttggaac ttctcacagt tatagccgta taacattc    600
gacaggaaat ttaggatgac aactactgac tgacttgtgt gtgtgatggc gataggacgt   660
ggtcaatgaa atcttcaacg aggatggaac gctgcgctct tcagtctttt ccaggctcct   720
cggcgaggag tttgtctcga ttgcctttcg tgctgctcga gatgctgacc cttctgcccg   780
tctttacatc aacgactaca atctcgaccg cgccaactat ggcaaggtca acgggttgaa   840
gacttacgtc tccaagtgga tctctcaagg agttcccatt gacggtattg gtgagccacg   900
acccctaaat gtcccccatt agagtctctt tctagagcca aggcttgaag ccattcaggg    960
actgacacga gagccttctc tacaggaagc cagtcccatc tcagcggcgg cggaggctct  1020
ggtacgctgg gtgcgctcca gcagctggca acggtacccg tcaccgagct ggccattacc  1080
gagctggaca ttcagggggc accgacgacg gattacaccc aagttgttca agcatgcctg  1140
agcgtctcca gtgcgtcgg catcaccgtg tggggcatca gtgacaaggt aagttgcttc  1200
ccctgtctgt gcttatcaac tgtaagcagc aacaactgat gctgtctgtc tttacctagg  1260
actcgtggcg tgccagcacc aaccctcttc tgtttgacgc aaacttcaac cccaagccgg  1320
catataacag cattgttggc atcttacaat ag                                1352

<210> SEQ ID NO 18
<211> LENGTH: 347
<212> TYPE: PRT
<213> ORGANISM: Trichoderma reesei

<400> SEQUENCE: 18

Met Lys Ala Asn Val Ile Leu Cys Leu Leu Ala Pro Leu Val Ala Ala
1               5                   10                  15

Leu Pro Thr Glu Thr Ile His Leu Asp Pro Glu Leu Ala Ala Leu Arg
            20                  25                  30

Ala Asn Leu Thr Glu Arg Thr Ala Asp Leu Trp Asp Arg Gln Ala Ser
        35                  40                  45

Gln Ser Ile Asp Gln Leu Ile Lys Arg Lys Gly Lys Leu Tyr Phe Gly
    50                  55                  60

Thr Ala Thr Asp Arg Gly Leu Leu Gln Arg Glu Lys Asn Ala Ala Ile
65                  70                  75                  80

Ile Gln Ala Asp Leu Gly Gln Val Thr Pro Glu Asn Ser Met Lys Trp
                85                  90                  95
```

Gln Ser Leu Glu Asn Asn Gln Gly Gln Leu Asn Trp Gly Asp Ala Asp
            100                 105                 110

Tyr Leu Val Asn Phe Ala Gln Gln Asn Gly Lys Ser Ile Arg Gly His
        115                 120                 125

Thr Leu Ile Trp His Ser Gln Leu Pro Ala Trp Val Asn Asn Ile Asn
    130                 135                 140

Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
            180                 185                 190

Leu Gly Glu Glu Phe Val Ser Ile Ala Phe Arg Ala Ala Arg Asp Ala
        195                 200                 205

Asp Pro Ser Ala Arg Leu Tyr Ile Asn Asp Tyr Asn Leu Asp Arg Ala
    210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
                245                 250                 255

Gly Gly Gly Gly Ser Gly Thr Leu Gly Ala Leu Gln Gln Leu Ala Thr
            260                 265                 270

Val Pro Val Thr Glu Leu Ala Ile Thr Glu Leu Asp Ile Gln Gly Ala
        275                 280                 285

Pro Thr Thr Asp Tyr Thr Gln Val Val Gln Ala Cys Leu Ser Val Ser
    290                 295                 300

Lys Cys Val Gly Ile Thr Val Trp Gly Ile Ser Asp Lys Asp Ser Trp
305                 310                 315                 320

Arg Ala Ser Thr Asn Pro Leu Leu Phe Asp Ala Asn Phe Asn Pro Lys
                325                 330                 335

Pro Ala Tyr Asn Ser Ile Val Gly Ile Leu Gln
            340                 345

<210> SEQ ID NO 19
<211> LENGTH: 2054
<212> TYPE: DNA
<213> ORGANISM: Aspergillus tubingensis

<400> SEQUENCE: 19
aacgtctgca gtcccgtact gtttaccaaa atgccaggcc actggtggat atacaacttt      60
gtaatacgtt gccggagtca gcccctactc cctgatgggt tcccactccc tagttacttc     120
ctactgggta gtaggctcct agagtggggt aaagtttgcc aagggtttag ccccagtctt     180
gtttatgctt ggctaggcag gacctgggta agttgatggc tcctgcattc ctacctgagt     240
atttccagct ataagcgaga tttgccatac tcttcagcga gtccggatgg tccgcgccga     300
ggttgaccct gccttcatca cctacacaaa gaactcctcg ccaactccc ggtggccttc      360 gagctccaaa gtaccttcgc gacctttggc cagtgtttct cgcagcgttt actgagccta     420
aggcttgcta caataaataa agagacataa ccttgcagta catacgtctt gtatgagcga     480
ggaactgtgt tcagtagtag atcagtgggt acataatcat gaacatgact tctgagccag     540
aaaaccttct gcagggaacc ggtgaagaaa ccccacttcc ccgcctccac taactgcagc     600
ccctttatcc gcctgccgtc catttagcca aatgtagtcc atttagccaa gtgcggtcca     660
tttagccaag tccagtgctt aggttggtgg ctacacagga aacggccatg aatgtagaca     720

```
caactataga actgtcccta gaaataggct cgaggttgtt agagcgttta aggtgatgcg      780
gcaaaatgca tatgactgag ttgcttcaac gtgcagggga aagggataaa tagtcttttt      840
cgcagaatat aaatagaggt agagcgggct cgcagcaata ttgaccagga cagggcttct      900
tttccagttg catacatcca ttcacagcat tcagctttct tcaatcatca tgaaggtcac      960
tgcggctttt gcaggtcttt tggtcacggc attcgccgct cctgccccag aacctgatct     1020
ggtgtcgcga agtgccggta tcaactacgt gcaaaactac aacggcaacc ttggtgattt     1080
cacctacgac gagagtgccg aacatttttc catgtactgg gaagatggag tgagctccga     1140
ctttgtcgtt ggtctgggct ggaccactgg ttcttctaag tgagtgactg tattctttaa     1200
ccaaggtcta ggatctaacg tctttcagcg ctatcaccta ctctgccgaa tacagcgctt     1260
ctggctccgc ttcctacctc gctgtgtacg gctgggtcaa ctatcctcaa gctgagtact     1320
acatcgtcga ggattacggt gattataacc cttgcagttc ggccacaagc cttggtaccg     1380
tgtactctga tggaagcacc taccaagtct gcaccgacac tcgaacaaac gaaccgtcca     1440
tcacgggaac aagcacgttc acgcagtact ctccgttcg agagagcacg cgcacatctg     1500
gaacggtgac tgttgccaac catttcaact tctgggcgca ccatgggttc ggcaatagcg     1560
acttcaatta tcaggtcgtg gcggtggaag catggagcgg tgctggcagc gctagtgtca     1620
caatctcttc ttgagagatt agtgccctag tagtcggaag atatcaacgc ggcagtttgc     1680
tctcaggtgg tgtgatgatc ggatccggtc tctggggtta cattgaggct gtataagttg     1740
ttgtggggcc gagctgtcag cggctgcgtt ttcagcttgc acagataatc aactctcgtt     1800
ttctatctct tgcgtttcct cgctgcttat cctatccata gataattatt ttgcccacta     1860
ccacaacttg ttcggtcgca gtagtcactc cgagcaaggc attgggaaat ggggatgcg      1920 gggtgctgcg tacccctctaa cctagggcat tttaaaggat atttacccte cagatattct     1980 atagatacag acttcttagg actgcgggta atatagagag cgaaatttct acagttcgat     2040
gcagttcaat gcga                                                       2054
```

<210> SEQ ID NO 20
<211> LENGTH: 211
<212> TYPE: PRT
<213> ORGANISM: Aspergillus tubingensis

<400> SEQUENCE: 20

```
Met Lys Val Thr Ala Ala Phe Ala Gly Leu Leu Val Thr Ala Phe Ala
1               5                   10                  15

Ala Pro Ala Pro Glu Pro Asp Leu Val Ser Arg Ser Ala Gly Ile Asn
            20                  25                  30

Tyr Val Gln Asn Tyr Asn Gly Asn Leu Gly Asp Phe Thr Tyr Asp Glu
        35                  40                  45

Ser Ala Gly Thr Phe Ser Met Tyr Trp Glu Asp Gly Val Ser Ser Asp
    50                  55                  60

Phe Val Val Gly Leu Gly Trp Thr Thr Gly Ser Ser Asn Ala Ile Thr
65                  70                  75                  80

Tyr Ser Ala Glu Tyr Ser Ala Ser Gly Ser Ala Ser Tyr Leu Ala Val
                85                  90                  95

Tyr Gly Trp Val Asn Tyr Pro Gln Ala Glu Tyr Tyr Ile Val Glu Asp
            100                 105                 110

Tyr Gly Asp Tyr Asn Pro Cys Ser Ser Ala Thr Ser Leu Gly Thr Val
        115                 120                 125
```

-continued

```
Tyr Ser Asp Gly Ser Thr Tyr Gln Val Cys Thr Asp Thr Arg Thr Asn
    130                 135                 140

Glu Pro Ser Ile Thr Gly Thr Ser Thr Phe Thr Gln Tyr Phe Ser Val
145                 150                 155                 160

Arg Glu Ser Thr Arg Thr Ser Gly Thr Val Thr Val Ala Asn His Phe
                165                 170                 175

Asn Phe Trp Ala His His Gly Phe Gly Asn Ser Asp Phe Asn Tyr Gln
            180                 185                 190

Val Val Ala Val Glu Ala Trp Ser Gly Ala Gly Ser Ala Ser Val Thr
        195                 200                 205

Ile Ser Ser
    210
```

<210> SEQ ID NO 21
<211> LENGTH: 1023
<212> TYPE: DNA
<213> ORGANISM: Gibberella zeae

<400> SEQUENCE: 21

```
atgaagtcca agttgttatt cccactcctc tctttcgttg gtcaaagtct tgccaccaac      60
gacgactgtc ctctcatcac tagtagatgg actgcggatc cttcggctca tgtctttaac     120
gacaccttgt ggctctaccc gtctcatgac atcgatgctg gatttgagaa tgatcctgat     180
ggaggccagt acgccatgag agattaccat gtctactcta tcgacaagat ctacggttcc     240
ctgccggtcg atcacggtac ggccctgtca gtggaggatg tcccctgggc ctctcgacag     300
atgtgggctc ctgacgctgc ccacaagaac ggcaaatact acctatactt ccctgccaaa     360
gacaaggatg atatcttcag aatcggcgtt gctgtctcac caacccccgg cggaccattc     420
gtccccgaca agagttggat ccctcacact ttcagcatcg accccgccag tttcgtcgat     480
gatgatgaca gagcctactt ggcatggggt ggtatcatgg gtggccagct tcaacgatgg     540
caggataaga acaagtacaa cgaatctggc actgagccag gaaacggcac cgctgccttg     600
agccctcaga ttgccaagct gagcaaggac atgcacactc tggcagagaa gcctcgcgac     660
atgctcattc ttgaccccaa gactggcaag ccgctccttt ctgaggatga agaccgacgc     720
ttcttcgaag gaccctggat tcacaagcgc aacaagattt actacctcac ctactctact     780
ggcacaaccc actatcttgt ctatgcgact tcaaagaccc cctatggtcc ttacacctac     840
cagggcagaa ttctggagcc agttgatggc tggactactc actctagtat cgtcaagtac     900
cagggtcagt ggtggctatt ttatcacgat gccaagacat ctggcaagga ctatcttcgc     960
caggtaaagg ctaagaagat ttggtacgat agcaaaggaa agatcttgac aaagaagcct    1020
tga                                                                  1023
```

<210> SEQ ID NO 22
<211> LENGTH: 340
<212> TYPE: PRT
<213> ORGANISM: Gibberella zeae

<400> SEQUENCE: 22

```
Met Lys Ser Lys Leu Leu Phe Pro Leu Leu Ser Phe Val Gly Gln Ser
1               5                   10                  15

Leu Ala Thr Asn Asp Asp Cys Pro Leu Ile Thr Ser Arg Trp Thr Ala
            20                  25                  30

Asp Pro Ser Ala His Val Phe Asn Asp Thr Leu Trp Leu Tyr Pro Ser
        35                  40                  45
```

```
His Asp Ile Asp Ala Gly Phe Glu Asn Asp Pro Asp Gly Gly Gln Tyr
        50                  55                  60

Ala Met Arg Asp Tyr His Val Tyr Ser Ile Asp Lys Ile Tyr Gly Ser
 65                  70                  75                  80

Leu Pro Val Asp His Gly Thr Ala Leu Ser Val Glu Asp Val Pro Trp
                 85                  90                  95

Ala Ser Arg Gln Met Trp Ala Pro Asp Ala Ala His Lys Asn Gly Lys
            100                 105                 110

Tyr Tyr Leu Tyr Phe Pro Ala Lys Asp Lys Asp Ile Phe Arg Ile
            115                 120                 125

Gly Val Ala Val Ser Pro Thr Pro Gly Gly Pro Phe Val Pro Asp Lys
        130                 135                 140

Ser Trp Ile Pro His Thr Phe Ser Ile Asp Pro Ala Ser Phe Val Asp
145                 150                 155                 160

Asp Asp Asp Arg Ala Tyr Leu Ala Trp Gly Gly Ile Met Gly Gly Gln
                165                 170                 175

Leu Gln Arg Trp Gln Asp Lys Asn Lys Tyr Asn Glu Ser Gly Thr Glu
            180                 185                 190

Pro Gly Asn Gly Thr Ala Ala Leu Ser Pro Gln Ile Ala Lys Leu Ser
            195                 200                 205

Lys Asp Met His Thr Leu Ala Glu Lys Pro Arg Asp Met Leu Ile Leu
210                 215                 220

Asp Pro Lys Thr Gly Lys Pro Leu Leu Ser Glu Asp Glu Asp Arg Arg
225                 230                 235                 240

Phe Phe Glu Gly Pro Trp Ile His Lys Arg Asn Lys Ile Tyr Tyr Leu
                245                 250                 255

Thr Tyr Ser Thr Gly Thr Thr His Tyr Leu Val Tyr Ala Thr Ser Lys
            260                 265                 270

Thr Pro Tyr Gly Pro Tyr Thr Tyr Gln Gly Arg Ile Leu Glu Pro Val
            275                 280                 285

Asp Gly Trp Thr Thr His Ser Ser Ile Val Lys Tyr Gln Gly Gln Trp
            290                 295                 300

Trp Leu Phe Tyr His Asp Ala Lys Thr Ser Gly Lys Asp Tyr Leu Arg
305                 310                 315                 320

Gln Val Lys Ala Lys Lys Ile Trp Tyr Asp Ser Lys Gly Lys Ile Leu
                325                 330                 335

Thr Lys Lys Pro
            340

<210> SEQ ID NO 23
<211> LENGTH: 1047
<212> TYPE: DNA
<213> ORGANISM: Fusarium oxysporum

<400> SEQUENCE: 23
atgcagctca agtttctgtc ttcagcattg ctgttctctc tgaccagcaa atgcgctgcg      60
caagacacta tgacattcc tcccctgatc accgacctct ggtccgcaga tccctcggct     120
catgttttcg aaggcaagct ctgggtttac ccatctcacg acatcgaagc caatgttgtc     180
aacggcacag gaggcgctca atcgccatg agggattacc ataccactc catgaagagc      240 atctatggta agatcccgt tgtcgaccac ggcgtcgctc tctcagtcga tgacgttccc     300
tgggcgaagc agcaaatgtg gctcctgac gcagctcata gaacggcaa atattatctg      360 tacttccccg ccaaggacaa ggatgagatc ttcagaattg agttgctgt ctccaacaag     420
```

```
cccagcggtc ctttcaaggc cgacaagagc tggatccctg gcacgtacag tatcgatcct    480
gctagctacg tcgacactga taacgaggcc tacctcatct ggggcggtat ctggggcggc    540
cagctccaag cctggcagga taaaagaaac tttaacgagt cgtggattgg agacaaggct    600
gctcctaacg gcaccaatgc cctatctcct cagatcgcca agctaagcaa ggacatgcac    660
aagatcaccg aaacaccccg cgatctcgtc attctcgccc ccgagacagg caagcctctt    720
caggctgagg acaacaagcg acgattcttc gagggcccct ggatccacaa gcgcggcaag    780
ctttactacc tcatgtactc caccggtgat acccacttcc ttgtctacgc tacttccaag    840
aacatctacg gtccttatac ctaccggggc aagattcttg atcctgttga tgggtggact    900
actcatggaa gtattgttga gtataaggga cagtggtggc ttttctttgc tgatgcgcat    960
acgtctggta aggattacct tcgacaggtg aaggcgagga agatctggta tgacaagaac   1020
ggcaagatct tgcttcaccg tccttag                                        1047
```

<210> SEQ ID NO 24
<211> LENGTH: 348
<212> TYPE: PRT
<213> ORGANISM: Fusarium oxysporum

<400> SEQUENCE: 24

```
Met Gln Leu Lys Phe Leu Ser Ser Ala Leu Leu Phe Ser Leu Thr Ser
1               5                   10                  15

Lys Cys Ala Ala Gln Asp Thr Asn Asp Ile Pro Pro Leu Ile Thr Asp
            20                  25                  30

Leu Trp Ser Ala Asp Pro Ser Ala His Val Phe Glu Gly Lys Leu Trp
        35                  40                  45

Val Tyr Pro Ser His Asp Ile Glu Ala Asn Val Val Asn Gly Thr Gly
    50                  55                  60

Gly Ala Gln Tyr Ala Met Arg Asp Tyr His Thr Tyr Ser Met Lys Ser
65                  70                  75                  80

Ile Tyr Gly Lys Asp Pro Val Val Asp His Gly Val Ala Leu Ser Val
                85                  90                  95

Asp Asp Val Pro Trp Ala Lys Gln Gln Met Trp Ala Pro Asp Ala Ala
            100                 105                 110

His Lys Asn Gly Lys Tyr Tyr Leu Tyr Phe Pro Ala Lys Asp Lys Asp
        115                 120                 125

Glu Ile Phe Arg Ile Gly Val Ala Val Ser Asn Lys Pro Ser Gly Pro
    130                 135                 140

Phe Lys Ala Asp Lys Ser Trp Ile Pro Gly Thr Tyr Ser Ile Asp Pro
145                 150                 155                 160

Ala Ser Tyr Val Asp Thr Asp Asn Glu Ala Tyr Leu Ile Trp Gly Gly
                165                 170                 175

Ile Trp Gly Gly Gln Leu Gln Ala Trp Gln Asp Lys Lys Asn Phe Asn
            180                 185                 190

Glu Ser Trp Ile Gly Asp Lys Ala Ala Pro Asn Gly Thr Asn Ala Leu
        195                 200                 205

Ser Pro Gln Ile Ala Lys Leu Ser Lys Asp Met His Lys Ile Thr Glu
    210                 215                 220

Thr Pro Arg Asp Leu Val Ile Leu Ala Pro Glu Thr Gly Lys Pro Leu
225                 230                 235                 240

Gln Ala Glu Asp Asn Lys Arg Arg Phe Phe Glu Gly Pro Trp Ile His
                245                 250                 255
```

```
Lys Arg Gly Lys Leu Tyr Tyr Leu Met Tyr Ser Thr Gly Asp Thr His
                260                 265                 270

Phe Leu Val Tyr Ala Thr Ser Lys Asn Ile Tyr Gly Pro Tyr Thr Tyr
                275                 280                 285

Arg Gly Lys Ile Leu Asp Pro Val Asp Gly Trp Thr Thr His Gly Ser
            290                 295                 300

Ile Val Glu Tyr Lys Gly Gln Trp Trp Leu Phe Phe Ala Asp Ala His
305                 310                 315                 320

Thr Ser Gly Lys Asp Tyr Leu Arg Gln Val Lys Ala Arg Lys Ile Trp
                325                 330                 335

Tyr Asp Lys Asn Gly Lys Ile Leu Leu His Arg Pro
                340                 345

<210> SEQ ID NO 25
<211> LENGTH: 535
<212> TYPE: PRT
<213> ORGANISM: Geobacillus stearothermophilus

<400> SEQUENCE: 25

Met Ser Lys Ile Lys Asn Pro Ile Leu Thr Gly Phe His Pro Asp Pro
1               5                   10                  15

Ser Ile Cys Arg Val Gly Asp Asp Tyr Tyr Ile Ala Val Ser Thr Phe
                20                  25                  30

Glu Trp Phe Pro Gly Val Arg Ile Tyr His Ser Lys Asp Leu Lys Asn
            35                  40                  45

Trp Arg Leu Val Ala Arg Pro Leu Asn Arg Leu Ser Gln Leu Asn Met
        50                  55                  60

Ile Gly Asn Pro Asp Ser Gly Val Trp Ala Pro His Leu Ser Tyr
65                  70                  75                  80

Ser Asp Gly Lys Phe Trp Leu Ile Tyr Thr Asp Val Lys Val Val Glu
                85                  90                  95

Gly Gln Trp Lys Asp Gly His Asn Tyr Leu Val Thr Cys Asp Thr Ile
            100                 105                 110

Asp Gly Ala Trp Ser Asp Pro Ile Tyr Leu Asn Ser Ser Gly Phe Asp
        115                 120                 125

Pro Ser Leu Phe His Asp Glu Asp Gly Arg Lys Tyr Leu Val Asn Met
    130                 135                 140

Tyr Trp Asp His Arg Val Asp His His Pro Phe Tyr Gly Ile Val Leu
145                 150                 155                 160

Gln Glu Tyr Ser Val Glu Gln Lys Lys Leu Val Gly Glu Pro Lys Ile
                165                 170                 175

Ile Phe Lys Gly Thr Asp Leu Arg Ile Thr Glu Gly Pro His Leu Tyr
            180                 185                 190

Lys Ile Asn Gly Tyr Tyr Tyr Leu Leu Thr Ala Glu Gly Gly Thr Arg
        195                 200                 205

Tyr Asn His Ala Ala Thr Ile Ala Arg Ser Thr Ser Leu Tyr Gly Pro
    210                 215                 220

Tyr Glu Val His Pro Asp Asn Pro Leu Leu Thr Ser Trp Pro Tyr Pro
225                 230                 235                 240

Arg Asn Pro Leu Gln Lys Ala Gly His Ala Ser Ile Val His Thr His
                245                 250                 255

Thr Asp Glu Trp Phe Leu Val His Leu Thr Gly Arg Pro Leu Pro Arg
            260                 265                 270

Glu Gly Gln Pro Leu Leu Glu His Arg Gly Tyr Cys Pro Leu Gly Arg
        275                 280                 285
```

```
Glu Thr Ala Ile Gln Arg Leu Glu Trp Lys Asp Gly Trp Pro Tyr Val
    290                 295                 300

Val Gly Gly Asn Gly Pro Ser Leu Glu Ile Asp Gly Pro Ser Val Glu
305                 310                 315                 320

Glu Val Ser Trp Glu Lys Asp Tyr Asp Glu Lys Asp Asp Phe Asp Gly
                325                 330                 335

Asp Thr Leu Asn His His Phe Gln Thr Leu Arg Ile Pro Leu Gly Glu
            340                 345                 350

Asp Ile Ala Thr Leu Lys Ala Arg Pro Gly His Leu Arg Leu Tyr Gly
            355                 360                 365

Arg Glu Ser Leu Thr Ser Arg Phe Thr Gln Ala Phe Val Ala Arg Arg
370                 375                 380

Trp Gln His Phe His Phe Val Ala Glu Thr Lys Val Ser Phe Arg Pro
385                 390                 395                 400

Thr Thr Phe Gln Gln Ser Ala Gly Leu Val Asn Tyr Asn Thr Gln
                405                 410                 415

Asn Trp Thr Thr Leu Gln Ile Thr Trp His Glu Glu Lys Gly Arg Ile
                420                 425                 430

Leu Glu Leu Met Thr Cys Asp His Leu Val Val Asp Gln Pro Leu Arg
            435                 440                 445

Gly Arg Glu Ile Val Val Pro Asp Asp Ile Glu Tyr Val Tyr Leu Arg
450                 455                 460

Val Thr Val Gln Ala Thr Thr Tyr Lys Tyr Ser Tyr Ser Phe Asp Gly
465                 470                 475                 480

Met Asn Trp Ile Asp Leu Pro Val Thr Phe Glu Ser Tyr Lys Leu Ser
                485                 490                 495

Asp Asp Tyr Ile Lys Ser Arg Ala Ala Phe Thr Gly Ala Phe Val Gly
            500                 505                 510

Met His Cys Arg Asp Gly Ser Gly Gln Asn Asn Tyr Ala Asp Phe Asp
            515                 520                 525

Tyr Phe Leu Tyr Lys Glu Leu
            530             535

<210> SEQ ID NO 26
<211> LENGTH: 744
<212> TYPE: PRT
<213> ORGANISM: Trichoderma reesei

<400> SEQUENCE: 26

Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Val
                20                  25                  30

Val Pro Pro Ala Gly Thr Pro Trp Gly Thr Ala Tyr Asp Lys Ala Lys
            35                  40                  45

Ala Ala Leu Ala Lys Leu Asn Leu Gln Asp Lys Val Gly Ile Val Ser
            50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
                100                 105                 110

Ala Ser Thr Trp Asp Val Asn Leu Ile Arg Glu Arg Gly Gln Phe Ile
            115                 120                 125
```

-continued

Gly Glu Glu Val Lys Ala Ser Gly Ile His Val Ile Leu Gly Pro Val
130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
        275                 280                 285

Thr Asp Phe Asn Gly Asn Asn Arg Leu Trp Gly Pro Ala Leu Thr Asn
290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
        355                 360                 365

Ala Asn Ile Leu Pro Leu Lys Lys Pro Ala Ser Ile Ala Val Val Gly
370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
        435                 440                 445

Thr Ser Ser Gly Ala Ser Ala Ala Arg Gly Lys Asp Val Ala Ile Val
450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val Val His
            500                 505                 510

Ser Val Gly Ala Ile Ile Leu Glu Gln Ile Leu Ala Leu Pro Gln Val
        515                 520                 525

Lys Ala Val Val Trp Ala Gly Leu Pro Ser Gln Glu Ser Gly Asn Ala
530                 535                 540

```
Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
595                 600                 605

Ser Tyr Thr Lys Phe Asn Tyr Ser Arg Leu Ser Val Leu Ser Thr Ala
        610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670

Ser Ala Pro Arg Thr Pro Pro Lys Gln Leu Arg Gly Phe Ala Lys Leu
        675                 680                 685

Asn Leu Thr Pro Gly Gln Ser Gly Thr Ala Thr Phe Asn Ile Arg Arg
690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
                725                 730                 735

Leu Thr Ser Thr Leu Ser Val Ala
            740

<210> SEQ ID NO 27
<211> LENGTH: 72
<212> TYPE: DNA
<213> ORGANISM: Artificial
<220> FEATURE:
<223> OTHER INFORMATION: synthetic primer

<400> SEQUENCE: 27
caaggcgcgc caagtataac ttcgtataat gtatgctata cgaagttatc ggccggcgta   60
ttgggtgtta cg                                                       72

<210> SEQ ID NO 28
<211> LENGTH: 73
<212> TYPE: DNA
<213> ORGANISM: Artificial
<220> FEATURE:
<223> OTHER INFORMATION: synthetic primer

<400> SEQUENCE: 28
gaaggcgcgc cacagataac ttcgtatagc atacattata cgaagttatc ctgggcttgt   60
gactggtcgc gag                                                      73

<210> SEQ ID NO 29
<211> LENGTH: 22
<212> TYPE: DNA
<213> ORGANISM: Artificial
<220> FEATURE:
<223> OTHER INFORMATION: synthetic primer

<400> SEQUENCE: 29
ccatgtcacc tgtcttgaac ac                                            22
```

-continued

```
<210> SEQ ID NO 30
<211> LENGTH: 31
<212> TYPE: DNA
<213> ORGANISM: Artificial
<220> FEATURE:
<223> OTHER INFORMATION: synthetic primer

<400> SEQUENCE: 30
caaggcgcgc catctctttc gatctcaaca g                              31

<210> SEQ ID NO 31
<211> LENGTH: 32
<212> TYPE: DNA
<213> ORGANISM: Artificial
<220> FEATURE:
<223> OTHER INFORMATION: synthetic primer

<400> SEQUENCE: 31
gattgcgatc gccgtctaca acgttttcaa cc                             32

<210> SEQ ID NO 32
<211> LENGTH: 23
<212> TYPE: DNA
<213> ORGANISM: Artificial
<220> FEATURE:
<223> OTHER INFORMATION: synthetic primer

<400> SEQUENCE: 32
ggtccaacct tgaatgtaac agc                                       23

<210> SEQ ID NO 33
<211> LENGTH: 22
<212> TYPE: DNA
<213> ORGANISM: Artificial
<220> FEATURE:
<223> OTHER INFORMATION: synthetic primer

<400> SEQUENCE: 33
gtgtcgctga acataaggtc tc                                        22

<210> SEQ ID NO 34
<211> LENGTH: 21
<212> TYPE: DNA
<213> ORGANISM: Artificial
<220> FEATURE:
<223> OTHER INFORMATION: synthetic primer

<400> SEQUENCE: 34
cctccattct tccaacaagc c                                         21

<210> SEQ ID NO 35
<211> LENGTH: 24
<212> TYPE: DNA
<213> ORGANISM: Artificial
<220> FEATURE:
<223> OTHER INFORMATION: synthetic primer

<400> SEQUENCE: 35
caccatgcag ctcaagtttc tgtc                                      24

<210> SEQ ID NO 36
<211> LENGTH: 32
<212> TYPE: DNA
<213> ORGANISM: Artificial
<220> FEATURE:
<223> OTHER INFORMATION: synthetic primer
```

```
<400> SEQUENCE: 36
ggttactagt caactgcccg ttctgtagcg ag                              32

<210> SEQ ID NO 37
<211> LENGTH: 29
<212> TYPE: DNA
<213> ORGANISM: Artificial
<220> FEATURE:
<223> OTHER INFORMATION: synthetic primer

<400> SEQUENCE: 37
catgcgatcg cgacgttttg gtcaggtcg                                  29

<210> SEQ ID NO 38
<211> LENGTH: 40
<212> TYPE: DNA
<213> ORGANISM: Artificial
<220> FEATURE:
<223> OTHER INFORMATION: synthetic primer

<400> SEQUENCE: 38
gacagaaact tgagctgcat ggtgtgggac aacaagaagg                      40

<210> SEQ ID NO 39
<211> LENGTH: 2415
<212> TYPE: DNA
<213> ORGANISM: Aspergillus japonicus

<400> SEQUENCE: 39
atggctgtgg cggctcttgc tctgctggct ctactgcctc aagctctggg gcaacataac    60
agcagctacg tggattacaa cgtcgaagcc aatccggact tgtttccaca atgtctagac   120
acaatctccc tgtccttccc cgactgccag agcggtcctc tgagcaagaa cctcgtctgc   180
gactcgactg cctcgcccta tgaccgcgcc gcggctctgg tctccctctt caccctcgag   240
gaacttatcg ccaacactgg taacaccagc ccgggtgtcc ctcgtctggg tctgcctcca   300
taccaggtct ggagtgaggc cctgcatggc ctggctcgcg ccaacttcac cgacaacggg   360
gcttacagct gggcgacgtc cttcccctca cccattctct ccgcagcggc cttcaatcgc   420
accctgatca accagatcgc ctccattatt tcgactcagg gccgtgcctt caacaacgcc   480
ggccgctttg gcctcgacgt ctactcgcca aacatcaata ccttccgcca tccagtctgg   540
ggtcgtggac aggaaactcc tggcgaggat gcgtacactc ttacggccgc ctacgcctac   600
gaatacatca cgggtatcca gggtggtgtg aacccagagc atctgaagct cgccgcgaca   660
gccaagcact tgccggcta cgacatcgag aactgggaca ccactcccg gctggggaac   720 gatgtcaaca ttacgcagca agacctggcc gagtactaca cgccgcagtt cctcgtcgcc   780
gcgcgcgacg cccacgtcca cagcttcatg tgctcctaca acgccgttaa cggagtgccc   840
agctgctcca cacccttctt tctgcagacc ctcctgcgcg caccttctc cttcgtcgac   900 cacggctacg tctccggcga ctgcggcgcc gtctacggcg tcttcaaccc ccacggctac   960
gcggccaacg agcccagcgc cgccgccgat gccatcctcg ccggcactga cattgactgc  1020
ggcacctcct atcaatatca cttcaacgag tccatcacca ccggggctgt cgcccgcgac  1080
gacatcgagc gtggtttcat ccggctgtac gccaacctcg tcgagctggg ctacttcgac  1140
ggcaacagca gcagcagcaa cccgtaccgc agcctgggct ggcccgacgt ccagaagaca  1200
gacgcatgga catttcccta cgaggcggca gtcgaaggca tcgtcctcct gaagaacgac  1260 ggcacccctcc ctcttgcctc cccctccgag ggcaagaaca aatccatcgc cctcatcggc  1320
```

```
cctgggcca acgccaccac ccagctccag gtaactact acggcgacgc gccatacctc     1380
atcagcccgg tcgacgcctt cacggccgcc gggtacacag tacactacgc ccccggcacg     1440
gagatctcga cgaactcgac ggcgaacttc agcgccgcgc tctccgcggc gcgcgccgcc     1500
gacaccatcg tattcttggg gggcatcgat aacaccatcg aagccgaagc caagaccgc     1560
agctcgatcg cctggcccgg caaccaactc gagctgatct cgcaactcgc ggcgcagaaa     1620
tccgacgacc agcccctggt ggtgtaccag atgggcggcg ccaggtcga ctcctccgcc     1680
ctcaaatcca acgcgaaggt caacgccctc tctggggcg gctacccggg ccaatccggc     1740
ggcctcgccc tgcgcgacat cctcacgggc gcgcgcgccc ccgccggccg cctcaccacg     1800
acccagtacc cggccgccta cgccgagagc ttctcggccc tcgacatgaa cctgcggccg     1860
aatgagacta cacagaaccc gggccagacc tacatgtggt acaccggcga gcccgtctac     1920
gccttcggcc acggcctgtt ctacaccacc ttcaacgctt cctcagccca agcagcgaag     1980
acgaagtata ccttcaacat caccgacctc acctccgccg cacacccaga caccacgacc     2040
gtcggccaac gcaccctctt caacttcaca gcctccatca cgaactccgg acagagggat     2100
tccgattaca ccgccctggt gtacgccaac acctcgactg cgggcccctc cccgtacccg     2160
aataaatggc tcgtcgggtt cgaccggctc gccgccgtgg cgaaggaggg cggcacggcc     2220
gagttgaatg tgccggtggc ggtggatcgg ttggcgaggg tggatgaagc gggtaacacc     2280
gtgctgtttc cggggcggta tgaggtggcc ctgaataatg agcgcgaggt cgtggtcgag     2340
gtggagttgg tgggtgagca ggttgtgctg ttgaagtggc cggaggaggt gcaggggtg     2400
gcggggatg agtag                                                       2415
```

<210> SEQ ID NO 40
<211> LENGTH: 804
<212> TYPE: PRT
<213> ORGANISM: Aspergillus japonicus

<400> SEQUENCE: 40

Met Ala Val Ala Ala Leu Ala Leu Leu Ala Leu Leu Pro Gln Ala Leu
1               5                   10                  15

Gly Gln His Asn Ser Ser Tyr Val Asp Tyr Asn Val Glu Ala Asn Pro
            20                  25                  30

Asp Leu Phe Pro Gln Cys Leu Asp Thr Ile Ser Leu Ser Phe Pro Asp
        35                  40                  45

Cys Gln Ser Gly Pro Leu Ser Lys Asn Leu Val Cys Asp Ser Thr Ala
    50                  55                  60

Ser Pro Tyr Asp Arg Ala Ala Ala Leu Val Ser Leu Phe Thr Leu Glu
65                  70                  75                  80

Glu Leu Ile Ala Asn Thr Gly Asn Thr Ser Pro Gly Val Pro Arg Leu
                85                  90                  95

Gly Leu Pro Pro Tyr Gln Val Trp Ser Glu Ala Leu His Gly Leu Ala
            100                 105                 110

Arg Ala Asn Phe Thr Asp Asn Gly Ala Tyr Ser Trp Ala Thr Ser Phe
        115                 120                 125

Pro Ser Pro Ile Leu Ser Ala Ala Phe Asn Arg Thr Leu Ile Asn
    130                 135                 140

Gln Ile Ala Ser Ile Ile Ser Thr Gln Gly Arg Ala Phe Asn Asn Ala
145                 150                 155                 160

Gly Arg Phe Gly Leu Asp Val Tyr Ser Pro Asn Ile Asn Thr Phe Arg
                165                 170                 175

-continued

```
His Pro Val Trp Gly Arg Gly Gln Glu Thr Pro Gly Glu Asp Ala Tyr
            180                 185                 190

Thr Leu Thr Ala Ala Tyr Ala Tyr Glu Tyr Ile Thr Gly Ile Gln Gly
            195                 200                 205

Gly Val Asn Pro Glu His Leu Lys Leu Ala Ala Thr Ala Lys His Phe
210                 215                 220

Ala Gly Tyr Asp Ile Glu Asn Trp Asp Asn His Ser Arg Leu Gly Asn
225                 230                 235                 240

Asp Val Asn Ile Thr Gln Gln Asp Leu Ala Glu Tyr Tyr Thr Pro Gln
                245                 250                 255

Phe Leu Val Ala Ala Arg Asp Ala His Val His Ser Phe Met Cys Ser
            260                 265                 270

Tyr Asn Ala Val Asn Gly Val Pro Ser Cys Ser Asn Thr Phe Phe Leu
            275                 280                 285

Gln Thr Leu Leu Arg Asp Thr Phe Ser Phe Val Asp His Gly Tyr Val
        290                 295                 300

Ser Gly Asp Cys Gly Ala Val Tyr Gly Val Phe Asn Pro His Gly Tyr
305                 310                 315                 320

Ala Ala Asn Glu Pro Ser Ala Ala Asp Ala Ile Leu Ala Gly Thr
                325                 330                 335

Asp Ile Asp Cys Gly Thr Ser Tyr Gln Tyr His Phe Asn Glu Ser Ile
            340                 345                 350

Thr Thr Gly Ala Val Ala Arg Asp Asp Ile Glu Arg Gly Phe Ile Arg
            355                 360                 365

Leu Tyr Ala Asn Leu Val Glu Leu Gly Tyr Phe Asp Gly Asn Ser Ser
    370                 375                 380

Ser Ser Asn Pro Tyr Arg Ser Leu Gly Trp Pro Asp Val Gln Lys Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ala Ser Pro Ser Glu Gly Lys
            420                 425                 430

Asn Lys Ser Ile Ala Leu Ile Gly Pro Trp Ala Asn Ala Thr Thr Gln
        435                 440                 445

Leu Gln Gly Asn Tyr Tyr Gly Asp Ala Pro Tyr Leu Ile Ser Pro Val
    450                 455                 460

Asp Ala Phe Thr Ala Ala Gly Tyr Thr Val His Tyr Ala Pro Gly Thr
465                 470                 475                 480

Glu Ile Ser Thr Asn Ser Thr Ala Asn Phe Ser Ala Ala Leu Ser Ala
                485                 490                 495

Ala Arg Ala Ala Asp Thr Ile Val Phe Leu Gly Gly Ile Asp Asn Thr
            500                 505                 510

Ile Glu Ala Glu Ala Gln Asp Arg Ser Ser Ile Ala Trp Pro Gly Asn
        515                 520                 525

Gln Leu Glu Leu Ile Ser Gln Leu Ala Ala Gln Lys Ser Asp Asp Gln
    530                 535                 540

Pro Leu Val Val Tyr Gln Met Gly Gly Gly Gln Val Asp Ser Ser Ala
545                 550                 555                 560

Leu Lys Ser Asn Ala Lys Val Asn Ala Leu Leu Trp Gly Gly Tyr Pro
                565                 570                 575

Gly Gln Ser Gly Gly Leu Ala Leu Arg Asp Ile Leu Thr Gly Ala Arg
            580                 585                 590
```

Ala Pro Ala Gly Arg Leu Thr Thr Thr Gln Tyr Pro Ala Tyr Ala
            595                 600                 605

Glu Ser Phe Ser Ala Leu Asp Met Asn Leu Arg Pro Asn Glu Thr Thr
    610                 615                 620

Gln Asn Pro Gly Gln Thr Tyr Met Trp Tyr Thr Gly Glu Pro Val Tyr
625                 630                 635                 640

Ala Phe Gly His Gly Leu Phe Tyr Thr Thr Phe Asn Ala Ser Ser Ala
                645                 650                 655

Gln Ala Ala Lys Thr Lys Tyr Thr Phe Asn Ile Thr Asp Leu Thr Ser
            660                 665                 670

Ala Ala His Pro Asp Thr Thr Val Gly Gln Arg Thr Leu Phe Asn
        675                 680                 685

Phe Thr Ala Ser Ile Thr Asn Ser Gly Gln Arg Asp Ser Asp Tyr Thr
690                 695                 700

Ala Leu Val Tyr Ala Asn Thr Ser Thr Ala Gly Pro Ser Pro Tyr Pro
705                 710                 715                 720

Asn Lys Trp Leu Val Gly Phe Asp Arg Leu Ala Val Ala Lys Glu
                725                 730                 735

Gly Gly Thr Ala Glu Leu Asn Val Pro Val Ala Val Asp Arg Leu Ala
            740                 745                 750

Arg Val Asp Glu Ala Gly Asn Thr Val Leu Phe Pro Gly Arg Tyr Glu
        755                 760                 765

Val Ala Leu Asn Asn Glu Arg Glu Val Val Val Glu Val Glu Leu Val
770                 775                 780

Gly Glu Gln Val Val Leu Leu Lys Trp Pro Glu Glu Val Gln Gly Val
785                 790                 795                 800

Ala Gly Asp Glu

<210> SEQ ID NO 41
<211> LENGTH: 1695
<212> TYPE: DNA
<213> ORGANISM: Fusarium verticillioides

<400> SEQUENCE: 41
atgctcttct cgctcgttct tcctacccct gcctttcaag ccagcctggc gctcggcgat      60
acatccgtta ctgtcgacac cagccagaaa ctccaggtca tcgatggctt tggtgtctca    120
gaagcctacg ccacgccaa acaattccaa aacctcggtc ctggaccaca gaaagagggc     180
ctcgatcttc tcttcaacac tacaaccggc gcaggcttat ccatcatccg aaacaagatc    240
ggctgcgacg cctccaactc catcaccagc accaacaccg acaacccaga taagcaggct    300
gtttaccatt tgacggcga tgatgatggt caggtatggt ttagcaaaca ggccatgagc    360
tatggtgtag atactatcta cgctaatgct tggtctgcgc ctgtatacat gaagtcagcc    420
cagagtatgg gccgtctctg cggtacacct ggtgtgtcgt gctcctctgg agattggaga    480
catcgttacg ttgagatgat agctgagtac ctctcctact acaagcaggc tggcatccca    540
gtgtcgcacg ttggattcct caatgagggt gacggctcgg actttatgct ctcaactgcc    600
gaacaggctg cagatgtcat tcctcttcta cacagcgctt tgcagtccaa gggccttggc    660
gatatcaaga tgacgtgctg tgataacatc ggttggaagt cacagatgga ctataccgcc    720
aagctggctg agcttgaggt ggagaagtat ctatctgtca tcacatccca cgagtactcc    780 agcagccca accagcctat gaacactaca ttgccaacct ggatgtccga gggagctgcc    840
aatgaccagg catttgccac agcgtggtac gtcaacggcg gttccaacga aggtttcaca    900

```
tgggcagtca agatcgcaca aggcatcgtc aatgccgacc tctcagcgta tatctactgg    960
gagggcgttg agaccaacaa caagggtct ctatctcacg tcatcgacac ggacggtacc    1020
aagtttacca tatcctcgat tctctgggcc attgctcact ggtcgcgcca tattcgccct    1080
ggtgcgcata gactttcgac ttcaggtgtt gtgcaagata cgattgttgg tgcgtttgag    1140
aacgttgatg gcagtgtcgt catggtgctc accaactctg gcactgctgc tcagactgtg    1200
gacctggggt ttcgggaag tagcttctca acagctcagg ctttcacttc ggatgctgag    1260
gcgcagatgg tcgataccaa ggtgactctg tccgacggtc gtgtcaaggt tacggtcccg    1320
gtgcacggtg tcgtcactgt gaagctcaca acagcaaaaa gctccaaacc ggtctcaact    1380
gctgtttctg cgcaatctgc ccccactcca actagtgtta agcacacctt gactcaccag    1440
aagacttctt caacaacact ctcgaccgcc aaggccccaa cctccactca gactacctct    1500
gtagttgagt cagccaaggc ggtgaaatac cctgtccccc ctgtagcatc caagggatcc    1560
tcgaagagtg ctcccaagaa gggtaccaag aagaccacta cgaagaaggg ctcccaccaa    1620
tcgcacaagg cgcatagtgc tactcatcgt cgatgccgcc atggaagtta ccgtcgtggc    1680
cactgcacca actaa                                                    1695
```

<210> SEQ ID NO 42
<211> LENGTH: 537
<212> TYPE: PRT
<213> ORGANISM: Fusarium verticillioides

<400> SEQUENCE: 42

```
Met Leu Phe Ser Leu Val Leu Pro Thr Leu Ala Phe Gln Ala Ser Leu
1               5                   10                  15

Ala Leu Gly Asp Thr Ser Val Thr Val Asp Thr Ser Gln Lys Leu Gln
            20                  25                  30

Val Ile Asp Gly Phe Gly Val Ser Glu Ala Tyr Gly His Ala Lys Gln
        35                  40                  45

Phe Gln Asn Leu Gly Pro Gly Pro Gln Lys Glu Gly Leu Asp Leu Leu
    50                  55                  60

Phe Asn Thr Thr Thr Gly Ala Gly Leu Ser Ile Ile Arg Asn Lys Ile
65                  70                  75                  80

Gly Cys Asp Ala Ser Asn Ser Ile Thr Ser Thr Asn Thr Asp Asn Pro
                85                  90                  95

Asp Lys Gln Ala Val Tyr His Phe Asp Gly Asp Asp Gly Gln Ser
            100                 105                 110

Ala Gln Ser Met Gly Arg Leu Cys Gly Thr Pro Gly Val Ser Cys Ser
        115                 120                 125

Ser Gly Asp Trp Arg His Arg Tyr Val Glu Met Ile Ala Glu Tyr Leu
    130                 135                 140

Ser Tyr Tyr Lys Gln Ala Gly Ile Pro Val Ser His Val Gly Phe Leu
145                 150                 155                 160

Asn Glu Gly Asp Gly Ser Asp Phe Met Leu Ser Thr Ala Glu Gln Ala
                165                 170                 175

Ala Asp Val Ile Pro Leu Leu His Ser Ala Leu Gln Ser Lys Gly Leu
            180                 185                 190

Gly Asp Ile Lys Met Thr Cys Cys Asp Asn Ile Gly Trp Lys Ser Gln
        195                 200                 205

Met Asp Tyr Thr Ala Lys Leu Ala Glu Leu Glu Val Glu Lys Tyr Leu
    210                 215                 220
```

Ser Val Ile Thr Ser His Glu Tyr Ser Ser Ser Pro Asn Gln Pro Met
225                 230                 235                 240

Asn Thr Thr Leu Pro Thr Trp Met Ser Glu Gly Ala Ala Asn Asp Gln
            245                 250                 255

Ala Phe Ala Thr Ala Trp Tyr Val Asn Gly Gly Ser Asn Glu Gly Phe
        260                 265                 270

Thr Trp Ala Val Lys Ile Ala Gln Gly Ile Val Asn Ala Asp Leu Ser
    275                 280                 285

Ala Tyr Ile Tyr Trp Glu Val Glu Thr Asn Asn Lys Gly Ser Leu
290                 295                 300

Ser His Val Ile Asp Thr Asp Gly Thr Lys Phe Thr Ile Ser Ser Ile
305                 310                 315                 320

Leu Trp Ala Ile Ala His Trp Ser Arg His Ile Arg Pro Gly Ala His
                325                 330                 335

Arg Leu Ser Thr Ser Gly Val Val Gln Asp Thr Ile Val Gly Ala Phe
            340                 345                 350

Glu Asn Val Asp Gly Ser Val Val Met Val Leu Thr Asn Ser Gly Thr
        355                 360                 365

Ala Ala Gln Thr Val Asp Leu Gly Val Ser Gly Ser Ser Phe Ser Thr
370                 375                 380

Ala Gln Ala Phe Thr Ser Asp Ala Glu Ala Gln Met Val Asp Thr Lys
385                 390                 395                 400

Val Thr Leu Ser Asp Gly Arg Val Lys Val Thr Val Pro Val His Gly
                405                 410                 415

Val Val Thr Val Lys Leu Thr Thr Ala Lys Ser Ser Lys Pro Val Ser
            420                 425                 430

Thr Ala Val Ser Ala Gln Ser Ala Pro Thr Pro Thr Ser Val Lys His
        435                 440                 445

Thr Leu Thr His Gln Lys Thr Ser Ser Thr Thr Leu Ser Thr Ala Lys
    450                 455                 460

Ala Pro Thr Ser Thr Gln Thr Thr Ser Val Val Glu Ser Ala Lys Ala
465                 470                 475                 480

Val Lys Tyr Pro Val Pro Pro Val Ala Ser Lys Gly Ser Ser Lys Ser
                485                 490                 495

Ala Pro Lys Lys Gly Thr Lys Lys Thr Thr Thr Lys Lys Gly Ser His
            500                 505                 510

Gln Ser His Lys Ala His Ser Ala Thr His Arg Arg Cys Arg His Gly
        515                 520                 525

Ser Tyr Arg Arg Gly His Cys Thr Asn
530                 535

<210> SEQ ID NO 43
<211> LENGTH: 1734
<212> TYPE: DNA
<213> ORGANISM: Fusarium verticillioides

<400> SEQUENCE: 43
atgaatcctt tatctctcgg ccttgccgcc ttgagccttc tgggctacgt gggtgtcaac     60
tttgttgcag ccttccccac ggattcaaac tcaggctccg aagtcttgat ttctgtcaat    120
ggccacgtta acaccaaga gcttgacgga tttggtgctt cacaagcatt ccaacgggcc     180
gaagacattc ttggaaaaga cggtctgtcc aaagaaggga ctcagcatgt actggacttg    240
ctgttcagca aggatatcgg tgcgggcttc tctatcctgc gtaatggcat ggctcaagc     300 aacagttctg acaagaactt catgaattca atcgagccat tctcgccagg ctcacccgga    360

```
gcaaagccac actacgtctg ggatggctat gatagcggac aactcaccgt cgctcaagaa    420
gcattcaaga gaggattgaa gttcctctat ggcgatgctt ggtccgctcc tggttacatg    480
aagacaaacc acgatgagaa taacgggggg tatttgtgtg gtgttacagg tgctgcctgc    540
gcttctggcg actggaagca ggcttacgca gactacttgc tgcagtgggt tgagttctac    600
cgcaagtcag gcgtcaaggt caccaaccta ggattcctta acgagcctca gttcgccgct    660
ccctacgccg catgctgtc taacggcaca caggctgccg acttcatacg tgtactgggc    720
aagacaatca gaaaacgagg tatccacgac cttacaatcg cctgctgtga tggcgagggc    780
tgggatctcc aagaagatat gatggctggt ttgactgctg gacctgatcc ggcaatcaac    840
tacctcagtg tcgttactgg gcacggctac gtttcaccac cgaaccatcc gctttcaaca    900
acaaagaaga cgtggctcac cgagtgggct gatctcacag gccagttcac gcccacacg     960 ttctacaaca atagcggtca gggggaaggt atgacctggg ctggccgtat ccagacggcg   1020
cttgtagatg ccaatgtcag cggctttctc tattggatcg gagccgagaa ctcgaccacc   1080
aacagtgctc tgatcaacat gatcggcgac aaggtcatcc cttccaagag gttctgggcc   1140
tttgcatcct tcagtcggtt tgctagacct ggtgctcgtc gcattgaagc cacgagctcc   1200
gttcctctgg tcacagtcag ttcatttctg aataccgacg tactgtcgc gacgcaggtg    1260 ctgaacaacg acacggttgc tcacagtgtg caactcgttg tctctggcac aggtcgaaat   1320
cctcatagct tgaagccgtt tttgaccgat aattctaatg atttgactgc cttgaagcat   1380
ttgaaggcta ctggaaaggg ttcatttcag actacgattc ctcctcgatc tcttgttagc   1440
tttgttacag atttctaaca aagacaatat tacttgaaga agacgactat gagggctgct   1500
ttgatcaagt tgactatgtc tagtatgttg gtgtaaatct cctaacaatc ttgttgggct   1560
gcttatttcg gcttagttac gcaacgtcat gttcagtgtg ccgaaagccg aaccacgaaa   1620
atagctcaca agaccattct ggattttgac acgataagat cctgccttt ttttcatact    1680 tgttcctctc tttcacttgg cgaaatatgc tgttttacgt atccatgctc tccc          1734
```

<210> SEQ ID NO 44
<211> LENGTH: 485
<212> TYPE: PRT
<213> ORGANISM: Fusarium verticillioides

<400> SEQUENCE: 44

```
Met Asn Pro Leu Ser Leu Gly Leu Ala Ala Leu Ser Leu Leu Gly Tyr
1               5                  10                  15

Val Gly Val Asn Phe Val Ala Ala Phe Pro Thr Asp Ser Asn Ser Gly
            20                  25                  30

Ser Glu Val Leu Ile Ser Val Asn Gly His Val Lys His Gln Glu Leu
        35                  40                  45

Asp Gly Phe Gly Ala Ser Gln Ala Phe Gln Arg Ala Glu Asp Ile Leu
    50                  55                  60

Gly Lys Asp Gly Leu Ser Lys Glu Gly Thr Gln His Val Leu Asp Leu
65                  70                  75                  80

Leu Phe Ser Lys Asp Ile Gly Ala Gly Phe Ser Ile Leu Arg Asn Gly
                85                  90                  95

Ile Gly Ser Ser Asn Ser Ser Asp Lys Asn Phe Met Asn Ser Ile Glu
            100                 105                 110

Pro Phe Ser Pro Gly Ser Pro Gly Ala Lys Pro His Tyr Val Trp Asp
        115                 120                 125
```

```
Gly Tyr Asp Ser Gly Gln Leu Thr Val Ala Gln Glu Ala Phe Lys Arg
            130                 135                 140

Gly Leu Lys Phe Leu Tyr Gly Asp Ala Trp Ser Ala Pro Gly Tyr Met
145                 150                 155                 160

Lys Thr Asn His Asp Glu Asn Gly Gly Tyr Leu Cys Gly Val Thr
                165                 170                 175

Gly Ala Ala Cys Ala Ser Gly Asp Trp Lys Gln Ala Tyr Ala Asp Tyr
                180                 185                 190

Leu Leu Gln Trp Val Glu Phe Tyr Arg Lys Ser Gly Val Lys Val Thr
                195                 200                 205

Asn Leu Gly Phe Leu Asn Glu Pro Gln Phe Ala Ala Pro Tyr Ala Gly
            210                 215                 220

Met Leu Ser Asn Gly Thr Gln Ala Ala Asp Phe Ile Arg Val Leu Gly
225                 230                 235                 240

Lys Thr Ile Arg Lys Arg Gly Ile His Asp Leu Thr Ile Ala Cys Cys
                245                 250                 255

Asp Gly Glu Gly Trp Asp Leu Gln Glu Asp Met Met Ala Gly Leu Thr
            260                 265                 270

Ala Gly Pro Asp Pro Ala Ile Asn Tyr Leu Ser Val Val Thr Gly His
            275                 280                 285

Gly Tyr Val Ser Pro Pro Asn His Pro Leu Ser Thr Thr Lys Lys Thr
            290                 295                 300

Trp Leu Thr Glu Trp Ala Asp Leu Thr Gly Gln Phe Thr Pro Tyr Thr
305                 310                 315                 320

Phe Tyr Asn Asn Ser Gly Gln Gly Glu Gly Met Thr Trp Ala Gly Arg
                325                 330                 335

Ile Gln Thr Ala Leu Val Asp Ala Asn Val Ser Gly Phe Leu Tyr Trp
                340                 345                 350

Ile Gly Ala Glu Asn Ser Thr Thr Asn Ser Ala Leu Ile Asn Met Ile
            355                 360                 365

Gly Asp Lys Val Ile Pro Ser Lys Arg Phe Trp Ala Phe Ala Ser Phe
            370                 375                 380

Ser Arg Phe Ala Arg Pro Gly Ala Arg Ile Glu Ala Thr Ser Ser
385                 390                 395                 400

Val Pro Leu Val Thr Val Ser Ser Phe Leu Asn Thr Asp Gly Thr Val
                405                 410                 415

Ala Thr Gln Val Leu Asn Asn Asp Thr Val Ala His Ser Val Gln Leu
                420                 425                 430

Val Val Ser Gly Thr Gly Arg Asn Pro His Ser Leu Lys Pro Phe Leu
            435                 440                 445

Thr Asp Asn Ser Asn Asp Leu Thr Ala Leu Lys His Leu Lys Ala Thr
450                 455                 460

Gly Lys Gly Ser Phe Gln Thr Thr Ile Pro Pro Arg Ser Leu Val Ser
465                 470                 475                 480

Phe Val Thr Asp Phe
                485

<210> SEQ ID NO 45
<211> LENGTH: 1374
<212> TYPE: DNA
<213> ORGANISM: Fusarium verticillioides
```

<400> SEQUENCE: 45

```
atgcactacg ctaccctcac cactttggtg ctggctctga ccaccaacgt cgctgcacag        60
caaggcacag caactgtcga cctctccaaa aatcatggac cggcgaaggc ccttggttca       120
ggcttcatat acggctggcc tgacaacgga acaagcgtcg acacctccat accagatttc       180
ttggtaactg acatcaaatt caactcaaac cgcggcggtg cgcccaaat cccatcactg        240
ggttgggcca gaggtggcta tgaaggatac ctcggccgct tcaactcaac cttatccaac       300
tatcgcacca cgcgcaagta aacgctgac tttatcttgt tgcctcatga cctctggggt        360
gcggatggcg gcagggttc aaactccccg tttcctggcg acaatggcaa ttggactgag        420
atggagttat tctggaatca gcttgtgtct gacttgaagg ctcataatat gctggaaggt       480
cttgtgattg atgtttggaa tgagcctgat attgatatct tttgggatcg cccgtggtcg       540
cagtttcttg agtattacaa tcgcgcgacc aaactacttc ggtgagtcta ctactgatcc       600
atacgtattt acagtgagct gactggtcga attagaaaaa cacttcccaa aactcttctc       660
agtggcccag ccatggcaca ttctcccatt ctgtccgatg ataaatgca tacctggctt       720
caatcagtag cgggtaacaa gacagtccct gatatttact cctggcatca gattggcgct       780
tgggaacgtg agccggacag cactatcccc gactttacca ccttgcgggc gcaatatggc       840
gttcccgaga agccaattga cgtcaatgag tacgctgcac gcgatgagca aaatccagcc       900
aactccgtct actacctctc tcaactagag cgtcataacc ttagaggtct tcgcgcaaac       960
tggggtagcg gatctgacct ccacaactgg atgggcaact tgatttacag cactaccggt      1020
accctcggagg ggacttacta ccctaatggt gaatggcagg cttacaagta ctatgcggcc    1080
atggcagggc agagacttgt gaccaaagca tcgtcggact tgaagtttga tgtctttgcc      1140
actaagcaag gccgtaagat taagattata gccggcacga ggaccgttca agcaaagtat      1200
aacatcaaaa tcagcggttt ggaagtagca ggacttccta agatgggtac ggtaaaggtc      1260
cggacttatc ggttcgactg ggctgggccg aatggaaagg ttgacgggcc tgttgatttg      1320
ggggagaaga agtatactta ttcggccaat acggtgagca gcccctctac ttga            1374
```

<210> SEQ ID NO 46
<211> LENGTH: 439
<212> TYPE: PRT
<213> ORGANISM: Fusarium verticillioides

<400> SEQUENCE: 46

```
Met His Tyr Ala Thr Leu Thr Thr Leu Val Leu Ala Leu Thr Thr Asn
  1               5                  10                  15

Val Ala Ala Gln Gln Gly Thr Ala Thr Val Asp Leu Ser Lys Asn His
             20                  25                  30

Gly Pro Ala Lys Ala Leu Gly Ser Gly Phe Ile Tyr Gly Trp Pro Asp
         35                  40                  45

Asn Gly Thr Ser Val Asp Thr Ser Ile Pro Asp Phe Leu Val Thr Asp
     50                  55                  60

Ile Lys Phe Asn Ser Asn Arg Gly Gly Ala Gln Ile Pro Ser Leu
 65                  70                  75                  80

Gly Trp Ala Arg Gly Gly Tyr Glu Gly Tyr Leu Gly Arg Phe Asn Ser
                 85                  90                  95

Thr Leu Ser Asn Tyr Arg Thr Thr Arg Lys Tyr Asn Ala Asp Phe Ile
            100                 105                 110

Leu Leu Pro His Asp Leu Trp Gly Ala Asp Gly Gly Gln Gly Ser Asn
        115                 120                 125
```

```
Ser Pro Phe Pro Gly Asp Asn Gly Asn Trp Thr Glu Met Glu Leu Phe
    130                 135                 140

Trp Asn Gln Leu Val Ser Asp Leu Lys Ala His Asn Met Leu Glu Gly
145                 150                 155                 160

Leu Val Ile Asp Val Trp Asn Glu Pro Asp Ile Asp Ile Phe Trp Asp
                165                 170                 175

Arg Pro Trp Ser Gln Phe Leu Glu Tyr Tyr Asn Arg Ala Thr Lys Leu
            180                 185                 190

Leu Arg Lys Thr Leu Pro Lys Thr Leu Leu Ser Gly Pro Ala Met Ala
        195                 200                 205

His Ser Pro Ile Leu Ser Asp Asp Lys Trp His Thr Trp Leu Gln Ser
210                 215                 220

Val Ala Gly Asn Lys Thr Val Pro Asp Ile Tyr Ser Trp His Gln Ile
225                 230                 235                 240

Gly Ala Trp Glu Arg Glu Pro Asp Ser Thr Ile Pro Asp Phe Thr Thr
                245                 250                 255

Leu Arg Ala Gln Tyr Gly Val Pro Glu Lys Pro Ile Asp Val Asn Glu
            260                 265                 270

Tyr Ala Ala Arg Asp Glu Gln Asn Pro Ala Asn Ser Val Tyr Tyr Leu
        275                 280                 285

Ser Gln Leu Glu Arg His Asn Leu Arg Gly Leu Arg Ala Asn Trp Gly
    290                 295                 300

Ser Gly Ser Asp Leu His Asn Trp Met Gly Asn Leu Ile Tyr Ser Thr
305                 310                 315                 320

Thr Gly Thr Ser Glu Gly Thr Tyr Tyr Pro Asn Gly Glu Trp Gln Ala
                325                 330                 335

Tyr Lys Tyr Tyr Ala Ala Met Ala Gly Gln Arg Leu Val Thr Lys Ala
            340                 345                 350

Ser Ser Asp Leu Lys Phe Asp Val Phe Ala Thr Lys Gln Gly Arg Lys
        355                 360                 365

Ile Lys Ile Ile Ala Gly Thr Arg Thr Val Gln Ala Lys Tyr Asn Ile
370                 375                 380

Lys Ile Ser Gly Leu Glu Val Ala Gly Leu Pro Lys Met Gly Thr Val
385                 390                 395                 400

Lys Val Arg Thr Tyr Arg Phe Asp Trp Ala Gly Pro Asn Gly Lys Val
                405                 410                 415

Asp Gly Pro Val Asp Leu Gly Glu Lys Lys Tyr Thr Tyr Ser Ala Asn
            420                 425                 430

Thr Val Ser Ser Pro Ser Thr
        435
```

<210> SEQ ID NO 47
<211> LENGTH: 1426
<212> TYPE: DNA
<213> ORGANISM: Fusarium verticillioides

<400> SEQUENCE: 47

```
atgtggttaa tcaaggcctg ttccgtcctc gccgctctct ccactgtagc tgctgacagc      60
cccggtccca ccatcgactt ctcctccaac actggagagc ctcagcatct cgctgctggt     120
atcctgtacg gtatacccga cgatgggaac cagatcccag atgatcttct ctctggcttt     180
ggcttcaact actatcgcgg tgcaggtgcc caagtctctc atggatggag ttatgacgag     240
gctggcttcc agcagcgttt tgaaagcgcg cataacaact acatcgtcac gcgtcgtcac     300
aacggcggct tgtcttgtt gctgaatgac ctctggggct tgattgttc ttctaacaac       360
```

```
gatacctcac ctggtccagg cgataatggc gattggtcgt cctatgacaa gttcgttcag      420
gcgattattg ccaatgtcaa gaagtacaac atgcaggaag gcttggtcat tgatatctgg      480
aacgagccag agggggggctg tttctggggc cgtagcattg accaatggct tcagatgtgg     540
ggtcgcggct ggcatcaatt caagtaagta ctagatacct ctgaggacgg atgggacaag      600
aactgactgt ctattcagtg atgccttcgg ggacagcgtg ttgacatccg gaccaactct      660
tgcaggcgag ccgggaacaa acgatgactg gtggacccaa tgggcccaat cgtcaagaa      720 caacgactcc atccccgacc aatacgcatg gcacgaggaa ggaggctcag gttccaactt      780
cgagaacagc tacggcgtcc tgcaacaaat tctcactaaa tacggtcttc ccaacgcca      840 aatcaacatc aacgaatacg ctacgttcaa tgaacaagtc cccgccggtt ctgccttctg      900
gatctcccag ttcgagcgcc gtaatgctat cggtcttcgc ggcaattggc taggaggcac      960
tcaacttcac gatctggccg ctagtcttct gtccaagcct gacccctcgg actacgcttc     1020
cacgggatac tttgccaatg gagactggtg ggtgtataac tactactctc acaacatgac     1080
gggacagcgc gtttcgactt cggtgtcttc cgatggaagg ctggatgctt atgcaacggt     1140
ggatactacg gcgcgcacgg ctagagtatt gcttggctgc catccgccta cgactggtac     1200
ttatgatgtg acattctctg gtctgacaaa gttgggtctg ccatcttctg gaacacttca     1260
ggttaggact tggaagtttg ctgtgggcag tgatgtgcat tacagccagg tgggttctcc     1320
tcaggatctg ggtaactatg gtcacactat tagcaacggt caggttacct tgccgttcta     1380
tcagactgat gatgtgacta catacgcatg ggagttcaaa ttctag                     1426
```

<210> SEQ ID NO 48
<211> LENGTH: 456
<212> TYPE: PRT
<213> ORGANISM: Fusarium verticillioides

<400> SEQUENCE: 48

```
Met Trp Leu Ile Lys Ala Cys Ser Val Leu Ala Ala Leu Ser Thr Val
1               5                   10                  15

Ala Ala Asp Ser Pro Gly Pro Thr Ile Asp Phe Ser Ser Asn Thr Gly
            20                  25                  30

Glu Pro Gln His Leu Ala Ala Gly Ile Leu Tyr Gly Ile Pro Asp Asp
        35                  40                  45

Gly Asn Gln Ile Pro Asp Asp Leu Leu Ser Gly Phe Gly Phe Asn Tyr
    50                  55                  60

Tyr Arg Gly Ala Gly Ala Gln Val Ser His Gly Trp Ser Tyr Asp Glu
65                  70                  75                  80

Ala Gly Phe Gln Gln Arg Phe Glu Ser Ala His Asn Asn Tyr Ile Val
                85                  90                  95

Thr Arg Arg His Asn Gly Gly Phe Val Leu Leu Leu Asn Asp Leu Trp
            100                 105                 110

Gly Phe Asp Cys Ser Ser Asn Asn Asp Thr Ser Pro Gly Pro Gly Asp
        115                 120                 125

Asn Gly Asp Trp Ser Ser Tyr Asp Lys Phe Val Gln Ala Ile Ile Ala
    130                 135                 140

Asn Val Lys Lys Tyr Asn Met Gln Glu Gly Leu Val Ile Asp Ile Trp
145                 150                 155                 160

Asn Glu Pro Glu Gly Gly Cys Phe Trp Gly Arg Ser Ile Asp Gln Trp
                165                 170                 175

Leu Gln Met Trp Gly Arg Gly Trp His Gln Phe Asn Asp Ala Phe Gly
            180                 185                 190
```

```
Asp Ser Val Leu Thr Ser Gly Pro Thr Leu Ala Gly Glu Pro Gly Thr
            195                 200                 205

Asn Asp Asp Trp Trp Thr Gln Trp Ala Gln Phe Val Lys Asn Asn Asp
        210                 215                 220

Ser Ile Pro Asp Gln Tyr Ala Trp His Glu Glu Gly Ser Gly Ser
225                 230                 235                 240

Asn Phe Glu Asn Ser Tyr Gly Val Leu Gln Gln Ile Leu Thr Lys Tyr
                245                 250                 255

Gly Leu Pro Gln Arg Gln Ile Asn Ile Asn Glu Tyr Ala Thr Phe Asn
            260                 265                 270

Glu Gln Val Pro Ala Gly Ser Ala Phe Trp Ile Ser Gln Phe Glu Arg
        275                 280                 285

Arg Asn Ala Ile Gly Leu Arg Gly Asn Trp Leu Gly Gly Thr Gln Leu
    290                 295                 300

His Asp Leu Ala Ala Ser Leu Leu Ser Lys Pro Asp Pro Ser Asp Tyr
305                 310                 315                 320

Ala Ser Thr Gly Tyr Phe Ala Asn Gly Asp Trp Trp Val Tyr Asn Tyr
                325                 330                 335

Tyr Ser His Asn Met Thr Gly Gln Arg Val Ser Thr Ser Val Ser Ser
            340                 345                 350

Asp Gly Arg Leu Asp Ala Tyr Ala Thr Val Asp Thr Thr Ala Arg Thr
        355                 360                 365

Ala Arg Val Leu Leu Gly Cys His Pro Pro Thr Thr Gly Thr Tyr Asp
    370                 375                 380

Val Thr Phe Ser Gly Leu Thr Lys Leu Gly Leu Pro Ser Ser Gly Thr
385                 390                 395                 400

Leu Gln Val Arg Thr Trp Lys Phe Ala Val Gly Ser Asp Val His Tyr
                405                 410                 415

Ser Gln Val Gly Ser Pro Gln Asp Leu Gly Asn Tyr Gly His Thr Ile
            420                 425                 430

Ser Asn Gly Gln Val Thr Leu Pro Phe Tyr Gln Thr Asp Asp Val Thr
        435                 440                 445

Thr Tyr Ala Trp Glu Phe Lys Phe
    450                 455

<210> SEQ ID NO 49
<211> LENGTH: 1506
<212> TYPE: DNA
<213> ORGANISM: Trichomonas saccarolyticum

<400> SEQUENCE: 49
atggtaaaaa taaagatacc aaaaaattct gatggcaaaa aattcaccag tagatggaga      60
tattgtgtag gtacaggaag gttgggactt gcgctgcaaa aagagtacat ggatacttta     120
aaatttgtga agaaaatat agacttcaag tatataagag acatggcct tttgtgcgac      180 gatgtaggta tttaccgtga ggacgtagta ggcaacgatg taaggccatt ttacaatttc     240
acgtatatag atagaatctt tgattcattt ttggaattag ggataaggcc atttgttgaa     300
gtcggattta tgcctaaaag attagcatct ggtacacaga cagtatttta ttgggaggga     360
aatgtcaccc ctcccaaaga ttatgaaaaa tggagcaacc ttataaaagc tgttgtttca     420
cattttatat caaggtatgg catagatgaa gtcgtaaaat ggccatttga aatatggaat     480
gagccaaacc taaagagtt ttggaaagat gctgatgaga aagaatactt caagctgtac     540
aaggttactg caaaggcgat taagaagta aatgagaatt tgcaggtagg aggacctgct     600
```

-continued

| | | | | | |
|---|---|---|---|---|---|
| atatgtggtg gtgctgacta ctggatagaa gatttttga atttctgcta tgaagaaaat | | | | | 660 |
| gttcctgttg attttgtatc gcgacacgca tatacgtcta agcaaggtga atatacgcca | | | | | 720 |
| catctcatat accaggagat tatgccatct gaatacatgc taaacgaatt caaaacagtg | | | | | 780 |
| agagagatca taaaaaactc acattttccg aaccttccgt ttcatataac ggagtacaat | | | | | 840 |
| acatcttaca gtccattaaa tcctgtacat gatacgcctt ttaatgcggc gtatcttgcg | | | | | 900 |
| aggatttaa gtgaaggcgg agattatgtt gattcattt cctattggac gtttagcgat | | | | | 960 |
| gtgtttgaag aaagagatgt gccaagatcg cagtttcatg gaggatttgg actagttgca | | | | | 1020 |
| ttgaataaga taccaaagcc gacttttcac atgtttaaat tttcaatgc tatgggagaa | | | | | 1080 |
| gaggtgcttt acagagataa ccatatgctt ataactagaa gggatgatgg gtcgattgca | | | | | 1140 |
| ttgattgctt ggaatgagat aatggagaaa acagaaaatc cagataagga atatgaactg | | | | | 1200 |
| gaaatacctg taggattcaa agatgtcttt ataaagaaac agatgataga tgaggatcac | | | | | 1260 |
| ggcaatcctt ggggtacgtg gatacacatg ggaaggccga gattcccaag taaagaacaa | | | | | 1320 |
| attaagactt taagggatat tgcaaagcct aaaatcaaaa caggtagagc cacatcaaat | | | | | 1380 |
| gatggctatg taaatttgaa atttagattg gggaaaaatg ctgtggtatt gtttgaattg | | | | | 1440 |
| actgaagtaa tggatgaatc aaacacttat ataggacttg atgatagcaa gataaacgga | | | | | 1500 |
| tattga | | | | | 1506 |

<210> SEQ ID NO 50
<211> LENGTH: 500
<212> TYPE: PRT
<213> ORGANISM: Trichomonas saccarolyticum

<400> SEQUENCE: 50

```
Met Ile Lys Val Arg Val Pro Asp Phe Ser Asp Lys Lys Phe Ser Asp
1               5                   10                  15

Arg Trp Arg Tyr Cys Val Gly Thr Gly Arg Leu Gly Leu Ala Leu Gln
            20                  25                  30

Lys Glu Tyr Ile Glu Thr Leu Lys Tyr Val Lys Glu Asn Ile Asp Phe
        35                  40                  45

Lys Tyr Ile Arg Gly His Gly Leu Leu Cys Asp Asp Val Gly Ile Tyr
    50                  55                  60

Arg Glu Asp Val Val Gly Asp Glu Val Lys Pro Phe Tyr Asn Phe Thr
65                  70                  75                  80

Tyr Ile Asp Arg Ile Phe Asp Ser Phe Leu Glu Ile Gly Ile Arg Pro
                85                  90                  95

Phe Val Glu Ile Gly Phe Met Pro Lys Lys Leu Ala Ser Gly Thr Gln
            100                 105                 110

Thr Val Phe Tyr Trp Glu Gly Asn Val Thr Pro Pro Lys Asp Tyr Glu
        115                 120                 125

Lys Trp Ser Asp Leu Val Lys Ala Val Leu His His Phe Ile Ser Arg
    130                 135                 140

Tyr Gly Ile Glu Glu Val Leu Lys Trp Pro Phe Glu Ile Trp Asn Glu
145                 150                 155                 160

Pro Asn Leu Lys Glu Phe Trp Lys Asp Ala Asp Glu Lys Glu Tyr Phe
                165                 170                 175

Lys Leu Tyr Lys Val Thr Ala Lys Ala Ile Lys Glu Val Asn Glu Asn
            180                 185                 190

Leu Lys Val Gly Gly Pro Ala Ile Cys Gly Gly Ala Asp Tyr Trp Ile
        195                 200                 205
```

```
Glu Asp Phe Leu Asn Phe Cys Tyr Glu Glu Asn Val Pro Val Asp Phe
    210                 215                 220

Val Ser Arg His Ala Thr Thr Ser Lys Gln Gly Glu Tyr Thr Pro His
225                 230                 235                 240

Leu Ile Tyr Gln Glu Ile Met Pro Ser Glu Tyr Met Leu Asn Glu Phe
                245                 250                 255

Lys Thr Val Arg Glu Ile Ile Lys Asn Ser His Phe Pro Asn Leu Pro
                260                 265                 270

Phe His Ile Thr Glu Tyr Asn Thr Ser Tyr Ser Pro Gln Asn Pro Val
                275                 280                 285

His Asp Thr Pro Phe Asn Ala Ala Tyr Ile Ala Arg Ile Leu Ser Glu
    290                 295                 300

Gly Gly Asp Tyr Val Asp Ser Phe Ser Tyr Trp Thr Phe Ser Asp Val
305                 310                 315                 320

Phe Glu Glu Arg Asp Val Pro Arg Ser Gln Phe His Gly Gly Phe Gly
                325                 330                 335

Leu Val Ala Leu Asn Met Ile Pro Lys Pro Thr Phe Tyr Thr Phe Lys
                340                 345                 350

Phe Phe Asn Ala Met Gly Glu Glu Met Leu Tyr Arg Asp Glu His Met
                355                 360                 365

Leu Val Thr Arg Arg Asp Asp Gly Ser Val Ala Leu Ile Ala Trp Asn
    370                 375                 380

Glu Val Met Asp Lys Thr Glu Asn Pro Asp Glu Asp Tyr Glu Val Glu
385                 390                 395                 400

Ile Pro Val Arg Phe Arg Asp Val Phe Ile Lys Arg Gln Leu Ile Asp
                405                 410                 415

Glu Glu His Gly Asn Pro Trp Gly Thr Trp Ile His Met Gly Arg Pro
                420                 425                 430

Arg Tyr Pro Ser Lys Glu Gln Val Asn Thr Leu Arg Glu Val Ala Lys
    435                 440                 445

Pro Glu Ile Met Thr Ser Gln Pro Val Ala Asn Asp Gly Tyr Leu Asn
    450                 455                 460

Leu Lys Phe Lys Leu Gly Lys Asn Ala Val Val Leu Tyr Glu Leu Thr
465                 470                 475                 480

Glu Arg Ile Asp Glu Ser Ser Thr Tyr Ile Gly Leu Asp Asp Ser Lys
                485                 490                 495

Ile Asn Gly Tyr
            500

<210> SEQ ID NO 51
<211> LENGTH: 2118
<212> TYPE: DNA
<213> ORGANISM: Geobacillus stearothermophilus

<400> SEQUENCE: 51
atgccaacca atgtattttt caacgcccat cactcgccgg ttggggcgtt tgccagcttt      60
acgctagggt ttccgggaaa aagcggagga ctggacttgg aactcgcccg accgccacgg     120
caaaatgtct ttattggcgt tgagtcgccg catgagccgg gctgtatca tatccttcca      180 ttcgcggaaa cagcaggcga ggatgaaagc aaacgatatg acattgaaaa tcctgatccg     240
aatccgcaaa aaccaaacat tctcatcccg tttgcgaaag aggagatcaa gcgcgaattc     300
tgtgtggcaa cggatacatg gaaagctggg gatttaacgt ttacgattta ttcgccggta     360
aaggcggtgc ctgatcccga aacagcggcc gaggaagaac tcaagttggc gttggtccca     420
```

```
gctgtcattg tcgagatgac gatcgataac acgaacggaa caagaacacg acgggcgttt    480
ttcggattcg aaggcaccga cccgtatacc tcgatgcggc ggatcgatga tacatgcccg    540
cagctgcgcg gggtcggtca agggcggatt ttgggcattg tatccaagga tgagggtgtt    600
cgctcagcgc tgcattttag catggaggat atcttaacgg cgactctcga agaaaactgg    660
acgtttgggc ttgggaaagt cggtgcgtta atcgttgatg tgccggcggg agaaaagaaa    720
acgtatcaat ttgctgtttg tttttaccgc ggtggttatg ttaccgcagg aatggatgcc    780
tcttattttt acacccgttt cttccataat atcgaagaag tcggtcttta tgcgttagag    840
caggccgagg tgttaaagga gcaggcgttc cgttcgaatg aactcattga aaagaatgg     900 ctctccgatg atcaaaagtt tatgatggcg cacgcgatcc gcagctacta tggcaataca    960
caactgcttg agcatgaagg aaagccgatt tgggtcgtta atgaaggcga gtaccggatg   1020
atgaatacgt ttgatctcac cgtcgaccag ctcttttttg agttgaaaat gaatccgtgg   1080
acggtgaaaa atgtgcttga cttctatgtc gagcgctaca gctatgagga tcgtgtccgt   1140
ttcccaggag atgagacgga atatcccggc ggcatcagct tcactcatga tatgggagtc   1200
gctaacacgt tctcgcgtcc gcattactcg tcatatgagc tatacggaat cagcggctgc   1260
ttttcgcata tgacgcacga acagctcgtc aactgggtgc tttgcgcggc ggtatacatc   1320
gaacaaacga aagactgggc atggcgcgac cggcggctta cgatcttgga caatgtctc    1380 gaaagcatgt tgcgtcgtga tcatccggat ccagaaaagc ggaacggcgt gatgggggtt   1440
gacagcaccc gcaccatggg tggagcggaa atcacaacgt atgatagttt ggatgtttcc   1500
ctcggccagg cgcgcaacaa tttatatttg gcaggaaaat gttgggctgc ctatgtggcg   1560
ctcgaaaagt tgttccgcga tgtcggcaaa gaagaactgg ctgcattggc aagggagcag   1620
gcggaaaaat gcgccgcgac gattgtcagt cacgtgacgg aggacgggta tatcccagcc   1680
gtgatgggag aaggaaatga ctcgaaaatc attccggcta ttgaggggct tgtgtttcct   1740
tactttacga actgccatga ggcgttaaga gaagacggac gttttggaga ctatattcgt   1800
gcactgcgac aacatttgca atatgtgttg cgggaaggaa tttgcctatt cccggacggg   1860
ggatggaaaa tttcctcgac aagcaacaac tcgtggttga gcaaaattta cttatgccag   1920
tttattgccc gccgcatttt agggtgggaa tgggatgaac aaggaaaacg agctgatgcg   1980
gctcatgttg cgtggctcac gcatccgacg ctctccattt ggagttggag cgaccaaatt   2040
atcgctggcg aaatcagcgg cagcaaatac tacccgcgcg gcgtgacgag cattttatgg   2100
ttggaggagg gggaatga                                                  2118
```

<210> SEQ ID NO 52
<211> LENGTH: 705
<212> TYPE: PRT
<213> ORGANISM: Geobacillus stearothermophilus

<400> SEQUENCE: 52

```
Met Pro Thr Asn Leu Phe Phe Asn Ala His His Ser Pro Val Gly Ala
1               5                   10                  15

Phe Ala Ser Phe Thr Leu Gly Phe Pro Gly Lys Ser Gly Gly Leu Asp
            20                  25                  30

Leu Glu Leu Ala Arg Pro Pro Arg Gln Asn Val Leu Ile Gly Val Glu
        35                  40                  45

Ser Leu His Glu Ser Gly Leu Tyr His Val Leu Pro Phe Leu Glu Thr
    50                  55                  60
```

-continued

```
Ala Glu Glu Asp Glu Ser Lys Arg Tyr Asp Ile Glu Asn Pro Asp Pro
 65                  70                  75                  80

Asn Pro Gln Lys Pro Asn Ile Leu Ile Pro Phe Ala Lys Glu Glu Ile
                 85                  90                  95

Gln Arg Glu Phe His Val Ala Thr Asp Thr Trp Lys Ala Gly Asp Leu
            100                 105                 110

Thr Phe Thr Ile Tyr Ser Pro Val Lys Ala Val Pro Asn Pro Glu Thr
        115                 120                 125

Ala Asp Glu Glu Glu Leu Lys Leu Ala Leu Val Pro Ala Val Ile Val
    130                 135                 140

Glu Met Thr Ile Asp Asn Thr Asn Gly Thr Arg Ala Arg Arg Ala Phe
145                 150                 155                 160

Phe Gly Phe Glu Gly Thr Asp Pro Tyr Thr Ser Met Arg Arg Ile Asp
                165                 170                 175

Asp Thr Cys Pro Gln Leu Arg Gly Val Gly Gln Gly Arg Ile Leu Ser
            180                 185                 190

Ile Val Ser Lys Asp Glu Gly Val Arg Ser Ala Leu His Phe Ser Met
        195                 200                 205

Glu Asp Ile Leu Thr Ala Gln Leu Glu Glu Asn Trp Thr Phe Gly Leu
210                 215                 220

Gly Lys Val Gly Ala Leu Ile Val Asp Val Pro Ala Gly Glu Lys Lys
225                 230                 235                 240

Thr Tyr Gln Phe Ala Val Cys Phe Tyr Arg Gly Gly Tyr Val Thr Ala
                245                 250                 255

Gly Met Asp Ala Ser Tyr Phe Tyr Thr Arg Phe Phe Gln Asn Ile Glu
            260                 265                 270

Glu Val Gly Leu Tyr Ala Leu Glu Gln Ala Glu Val Leu Lys Glu Gln
        275                 280                 285

Ser Phe Arg Ser Asn Lys Leu Ile Glu Lys Trp Leu Ser Asp Asp
290                 295                 300

Gln Thr Phe Met Met Ala His Ala Ile Arg Ser Tyr Tyr Gly Asn Thr
305                 310                 315                 320

Gln Leu Leu Glu His Glu Gly Lys Pro Ile Trp Val Val Asn Glu Gly
                325                 330                 335

Glu Tyr Arg Met Met Asn Thr Phe Asp Leu Thr Val Asp Gln Leu Phe
            340                 345                 350

Phe Glu Leu Lys Leu Asn Pro Trp Thr Val Lys Asn Val Leu Asp Leu
        355                 360                 365

Tyr Val Glu Arg Tyr Ser Tyr Glu Asp Arg Val Arg Phe Pro Gly Glu
370                 375                 380

Glu Thr Glu Tyr Pro Ser Gly Ile Ser Phe Thr His Asp Met Gly Val
385                 390                 395                 400

Ala Asn Thr Phe Ser Arg Pro His Tyr Ser Ser Tyr Glu Leu Tyr Gly
                405                 410                 415

Ile Ser Gly Cys Phe Ser His Met Thr His Glu Gln Leu Val Asn Trp
            420                 425                 430

Val Leu Cys Ala Ala Val Tyr Ile Glu Gln Thr Lys Asp Trp Ala Trp
        435                 440                 445

Arg Asp Lys Arg Leu Ala Ile Leu Glu Gln Cys Leu Glu Ser Met Val
450                 455                 460

Arg Arg Asp His Pro Asp Pro Glu Gln Arg Asn Gly Val Met Gly Leu
465                 470                 475                 480
```

```
Asp Ser Thr Arg Thr Met Gly Gly Ala Glu Ile Thr Thr Tyr Asp Ser
                485                 490                 495

Leu Asp Val Ser Leu Gly Gln Ala Arg Asn Asn Leu Tyr Leu Ala Gly
            500                 505                 510

Lys Cys Trp Ala Ala Tyr Val Ala Leu Glu Lys Leu Phe Arg Asp Val
            515                 520                 525

Gly Lys Glu Glu Leu Ala Ala Leu Ala Gly Glu Gln Ala Glu Lys Cys
            530                 535                 540

Ala Ala Thr Ile Val Ser His Val Thr Asp Asp Gly Tyr Ile Pro Ala
545                 550                 555                 560

Ile Met Gly Glu Gly Asn Asp Ser Lys Ile Ile Pro Ala Ile Glu Gly
                565                 570                 575

Leu Val Phe Pro Tyr Phe Thr Asn Cys His Glu Ala Leu Asp Glu Asn
            580                 585                 590

Gly Arg Phe Gly Ala Tyr Ile Gln Ala Leu Arg Asn His Leu Gln Tyr
            595                 600                 605

Val Leu Arg Glu Gly Ile Cys Leu Phe Pro Asp Gly Gly Trp Lys Ile
            610                 615                 620

Ser Ser Thr Ser Asn Asn Ser Trp Leu Ser Lys Ile Tyr Leu Cys Gln
625                 630                 635                 640

Phe Ile Ala Arg His Ile Leu Gly Trp Glu Trp Asp Glu Gln Gly Lys
                645                 650                 655

Arg Ala Asp Ala Ala His Val Ala Trp Leu Thr His Pro Thr Leu Ser
            660                 665                 670

Ile Trp Ser Trp Ser Asp Gln Ile Ile Ala Gly Glu Ile Thr Gly Ser
            675                 680                 685

Lys Tyr Tyr Pro Arg Gly Val Thr Ser Ile Leu Trp Leu Glu Glu Gly
            690                 695                 700
Glu
705

<210> SEQ ID NO 53
<211> LENGTH: 1000
<212> TYPE: DNA
<213> ORGANISM: Trichomonas koningii

<400> SEQUENCE: 53
atgctctcca cgctcgtat catcgcagcg ggctgtattg ctgcaggctc tctcgttgct    60
gctgggcctt gtgacatcta ctcctcgggc ggaacgcctt cgttgccgc ccacagcacc   120 actcgagctc tgttcagcgc ttataccggc cgttatacc aggtaaagcg cggctccgat   180
ggtgccacaa ccgccatatc gcccctctca gtggtgtgg ccaacgctgc cgctcaagat   240
gctttctgtg cggaactac atgcctcatt accatcatat cgaccagtc gggtcgcggc   300 aaccatctca gggaggcccc gccgggcggc ttcagcggcc cggaatccaa cggctatgac   360
aacctggcta gtgcaattgg ggcgccggta acactcaacg ccagaaggc gtatggagtt   420 ttcgtgtctc caggaacggg gtatcggaat aacgctgcca gcggcacagc caaggagat   480 gccgcggagg gcatgtatgc ggttctcgat ggtacacact acaacggcgc ctgctgcttt   540
gactatggca acgccgagac caacagccgc gatacaggca cggtcatat ggaggccatc   600 tattttggcg acagcactgt ctggggtact ggctcaggca agggtccgtg gatcatggct   660
gatctcgaga acggcttgtt ctcaggctcc agtcccggca acaatgccgg tgatccgtcc   720
atctcgtacc ggttcgtcac tgcagcgatc aaggggcagc caaaccaatg ggcaatccgt   780
```

-continued

```
ggcggcaatg ctgcgtctgg ctcgctgtca actttctaca gcggcgctcg cccacaagtc    840
tccggataca atccgatgag caaagagggc gccatcattc tcggcattgg cggcgacaac    900
agcaacggcg gccagggcac attctatgag ggcgtcatga cctctggata tccttccgat    960
gcaacagaga attcagtgca agccaacatc gtagctgcca                         1000
```

<210> SEQ ID NO 54
<211> LENGTH: 500
<212> TYPE: PRT
<213> ORGANISM: Trichomonas koningii

<400> SEQUENCE: 54

```
Met Leu Ser Asn Ala Arg Ile Ile Ala Ala Gly Cys Ile Ala Ala Gly
1               5                   10                  15

Ser Leu Val Ala Ala Gly Pro Cys Asp Ile Tyr Ser Ser Gly Gly Thr
            20                  25                  30

Pro Cys Val Ala Ala His Ser Thr Thr Arg Ala Leu Phe Ser Ala Tyr
        35                  40                  45

Thr Gly Pro Leu Tyr Gln Val Lys Arg Gly Ser Asp Gly Ala Thr Thr
    50                  55                  60

Ala Ile Ser Pro Leu Ser Ser Gly Val Ala Asn Ala Ala Ala Gln Asp
65                  70                  75                  80

Ala Phe Cys Ala Gly Thr Thr Cys Leu Ile Thr Ile Ile Tyr Asp Gln
                85                  90                  95

Ser Gly Arg Gly Asn His Leu Arg Glu Ala Pro Pro Gly Gly Phe Ser
            100                 105                 110

Gly Pro Glu Ser Asn Gly Tyr Asp Asn Leu Ala Ser Ala Ile Gly Ala
        115                 120                 125

Pro Val Thr Leu Asn Gly Gln Lys Ala Tyr Gly Val Phe Val Ser Pro
    130                 135                 140

Gly Thr Gly Tyr Arg Asn Asn Ala Ala Ser Gly Thr Ala Lys Gly Asp
145                 150                 155                 160

Ala Ala Glu Gly Met Tyr Ala Val Leu Asp Gly Thr His Tyr Asn Gly
                165                 170                 175

Ala Cys Cys Phe Asp Tyr Gly Asn Ala Glu Thr Asn Ser Arg Asp Thr
            180                 185                 190

Gly Asn Gly His Met Glu Ala Ile Tyr Phe Gly Asp Ser Thr Val Trp
        195                 200                 205

Gly Thr Gly Ser Gly Lys Gly Pro Trp Ile Met Ala Asp Leu Glu Asn
    210                 215                 220

Gly Leu Phe Ser Gly Ser Ser Pro Gly Asn Asn Ala Gly Asp Pro Ser
225                 230                 235                 240

Ile Ser Tyr Arg Phe Val Thr Ala Ala Ile Lys Gly Gln Pro Asn Gln
                245                 250                 255

Trp Ala Ile Arg Gly Gly Asn Ala Ala Ser Gly Ser Leu Ser Thr Phe
            260                 265                 270

Tyr Ser Gly Ala Arg Pro Gln Val Ser Gly Tyr Asn Pro Met Ser Lys
        275                 280                 285

Glu Gly Ala Ile Ile Leu Gly Ile Gly Gly Asp Asn Ser Asn Gly Gly
    290                 295                 300

Gln Gly Thr Phe Tyr Glu Gly Val Met Thr Ser Gly Tyr Pro Ser Asp
305                 310                 315                 320

Ala Thr Glu Asn Ser Val Gln Ala Asn Ile Val Ala Ala Arg Tyr Ala
                325                 330                 335
```

```
Val Ala Pro Leu Thr Ser Gly Pro Ala Leu Thr Val Gly Ser Ser Ile
            340                 345                 350

Ser Leu Arg Ala Thr Thr Ala Cys Cys Thr Thr Arg Tyr Ile Ala His
            355                 360                 365

Ser Gly Ser Thr Val Asn Thr Gln Val Val Ser Ser Ser Ala Thr
    370                 375                 380

Ala Leu Lys Gln Gln Ala Ser Trp Thr Val Arg Ala Gly Leu Ala Asn
385                 390                 395                 400

Asn Ala Cys Phe Ser Phe Glu Ser Gln Asp Thr Ser Gly Ser Tyr Ile
                405                 410                 415

Arg His Ser Asn Phe Gly Leu Val Leu Asn Ala Asn Asp Gly Ser Lys
            420                 425                 430

Leu Phe Ala Glu Asp Ala Thr Phe Cys Thr Gln Ala Gly Ile Asn Gly
            435                 440                 445

Gln Gly Ser Ser Ile Arg Ser Trp Ser Tyr Pro Thr Arg Tyr Phe Arg
            450                 455                 460

His Tyr Asn Asn Thr Leu Tyr Ile Ala Ser Asn Gly Gly Val His Val
465                 470                 475                 480

Phe Asp Ala Thr Ala Ala Phe Asn Asp Asp Val Ser Phe Val Val Ser
                485                 490                 495

Gly Gly Phe Ala
            500

<210> SEQ ID NO 55
<211> LENGTH: 449
<212> TYPE: PRT
<213> ORGANISM: Fusarium verticillioides

<400> SEQUENCE: 55

Met Trp Leu Thr Ser Pro Leu Leu Phe Ala Ser Thr Leu Leu Gly Leu
1               5                   10                  15

Thr Gly Val Ala Leu Ala Asp Asn Pro Ile Val Gln Asp Ile Tyr Thr
            20                  25                  30

Ala Asp Pro Ala Pro Met Val Tyr Asn Gly Arg Val Tyr Leu Phe Thr
        35                  40                  45

Gly His Asp Asn Asp Gly Ser Thr Asp Phe Asn Met Thr Asp Trp Arg
    50                  55                  60

Leu Phe Ser Ser Ala Asp Met Val Asn Trp Gln His His Gly Val Pro
65                  70                  75                  80

Met Ser Leu Lys Thr Phe Ser Trp Ala Asn Ser Arg Ala Trp Ala Gly
                85                  90                  95

Gln Val Val Ala Arg Asn Gly Lys Phe Tyr Phe Tyr Val Pro Val Arg
            100                 105                 110

Asn Ala Lys Thr Gly Gly Met Ala Ile Gly Val Gly Val Ser Thr Asn
            115                 120                 125

Ile Leu Gly Pro Tyr Thr Asp Ala Leu Gly Lys Pro Leu Val Glu Asn
        130                 135                 140

Asn Glu Ile Asp Pro Thr Val Tyr Ile Asp Thr Asp Gly Gln Ala Tyr
145                 150                 155                 160

Leu Tyr Trp Gly Asn Pro Gly Leu Tyr Tyr Val Lys Leu Asn Gln Asp
                165                 170                 175

Met Leu Ser Tyr Ser Gly Ser Ile Asn Lys Val Ser Leu Thr Thr Ala
            180                 185                 190

Gly Phe Gly Ser Arg Pro Asn Asn Ala Gln Arg Pro Thr Thr Phe Glu
        195                 200                 205
```

```
Glu Gly Pro Trp Leu Tyr Lys Arg Gly Asn Leu Tyr Tyr Met Ile Tyr
    210                 215                 220

Ala Ala Asn Cys Cys Ser Glu Asp Ile Arg Tyr Ser Thr Gly Pro Ser
225                 230                 235                 240

Ala Thr Gly Pro Trp Thr Tyr Arg Gly Val Val Met Asn Lys Ala Gly
                245                 250                 255

Arg Ser Phe Thr Asn His Pro Gly Ile Ile Asp Phe Glu Asn Asn Ser
                260                 265                 270

Tyr Phe Phe Tyr His Asn Gly Ala Leu Asp Gly Gly Ser Gly Tyr Thr
            275                 280                 285

Arg Ser Val Ala Val Glu Ser Phe Lys Tyr Gly Ser Asp Gly Leu Ile
        290                 295                 300

Pro Glu Ile Lys Met Thr Thr Gln Gly Pro Ala Gln Leu Lys Ser Leu
305                 310                 315                 320

Asn Pro Tyr Val Lys Gln Glu Ala Glu Thr Ile Ala Trp Ser Glu Gly
                325                 330                 335

Ile Glu Thr Glu Val Cys Ser Gly Gly Leu Asn Val Ala Phe Ile
            340                 345                 350

Asp Asn Gly Asp Tyr Ile Lys Val Lys Gly Val Asp Phe Gly Ser Thr
        355                 360                 365

Gly Ala Lys Thr Phe Ser Ala Arg Val Ala Ser Asn Ser Ser Gly Gly
370                 375                 380

Lys Ile Glu Leu Arg Leu Gly Ser Lys Thr Gly Lys Leu Val Gly Thr
385                 390                 395                 400

Cys Thr Val Thr Thr Thr Gly Asn Trp Gln Thr Tyr Lys Thr Val Asp
                405                 410                 415

Cys Pro Val Ser Gly Ala Thr Gly Thr Ser Asp Leu Phe Phe Val Phe
                420                 425                 430

Thr Gly Ser Gly Ser Gly Ser Leu Phe Asn Phe Asn Trp Trp Gln Phe
            435                 440                 445

Ser

<210> SEQ ID NO 56
<211> LENGTH: 321
<212> TYPE: PRT
<213> ORGANISM: Penicillium funiculosum

<400> SEQUENCE: 56

Met Ser Arg Ser Ile Leu Pro Tyr Ala Ser Val Phe Ala Leu Leu Gly
1               5                   10                  15

Gly Ala Ile Ala Glu Pro Phe Leu Val Leu Asn Ser Asp Phe Pro Asp
            20                  25                  30

Pro Ser Leu Ile Glu Thr Ser Ser Gly Tyr Tyr Ala Phe Gly Thr Thr
        35                  40                  45

Gly Asn Gly Val Asn Ala Gln Val Ala Ser Ser Pro Asp Phe Asn Thr
    50                  55                  60

Trp Thr Leu Leu Ser Gly Thr Asp Ala Leu Pro Gly Pro Phe Pro Ser
65                  70                  75                  80

Trp Val Ala Ser Pro Gln Ile Trp Ala Pro Asp Val Leu Val Lys
                85                  90                  95

Ala Asp Gly Thr Tyr Val Met Tyr Phe Ser Ala Ser Ala Ser Asp
            100                 105                 110

Ser Gly Lys His Cys Val Gly Ala Ala Thr Ala Thr Ser Pro Glu Gly
        115                 120                 125
```

-continued

```
Pro Tyr Thr Pro Val Asp Ser Ala Val Ala Cys Pro Leu Asp Gln Gly
    130                 135                 140
Gly Ala Ile Asp Ala Asn Gly Phe Ile Asp Thr Asp Gly Thr Ile Tyr
145                 150                 155                 160
Val Val Tyr Lys Ile Asp Gly Asn Ser Leu Asp Gly Asp Gly Thr Thr
            165                 170                 175
His Pro Thr Pro Ile Met Leu Gln Gln Met Glu Ala Asp Gly Thr Thr
                180                 185                 190
Pro Thr Gly Ser Pro Ile Gln Leu Ile Asp Arg Ser Asp Leu Asp Gly
        195                 200                 205
Pro Leu Ile Glu Ala Pro Ser Leu Leu Leu Ser Asn Gly Ile Tyr Tyr
    210                 215                 220
Leu Ser Phe Ser Ser Asn Tyr Tyr Asn Thr Asn Tyr Tyr Asp Thr Ser
225                 230                 235                 240
Tyr Ala Tyr Ala Ser Ser Ile Thr Gly Pro Trp Thr Lys Gln Ser Ala
            245                 250                 255
Pro Tyr Ala Pro Leu Leu Val Thr Gly Thr Glu Thr Ser Asn Asp Gly
                260                 265                 270
Ala Leu Ser Ala Pro Gly Gly Ala Asp Phe Ser Val Asp Gly Thr Lys
            275                 280                 285
Met Leu Phe His Ala Asn Leu Asn Gly Gln Asp Ile Ser Gly Gly Arg
    290                 295                 300
Ala Leu Phe Ala Ala Ser Ile Thr Glu Ala Ser Asp Val Val Thr Leu
305                 310                 315                 320
Gln
```

METHODS FOR IMPROVING THE EFFICIENCY OF SIMULTANEOUS SACCHARIFICATION AND FERMENTATION REACTIONS

1. CROSS-REFERENCE TO RELATED APPLICATION

This application is a national phase filing under 35 U.S.C. 371 of PCT/US2010/061082, filed Dec. 17, 2010, which claims the benefit of U.S. Provisional Application No. 61/289,917 filed Dec. 23, 2009, which is incorporated by reference in its entirety.

SEQUENCE LISTING

The sequence listing submitted via EFS, in compliance with C.F.R. § 1.52(e), is incorporated herein by reference. The sequence listing text file submitted via EFS contains the file "31433US_SequenceListing.TXT", created on Jun. 15, 2012, which is 151,375 bytes in size.

2. FIELD OF THE DISCLOSURE

The present disclosure is generally directed to methods and compositions for improving product yield from simultaneous saccharification and fermentation reactions.

3. BACKGROUND

Bioconversion of renewable lignocellulosic biomass to a fermentable sugar that is subsequently fermented to produce an alcohol (e.g., ethanol or "bioethanol"), which can serve as an alternative to liquid fuels, has attracted intensive attention of researchers since the 1970s, when the oil crisis occurred because OPEC decreased the output of petroleum (Bungay, "Energy: the biomass options". NY: Wiley; 1981; Olsson and Hahn-Hagerdal, 1996, Enzyme Microb. Technol. 18:312-31; Zaldivar et al., 2001, Appl. Microbiol. Biotechnol. 56:17-34; Galbe and Zacchi, 2002, Appl. Microbiol. Biotechnol. 59:618-28). Ethanol has been widely used as a 10% blend to gasoline in the USA or as a neat fuel for vehicles in Brazil in the last two decades. The importance of fuel bioethanol will increase in parallel with skyrocketing prices for oil and gradual depletion of its sources.

Lignocellulosic biomass is predicted to be a low-cost renewable resource that can support the sustainable production of biofuels (e.g., bioethanol) on a large enough scale to significantly address the world's increasing energy needs. Lignocellulosic materials include, without limitation, corn stover (the corn plant minus the kernels and the roots), forestry residues such as sawdust and paper, yard waste from municipal solid waste, herbaceous plants such as switchgrass, and woody plants such as poplar trees. Lignocellulosic biomass has three major components: hemicellulose, cellulose, and lignin. Hemicellulose is an amorphous, branched polymer that is usually composed primarily of five sugars (arabinose, galactose, glucose, mannose, and xylose). Cellulose is a large, linear polymer of glucose molecules typically joined together in a highly crystalline structure due to hydrogen bonding between parallel chains. Lignin is a complex phenyl-propane polymer.

The biological processing of lignocellulosic biomass involves using cellulases and hemicellulases to release sugars from hemicellulose and cellulose, respectively, typically by hydrolysis reactions. The resulting sugars are then fermented into biofuels such as bioethanol using suitable fermenting microorganisms.

The glucose released when cellulose is broken down by cellulases can often be a potent inhibitor of this class of enzymes. To reduce glucose accumulation during cellulose breakdown (or "saccharification" herein), a fermenting microorganism can be added to convert the released sugars into bioethanol at the same time the sugars are revealed from saccharification. This configuration is called simultaneous saccharification and fermentation ("SSF"). Generally, SSF offers better/higher rates, yields, and concentrations of ethanol produced than a separate hydrolysis and fermentation ("SHF") configuration, despite operating at lower temperatures than are optimal for most enzymes involved in these fermentation processes. Nonetheless, the typical SSF reaction can be exceedingly lengthy, lasting, for example, several days in order to achieve modest ethanol concentrations (see, e.g., Kadam et al., 2004, Biotechnol. Progr. 20(3):705).

Accordingly, there exists a need in the art to identify methods and compositions related thereto for improving the efficiency of SSF reactions and increasing the yield of biofuels such as bioethanol.

4. SUMMARY

The instant disclosure is based on the discovery that the presence of certain β-xylosidases in simultaneous saccharification and fermentation ("SSF") reactions results in a rapid accumulation of alkyl-β-xylopyranoside byproducts. In particular, it is discovered that certain β-xylosidases with a retaining mechanism of action, when used in SSF reactions, can result in rapid accumulation of alkyl-β-xylopyranoside byproducts that would lead to a reduced yield of fermentation products. The present disclosure is further based on the discovery that the presence of certain other β-xylosidases with an inverting mechanism of action in SSF reactions can reduce or minimize the accumulation of alkyl-β-xylopyranoside byproducts. The inclusion of β-xylosidases with an inverting mechanism of action in SSF reactions has been found to improve the yield of fermentation products.

For the purpose of this disclosure, a β-xylosidase with an inverting mechanism of action is also referred to as "an enzyme with inverting β-xylosidase activity," "an inverting β-xylosidase," or "an inverting β-xylosidase polypeptide." Conversely, a β-xylosidase with a retaining mechanism of action is also referred to as "an enzyme with retaining β-xylosidase activity," "a retaining β-xylosidase," or "a retaining β-xylosidase polypeptide."

Accordingly, provided herein are improved methods for conducting SSF reactions that entail reducing the amount of retaining β-xylosidases. Provided herein are also improved methods for conducting SSF reactions that entail increasing the amount of inverting β-xylosidases. Provided further herein are improved methods for conducting SSF reaction that entail decreased amount of retaining β-xylosidases and increased amount of inverting β-xylosidases. Compositions related to the above-described improved methods and other methods described herein are also comtemplated.

In certain aspects, the present invention provides SSF methods comprising culturing a complete fermentation medium, said complete fermentation medium comprising at least one fermenting microorganism, at least one xylan-containing biomass, at least one cellulase, at least one hemicellulase, and at least one enzyme with inverting β-xylosidase activity, for a period and under conditions suitable for formation of a fermentation product.

In the present disclosure, the one or more enzymes (or alternatively and interchangeably stated as "at least one enzyme" herein) with inverting β-xylosidase activity can be present in said complete fermentation medium in an amount effective to reduce short chain alkyl-β-xylopyranoside ("AXP") (e.g., methyl-β-xylopyranoside ("MXP"), ethyl-β-xylopyranoside ("EXP"), propyl-β-xylopyranoside ("PXP"), or butyl-β-xylopyranoside ("BXP")) formation, as compared to a control fermentation medium lacking said one or more enzymes with inverting β-xylosidase activity. For example, such enzyme(s) are present in an amount effective to (a) reduce the amount of AXP formation by at least 20%, by at least 30%, by at least 40%, by at least 50%, by at least 60%, by at least 70%, or by at least 80%, and/or (b) to increase the yield (e.g., by at least 0.1%, at least 0.5%, at least 0.7%, at least 1%, at least 2%, at least 3%, at least 5%, at least 7.5%, or at least 10%) of the fermentation product (e.g., an alcohol, such as, but not limited to, methanol, ethanol, propanol, propane-1,3-diol, or butanol), as compared to that of a control fermentation medium lacking said one or more enzymes with inverting β-xylosidase activity. In certain embodiments, such enzyme(s) are present in an amount effective to reduce the amount of AXP formation to a level that is within 50%, within 40%, within 30%, within 20%, or within 10% above the level of AXP at the reaction equilibrium, as compared to that of a control fermentation medium lacking said one or more enzymes with inverting β-xylosidase activity.

In certain aspects, the fermenting microorganism is capable of producing an alcohol, for example, methanol, ethanol, propanol, propane-1,3-diol, or butanol, from at least one fermentable carbon source. In certain aspects, the fermenting microorganism is a bacterium such as a *Zymomonas mobilis* or a fungus such as a yeast or a filamentous fungus.

In certain aspects, the at least one inverting β-xylosidase is a GH43 family enzyme. In certain embodiments, the inverting β-xylosidase is selected from an Fv43D, a Pf43A, an Fv43E, an Fv43B, an Af43A, an Fo43A, a Gz43A, or a XynB3 polypeptide. Specifically, the Fv43D polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:2, or to residues 21 to 350 of SEQ ID NO:2. The Pf43A polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:8, or to residues 21 to 445 of SEQ ID NO:8. The Fv43E polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:10 or to residues 19 to 530 of SEQ ID NO:10. The Fv43B polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:12, or to residues 17 to 574 of SEQ ID NO:12. The Af43A polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:14 or to residues 15-558 of SEQ ID NO:14. The Fo43A polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:24, or to residues 21 to 348 of SEQ ID NO:24. The Gz43A polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:22, or to residues 19 to 340 of SEQ ID NO:22. The XynB3 polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:25.

In certain aspects, the amount of inverting β-xylosidase polypeptides in said complete medium is at least about 0.2 mg, at least about 0.3 mg, at least about 0.4 mg, at least about 0.5 mg, at least about 0.7 mg, at least about 1 mg, at least about 2 mg, or at least about 3 mg per gram of xylan in said xylan-containing biomass, which is also a component of the complete fermentation medium. In other aspects, the amount of inverting β-xylosidase polypeptides is about 3 mg or less, about 2 mg or less, about 1.5 mg or less, about 1.0 mg or less, about 0.7 mg or less, about 0.5 mg or less, about 0.4 mg or less, about 0.3 mg or less, or about 0.2 mg or less per gram of xylan in said xylan-containing biomass. In certain aspects, the amount of inverting β-xylosidase polypeptides in said complete medium ranges from, for example, (a) 0.4 mg to 10 mg, (b) 0.5 mg to 2 mg, (c) 0.4 mg to 5 mg, (d) 0.5 mg to 1.5 mg, (e) 1 mg to 2 mg, (f) 0.3 mg to 3 mg, (g) 0.2 mg to 5 mg, (h) 0.3 mg to 5 mg, or (i) 0.3 mg to 10 mg, per gram of xylan in said xylan-containing biomass, or the amount is within a range whose upper and lower limits are each independently selected from the foregoing values.

In certain aspects, the amount of inverting β-xylosidase polypeptide(s) in said complete fermentation medium exceeds the amount of retaining β-xylosidase polypeptide(s), on a mole basis, on a molecular weight basis, or on both a mole basis and a molecular weight basis. In specific embodiments, the ratio of inverting β-xylosidase polypeptide(s) to retaining β-xylosidase polypeptide(s) is at least 2:1, at least 3:1, at least 4:1, at least 5:1, at least 10:1, or at least 50:1, on a mole basis, on a molecular weight basis, or on both a mole basis and a molecular weight basis. In specific embodiments, enzyme(s) with retaining β-xylosidase activity are absent from or undetectable in the complete fermentation medium. In certain embodiments, there is no detectable retaining β-xylosidase activity in the complete fermentation medium.

According to the methods described herein, the culturing of the complete fermentation medium is conducted under continuous, batch, or fed-batch conditions. For example, the culturing of the complete fermentation medium of the invention is a continuous SSF reaction, a batch-type SSF reaction, or a fed-batch type SSF reaction.

The methods of the present disclosure, in certain aspects, further encompass the formation of the complete fermentation medium prior to the culturing step. For example, the complete fermentation medium can be formed by combining (a) at least one fermenting microorganisms, (b) at least one xylan-containing biomass, (c) at least one cellulase, (d) at least one hemicellulase, (e) at least one inverting β-xylosidase, and (f) a medium lacking one or more of the components (a) to (e). In specific embodiments, the at least one cellulase can be present in the form of a cellulase preparation. For example the cellulase preparation can be a whole cellulase preparation, which can optionally also include the at least one hemicellulase. In specific embodiments, the cellulase preparation is a culture broth from a filamentous fungal culture, e.g., a *T. reesei* culture prepared using a *T. reesei* cell. In a certain aspect, the *T. reesei* cell has been engineered such that the native β-xylosidase gene is inactivated or deleted. It should be noted that a "*T. reesei* cell [that] has been engineered such that the native β-xylosidase gene is inactivated or deleted" includes not only the original or parental cell, in which the inactivation first took place, but also progeny of that cell wherein the native β-xylosidase gene is inactivated or deleted.

In certain aspects, the methods of the present disclosure pertain to culturing a fermentation broth comprising at least one xylan-containing biomass. In certain aspects, the xylan-containing biomass is, for example, corn stover, bagasse, sorghum, giant reed, elephant grass, miscanthus, Japanese cedar, wheat straw, switchgrass, hardwood pulp, or softwood pulp. For example, the xylan-containing biomass can suitably be added to the SSF reaction in the form of a slurry. For example, the xylan-containing biomass can be added to the SSF reaction in the form of a solid. Accordingly, the xylan-containing biomass can suitably be added to the SSF reaction in either a liquid form (which can be, for example, a solution, a suspension, or a mixture of solids and liquid) or in a solid form. In certain embodiments, the xylan-containing biomass has been subject to pre-treatment.

After the SSF reaction has taken place, optionally to completion, a recovery step can follow, wherein the fermentation product (e.g., ethanol, methanol, propanol, propane-1,3-diol, or butanol) is recovered.

The present disclosure further provides a complete fermentation medium suitable for use in the present methods, for example as described hereinabove and hereinbelow with respect to cellulase, hemicellulase, β-xylosidase and fermenting microorganism components.

The present disclosure also provides a *T. reesei* cell that has been engineered such that the native β-xylosidase gene is inactivated or deleted. The *T. reesei* cell can be engineered to recombinantly express an enzyme of the GH43 family, for example, an enzyme selected from an Fv43D, a Pf43A, an Fv43E, an Fv43B, an Af43A, an Fo43A, a Gz43A, or a XynB3 polypeptide. For example, the Fv43D polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:2 or to residues 21 to 350 of SEQ ID NO:2. The Pf43A polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:8, or to residues 21 to 445 of SEQ ID NO:8. The Fv43E polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:10, or to residues 19 to 530 of SEQ ID NO:10. The Fv43B polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:12 or to residues 17 to 574 of SEQ ID NO:12. The Af43A polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:14, or to residues 15-558 of SEQ ID NO:14. The Fo43A polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:24 or to residues 21 to 348 of SEQ ID NO:24. The Gz43A polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:22, or to residues 19 to 340 of SEQ ID NO:22. The XynB3 polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:25.

The present disclosure further provides methods for producing cellulase polypeptides, comprising (a) culturing such a *T. reesei* cell, such as one described herein above and/or herein below, under conditions that allow the production of one or more cellulase polypeptides, and (b) recovering the cellulase polypeptides, for example, by recovering a culture broth comprising the cellulase polypeptides. The present disclosure further provides a culture broth produced by the *T. reesei* cell, and its use in saccharification reactions, including, for example, SSF reactions.

In certain aspects, the present disclosure provides a complete fermentation medium composition, comprising, at least one inverting β-xylosidase, at least one fermenting microorganism, at least one xylan-containing biomass, at least one cellulase, at least one hemicellulase, and a fermentation medium. The inverting β-xylosidase is, for example, a GH43 family enzyme. The inverting β-xylosidase can, in certain aspects, be one selected from an Fv43D, a Pf43A, an Fv43E, an Fv43B, an Af43A, an Fo43A, a Gz43A, or a XynB3 polypeptide. The fermenting microorganism is suitably one that is capable of fermenting a suitable carbon source such as a xylan-containing biomass, or sugars, such as glucose, xylose, arabinose, mannose, galactose, or oligosaccharides, directly or indirectly into a desired fermentation product, including, for example, methanol ("MeOH"), ethanol ("EtOH"), propanol, propane-1,3-diol, or butanol. The fermenting microorganism can be selected from a fungus, such as, for example, a yeast or a filamentous fungus, a bacterium, such as a *Zymomonas mobillis* or a *Clostridium thermocellum*. Suitable carbon sources or substrates include, for example, xylan-containing biomass substrates, selected from, for example, lingocellulosic substrates or other carbohydrate-containing raw materials.

Certain of the lignocellulosic substrates can, for example, comprise cellulose, hemicellulose, and/or lignin.

The cellulase is, for example, a β-glucosidase, an endoglucanase, or a cellobiohydrolase polypeptide. Enzymes are referred to herein either by their names, or by the enzyme families to which they belong (e.g., the GH43 family enzyme; or enzyme classified in or under EC 3.2.1.91); when they are referred to by their names, they can also be referred to interchangeably as a "[name] polypeptide (e.g., a β-glucosidase can also be referred to, interchangeably, as a β-glucosidase polypeptide). The cellulase can also be, for example, in the form of a whole cellulase preparation. The hemicellulase is, for example, a xylanase, a β-xylosidase, an L-α-arabinofuranosidase, or an accessory protein. The whole cellulase preparation can comprise one or more of the hemicellulase polypeptides in certain embodiments.

The fermentation medium can be one that results from a partial saccharification process, or one that comprises certain amounts of the products of saccharification. Such a composition can be suitably used in a saccharification reaction, including, for example, an SSF reaction, under conditions that allow production of the fermentation product(s) of interest.

In certain aspects, the one or more cellulases and/or the one or more hemicellulases are produced by a genetically engineered microorganism wherein the gene encoding the one or more (if more than one native β-xylosidase is present) native β-xylosidases have been deleted or there is no detectable native β-xylosidase activity. In certain embodiments, the microorganism engineered to produce the one or more cellulases and/or one or more hemicellulases does not comprise a retaining β-xylosidase or has no detectable retaining β-xylosidase activity.

In some aspects, the instant disclosure pertains to an improved method for conducting an SSF reaction on a xylan-containing biomass, in order to obtain a bioethanol fermentation product, wherein the method comprises culturing a fermentation medium comprising at least one cellulase, at least one hemicellulase, and at least one fermenting microorganism, wherein the improvement comprises the use of an enzyme with inverting β-xylosidase activity.

In related aspects, the instant disclosure also provides methods of improving production of alkyl-β-xylopyranosides, which are known to be useful and valuable for a number of industrial applications, in situations where such production is desirable. For example, alkyl-β-xylopyranoside can suitably be used as chemical intermediates in the synthesis of alkyl-glucosides, which is useful as biodegradable surfactants and emulsifiers (see, e.g., K. Schmid & H. Tesmann, 2001, Alkyl Polyglucosides, in Detergency of Specialty Surfactants, Surfactant science series, vol. 98; (F. E. Fried ed.); Marcel Dekker Inc., NY, pp. 1-70). These compounds are also inducers themselves or can be used to prepare inducers of xylanase production in a number of microorganisms (see, e.g., M. Marui et al., 1985, Agric. Biol. Chem. 49(12):3399-3407; H. Shinoyama et al., 1988, Agric. Biol. Chem. 52(9): 2197-2202). Various alkyl-pyranosides can, in addition, be used as primers for chondroitin sulphate and stimulants of the biosynthesis of proteoglycans (see, e.g., H. Shinoyama et al., 1988, Agric. Biol. Chem. 52(9): 2197-2202). The inclusion or increased production of β-xylosidases with a retaining mechanism of action in SSF reactions can be used to improve the yield of these useful alkyl-β-xylopyranosides in another aspect of the present invention.

Accordingly, in certain embodiments, the method of the disclosure comprises increasing an amount of retaining β-xylosidases. Provided herein are also improved methods of conducting SSF reactions that entail increasing the amount of retaining β-xylosidases. In a further example, an improved method of conducting SSF reactions that entails increasing the amount of retaining β-xylosidases while decreasing the amount of inverting β-xylosidases is contemplated.

In other aspects, the present invention provides SSF methods comprising culturing a complete fermentation medium, said complete fermentation medium comprising at least one fermenting microorganism, at least one xylan-containing biomass, at least one cellulase, at least one hemicellulase, and at least one enzyme with retaining β-xylosidase activity, for a period and under conditions suitable for formation of alkyl-β-xylopyranoside, such as, for example, methyl-β-xylopyranoside ("MXP"), ethyl-β-xylopyranoside ("EXP"), propyl-β-xylopyranoside ("PXP"), or butyl-β-xylopyranoside ("BXP").

In certain aspects, the at least one enzyme with retaining β-xylosidase activity can be present in said complete fermentation medium in an amount effective to increase short chain alkyl-β-xylopyranoside ("AXP") (e.g., methyl-β-xylopyranoside ("MXP"), ethyl-β-xylopyranoside ("EXP"), propyl-β-xylopyranoside ("PXP"), or butyl-β-xylopyranoside ("BXP")) formation, as compared to a control fermentation medium lacking or having lesser amount of said enzymes with retaining β-xylosidase activity. For example, such enzyme(s) are present in an amount effective to increase the amount of AXP formation by at least 20%, by at least 30%, by at least 40%, by at least 50%, by at least 60%, by at least 70%, or by at least 80%, as compared to that of a control fermentation medium lacking or having a lesser amount of said one or more enzymes with retaining β-xylosidase activity.

In certain aspects, the fermenting microorganism is capable of producing a number of short chain alkyl-β-xylopyranoside ("AXP") compounds, including, without limitation, methyl-β-xylopyranoside ("MXP"), ethyl-β-xylopyranoside ("EXP"), propyl-β-xylopyranoside ("PXP"), or butyl-β-xylopyranoside ("BXP") compounds. In some aspects the fermenting microorganism is a bacterium such as a *Zymomonas mobilis* or a fungus such as a yeast or a filamentous fungus.

In certain aspects, the at least one retaining β-xylosidase is a GH3, GH30, GH31, GH39, GH52, GH54, or GH116 family enzyme. In certain embodiments, the retaining β-xylosidase is selected from a XlnD, an Fv30A, an Fv30B, an Fv39A, an Fv39B, a XynB, a XylA, or a Xyl1 polypeptide. Specifically, the XlnD polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:40, or to residues 18-804 of SEQ ID NO:40. The Fv30A polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:42, or to residues 20-537 of SEQ ID NO:42. The Fv30B polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:44 or to residues 25-485 of SEQ ID NO:44. The Fv39A polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:46, or to residues 20-439 of SEQ ID NO:46. The Fv39B polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:48 or to residues 19-456 of SEQ ID NO:48. The XynB polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:50. The XylA, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:52. The Xyl1 polypeptide, if present in the complete fermentation medium, is a polypeptide comprising at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:54, or to residues 22-500 of SEQ ID NO:54.

In certain aspects, the amount of retaining β-xylosidase polypeptides in said complete medium is at least about 0.2 mg, at least about 0.5 mg, at least about 0.7 mg, at least about 1 mg, at least about 2 mg, or at least about 5 mg per gram of xylan in said xylan-containing biomass, which is also a component of the complete fermentation medium. In other aspects, the amount of inverting β-xylosidase polypeptide(s) is about 10 mg or less, about 5 mg or less, about 2 mg or less, about 1 mg or less, about 0.7 mg or less, about 0.5 mg or less, or about 0.2 mg or less per gram of xylan in said xylan-containing biomass. In certain aspects, the amount of retaining β-xylosidase polypeptides in said complete medium ranges from, for example, (a) 0.2 mg to 10 mg, (b) 0.2 mg to 5 mg, (c) 0.5 mg to 5 mg, (d) 1 mg to 10 mg, (e) 2 mg to 10 mg, (f) 0.2 to 5 mg, (g) 0.2 mg to 2 mg, or (h) 0.5 mg to 10 mg, per gram of xylan in said xylan-containing biomass, or the amount is within a range whose upper and lower limits are each independently selected from the foregoing values.

In certain aspects, the amount of retaining β-xylosidase polypeptide(s) in said complete fermentation medium exceeds the amount of inverting β-xylosidase polypeptide(s), on a mole basis, on a molecular weight basis, or on both a mole basis and a molecular weight basis. In specific embodiments, the ratio of retaining β-xylosidase polypeptides to inverting β-xylosidase polypeptides is at least 2:1, at least 3:1, at least 4:1, at least 5:1, at least 10:1, or at least 50:1, on a mole basis, on a molecular weight basis, or on both a mole basis and a molecular weight basis. In specific embodiments, enzymes with inverting β-xylosidase activity are absent from or undetectable in the complete fermentation medium. In certain embodiments, there is no detectable inverting β-xylosidase activity in the complete fermentation medium.

According to the method describe herein, the culturing of the complete fermentation medium is conducted under continuous, batch, or fed-batch conditions. For example, the culturing of the complete fermentation medium of the invention is a continuous SSF reaction, a batch-type SSF reaction, or a fed-batch type SSF reaction.

The methods of the present disclosure, in certain aspects, further encompass the formation of the complete fermentation medium prior to the culturing step. For example, the complete fermentation medium can be formed by combining (a) at least one fermenting microorganisms, (b) at least one xylan-containing biomass, (c) at least one cellulase, (d) at least one hemicellulase, (e) at least one retaining β-xylosidase, and (f) a medium lacking one or more of the components (a) to (e). In specific embodiments, the at least one cellulase can be present in the form of a cellulase preparation. For example the cellulase preparation can be a whole cellulase preparation, which can optionally also include the at least one hemicellulase. In specific embodiments, the cellulase preparation is a culture broth from a filamentous fungal culture, e.g., a T. reesei culture prepared using a T. reesei cell. In a certain aspect, the T. reesei cell has been engineered such that either the native retaining β-xylosidase gene is overexpressed or that a foreign retaining β-xylosidase gene is introduced and expressed therein. It should be noted that a "T. reesei cell [that] has been engineered such that either the native retaining β-xylosidase gene is overexpressed or that a foreign retaining β-xylosidase gene is introduced and expressed therein" includes not only the original or parental cell, in which the inactivation first took place, but also progeny of that cell.

In certain aspects, the methods of the present disclosure pertain to culturing a fermentation broth comprising at least one xylan-containing biomass. In certain aspects, the xylan-containing biomass is, for example, corn stover, bagasse, sorghum, giant reed, elephant grass, miscanthus, Japanese cedar, wheat straw, switchgrass, hardwood pulp, or softwood pulp. For example, the xylan-containing biomass can suitably be added to the SSF reaction in the form of a slurry. For example, the xylan-containing biomass can be added to the SSF reaction in the form of a solid. Accordingly, the xylan-containing biomass can suitably be added to the SSF reaction in either a liquid form (which can be, for example, a solution, a suspension, or a mixture of solids and liquid) or in a solid form. In certain embodiments, the xylan-containing biomass has been subject to pre-treatment.

After the SSF reaction has taken place, optionally to completion, a recovery step can follow, wherein the AXP product (e.g., MXP, EXP, PXP, or BXP) is recovered.

The present disclosure further provides a complete fermentation medium suitable for use in the present methods, for example as described hereinabove and hereinbelow with respect to cellulase, hemicellulase, β-xylosidase and fermenting microorganism components.

The present disclosure also provides a T. reesei cell that has been engineered such that the native retaining β-xylosidase gene is overexpressed, or that a foreign retaining β-xylosidase gene is expressed therein. The T. reesei cell can be engineered to recombinantly express an enzyme of the GH3, GH30, GH31, GH39, GH52, GH54, or GH116 family, for example, one selected from a XlnD, an Fv30A, an Fv30B, an Fv39A, an Fv39B, a XynB, a XylA, or a Xyl1 polypeptide. For example, the XlnD polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:40 or to residues 18-804 of SEQ ID NO:40. The Fv30A polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:42, or to residues 20-537 of SEQ ID NO:42. The Fv30B polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:44, or to residues 25-485 of SEQ ID NO:44. The Fv39A polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:46 or to residues 20-439 of SEQ ID NO:46. The Fv39B polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:48, or to residues 19-456 of SEQ ID NO:48 The XynB polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:50. The XylA polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:52, or to residues 19-705 of SEQ ID NO:52. The Xyl1 polypeptide has at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence corresponding to SEQ ID NO:54, or to residues 22-500 of SEQ ID NO:54.

The present disclosure further provides methods for producing cellulase polypeptides, comprising (a) culturing such a *T. reesei* cell, such as one described herein above and/or herein below, under conditions that allow the production of one or more cellulase polypeptides and (b) recovering the cellulase polypeptides, for example, by recovering a culture broth comprising the cellulase polypeptides. The present disclosure further provides a culture broth produced by the *T. reesei* cell, and its use in saccharification reactions, including, for example, SSF reactions.

In certain aspects, the present disclosure provides a complete fermentation medium composition, comprising, at least one retaining β-xylosidase, at least one fermenting microorganism, at least one xylan-containing biomass, at least one cellulase, at least one hemicellulase, and a fermentation medium. The retaining β-xylosidase is, for example, either a native retaining β-xylosidase that is overexpressed or a foreign β-xylosidase that is introduced into a suitable host cell. The retaining β-xylosidase is, for example, a GH3, GH30, GH31, GH39, GH52, GH54, or GH 116 family enzyme. The retaining β-xylosidase can, in certain aspects, be one selected from a XlnD, an Fv30A, an Fv30B, an Fv39A, an Fv39B, a XynB, a XylA, or a Xyl1 polypeptide. The fermenting microorganism is suitably one that is capable of fermenting a suitable carbon source such as a xylan-containing biomass, or sugars, such as glucose, xylose, arabinose, mannose, galactose, or oligosaccharides, directly or indirectly into a desired fermentation product, including, for example, methanol, ethanol, propanol, propane-1,3-diol, or butanol. The fermenting microorganism can be a fungus, such as, for example, a yeast or a filamentous fungus, or a bacterium, such as a *Zymomonas mobillis* or a *Clostridium thermocellum*. Suitable carbon sources or substrates can be, for example, xylan-containing biomass substrates, selected from, for example, lingocellulosic substrates or other carbohydrate-containing raw materials. Certain of the lignocellulosic substrates can, for example, comprise cellulose, hemicellulose, and/or lignin.

The cellulase is, for example, a β-glucosidase, an endoglucanase, or a cellobiohydrolase polypeptide. The cellulase can also be, for example, in the form of a whole cellulase preparation. The hemicellulase is, for example, a xylanase, a β-xylosidase, an L-α-arabinofuranosidase, or an accessory protein. The whole cellulase preparation can comprise one or more hemicellulase polypeptides in certain embodiments.

The fermentation medium can be one that results from a partial saccharification process, or one that comprises certain amounts of the products of saccharification. Such a composition can be suitably used in a saccharification reaction, including, for example, an SSF reaction, under conditions that allow production of the AXP compounds, including, for example, MXP, EXP, PXP, or BXP.

In certain aspects, the one or more cellulases or the one or more hemicellulases are produced by a genetically engineered microorganism wherein the gene encoding the one or more (if more than one native β-xylosidase is present) native β-xylosidases have been overexpressed or a gene encoding a foreign β-xylosidase has been introduced and/or expressed. In certain embodiments, the microorganism engineered to produce one or more cellulases and/or one or more hemicellulases has an increased expression of retaining β-xylosidase activity over a control microorganism which did not undergo the same genetic engineering. In certain embodiments, the microorganism engineered to produce one or more cellulases and/or one or more hemicellulases does not comprises an inverting β-xylosidase or has no detectable inverting β-xylosidase activity.

In certain related aspects, the instant disclosure pertains to an improved method for conducting an SSF reaction on a xylan-containing biomass, in order to obtain an AXP product wherein the method comprises culturing a fermentation medium comprising at least one cellulase, at least one hemicellulase, and at least one fermenting microorganism, wherein the improvement comprises the use of a cellulase preparation made from a *T. reesei* cell, which has been engineered to overexpress the native β-xylosidase gene, or to express a foreign β-xylosidase. In some embodiments, the native β-xylosidase gene that is overexpressed or the foreign β-xylosidase gene that is expressed is a gene encoding a retaining β-xylosidase.

All publications, patents, patent applications, GenBank sequences and ATCC deposits cited herein are hereby expressly incorporated by reference for all purposes.

5. BRIEF DESCRIPTION OF THE FIGURES AND TABLES

Table 1: EXP formation with recombinant *Zymomonas mobilis* under the SSF conditions from cob and glucose/xylose.

Table 2: EXP formation using various types of biomass substrates.

Table 3: Time course of EXP and/or xylose formation (expressed as RI area, proportional to mg/mL) from xylobiose (20 mg/mL) in 50 mM NaCitrate, pH 4.7 plus 0.9 M EtOH at 46° C. in the presence of Multifect® Xylanase ("ME," 560 μg/mL) and purified Fv43D (36 μg/mL) or Fv3A (54 μg/mL).

Table 4: Primer sequences for construction of bxl1 deletion cassette.

Table 5: Primer sequences for construction of *F. verticillioides* β-xylosidase Fv43D expression cassette.

Table 6: provides a summary of the sequence identifiers for certain enzymes used in SSF reactions.

FIG. 1: HPLC chromatograms of samples taken after 48 hrs of incubation at 46° C. of xylose (10 mg/mL) in 50 mM sodium citrate, pH 4.6, Multifect® Xylanase (1.35 mg/mL) and with no alcohol, with ethanol ("EtOH"), with methanol ("MeOH"), or with n-propanol ("n-PrOH"), each at 0.72 M. HPLC conditions: column HPX-87H at 60° C., 0.60 mL/min 0.01 N $H_2SO_4$, RI detector.

Figures 1, 1A, 2:
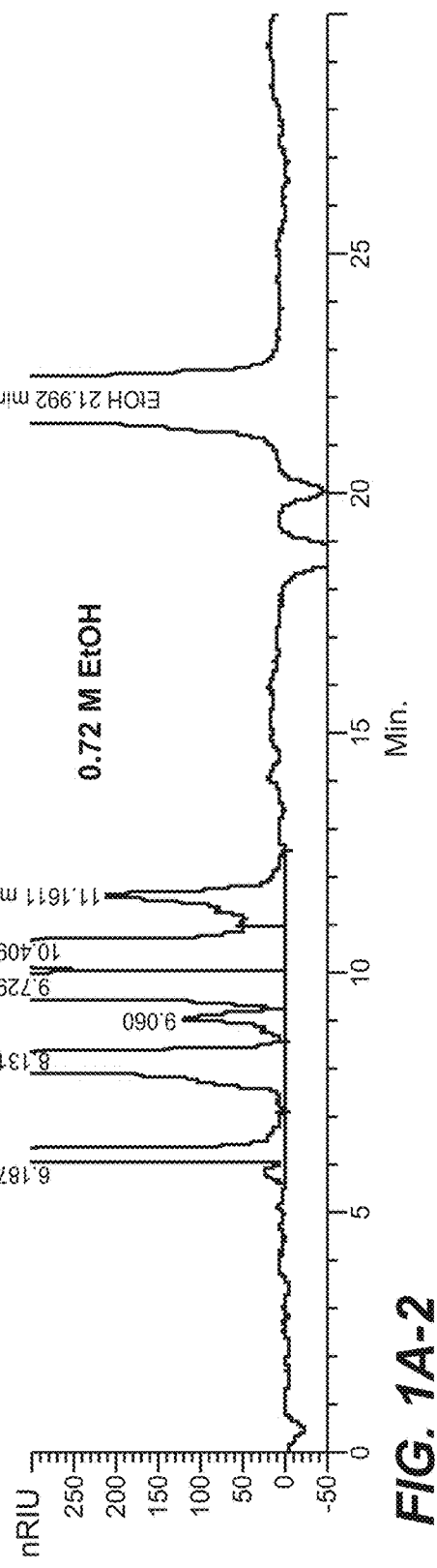
Figures 1, 1B:
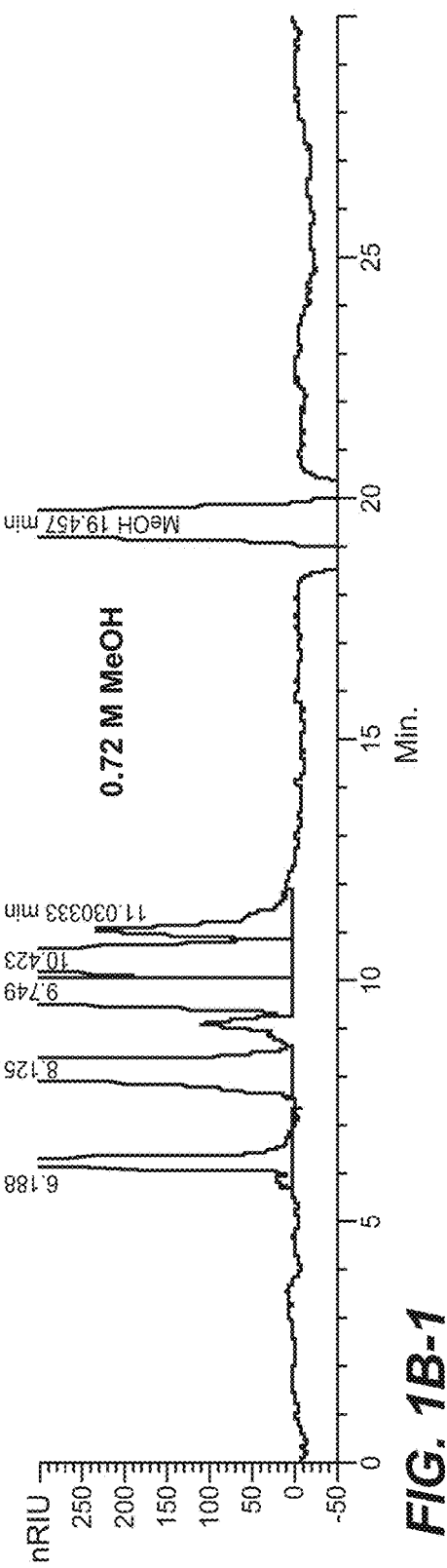
Figures 1, 1B, 2:
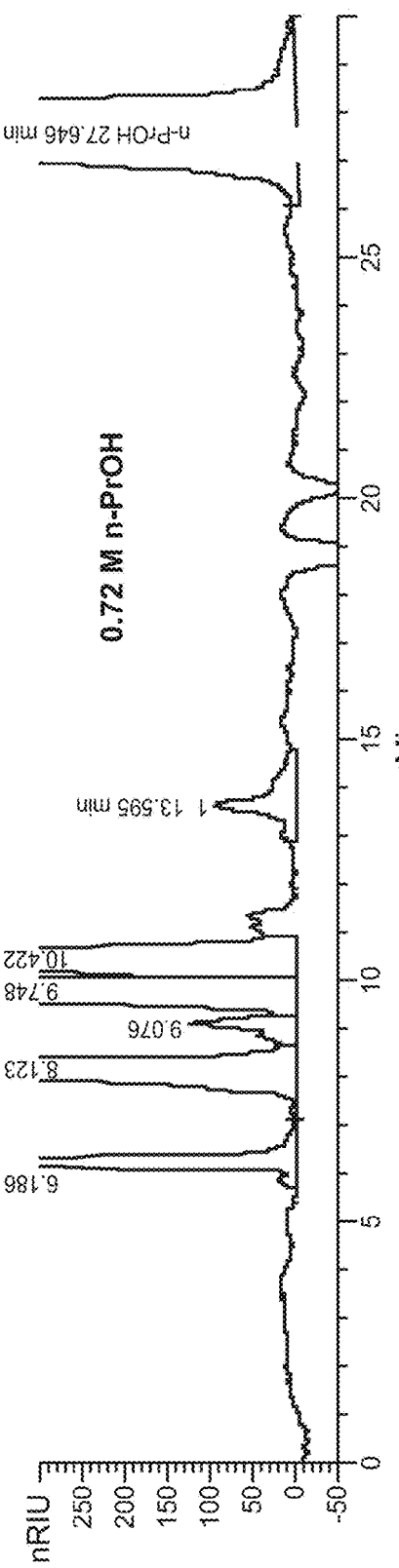
Figure 2:
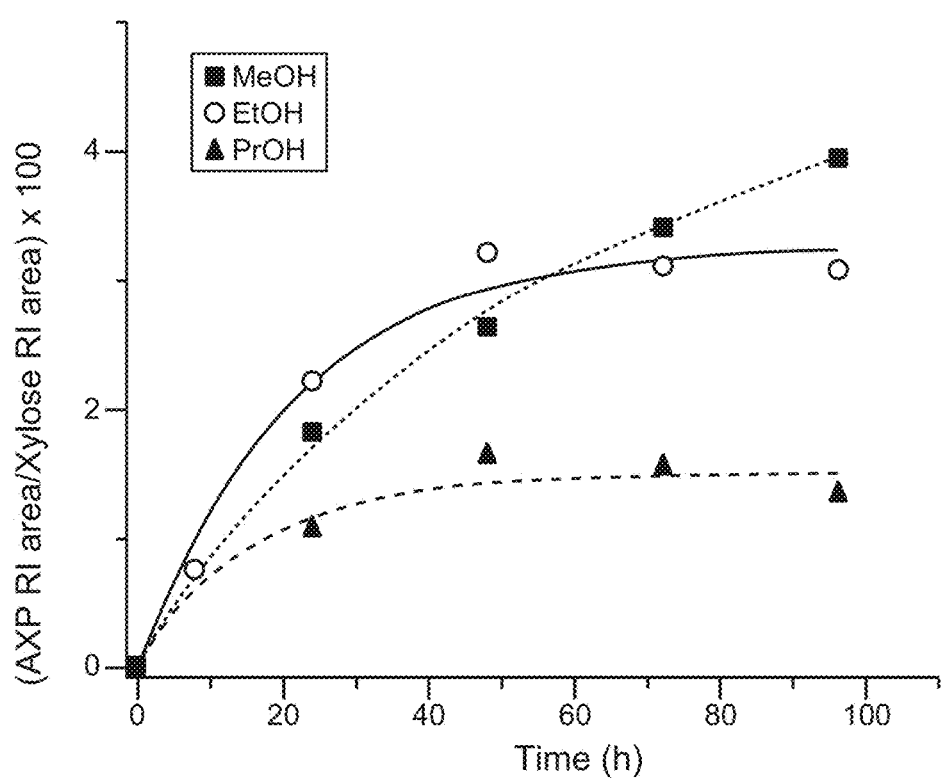

FIG. 2: Time course following the appearance/formation of alkyl-xylopyranosides ("AXP") under the same conditions as those described in the experiments of FIG. 1. The amounts of fermentation products formed are expressed as ratios of the areas of the product peaks compared to those of the xylose peaks.

Figure 3B:
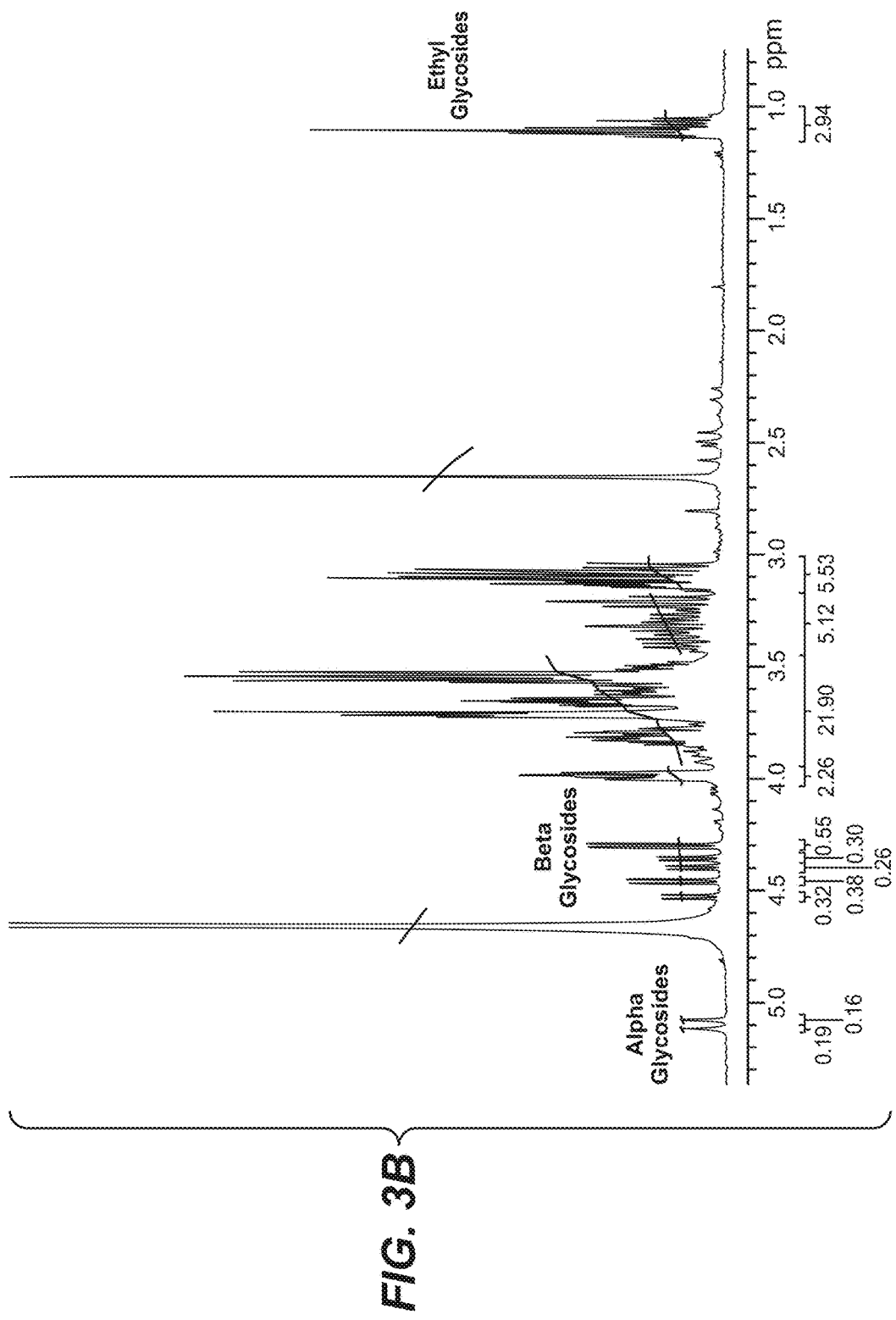

FIG. 3: NMR spectrum indicating the presence of ethyl-β-xylopyranoside.

Figure 4:
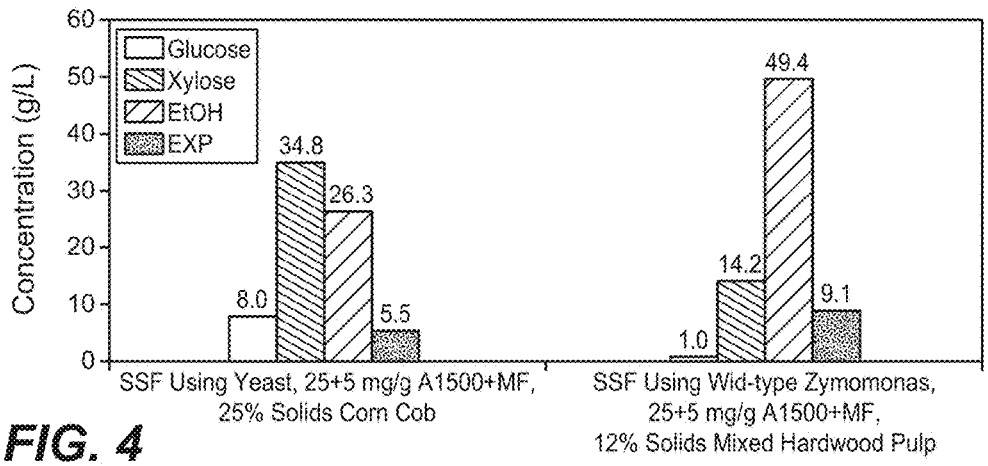

FIG. 4: EXP formation with yeast and wild-type *Zymomonas mobilis* under SSF conditions.

Figure 5:
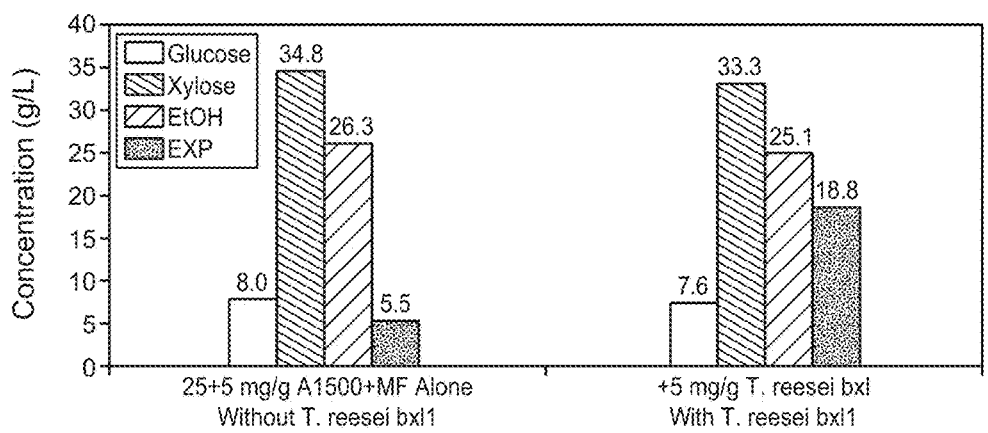

FIG. 5: EXP formation under the yeast SSF conditions with and without the addition of *T. reesei* Bxl1.

Figure 6:
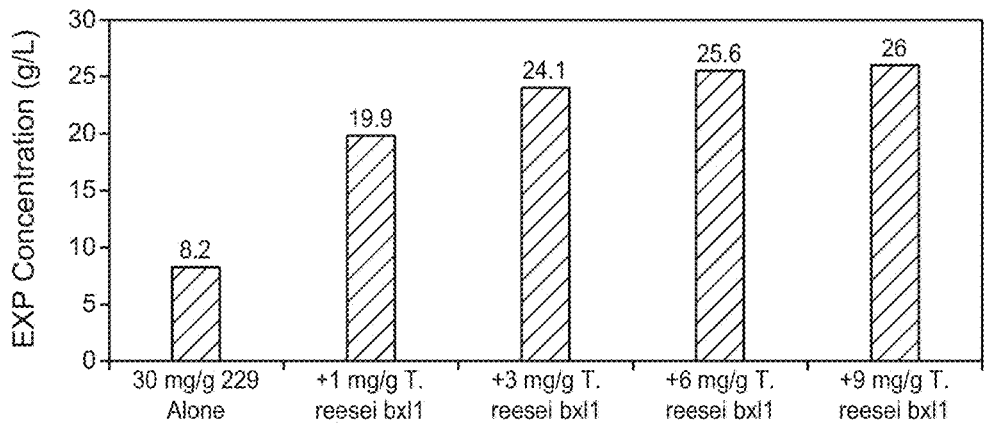

FIG. 6: EXP dose response following addition of *T. reesei* Bxl1 to the enzyme complex produced from integrated *T. reesei* strain #229 under the recombinant *Zymomonas* SSF conditions.

Figure 7:
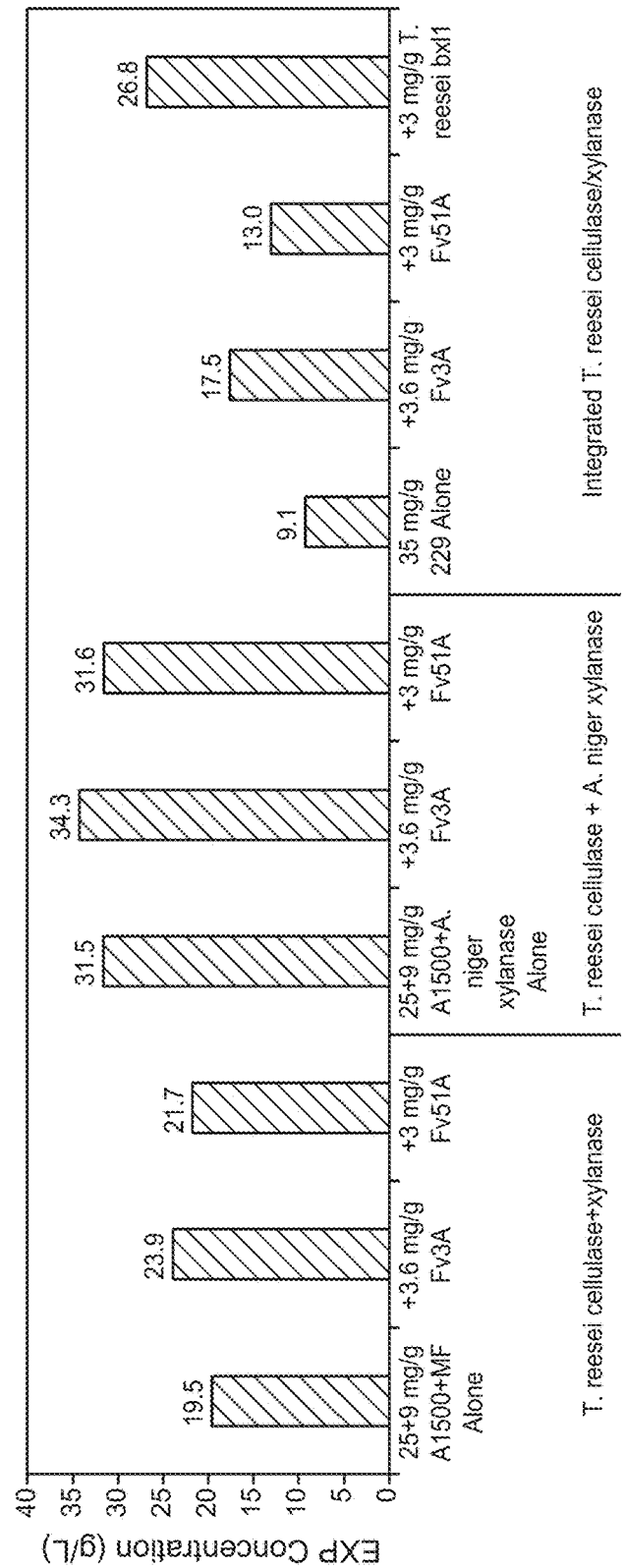

FIG. 7: EXP formation during an SSF reaction with the following enzyme configurations/mixtures for saccharification: Accellerase™ 1500 ("A1500")+Multifect® Xylanase, Accellerase™ 1500 ("A1500")+XlnA, and an enzyme complex produced from the integrated *T. reesei* strain #229 with the addition of a hemicellulase (Fv3A, Fv51A, or Bxl1).

Figure 8:
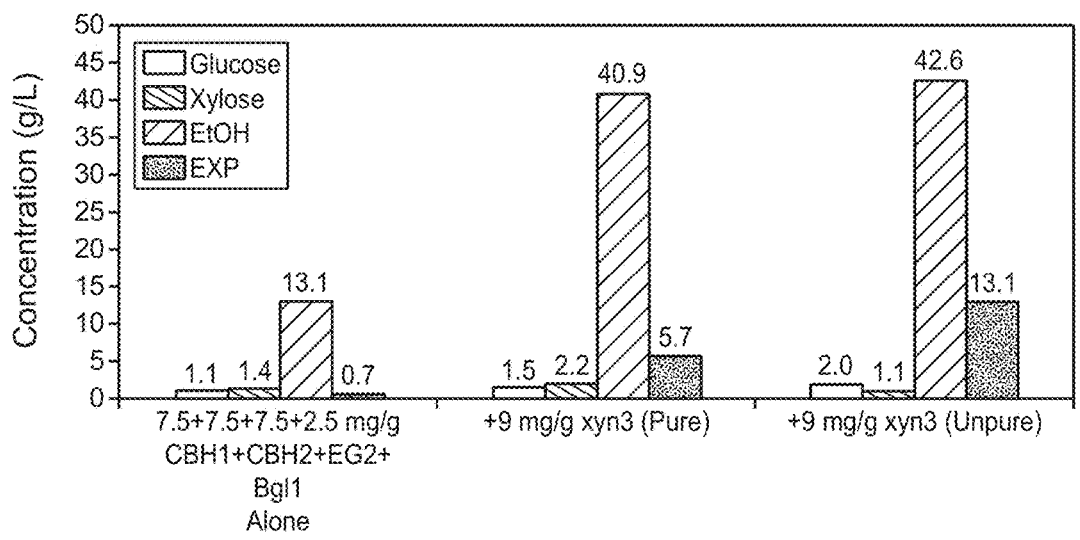

FIG. 8: EXP formation during an SSF reaction using various purified cellulase enzymes and XynB3 for saccharification.

Figure 9:
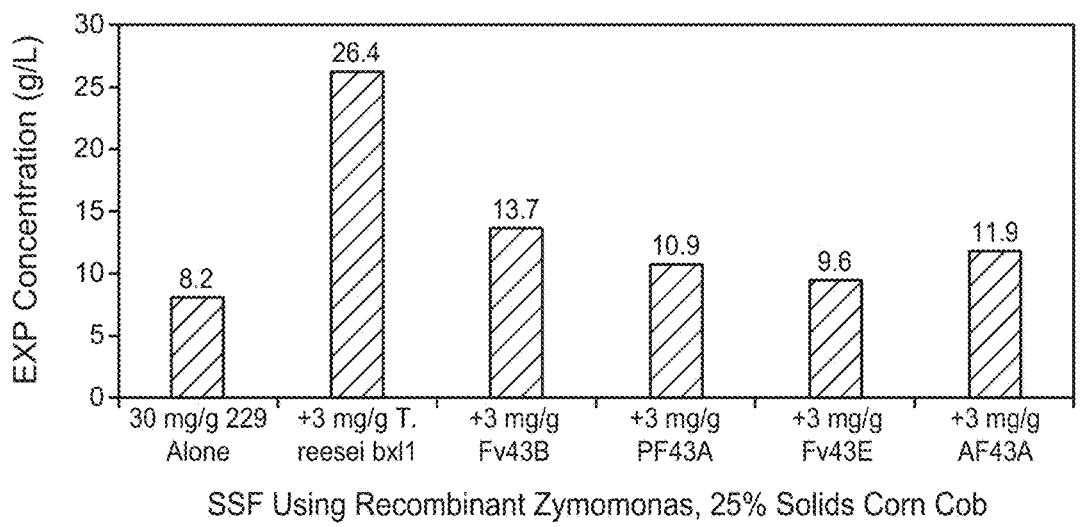

FIG. 9: EXP formation during an SSF reaction using an enzyme complex produced from the integrated *T. reesei* strain #229 in the presence of *T. reesei* Bxl1, or in the presence of certain other GH43 family β-xylosidase enzymes.

Figure 10:
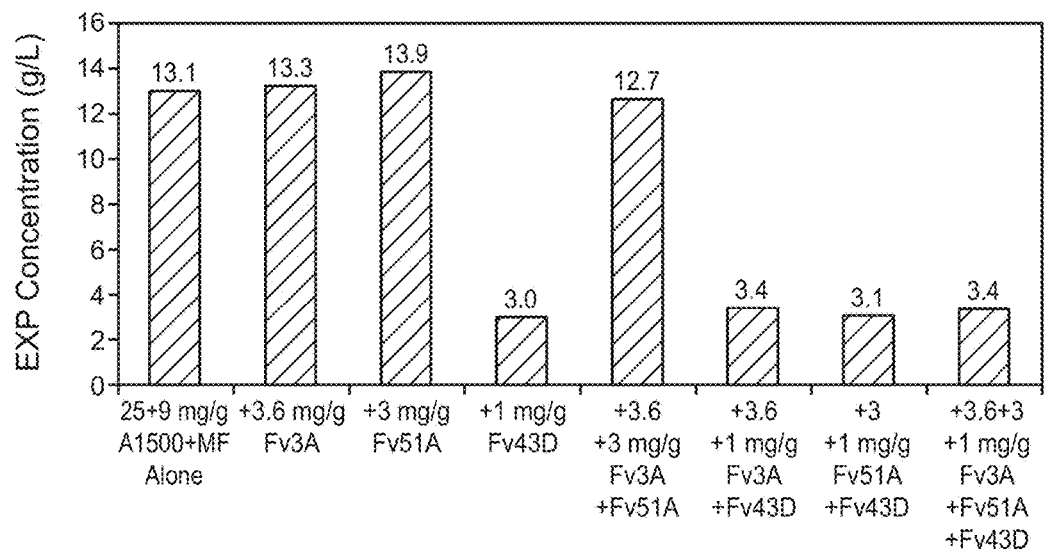

FIG. 10: Reduced EXP formation observed from the addition of Fv43D under the recombinant *Zymomonas* SSF conditions.

Figure 11:
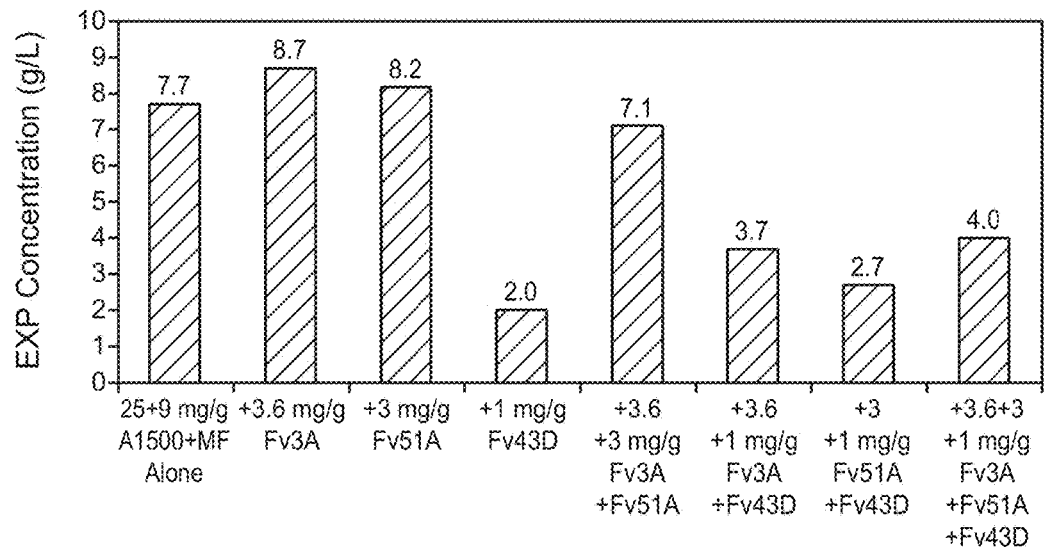

FIG. 11: Reduced EXP formation observed from the addition of Fv43D under the yeast SSF conditions.

Figure 12:
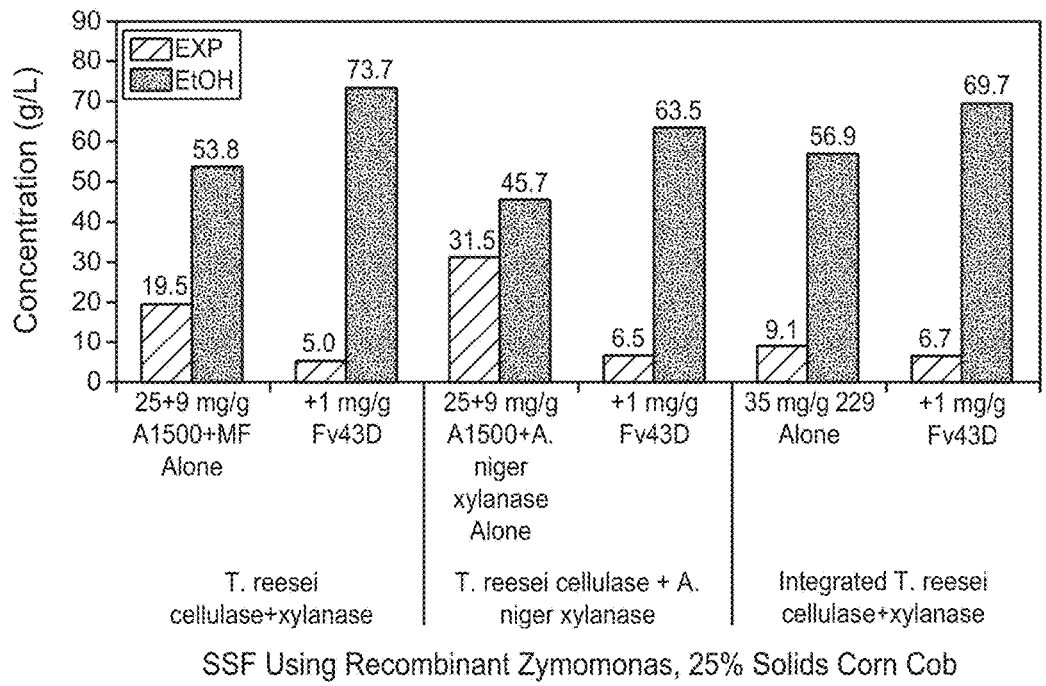

FIG. 12: Reduced EXP formation observed after the addition of Fv43D to Accellerase™ 1500+Multifect® Xylanase, to Accellerase™ 1500+XlnA, and to an enzyme complex produced from the integrated *T. reesei* strain #229 under the recombinant *Zymomonas* SSF conditions.

Figure 13:
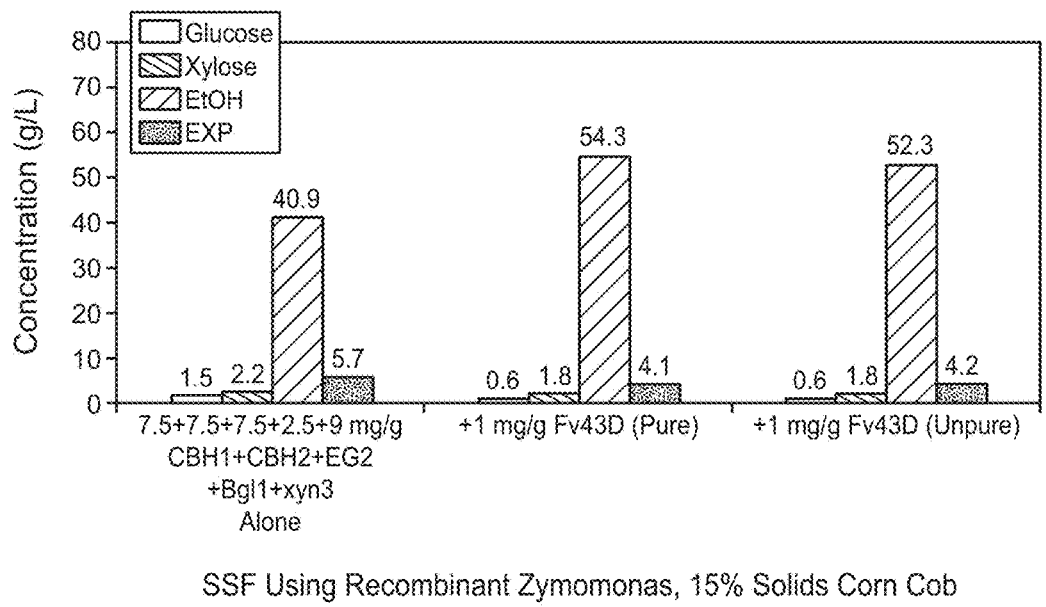

FIG. 13: Reduced EXP formation observed from the addition of Fv43D to purified cellulase enzymes and XynB3.

Figure 14A:
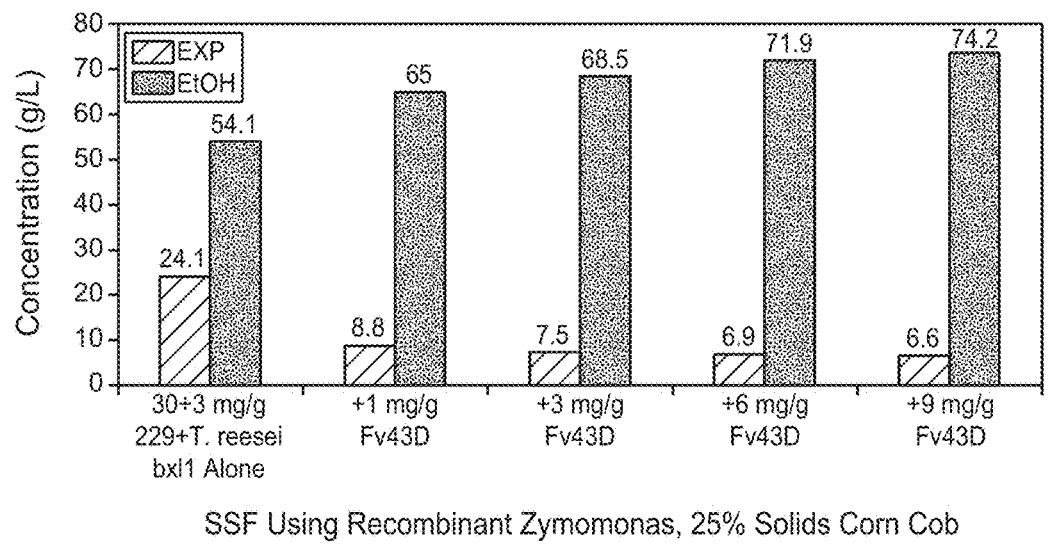
Figure 14B:
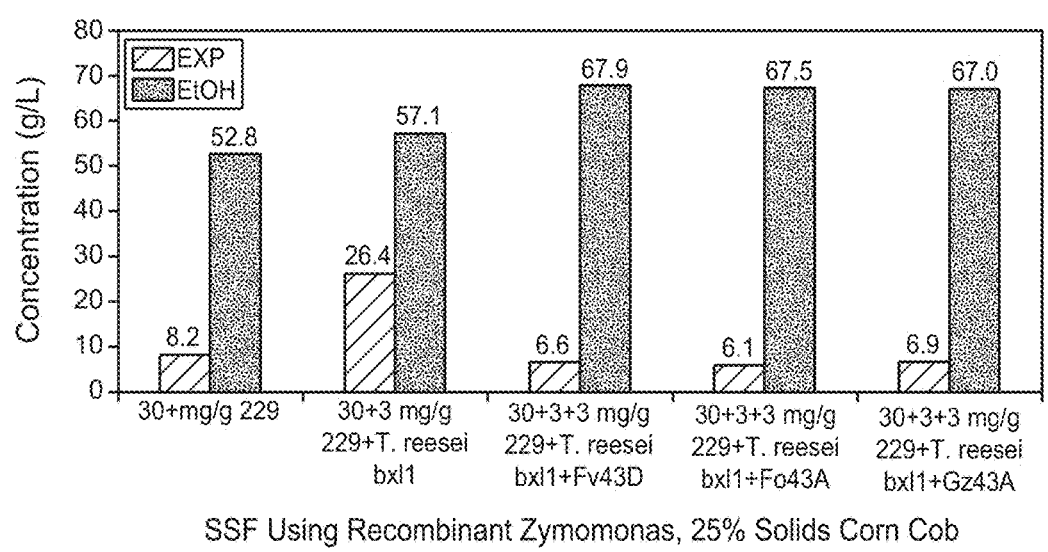

FIGS. 14A-14B: FIG. 14A shows EXP reduction dose response from the addition of Fv43D to the enzyme composition or blend produced from the *T. reesei* integrated strain #229+*T. reesei* Bxl1 under the recombinant *Zymomonas* SSF conditions. FIG. 14B shows EXP reduction from the addition of Fo43A or Gz43A to the enzyme complex produced from the integrated *T. reesei* strain #229+*T. reesei* Bxl1 under the recombinant *Zymomonas* SSF conditions.

Figure 15:
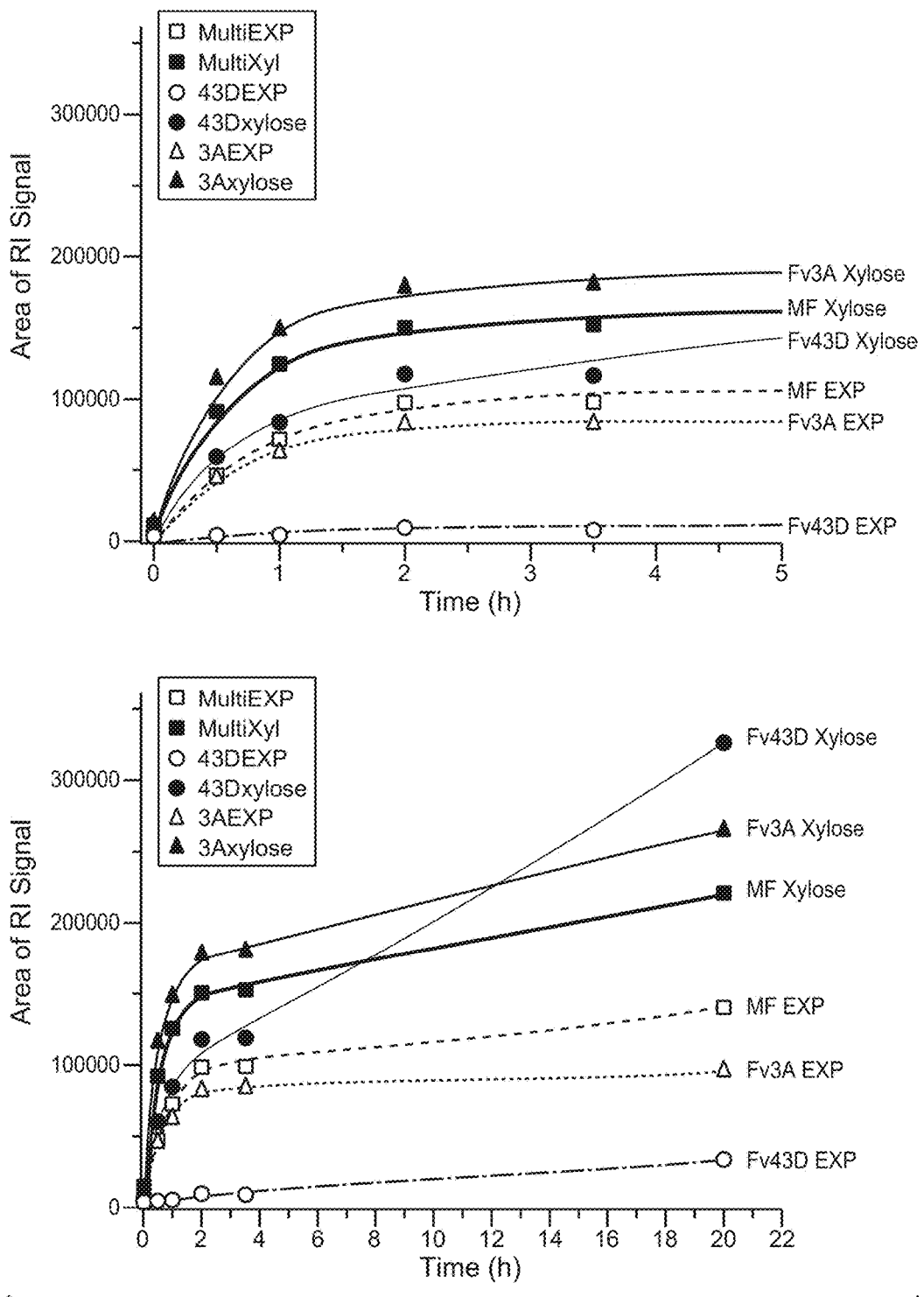

FIG. 15: Time course of xylose and EXP formation (expressed as RI area, which is proportional to mg/mL) from xylobiose (20 mg/mL) in 50 mM sodium citrate, pH 4.7 plus 0.9 M ethanol at 46° C. in the presence of Multifect® Xylanase (560 μg/mL) and purified Fv43D (36 μg/mL) and Fv3A (54 μg/mL).

Figure 16:
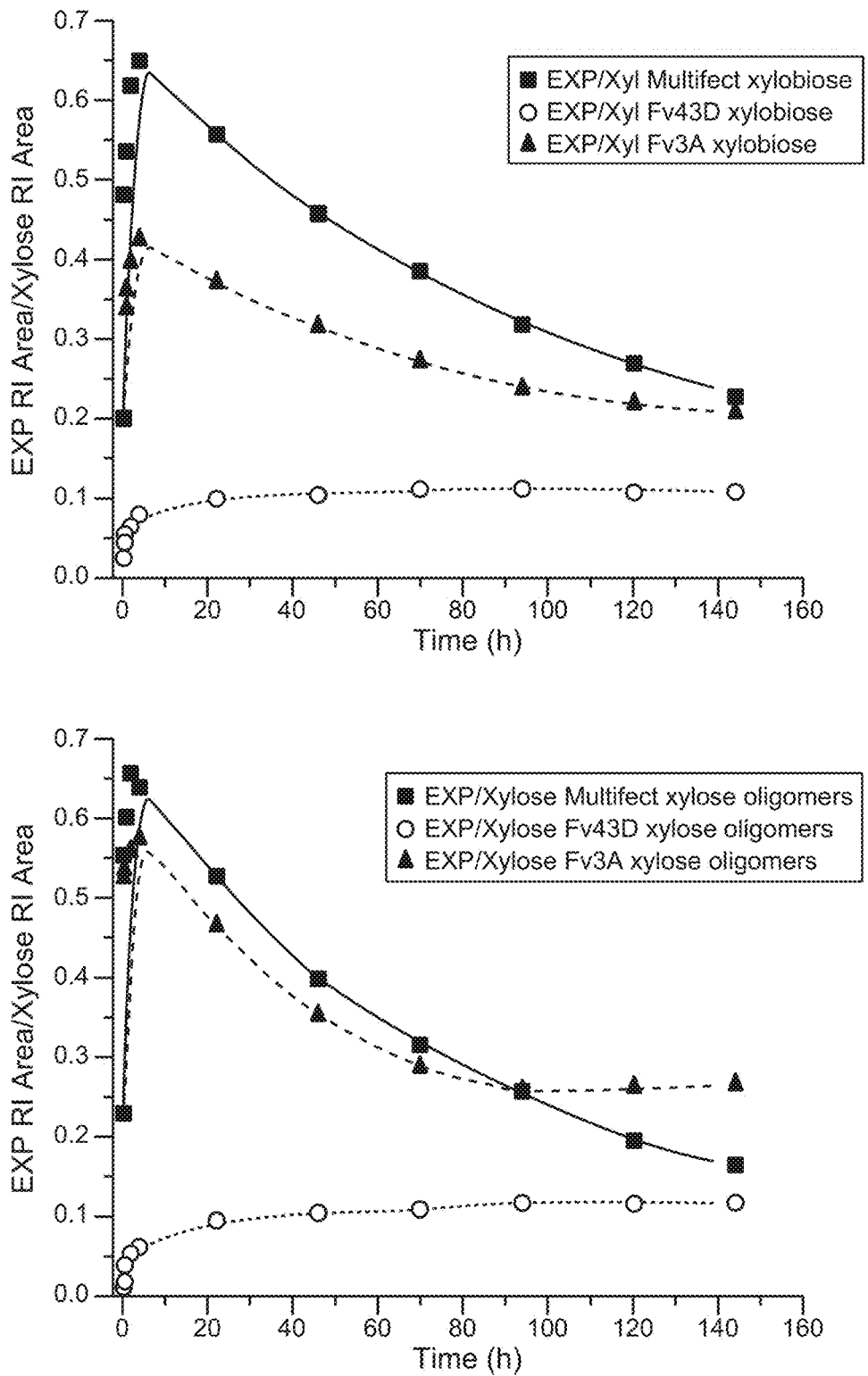

FIG. 16: Time course of formation of xylose and EXP from xylobiose (20 mg/mL, left) or xylose oligomers (20 mg/mL, right), in 50 mM sodium citrate, pH 4.7 plus 0.9 M ethanol at 46° C. in the presence of Multifect® Xylanase (560 μg/mL), Fv43D (36 μg/mL), or Fv3A (54 μg/mL). The results are expressed as ratios of the amount of EXP to the amount of xylose formed.

Figure 17:
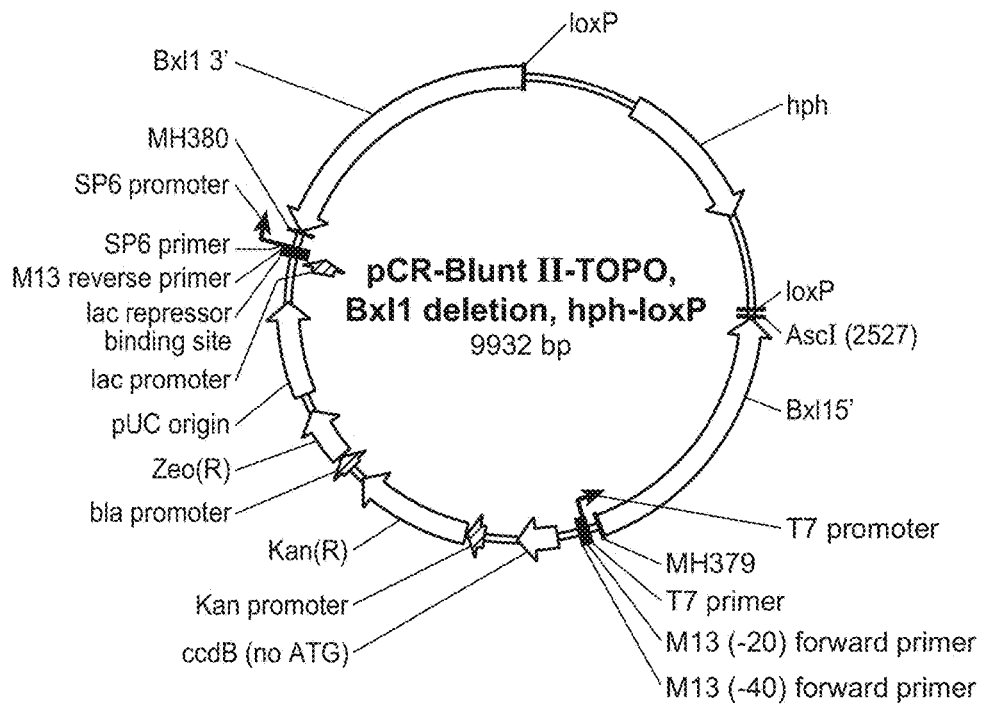

FIG. 17: Plasmid map of pCR-Blunt II-TOPO, bxl1 deletion, hph-loxP.

Figure 18:
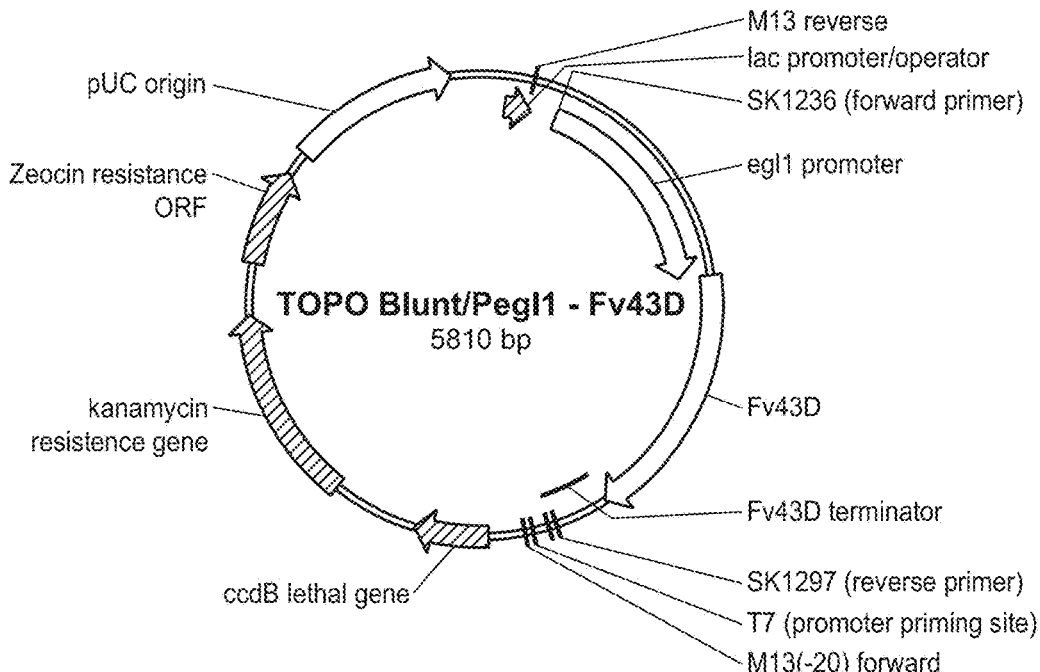

FIG. 18: Plasmid map of TOPO Blunt/Pegl1-Fv43D.

FIGS. 19A-19B: FIG. 19A: Fv43D nucleotide sequence (SEQ ID NO:1). FIG. 19B: Fv43D amino acid sequence (SEQ ID NO:2). SEQ ID NO:2 is the sequence of the immature Fv43D. Fv43D has a predicted signal sequence corresponding to residues 1 to 20 of SEQ ID NO:2 (underlined); cleavage of the signal sequence is predicted to yield a mature protein having a sequence corresponding to residues 21 to 350 of SEQ ID NO:2. Signal sequence predictions were made with the SignalP algorithm (available at: www.cbs.dtu.dk). The predicted conserved domain residues are in boldface type. Domain predictions were made based on the Pfam, SMART, or NCBI databases.

FIGS. 20A-20B: FIG. 20A: *T. reesei* Bxl1 nucleotide sequence (SEQ ID NO:3). FIG. 20B: *T. reesei* Bxl1 amino acid sequence (SEQ ID NO:4). The signal sequence is underlined. The predicted conserved domain residues are in bold face type. Domain predictions were made based on the Pfam, SMART, or NCBI databases.

FIGS. 21A-21B: FIG. 21A: Fv3A nucleotide sequence (SEQ ID NO:5). FIG. 21B: Fv3A amino acid sequence (SEQ ID NO:6). SEQ ID NO:6 is the sequence of the immature Fv3A. Fv3A has a predicted signal sequence corresponding to residues 1 to 23 of SEQ ID NO:6 (underlined); cleavage of the signal sequence is predicted to yield a mature protein having a sequence corresponding to residues 24 to 766 of SEQ ID NO:6. Signal sequence predictions were made with the SignalP algorithm (available at: www.cbs.dtu.dk). The predicted conserved domain residues are in boldface type. Domain predictions were made based on the Pfam, SMART, or NCBI databases.

FIGS. 22A-22B: FIG. 22A: Pf43A nucleotide sequence (SEQ ID NO:7). FIG. 22B: Pf43A amino acid sequence (SEQ ID NO:8). SEQ ID NO:8 is the sequence of the immature Pf43A. Pf43A has a predicted signal sequence corresponding to residues 1 to 20 of SEQ ID NO:8 (underlined); cleavage of the signal sequence is predicted to yield a mature protein having a sequence corresponding to residues 21 to 445 of SEQ ID NO:8. Signal sequence predictions were made with the SignalP algorithm (available at: www.cbs.dtu.dk). The predicted conserved domain residues are in boldface type, the predicted carbohydrate binding module ("CBM") residues are in uppercase type, and the predicted linker separating the CD and CBM is in italics. Domain predictions were made based on the Pfam, SMART, or NCBI databases.

FIGS. 23A-23B: FIG. 23A: Fv43E nucleotide sequence (SEQ ID NO:9). FIG. 23B: Fv43E amino acid sequence (SEQ ID NO:10). SEQ ID NO:10 is the sequence of the immature Fv43E. Fv43E has a predicted signal sequence corresponding to residues 1 to 18 of SEQ ID NO:10 (underlined); cleavage of the signal sequence is predicted to yield a mature protein having a sequence corresponding to residues 19 to 530 of SEQ ID NO:10. Signal sequence predictions were made with the SignalP algorithm (available at: www.cbs.dtu.dk). The predicted conserved domain residues are in boldface type. Domain predictions were made based on the Pfam, SMART, or NCBI databases.

FIGS. 24A-24B: FIG. 24A: Fv43B nucleotide sequence (SEQ ID NO:11). FIG. 24B: Fv43B amino acid sequence (SEQ ID NO:12). SEQ ID NO:12 is the sequence of the immature Fv43B. Fv43B has a predicted signal sequence corresponding to residues 1 to 16 of SEQ ID NO:12 (underlined); cleavage of the signal sequence is predicted to yield a mature protein having a sequence corresponding to residues 17 to 574 of SEQ ID NO:12. Signal sequence predictions were made with the SignalP algorithm (available at: www.cbs.dtu.dk). The predicted conserved domain residues are in boldface type. Domain predictions were made based on the Pfam, SMART, or NCBI databases.

FIGS. 25A-25B: FIG. 25A: Af43A nucleotide sequence (SEQ ID NO:13). FIG. 25B: Af43A amino acid sequence (SEQ ID NO:14). SEQ ID NO:14 is the sequence of the immature Af43A. Af43A does not have a predicted signal sequence, which can be derived using the SignalP algorithm (available at: www.cbs.dtu.dk). The predicted conserved domain residues are in boldface type. Domain predictions were made based on the Pfam, SMART, or NCBI databases.

FIGS. 26A-26B: FIG. 26A: Fv51A nucleotide sequence (SEQ ID NO:15). FIG. 26B: Fv51A amino acid sequence (SEQ ID NO:16). SEQ ID NO:16 is the sequence of the immature Fv51A. Fv51A has a predicted signal sequence corresponding to residues 1 to 19 of SEQ ID NO:16 (underlined); cleavage of the signal sequence is predicted to yield a mature protein having a sequence corresponding to residues 20 to 660 of SEQ ID NO:16. Signal sequence predictions were made with the SignalP algorithm (available at: www.cbs.dtu.dk). The predicted L-α-arabinfuranosidase conserved domain residues are in boldface type. Domain predictions were made based on the Pfam, SMART, or NCBI databases.

FIGS. 27A-27B: FIG. 27A: T. reesei Xyn3 nucleotide sequence (SEQ ID NO:17). FIG. 27B: T. reesei Xyn3 amino acid sequence (SEQ ID NO:18). SEQ ID NO:18 is the sequence of the immature T. reesei Xyn3. T. reesei Xyn3 has a predicted signal sequence corresponding to residues 1 to 16 of SEQ ID NO:18 (underlined); cleavage of the signal sequence is predicted to yield a mature protein having a sequence corresponding to residues 17 to 347 of SEQ ID NO:18. Signal sequence predictions were made with the SignalP algorithm (available at: www.cbs.dtu.dk). The predicted conserved domain residues are in bold face type. Domain predictions were made based on the Pfam, SMART, or NCBI databases.

FIGS. 28A-28B: FIG. 28A: XlnA nucleotide sequence (SEQ ID NO:19). FIG. 28B: XlnA amino acid sequence (SEQ ID NO:20). SEQ ID NO:20 is the sequence of the immature XlnA protein. XlnA has a predicted signal sequence corresponding to residues 1 to 27 of SEQ ID NO:20 (underlined); cleavage of the signal sequence is predicted to yield a mature protein having a sequence corresponding to residues 28 to 211 of SEQ ID NO:20. Signal sequence predictions were made with the SignalP algorithm (available at: www.cbs.dtu.dk). SEQ ID NO:19 is the genomic sequence of XlnA; the initiation and termination codon residues are shown in bold face type in FIG. 28A, and intron A of the XlnA gene is underlined in FIG. 28A.

FIG. 29: FIG. 29 shows the "α" and "β" anomer configurations of glucose. Anomers are identified as "α" or "β" based on the relation between the stereochemistry of the exocyclic oxygen atom at the anomeric carbon and the oxygen attached to the configurational atom (defining the sugar as D or L), which is often the furthest chiral center in the ring. The α anomer is the one in which these two positions have the same configuration; they are the opposite in the β anomer. Thus the structure of α-D-glucose has the same stereochemistry at both C1 and C5 whereas β-D-glucose has opposite stereochemistry at C1 compared to C5.

FIGS. 30A-30B: FIG. 30A: Gz43A nucleotide sequence (SEQ ID NO:21). FIG. 30B: Gz43A amino acid sequence (SEQ ID NO:22). SEQ ID NO:22 is the sequence of the immature Gz43A. Gz43A has a predicted signal sequence corresponding to residues 1 to 18 of SEQ ID NO:22 (underlined); cleavage of the signal sequence is predicted to yield a mature protein having a sequence corresponding to residues 19 to 340 of SEQ ID NO:22. Signal sequence predictions were made with the SignalP algorithm (available at: www.cbs.dtu.dk). The predicted conserved domain residues are in boldface type. Domain predictions were made based on the Pfam, SMART, or NCBI databases.

FIGS. 31A-31B: FIG. 31A: Fo43A nucleotide sequence (SEQ ID NO:23). FIG. 31B: Fo43A amino acid sequence (SEQ ID NO:24). SEQ ID NO:24 is the sequence of the immature Fo43A. Fo43A has a predicted signal sequence corresponding to residues 1 to 20 of SEQ ID NO:24 (underlined); cleavage of the signal sequence is predicted to yield a mature protein having a sequence corresponding to residues 21 to 348 of SEQ ID NO:24. Signal sequence predictions were made with the SignalP algorithm (available at: www.cbs.dtu.dk). The predicted conserved domain residues are in boldface type. Domain predictions were made based on the Pfam, SMART, or NCBI databases.

FIGS. 32-1 to 32-2: Alignment of GH43 family hydrolases. Amino acid residues that are highly conserved among members of the family are shown in bold and underline type.

FIG. 33: XynB3 amino acid sequence (SEQ ID NO:25).

FIG. 34: T. reesei Bgl1 amino acid sequence (SEQ ID NO:45). The signal sequence is underlined. The predicted conserved domain residues are in bold face type. The coding sequence is described in Barnett et al., 1991, Bio-Technology 9(6):562-567.

FIGS. 35A-35B: FIG. 35A: XlnD nucleotide sequence (SEQ ID NO:39). FIG. 35B: XlnD amino acid sequence (SEQ ID NO:40). SEQ ID NO:40 is the sequence of the immature XlnD. XlnD has a predicted signal sequence corresponding to residues 1 to 17 of SEQ ID NO:40 (underlined); cleavage of the signal sequence is predicted to yield a mature protein having a sequence corresponding to residues 18 to 804 of SEQ ID NO:40. Signal sequence predictions were made with the SignalP algorithm (available at: www.cbs.dtu.dk).

FIGS. 36A-36B: FIG. 36A: Fv30A nucleotide sequence (SEQ ID NO:41). FIG. 36B: Fv30A amino acid sequence (SEQ ID NO:42). SEQ ID NO:42 is the sequence of the immature Fv30A. Fv30A has a predicted signal sequence corresponding to residues 1 to 19 of SEQ ID NO:42 (underlined); cleavage of the signal sequence is predicted to yield a mature protein having a sequence corresponding to residues 20 to 537 of SEQ ID NO:42. Signal sequence predictions were made with the SignalP algorithm (available at: www.cbs.dtu.dk).

FIGS. 37A-37B: FIG. 37A: Fv30B nucleotide sequence (SEQ ID NO:43). FIG. 37B: Fv30B amino acid sequence (SEQ ID NO:44). SEQ ID NO:44 is the sequence of the immature Fv30B. Fv30B has a predicted signal sequence corresponding to residues 1 to 24 of SEQ ID NO:44 (underlined); cleavage of the signal sequence is predicted to yield a mature protein having a sequence corresponding to residues 25 to 485 of SEQ ID NO:44. Signal sequence predictions were made with the SignalP algorithm (available at: www.cbs.dtu.dk).

FIGS. 38A-38B: FIG. 38A: Fv39A nucleotide sequence (SEQ ID NO:45). FIG. 38B: Fv39A amino acid sequence (SEQ ID NO:46). SEQ ID NO:46 is the sequence of the immature Fv39A. Fv39A has a predicted signal sequence corresponding to residues 1 to 19 of SEQ ID NO:46 (underlined); cleavage of the signal sequence is predicted to yield a mature protein having a sequence corresponding to residues 20 to 439 of SEQ ID NO:46. Signal sequence predictions were made with the SignalP algorithm (available at: www.cbs.dtu.dk).

FIGS. 39A-39B: FIG. 39A: Fv39B nucleotide sequence (SEQ ID NO:47). FIG. 39B: Fv39B amino acid sequence (SEQ ID NO:48). SEQ ID NO:48 is the sequence of the immature Fv39B. Fv39B has a predicted signal sequence corresponding to residues 1 to 18 of SEQ ID NO:48 (underlined); cleavage of the signal sequence is predicted to yield a mature protein having a sequence corresponding to residues 19 to 456 of SEQ ID NO:48. Signal sequence predictions were made with the SignalP algorithm (available at: www.cbs.dtu.dk).

FIGS. 40A-40B: FIG. 40A: XynB nucleotide sequence (SEQ ID NO:49). FIG. 40B: XynB amino acid sequence (SEQ ID NO:50). XynB does not have a predicted signal sequence from the SignalP algorithm (available at: www.cbs.dtu.dk).

FIGS. 41A-41B: FIG. 41A: XylA nucleotide sequence (SEQ ID NO:51). FIG. 41B: XylA amino acid sequence (SEQ ID NO:52). XylA does not have a predicted signal sequence from the SignalP algorithm (available at: www.cbs.dtu.dk), but has a signal sequence predicted from the Uniprot algorithm (available at: www.uniprot.org/uniprot) that corresponds to residues 1 to 18 of SEQ ID NO:52 (underlined); cleavage of the signal sequence is predicted to yield a mature protein having a sequence corresponding to residues 19-705 of SEQ ID NO:52.

FIGS. 42A-42B: FIG. 42A: Xyl1 nucleotide sequence (SEQ ID NO:53). FIG. 42B: Xyl1 amino acid sequence (SEQ ID NO:54). SEQ ID NO:54 is the sequence of the immature Xyl1. Xyl1 has a predicted signal sequence corresponding to residues 1 to 21 of SEQ ID NO:54 (underlined); cleavage of the signal sequence is predicted to yield a mature protein having a sequence corresponding to residues 22 to 500 of SEQ ID NO:54. Signal sequence predictions were made with the SignalP algorithm (available at: www.cbs.dtu.dk).

FIGS. 43A-43B: FIG. 43A: EXP and ethanol concentrations measured on Day 1 from an SSF reaction employing the bxl1⁻ *T. reesei* strain #229, where 0.5 or 1.5 mg/g xylan of purified *T. reesei* Bxl1 was added to the SSF reaction or where 1 mg/g xylan of purified Fv43D was added; FIG. 43B: EXP and ethanol concentrations measured on Day 3 from an SSF reaction employing the bxl1⁻ *T. reesei* #229, where 0.5 or 1.0 mg/g xylan or purified *T. reesei* Bxl1 was added to the SSF reaction or where 1 mg/g xylan of purified Fv43D was added. Conditions of the SSF reaction(s) are described below in Example 6.

6. DETAILED DESCRIPTION

The meanings of abbreviations used herein are listed below: "min" means minute, "mins" means minutes; "hr" means hour, "hrs" means hours, "d" means day(s), "A" means microliter(s), "mL" means milliliter(s), "L" means liter(s), "nm" means to nanometer(s), "mm" means millimeter(s), "cm" means centimeter(s), "µm" means micrometer(s), "mM" means millimolar(s), "M" means molar(s), "mmol." means millimole(s), "µmole" means micromole(s), "g" means gram(s), "µg" means microgram(s), "mg" means to milligram(s), "kg" means kilogram(s), "RPM" or "rpm" means revolutions per minute, "vol. %" means volume %, "wt. %" means weight %, and "RPS" means revolutions per second.

6.1. Common Definitions

Unless otherwise noted, all U.S. patents and U.S. patent applications cited to herein are incorporated by reference in their entirety. Moreover, when an amount, concentration, or other value or parameter is given as a range, a preferred range, or a list of upper preferable value, or lower preferable values, it should be understood as specifically disclosing all ranges or numbers along the continuum formed in those ranges. When a range of numerical values is recited herein, unless otherwise noted, the range is intended to encompass the endpoints of that range, and all intergers and fractions within the range. It is not intended that the scope of the invention be limited to the specific values recited when defining a range.

As used herein, the articles "a", "an", and "the" preceding an element or component of the invention are intended to be nonrestrictive regarding the number of instances (e.g., occurrences) of the element or component. Thus "a", "an", and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the term "consisting essentially of" and "consisting of." Similarly, the term "consisting essentially of" is intended to include embodiments encompassed by the term "consisting of."

As used herein, the term "about" modifying the quanity of an ingredient or reactant, or the quantity of a parameter of the invention, refers to variation in the numerical quantity that can occur, for example, through typical measuring and liquid handling procedures used for making concentrates or solutions in the real world, through inadvertent errors in these procedures, through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about" the claims include equivalents to the quanities they recite.

The term "simultaneous saccharification and fermentation" or "SSF" refers to a process or reaction configuration wherein biomass is saccharified and the fermentable sugars produced from the saccharification are used by an enzyme and/or by a fermenting microorganism to produce a product all at the same time, typically in the same reaction vessel.

The term "hybrid saccharification and fermentation" or "HSF" refers to a process or reaction configuration wherein biomass is saccharified to a limited extent (incomplete or partial saccharification), followed by continued saccharification and fermentation occurring simultaneously.

The terms "separate saccharification and fermentation," "separate hydrolysis and fermentation," and "SHF" are used interchangeably herein. They refer to a process or reaction configuration wherein biomass is saccharified or hydrolyzed to substantial completion (e.g., about 60% or more complete, about 70% or more complete, about 80% or more complete, about 90% or more complete, or about 95% or more complete) or to completion (e.g., about 99% or more complete, or about 100% complete, such that all fermentable sugars that would be released from a given saccharification reaction are released), followed by a separate and distinct fermentation step, wherein the fermentation sugars produced by the saccharification or hydrolysis step is fermented to produce a fermentation product.

The term "fermentable sugar" refers to oligosaccharides and monosaccharides that can be used as a carbon source by a microorganism in a fermentation process.

The term "partial saccharification" refers to limited saccharification of biomass where the fermentable sugars released are less than the total of fermentable sugars that would be released if saccharification is run to completion.

The term "cellulosic" refers to a composition comprising cellulose and additional components, including, for example, hemicellulose.

The term "saccharification" refers to the production of fermentable sugars from polysaccharides or polysaccharide-containing materials.

The term "biomass" refers to any cellulosic or lignocellulosic material and includes materials comprising cellulose, and optionally further comprising hemicellulose, lignin, starch, oligosaccharides, and/or monosaccharides. Biomass can also comprise additional components, such as proteins and/or lipids. Biomass can be derived from a single source, or biomass can comprise a mixture derived from more than one source. For example, biomass can comprise a mixture of corn cobs and corn stover, or a mixture of grass and leaves. Biomass incudes, but is not limited to, bioenergy crops, agricultural residues, municipal solid waste, industrial solid waste, sludge from paper manufacture, yard waste, wood and forestry waste. Examples of biomass include, without limitation, corn cobs, crop residues such as corn husks, corn stover, grasses, wheat, wheat straw, barley straw, hay, rice straw, switchgrass, wasted paper, sugar cane bagasse, sorghum, giant reed, elephant grass, miscanthus, Japanese cedar, components obtained from milling of grains, tress, branches, roots, leaves, wood chips, sawdust, shrubs and bushes, vegetables, fruits, flowers and animal manure.

The term "saccharification enzyme" refers to an enzyme that can catalyze conversion of a component of biomass to fermentable sugars. It is often the case that the enzyme is more effective at producing fermentable sugars when the biomass is pretreated.

6.2. Detailed Description

Production of a substance or fermentation product from cellulosic material typically involves three major steps. These three steps are (1) pretreatment or pre-hydrolysis, (2) enzymatic hydrolysis or saccharification, and (3) fermentation, after which the substance or fermentation product can be recovered. Exemplified below is a process for producing ethanol, but it will be understood that similar processes can be used to produce other substances.

Pretreatment.

In the pretreatment or pre-hydrolysis step, the cellulosic material (including, for example, a lignocellulosic material) is heated to break down the lignin and carbohydrate structure, to solubilize most of the hemicellulose, and to make the cellulose fraction accessible to cellulolytic enzymes. The heating step is performed either directly using steam or in a slurry or mixture where a catalyst may optionally be added to the material to accelerate the reactions. Suitable catalysts include, for example, strong acids, such as sulfuric acid and $SO_2$, or strong bases, such as sodium hydroxide. The pretreatment step facilitates the penetration of the enzymes and microorganisms. Cellulosic biomass may also be subject to a hydrothermal steam explosion pre-treatment (see, e.g., U.S. Patent Publication No. 2002/0164730).

Saccharification.

In the enzymatic hydrolysis step, also known as the saccharification step, enzymes as described herein are added to the pretreated material to convert the cellulose fraction to glucose and/or other sugars. The saccharification step is generally performed in stirred-tank reactors or fermentors under controlled pH, temperature, and mixing conditions. A saccharification step may, in certain cases, last up to 200 hrs. Saccharification can be carried out at temperatures from about 30° C. to about 65° C., in particular about 50° C., and at a pH of between about 4 and about 5, in particular at about pH 4.5. To produce glucose that can be metabolized by a fermenting microorganism such as a fungus (e.g., a yeast or a filamentous fungus) or a bacterium (e.g., a *Zymomonas mobillis* or a *Clostridium thermocellum*) the enzymatic hydrolysis step is typically performed in the presence of a β-glucosidase.

Fermentation.

In the fermentation step, sugars, released from the cellulosic material as a result of the pretreatment and enzymatic hydrolysis steps, are fermented to ethanol (or other substances) by a fermenting organism, such as a fungus (e.g., a yeast or a filamentous fungus) or a bacterium (e.g., a *Zymomonas mobillis* or a *Clostridium thermocellum*).

SSF.

The present disclosure provides methods and compositions for improving the yield of reactions in which the fermentation step is carried out, rather than in a distinct or separate step following the enzymatic hydrolysis step, simultaneously with the enzymatic hydrolysis step in the same vessel, preferably under controlled pH, temperature, and mixing conditions. In certain aspects, the saccharification and fermentation are performed simultaneously in the same vessel, and as such is a simultaneous saccharification and fermentation, or "SSF." This process, as described herein, encompasses, also processes that are carried out using a "hybrid saccharification and fermentation" or "HSF" configuration. In certain aspects, an SSF reaction is initiated (e.g., by the addition of fermenting microorganism to a saccharification reaction, or by instituting a set of conditions to favor fermentation) when no more than 30%, no more than 25%, no more than 20%, no more than 15%, no more than 10%, or no more than 5% of the biomass is saccharified. As used herein, the term "SSF" also encompasses the co-fermentation of multiple sugars (Sheehan and Himmel, 1999, Enzymes, energy and the environment: A strategic perspective on the U.S. Department of Energy's research and development activities for bioethanol, Biotechnol. Prog. 15: 817-827).

6.3 Enzymatic Hydrolysis

The cell walls of higher plants are comprised of a variety of carbohydrate polymer (CP) components. These CP components interact through covalent and non-covalent means, providing the structural integrity plants require to form rigid cell walls and to resist turgor pressure. The major CP found in plants is cellulose, which forms the structural backbone of the plant cell walls. During cellulose biosynthesis, chains of poly-β-1,4-D-glucose self associate through hydrogen bonding and hydrophobic interactions to form cellulose microfibrils, which further self-associate to form larger fibrils. Cellulose microfibrils are somewhat irregular and contain regions of varying crystallinity. The degree of crystallinity of cellulose fibrils depends on how tightly ordered the hydrogen bonding is between any two component cellulose chains. Areas with less-ordered bonding, and therefore more accessible glucose chains, are referred to as amorphous regions.

The general model for converting or depolymerizing cellulose into glucose involves three enzymatic activities. Endoglucanases cleave cellulose chains internally to generate shorter chains and increase the number of accessible ends, which are then acted upon by exoglucanases. Exoglucanases are specific for either the reducing ends or the non-reducing ends of the shorter chains, and are capable of liberating cellobiose, the dimer of glucose. Examples of exoglucanases include, without limitation, various cellobiohydrolases. The accumulating cellobiose is then cleaved to form glucose by cellobiases. Examples of cellobiases include, without limitation, various β-1,4-glucosidases.

Hemicellulose contains a set of different sugar monomers from those of cellulose, which contains anhydro-glucose. For instance, aside from glucose, sugar monomers in hemicellulose can include xylose, mannose, galactose, rhamnose, and arabinose. Hemicelluloses contain mostly D-pentose sugars and occasionally small amounts of L-sugars as well. Xylose is the sugar monomer present in the largest amount, but mannuronic acid and galacturonic acid also tend to be present. Hemicelluloses include, for example, xylan, glucuronoxylan, arabinoxylan, glucomannan, and xyloglucan.

Enzymes and multi-enzyme compositions of the present disclosure are useful for saccharification of hemicellulose materials, e.g., xylan, arabinoxylan and xylan- or arabinoxylan-containing substrates. Arabinoxylan is a polysaccharide composed of xylose and arabinose, wherein L-α-arabinofuranose residues are attached as branch-points to a β-(1, 4)-linked xylose polymeric backbone.

Due to the complexity of most biomass sources, which can contain cellulose, hemicellulose, pectin, lignin, protein, and ash, among other components, in certain aspects the enzyme blends of the disclosure can contain enzymes with a range of substrate specificities that work together to degrade biomass into fermentable sugars in an efficient manner. One example of a multi-enzyme complex for lignocellulose saccharification comprises a mixture of cellobiohydrolase(s), xylanase(s), endoglucanase(s), β-glucosidase(s), β-xylosidase(s), and, optionally, various accessory proteins.

Accordingly, the present disclosure contemplates the use of one or more enzymes that are capable, individually or collectively, of producing a carbohydrate that can be used as an energy-source by the fermenting organism(s) in an SSF reaction for producing a fermentation product, such as ethanol.

In certain aspects, multi-enzyme compositions are used in an SSF reaction for hydrolysis of carbohydrates or carbohydrate-containing biomass substrates to produce sugars that are fermented in the same reaction by a fermenting microorganism. The multi-enzyme compositions (including products of manufacture, enzyme ensembles, or "blends") comprise a mixture (or "blend") of enzymes that, in certain aspects, is non-naturally occurring. As used herein, the term "blend" refers to:

(1) a composition made by combining component enzymes, whether in the form of a fermentation broth or in the form of partially or completely isolated or purified polypeptides;

(2) a composition produced by an organism modified to express one or more component enzymes; optionally, the organism can be modified to delete one or more genes or inactivate one or more gene products, wherein the genes encode proteins that affect xylan hydrolysis, hemicellulose hydrolysis and/or cellulose hydrolysis;

(3) a composition made by combining component enzymes simultaneously, separately, or sequentially during an SSF reaction; and (4) an enzyme mixture produced in situ, e.g., during an SSF reaction;

(5) a combination of any or all of (1)-(4) above.

It is also to be understood that any of the enzymes described specifically herein can be combined with any one or more of the enzymes described herein or with any other available and suitable enzymes, to produce a multi-enzyme composition. The disclosure is not restricted or limited to the specific exemplary combinations listed or exemplified herein.

In the methods of the present disclosure, any of the enzyme(s) described herein can be added prior to or during the SSF reaction, including during or after the propagation of the fermenting microorganism(s). The enzymes can be added individually, as an enzyme blend, or as a fermentation broth, etc.

The enzymes referenced herein can be derived or obtained from any suitable origins, including, for example, from bacterial, fungal, yeast, or mammalian origins. The term "obtained" is meant that the enzyme can be isolated from an organism, which naturally produces the enzyme as a native enzyme, or that the enzyme can be produced recombinantly in a host organism, wherein the recombinantly produced enzyme is either native or foreign to the host organism, has a modified amino acid sequence, e.g., having one or more amino acids, which are deleted, inserted and/or substituted, or is an enzyme produced by nucleic acid shuffling processes known in the art. For example, the recombinantly produced enzyme can be one that is a mutant and/or a fragment of a native amino acid sequence. By "a native enzyme" it is meant to encompass the product of a gene in its natural location in the genome of an organism, and also to encompass natural variants; by a "foreign enzyme" it is meant to encompass the product of a gene not normally found in the host organism, but that is introduced into the host organism by gene transfer, or gene inserted into a non-native organism, or chimeric genes, which includes enzymes that are obtained recombinantly, such as by site-directed mutagenesis or shuffling.

The enzymes can, in certain aspects, be purified. The term "purified," as used herein to modify substances like enzymes, proteins, polypeptides, polynucleotides, and other components, refers to enzymes free or substantially free from other components of the organisms from which they are derived. In certain aspects, the term "purified" also encompasses situations wherein the enzymes are free or substantially free from components of the native organisms from which they are obtained. Enzymes can be deemed "purified," but remain associated or in the presence of minor amounts of other proteins. The term "other proteins," as used herein, refers, in particular, to other enzymes. The term "purified" as used herein also refers to the removal of other components, particularly the removal of other proteins and more particularly other enzymes present in the originating cells of the enzymes of the disclosure. Accordingly, an enzyme can be, for example, a "substantially pure polypeptide," which is substantially free from other components. The organism in which a given enzyme is produced can be, for example, a host organism suitable for recombinantly produced enzymes. For example, a substantially pure polypeptide can refer to a polypeptide present at a level of 50 wt. % or more, 60 wt. % or more, 70 wt. % or more, 80 wt. % or more, 90 wt. % or more, 95 wt. % or more, 98% or more, or 99% or more in a mixture to which it is a part. A polypeptide substantially free of other components is one that is in a mixture that contains less than 40 wt. %, less than 30 wt. %, less than 20 wt. %, less than 10 wt. %, less than 5 wt. %, less than 2 wt. %, or less than 1 wt. % of other components.

6.3.1. Cellulases

Enzyme blends of the disclosure can comprise one or more cellulases. Cellulases are enzymes that hydrolyze cellulose (β-1,4-glucan or β-D-glucosidic linkages) to form glucose, cellobiose, cellooligosaccharides, and the like. Cellulases are traditionally divided into three major classes: endoglucanases (EC 3.2.1.4) ("EG"), exoglucanases or cellobiohydrolases (EC 3.2.1.91) ("CBH") and β-glucosidases (β-D-glucoside glucohydrolase; EC 3.2.1.21) ("BG") (Knowles et al., 1987, Trends in Biotechnol. 5(9):255-261, and Schulein, 1988, Methods of Enzymology 160:234-242). Endoglucanases act mainly on the amorphous parts of the cellulose fiber, whereas cellobiohydrolases are capable of degrading crystalline cellulose.

Cellulases for use in accordance with the methods and compositions of the disclosure can be obtained from, inter alia, one or more of the following organisms: *Crinipellis scapella, Macrophomina phaseolina, Myceliophthora thermophila, Sordaria fimicola, Volutella colletotrichoides, Thielavia terrestris, Acremonium* sp., *Exidia glandulosa, Fomes fomentarius, Spongipellis* sp., *Rhizophlyctis rosea, Rhizomucor pusillus, Phycomyces niteus, Chaetostylum fresenii, Diplodia gossypina, Ulospora bilgramii, Saccobolus dilutellus, Penicillium verruculosum, Penicillium chrysogenum, Thermomyces verrucosus, Diaporthe syngenesia, Colletotrichum lagenarium, Nigrospora* sp., *Xylaria hypoxylon, Nectria pinea, Sordaria macrospora, Thielavia thermophila, Chaetomium mororum, Chaetomium virscens, Chaetomium brasiliensis, Chaetomium cunicolorum, Syspastospora boninensis, Cladorrhinum foecundissimum, Scytalidium thermophila, Gliocladium catenulatum, Fusarium oxysporum* ssp. *lycopersici, Fusarium oxysporum* ssp. *passiflora, Fusarium solani, Fusarium anguioides, Fusarium poae, Humicola nigrescens, Humicola grisea, Panaeolus retirugis, Trametes sanguinea, Schizophyllum commune, Trichothecium roseum, Microsphaeropsis* sp., *Acsobolus stictoideus spej., Poronia punctata, Nodulisporum* sp., *Trichoderma* sp. (e.g., *Trichoderma reesei*) and *Cylindrocarpon* sp.

In specific embodiments, a cellulase for use in the composition of the disclosure is capable of achieving at least 0.1, at least 0.2, at least 0.3, at least 0.4, or at least 0.5 fraction product as determined by a calcofluor assay as described in the following subsection. In some embodiments, a cellulase for use in the composition of the disclosure is a whole cellulase and/or is capable of achieving at least 0.1, at least 0.2, at least 0.3, at least 0.4, or at least 0.5 fraction product as determined by a calcofluor assay as described in the following subsection. In some embodiments, a cellulase for use in the composition of the disclosure is a whole cellulase and/or is capable of achieving about 0.1 to about 0.5, or about 0.1 to about 0.4, or about 0.2 to about 0.4, or about 0.3 to about 0.4, or about 0.2 to about 0.5, or about 0.3 to about 0.5 fraction product as determined by a calcofluor assay.

6.3.1.1. Cellulase Activity Assay Using Calcofluor White

Phosphoric acid swollen cellulose (PASC) is prepared from Avicel PH-101 using an adapted protocol of Walseth, 1971, TAPPI 35:228, and of Wood, 1971, Biochem. J. 121:353-362. In short, in an exemplary method, Avicel is solubilized in concentrated phosphoric acid then precipitated using cold deionized water. After the cellulose is collected and washed with water to achieve neutral pH, it is diluted to 1% solids in 50 mM sodium acetate buffer, at pH 5.0.

All enzyme dilutions are made with a 50 mM sodium acetate buffer, pH 5.0. GC220 Cellulase (Danisco US Inc., Genencor) is diluted to 2.5, 5, 10, and 15 mg protein/g PASC, to produce a linear calibration curve. Samples to be tested are diluted to fall within the range of the calibration curve, i.e., to obtain a response of 0.1 to 0.4 fraction product. One hundred and fifty (150) μL of cold 1% PASC is added to each 20 μL of enzyme solution in suitable vessles, for example, 96-well microtiter plates. The plates are covered and incubated for 2 hrs at 50° C., spun at 200 rpm, in an incubator/shaker. The reactions are then quenched using 100 μL of 50 μg/mL Calcofluor in 100 mM Glycine, pH 10. Fluorescence is read on a fluorescence microplate reader at excitation wavelength Ex=365 nm and emission wavelength Em=435 nm. The result is expressed as the fraction product according to the equation:

$$FP=1-(FI\text{ sample}-FI\text{ buffer with cellobiose})/(FI\text{ zero enzyme}-FI\text{ buffer with cellobiose}),$$

wherein "FP" is fraction product and "FI" is fluorescence units.

6.3.1.2. β-Glucosidase

The enzyme blends of the disclosure optionally comprise one or more β-glucosidases. The term "β-glucosidase" as used herein refers to a β-D-glucoside glucohydrolase classified in or under EC 3.2.1.21, and/or to an enzyme that is a member of certain glycosyl hydrolase ("GH") families, including, without limitation, GH families 1, 3, 9 or 48. In certain aspects, the term refers to an enzyme that is capable of catalyzing the hydrolysis of cellobiose to release β-D-glucose.

β-glucosidases can be obtained from any suitable microorganisms. They can be obtained or produced by recombinant means, or can be obtained from commercial sources. Suitable β-glucosidases can, for example, be obtained from microorganisms such as bacteria and fungi. For example, a suitable β-glucosidase can be obtained from a filamentous fungus.

In certain aspects, a suitable β-glucosidase can be obtained from *Aspergillus aculeatus* (Kawaguchi et al., 1996, Gene 173: 287-288), *Aspergillus kawachi* (Iwashita et al., 1999, Appl. Environ. Microbiol. 65: 5546-5553), *Aspergillus oryzae* (PCT patent application publication WO 2002/095014), *Cellulomonas biazotea* (Wong et al., 1998, Gene 207:79-86), *Penicillium funiculosum* (PCT patent application publication WO 200478919), *Saccharomycopsis fibuligera* (Machida et al., 1988, Appl. Environ. Microbiol. 54: 3147-3155), *Schizosaccharomyces pombe* (Wood et al., 2002, Nature 415: 871-880), or *Trichoderma reesei*. For example, suitable β-glucosidases from *Trichoderma reesei* can include β-glucosidase 1 (U.S. Pat. No. 6,022,725), *Trichoderma reesei* β-glucosidase 3 (U.S. Pat. No. 6,982, 159), *Trichoderma reesei* β-glucosidase 4 (U.S. Pat. No. 7,045,332), *Trichoderma reesei* β-glucosidase 5 (U.S. Pat. No. 7,005,289), *Trichoderma reesei* β-glucosidase 6 (U.S. Patent Application Publication 20060258554), or *Trichoderma reesei* β-glucosidase 7 (U.S. Patent Application Publication 20060258554).

In some embodiments, suitable β-glucosidases can be produced by expressing genes encoding β-glucosidases. For example, a suitable β-glucosidase can be secreted into the extracellular space e.g., by certain Gram-positive organism, (such as *Bacillus* or Actinomycetes), or by a eukaryotic host (e.g., *Trichoderma, Aspergillus, Saccharomyces,* or *Pichia*).

Suitable β-glucosidases can also be obtained from commercial sources. Examples of commercial β-glucosidase preparation suitable for use in the methods, compositions and other embodiments of the present disclosure include, without limitation, *Trichoderma reesei* β-glucosidase in Accellerase™ BG (Danisco US Inc., Genencor); NOVOZYM™ 188 (a β-glucosidase from *Aspergillus niger*); *Agrobacterium* sp. β-glucosidase, and *Thermatoga maritima* β-glucosidase available from Megazyme (Megazyme International Ireland Ltd., Bray Business Park, Bray, Co. Wicklow, Ireland.).

In certain aspects, a suitable β-glucosidase can be a component of a whole cellulase, as described in Section 6.3.1.5 below.

β-glucosidase activity can be determined by means that are known in the art. For example, the assay described by Chen et al., 1992, in Biochimica et Biophysica Acta 121: 54-60 can be used. In that assay, one unit pNPG denotes 1 μmoL of Nitrophenol liberated from para-nitrophenyl-B-D-glucopyranoside in 10 mins at 50° C. (or 122° F.) and pH 4.8.

6.3.1.3. Endoglucanases

The enzyme blends of the disclosure optionally comprise one or more endoglucanase. The term "endoglucanase" refers to any polypeptides classified in EC 3.2.1.4.

In some aspects, a *Trichoderma reesei* EG1 (Penttila et al., 1986, Gene 63:103-112) and/or *T. reesei* EGII (Saloheimo et al., 1988, Gene 63:11-21) are used in the methods and compositions of the present disclosure. In other aspects, the endoglucanase can be a *T. reesei* endoglucanase VI (see, e.g., U.S. Pat. No. 7,351,568), endoglucanase VII (see, e.g., U.S. Pat. No. 7,449,319), or endoglucanase VIII (see, e.g., U.S. Pat. No. 7,049,125).

In specific embodiments, a suitable endoglucanase can be a *Thielavia terrestris* thermostable endoglucanase (Kvesitadaze et al., 1995, Appl. Biochem. Biotechnol. 50:137-143); *Trichoderma reesei* EGIII (Okada et al., 1988, Appl. Environ. Microbiol. 64:555-563), EGIV (Saloheimo et al., 1997, Eur. J. Biochem. 249:584-591), EG5 (Saloheimo et al., 1994, Mol. Microbiol. 13:219-228), EGVI (U.S. Patent Application Publication No. 20070213249), or EGVII (U.S. Patent Application Publication No. 20090170181); *Acidothermus cellulolyticus* EI endoglucanase (U.S. Pat. No. 5,536,655); *Humicola insolens* endoglucanase V (EGV) (Protein Data Bank entry 4ENG); *Staphylotrichum coccosporum* endoglucanase (U.S. Patent Application Publication No. 20070111278); *Aspergillus aculeatus* endoglucanase F1-CMC (Ooi et al., 1990, Nucleic Acid Res. 18:5884); *Aspergillus kawachii* IFO 4308 endoglucanase CMCase-1 (Sakamoto et al., 1995, Curr. Genet. 27:435-439); or *Erwinia carotovara* (Saarilahti et al., 1990, Gene 90:9-14); *Acremonium thermophilum* ALKO4245 endoglucanase (U.S. Patent Publication No. 20070148732).

Suitable endoglucanases for use in the methods and compositions of the present disclosure can also be those described in, e.g., PCT patent application publications WO 91/17243, WO 91/17244, WO 91/10732, or U.S. Pat. No. 6,001,639.

6.3.1.4. Cellobiohydrolases

The term "cellobiohydrolase" as used herein refers to any cellobiohydrolases that are classified in EC 3.2.1.91. The methods and compositions of the present disclosure can suitably comprise one or more cellobiohydrolases ("CBH").

In some aspects, a *Trichoderma reesei* GBHI (Shoemaker et al., 1983, Bio/Technology 1:691-696) and/or GBHI (Teeri et al., 1983, Bio/Technology 1:696-699) can be used in the methods and compositions of the present disclosure.

In some aspects, a suitable CBH can be an *Agaricus bisporus* CBH1 (Swiss Prot Accession no. Q92400); *Aspergillus aculeatus* CBH1 (Swiss Prot Accession No. O59843); *Aspergillus nidulans* CBHA (GenBank Accession No. AF420019); *Aspergillus nidulans* CBHB (GenBank Accession No. AF420020); *Aspergillus niger* CBHA (GenBank Accession No. AF156268); *Aspergillus niger* CBHB (GenBank Accession No. AF156269); *Claviceps purpurea* CBH1 (Swiss Prot Accession No. O00082); *Cochliobolus carbonarum* CBH1 (Swiss Prot Accession No. Q00328); *Cryphonectria parasitica* CBH1 (Swiss Prot Accession No. Q00548); *Fusarium oxysporum* CBH1 (Cel7A) (Swiss Prot Accession No. P46238); *Humicola grisea* cbh1.2 (GenBank Accession No. U50594); *Humicola grisea* var. *thermoidea* CBH1 (GenBank Accession No. D63515); *Humicola grisea* var. *thermoidea* CBHI.2 (GenBank Accession No. AF123441); *Humicola grisea* var. *thermoidea* exo1 (GenBank Accession No. AB003105); *Melanocarpus albomyces* Cel7B (GenBank Accession No. AJ515705), *Neurospora crassa* CBHI (GenBank Accession No. X77778); *Penicillium funiculosum* CBHI (Cel17A) (U.S. Patent Publication No. 20070148730); *Penicillium janthinellum* GBHI (GenBank Accession No. S56178); *Phanerochaete chrysosporium* CBH (GenBank Accession No. M22220); *Phanerochaete chrysosporium* CBHI-2 (Cel7D) (GenBank Accession No. L22656); *Talaromyces emersonii* Cbh1A (GenBank Accession No. AF439935); *Trichoderma viride* CBH1 (GenBank Accession No. X53931), or *Volvariella volvacea* V14 Cbh1 (GenBank Accession No. AF156693).

6.3.1.5. Whole Cellulases

In certain aspects, an enzyme blend of the disclosure comprises a whole cellulase. As used herein, a "whole cellulase" refers to both naturally occurring and non-naturally occurring cellulase-containing compositions comprising: (1) an endoglucanase, which cleaves internal β-1,4 linkages of a cellulose, resulting in shorter glucooligosaccharides, (2) a cellobiohydrolase, which acts in an "exo" manner to release cellobiose units from the shorter glucooligosaccharides; examples of cellobiose units include β-1,4 glucose-glucose disaccharide, and (3) a β-glucosidase, which catalyzes the release of glucose monomers from short cellooligosaccharides or cellobioses, which are glucose dimmers.

A "naturally occurring cellulase-containing" composition is one produced by a naturally occurring source, which comprises one or more cellobiohydrolase-type, one or more endoglucanase-type, and one or more β-glucosidase-type components or activities, wherein each of these components or activities is found at the ratios and levels produced in nature, untouched by the human hand. Accordingly, a naturally occurring cellulase-containing composition is, for example, one that is produced by an organism unmodified with respect to the cellulolytic enzymes such that the ratios or levels of the component enzymes are unaltered from that produced by the native organism in nature. A "non-naturally occurring cellulase-containing composition" refers to a composition produced by: (1) combining component cellulolytic enzymes either in a naturally occurring ratio or a non-naturally occurring, i.e., altered, ratio; or (2) modifying an organism to overexpress or underexpress one or more cellulolytic enzymes; or (3) modifying an organism such that at least one cellulolytic enzyme is deleted. A "non-naturally occurring cellulase containing" composition can also refer to a composition resulting from adjusting the culture conditions for a naturally-occurring organism, such that the naturally-occurring organism grows under a non-native condition, and produces an altered level or ratio of enzymes. Accordingly, in some embodiments, the whole cellulase preparation of the present disclosure can have one or more EGs and/or CBHs and/or β-glucosidases deleted and/or overexpressed. In the present disclosure, a whole cellulase preparation can be from any microorganism that is capable of hydrolyzing a cellulosic material. In some embodiments, the whole cellulase preparation is a filamentous fungal whole cellulase. For example, the whole cellulase preparation can be from an *Acremonium, Aspergillus, Emericella, Fusarium, Humicola, Mucor, Myceliophthora, Neurospora, Penicillium, Scytalidium, Thielavia, Tolypocladium*, or *Trichoderma* species. The whole cellulase preparation is, for example, an *Aspergillus aculeatus, Aspergillus awamori, Aspergillus foetidus, Aspergillus japonicus, Aspergillus nidulans, Aspergillus niger*, or *Aspergillus oryzae* whole cellulase. Moreover, the whole cellulase preparation can be a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* whole cellulase preparation. The whole cellulase preparation can also be a *Chrysosporium lucknowense, Humicola insolens, Humicola lanuginosa, Mucor miehei, Myceliophthora thermophila, Neurospora crassa, Penicillium purpurogenum, Penicillium funiculosum, Scytalidium thermophilum*, or *Thielavia terrestris* whole cellulase preparation. Moreover, the whole cellulase preparation can be a *Trichoderma harzianum, Trichoderma koningii, Trichoderma longibrachiatum, Trichoderma reesei* (e.g., RL-P37 (Sheir-Neiss G et al. Appl. Microbiol. Biotechnol. 1984, 20, pp. 46-53), QM9414 (ATCC No. 26921), NRRL 15709, ATCC 13631, 56764, 56466, 56767), or a *Trichoderma viride* (e.g., ATCC 32098 and 32086) whole cellulase preparation.

The whole cellulase preparation can, in particular, suitably be a *Trichoderma reesei* RutC30 whole cellulase preparation, which is available from the American Type Culture Collection as *Trichoderma reesei* ATCC 56765. For example, the whole cellulase preparation can also suitably be a whole cellulase of *Penicillium funiculosum*, which is available from the American Type Culture Collection as *Penicillium funiculosum* ATCC Number: 10446.

The whole cellulase preparation can also be obtained from commercial sources. Examples of commercial cellulase preparations suitable for use in the methods and compositions of the present disclosure include, for example, CELLUCLAST™ and Cellic™ (Novozymes A/S) and LAMINEX™ BG, IndiAge™ 44L, Primafast™ 100, Primafast™ 200, Spezyme™ CP, Accellerase™ 1000, and Accellerase™ 1500 (Danisco US. Inc., Genencor).

Suitable whole cellulase preparations can be made using any microorganism cultivation methods known in the art, especially fermentation, resulting in the expression of enzymes capable of hydrolyzing a cellulosic material. As used herein, "fermentation" refers to shake flask cultivation, small- or large-scale fermentation, such as continuous, batch, fed-batch, or solid state fermentations in laboratory or industrial fermenters performed in a suitable medium and under conditions that allow the cellulase and/or enzymes of interest to be expressed and/or isolated.

Generally, the microorganism is cultivated in a cell culture medium suitable for production of enzymes capable of hydrolyzing a cellulosic material. The cultivation takes place in a suitable nutrient medium comprising carbon and nitrogen sources and inorganic salts, using procedures and variations known in the art. Suitable culture media, temperature ranges and other conditions for growth and cellulase production are known in the art. As a non-limiting example, a typical temperature range for the production of cellulases by *Trichoderma reesei* is 24° C. to 28° C.

The whole cellulase preparation can be used as it is produced by fermentation with no or minimal recovery and/or purification. For example, once cellulases are secreted into the cell culture medium, the cell culture medium containing the cellulases can be used directly. The whole cellulase preparation can comprise the unfractionated contents of fermentation material, including the spent cell culture medium, extracellular enzymes and cells. On the other hand, the whole cellulase preparation can also be subject to further processing in a number of routine steps, e.g., precipitation, centrifugation, affinity chromatography, filtration, or the like. For example, the whole cellulase preparation can be concentrated, and then used without further purification. The whole cellulase preparation can, for example, be formulated to comprise certain chemical agents that decrease cell viability or kill the cells after fermentation. The cells can, for example, be lysed or permeabilized using methods known in the art.

The endoglucanase activity of the whole cellulase preparation can be determined using carboxymethyl cellulose (CMC) as a substrate. A suitable assay measures the production of reducing ends created by the enzyme mixture acting on CMC wherein 1 unit is the amount of enzyme that liberates 1 µmoL of product/min (Ghose, T. K., Pure & Appl. Chem. 1987, 59, pp. 257-268).

The whole cellulase can be a β-glucosidase-enriched cellulase. The β-glucosidase-enriched whole cellulase generally comprises a β-glucosidase and a whole cellulase preparation. The β-glucosidase-enriched whole cellulase compositions can be produced by recombinant means. For example, such a whole cellulase preparation can be achieved by expressing a β-glucosidase in a microorganism capable of producing a whole cellulase. The β-glucosidase-enriched whole cellulase composition can also, for example, comprise a whole cellulase preparation and a β-glucosidase. For instance, the β-glucosidase-enriched whole cellulase composition can suitably comprise at least 5 wt. %, 7 wt. %, 10 wt. %, 15 wt. % or 20 wt. %, and up to 25 wt. %, 30 wt. %, 35 wt. %, 40 wt. %, or 50 wt. % β-glucosidase based on the total weight of proteins in that blend/composition.

In certain aspects, a suitable whole cellulase can be obtained from a microorganism that is or has been genetically engineered to reduce or eliminate retaining β-xylosidase activity. In other aspects, a suitable whole cellulase can be obtained from a microorganism that is or has been genetically engineered to increase inverting β-xylosidase activity. In yet further aspects, a suitable whole cellulase can be obtained from a microorganism that is or has been genetically engineered to not only have reduced or eliminated retaining β-xylosidase activity, but also have increased inverting β-xylosidase activity. For example, a whole cellulase can suitably be obtained from *Trichoderma reesei* that has been engineered such that the native bxl1 gene is deleted. In another example, a whole cellulase can suitably be obtained from *Trichoderma reesei* that has been engineered to recombinantly express an enzyme with inverting β-xylosidase activity. In yet another example, a whole cellulase can suitably be obtained from *Trichoderma reesei* that has been engineered such that its native bxl1 gene is deleted and that it recombinantly expresses an enzyme with inverting β-xylosidase activity. Examples of enzymes with inverting β-xylosidase activity include, without limitation, Fv43D and others described herein in Section 6.4.

β-xylosidase activity can be determined by measuring the level of hydrolysis of an artificial substrate p-nitrophenyl-β-xylopyranoside. The hydrolysis reaction can be followed using $^1$H-NMR analysis during the course of the reaction. The anomeric proton of the residue contributing the reducing end of a glycosidic bond has a distinct chemical shift depending upon its axial or equatorial orientation as does the anomeric proton of the newly formed reducing sugar after hydrolysis. Mutarotation of the newly formed reducing sugar anomeric proton to the equilibrium mixture of axial and equatorial forms is slower in comparison to the hydrolysis reaction. Thus the $^1$H-NMR determination of the orientation of the first formed reducing end anomeric proton in comparison to the form present in the substrate is an assay for mechanisms that retain configuration versus those that invert configuration. The experimental methods are described in, e.g., Pauly et al., 1999, Glycobiology 9:93-100.

Alternatively, the level of hydrolysis can be determined by distinguishing transglycosylase activity of the retaining enzymes, which is absent in inverting enzymes. An example of such an assay is shown in FIG. 16. Xylobiose or xylose oligomers, in the presence of a retaining enzyme (e.g., Multifect® Xylanase or Fv3A), show a rapid rise in EXP/xylose to 7-8 times the equilibrium ratio in the presence of EtOH after which EXP/xylose falls toward the equilibrium ratio. In the case of the inverting enzymes (e.g., Fv43D), under the same conditions, EXP/xylose increases monotonically toward the equilibrium ratio.

6.3.2. Hemicellulases

A wide variety of fungi and bacteria are capable of enzymatically hydrolyzing hemicelluloses. Similar to cellulose degradation, hemicellulose hydrolysis involves coordinated actions of a number of enzymes. Hemicellulases are often grouped into three general categories: the endo-acting enzymes that attack internal bonds within polysaccharide chains, the exo-acting enzymes that act processively from either the reducing or the nonreducing end of the polysaccharide chain, and the accessory enzymes, acetylesterases, and/or esterases that hydrolyze lignin glycoside bonds. Examples of esterases can include coumaric acid esterase and ferulic acid esterase (Wong et al., 1988, Microbiol. Rev. 52:305-317; Tenkanen and Poutanen, 1992, Significance of esterases in the degradation of xylans, in Xylans and Xylanases, Visser et al., eds., Elsevier, New York, N.Y., pp. 203-212; Coughlan and Hazlewood, 1993, Hemicellulose and hemicellulases, Portland, London, UK; Brigham et al., 1996, Hemicellulases: Diversity and applications, in Handbook on Bioethanol: Production and Utilization, Wyman, ed., Taylor & Francis, Washington, D.C., pp. 119-141).

Suitable hemicellulases for use with the compositions and/or methods of the present disclosure include, for example, xylanases, arabinofuranosidases, acetyl xylan esterase, glucuronidases, endo-galactanase, mannanases, endo or exo arabinases, exo-galactanases, and mixtures thereof. Examples of endo-acting hemicellulases and ancillary enzymes include, without limitation, endoarabinanase, endoarabinogalactanase, endoglucanase, endomannanase, endoxylanase, and feraxan endoxylanase. Examples of exo-acting hemicellulases and ancillary enzymes include, without limitation, α-L-arabinosidase, β-L-arabinosidase, α-1, 2-L-fucosidase, α-D-galactosidase, β-D-galactosidase, β-D-glucosidase, β-D-glucuronidase, β-D-mannosidase, β-D-xylosidase, exoglucosidase, exocellobiohydrolase, exomannobiohydrolase, exomannanase, exoxylanase, xylan α-glucuronidase, and coniferin β-glucosidase. Examples of esterases include, without limitation, acetyl esterases (acetylgalactan esterase, acetylmannan esterase, and acetylxylan esterase) and aryl esterases (coumaric acid esterase and ferulic acid esterase).

In certain aspects, the hemicellulase is an exo-acting hemicellulase. Preferably, the exo-acting hemicellulase has the ability to hydrolyze hemicellulose under acidic conditions, for example, at or below pH 7.

In certain aspects, the hemicellulase is added in an effective amount. For example, the hemicellulase is added to the multienzyme blends of the present disclosure in an amount of about 0.001 wt. % or more, about 0.002 wt. % or more, about 0.0025 wt. % or more, about 0.005 wt. % or more, or about 0.01 wt. % or more relative to the weight of solids in the complete fermentation medium. In another example, the hemicellulase is added to the multienzyme blends of the present disclosure in an amount of about 0.001 wt. % to about 5.0 wt. %, for example, about 0.025 wt. % to about 4.0 wt. %, about 0.005 wt. % to about 2.0 wt. % relative to the weight of solids in the complete fermentation medium.

6.3.2.1. Xylanases

The enzyme blends of the disclosure optionally comprise one or more xylanases. The term "xylanase" as used herein refers to any xylanase classified in or under EC 3.2.1.8. Suitable xylanases include, for example, a *Caldocellum saccharolyticum* xylanase (Luthi et al., 1990, Appl. Environ. Microbiol. 56(9):2677-2683), a *Thermatoga maritima* xylanase (Winterhalter & Liebel, 1995, Appl. Environ. Microbiol. 61(5):1810-1815), a *Thermatoga* Sp. Strain FJSS-B.1 xylanase (Simpson et al., 1991, Biochem. J. 277, 413-417), a *Bacillus circulans* xylanase (BcX) (U.S. Pat. No. 5,405,769), an *Aspergillus nigerxylanase* (Kinoshita et al., 1995, J. Ferment. Bioeng. 79(5):422-428); a *Streptomyces lividans* xylanase (Shareck et al., 1991, Gene 107:75-82; Morosoli et al., 1986, Biochem. J. 239:587-592; Kluepfel et al., 1990, Biochem. J. 287:45-50); *Bacillus subtilis* xylanase (Bernier et al., 1983, Gene 26(1):59-65); a *Cellulomonas fimi* xylanase (Clarke et al., 1996, FEMS Microbiol. Lett. 139:27-35), a *Pseudomonas fluorescens* xylanase (Gilbert et al., 1988, J. Gen. Microbiol. 134:3239-3247); a *Clostridium thermocellum* xylanase (Dominguez et al., 1995, Nat. Struct. Biol. 2(7):569-76); a *Bacillus pumilus* xylanase (Nuyens et al., 2001, Appl. Microbiol. Biotech. 56:431-434; Yang et al., 1988, Nucleic Acids Res. 16(14B):7187); a *Clostridium acetobutylicum* P262 xylanase (Zappe et al., 1990, Nucleic Acids Res. 18(8):2179) or a *Trichoderma harzianum* xylanase (Rose et al., 1987, J. Mol. Biol. 194(4):755-756).

Xylanases can suitably be obtained from a number of sources, including, for example, fungal and bacterial organisms, such as *Aspergillus, Disporotrichum, Penicillium, Neurospora, Fusarium, Trichoderma, Humicola, Thermomyces,* and *Bacillus*. Certain commercially available preparations comprising xylanase(s) can also be used in the compositions and methods of the present disclosure; those include Multifect® xylanase, Laminex® BG and Spezyme® CP (Danisco US, Genencor), and Celluclast® and Viscozyme® (Novozymes A/S).

In certain aspects, the xylanase does not have retaining β-xylosidase activity and/or inverting β-xylosidase activity. An enzyme can be tested for retaining vs. inverting activity as described in Section 6.3.1.5 above.

6.3.2.2. β-Xylosidases

The enzyme blends of the disclosure optionally comprise one or more β-xylosidases.

As used herein, the term "β-xylosidase" refers to any β-xylosidase classified in or under EC 3.2.1.37. Suitable β-xylosidases include, for example *Talaromyces emersonii* Bxl1 (Reen et al., 2003, Biochem. Biophys. Res. Commun. 305(3):579-85); as well as β-xylosidases obtained from *Geobacillus stearothermophilus* (Shallom et al., 2005, Biochem. 44:387-397); *Scytalidium thermophilum* (Zanoelo et al., 2004, J. Ind. Microbiol. Biotechnol. 31:170-176); *Trichoderma lignorum* (Schmidt, 1988, Methods Enzymol. 160:662-671); *Aspergillus awamori* (Kurakake et al., 2005, Biochim. Biophys. Acta 1726:272-279); *Aspergillus versicolor* (Andrade et al., Process Biochem. 39:1931-1938); *Streptomyces* sp. (Pinphanichakarn et al., 2004, World J. Microbiol. Biotechnol. 20:727-733); *Thermotoga maritima* (Xue and Shao, 2004, Biotechnol. Lett. 26:1511-1515); *Trichoderma* sp. SY (Kim et al., 2004, J. Microbiol. Biotechnol. 14:643-645); *Aspergillus niger* (Oguntimein and Reilly, 1980, Biotechnol. Bioeng. 22:1143-1154); or *Penicillium wortmanni* (Matsuo et al., 1987, Agric. Biol. Chem. 51:2367-2379).

In certain aspects, the β-xylosidase does not have retaining β-xylosidase activity. In other aspects, the β-xylosidase has inverting β-xylosidase activity. In yet further aspects, the β-xylosidase has no retaining β-xylosidase activity but has inverting β-xylosidase activity. An enzyme can be tested for retaining vs. inverting activity as described in Section 6.3.1.5 above.

6.3.2.3. L-α-Arabinofuranosidases

The enzyme blends of the disclosure optionally comprise one or more L-α-arabinofuranosidases.

As used herein, the term "L-α-arabinofuranosidase" refers to any enzyme classified in or under EC 3.2.1.55. Suitable L-α-arabinofuranosidase can be obtained from, for example, *Aspergillus oryzae* (Numan & Bhosle, 2006, J. Ind. Microbiol. Biotechnol. 33:247-260); *Aspergillus sojae* (Oshima et al., 2005, J. Appl. Glycosci. 52:261-265); *Bacillus brevis* (Numan & Bhosle, 2006, J. Ind. Microbiol. Biotechnol. 33:247-260); *Bacillus stearothermophilus* (Kim et al., 2004, J. Microbiol. Biotechnol. 14:474-482); *Bifidobacterium breve* (Shin et al., 2003, Appl. Environ. Microbiol. 69:7116-7123; *Bifidobacterium longum* (Margolles et al., 2003, Appl. Environ. Microbiol. 69:5096-5103); *Clostridium thermocellum* (Taylor et al., 2006, Biochem. J. 395:31-37); *Fusarium oxysporum* (Panagiotou et al., 2003, Can. J. Microbiol. 49:639-644); *Fusarium oxysporum* f. sp. *dianthi* (Numan & Bhosle, 2006, J. Ind. Microbiol. Biotechnol. 33:247-260); *Geobacillus stearothermophilus* T-6 (Shallom et al., 2002, J. Biol. Chem. 277:43667-43673); *Hordeum vulgare* (Lee et al., 2003, J. Biol. Chem. 278:5377-5387); *Penicillium chrysogenum* (Sakamoto et al., 2003, Biophys. Acta 1621:204-210); *Penicillium* sp. (Rahman et al., 2003, Can. J. Microbiol. 49:58-64); *Pseudomonas cellulosa* (Numan & Bhosle, 2006, J. Ind. Microbiol. Biotechnol. 33:247-260); *Rhizomucor pusillus* (Rahman et al., 2003, Carbohydr. Res. 338:1469-1476); *Streptomyces chartreusis* (Numan & Bhosle, 2006, J. Ind. Microbiol. Biotechnol. 33:247-260); *Streptomyces thermoviolacus* (Numan & Bhosle, 2006, J. Ind. Microbiol. Biotechnol. 33:247-260); *Thermoanaerobacter ethanolicus* (Numan & Bhosle, 2006, J. Ind. Microbiol. Biotechnol. 33:247-260); *Thermobacillus xylanilyticus* (Numan & Bhosle, 2006, J. Ind. Microbiol. Biotechnol. 33:247-260); *Thermomonospora fusca* (Tuncer and Ball, 2003, Folia Microbiol. (Praha) 48:168-172); *Thermotoga maritima* (Miyazaki, 2005, Extremophiles 9:399-406); *Trichoderma* sp. SY (Jung et al., 2005, Agric. Chem. Biotechnol. 48:7-10); *Aspergillus kawachii* (Koseki et al., 2006, Biochim. Biophys. Acta 1760:1458-1464); *Fusarium oxysporum* f. sp. *dianthi* (Chacon-Martinez et al., 2004, Physiol. Mol. Plant. Pathol. 64:201-208); *Thermobacillus xylanilyticus* (Debeche et al., 2002, Protein Eng. 15:21-28); *Humicola insolens* (Sorensen et al., 2007, Biotechnol. Prog. 23:100-107); *Meripilus giganteus* (Sorensen et al., 2007, Biotechnol. Prog. 23:100-107); or *Raphanus sativus* (Kotake et al., 2006, J. Exp. Bot. 57:2353-2362).

In certain aspects, the L-α-arabinofuranosidase does not have retaining β-xylosidase activity. In other aspects, the L-α-arabinofuranosidase has inverting β-xylosidase activity. In yet further aspects, the L-α-arabinofuranosidase has no retaining β-xylosidase but has inverting β-xylosidase activity. An enzyme can be tested for retaining vs. inverting activity as described in Section 6.3.1.5 above.

6.3.3. Accessory Proteins

A number of polypeptides having cellulolytic enhancing activity can also be used in conjunction with the above-noted enzymes and/or cellulolytic proteins to further degrade the cellulose component of the biomass substrate, (see, e.g., Brigham et al., 1995, in Handbook on Bioethanol (Charles E. Wyman, ed.), pp. 119-141, Taylor & Francis, Washington D.C.; Lee, 1997, J. Biotechnol. 56: 1-24).

The optimum amounts of such a polypeptide having cellulolytic enhancing activity and of cellulolytic proteins depend on a number of factors including, without limitation, the specific mixture of component cellulolytic proteins, the cellulosic substrate, the concentration of cellulosic substrate, the pretreatment(s) of the cellulosic substrate, the temperature, time, and pH, and the nature of the fermenting organism.

The enzyme blends/compositions of the disclosure can, for example, suitably further comprise one or more accessory proteins. Examples of accessory proteins include, without limitation, mannanases (e.g., endomannanases, exomannanases, and β-mannosidases), galactanases (e.g., endo- and exo-galactanases), arabinases (e.g., endo-arabinases and exo-arabinases), ligninases, amylases, glucuronidases, proteases, esterases (e.g., ferulic acid esterases, acetyl xylan esterases, coumaric acid esterases or pectin methyl esterases), lipases, glycoside hydrolase Family 61 polypeptides, xyloglucanases, CIP1, CIP2, swollenin, expansins, and cellulose disrupting proteins. Examples of accessory proteins can also include CIP1-like proteins, CIP2-like proteins, cellobiose dehydrogenases and manganese peroxidases. In particular embodiments, the cellulose disrupting proteins are cellulose binding modules.

6.4 Enzymes with Inverting β-xylosidase Activity

According to the present disclosure, an enzyme with inverting β-xylosidase activity is used to reduce AXP (e.g., EXP) formation in SSF reactions. Thus, the present disclosure pertains, in one aspect, to a composition comprising at least one inverting β-xylosidase polypeptide. In another aspect, the present disclosure pertains to a method of producing a desired fermentation product in an SSF reaction comprising culturing a complete fermentation medium, said complete fermentation medium comprises at least one inverting β-xylosidase polypeptide.

Suitable inverting β-xylosidase polypeptides can be selected from those that are members of the glycoside hydrolase family 43 ("GH43"). GH43 family enzymes have a number of known activities. For example, a GH43 family enzyme can be one that is classified under EC 3.2.1.55 and can have L-α-arabinofuranosidase activity. In another example, a GH43 family enzyme can be one that is classified under EC 3.2.1.99, and can have endo-arabinanase activity. In yet another example, a GH43 family enzyme can be classified under EC 3.2.1.145, and can have galactan 1,3-β-galactosidase activity. In other examples, GH43 family of enzymes can be classified under EC 3.2.1.37 and can have β-xylosidase activity. Whilst GH43 family of β-xylosidases, such as those described above, often can only perform inverting hydrolysis, various β-xylosidases from the GH3, -39, -52, and -54 families, in contrast, have been reported to have retaining activities and to be able to perform both hydrolysis and transglycosylation reactions. (Smaali et al., 2006, Appl. Microbiol. Biotechnol. 73:582-590).

GH43 family enzymes typically display a five-bladed-β-propeller three-dimensional conformation. The "propeller" part of the structure is based upon a five-fold repeat of "blade"-like conformation that comprises four-stranded β-sheets. The catalytic general base, an aspartate, the catalytic general acid, a glutamate, and an aspartate residue that modulates the pKa of the general base have been identified through the crystal structure of *Cellvibrio japonicus* CjArb43A, and have been confirmed by site-directed mutagenesis (see Nurizzo et al., 2002, Nat. Struct. Biol. 9(9) 665-8). The catalytic residues are arranged in three conserved blocks, which spread widely throughout the amino acid sequence (Pons et al., 2004, Proteins: Structure, Function and Bioinformatics 54:424-432). For GH43 family of β-xylosidase enzymes, the predicted catalytic residues are shown as the bold and underlined type face fonts in the sequences of FIG. 32. The crystal structure of *Geobacillus stearothermophilus* xylosidase (Brux et al. 2006, J. Mol. Bio. 359:97-109) suggests several additional residues that might be important for substrate binding in that enzyme.

As described in Section 6.3.1.5 above, inverting β-xylosidase activity can be determined by suitable assays.

Accordingly, in certain aspects, the enzyme with inverting β-xylosidase activity herein is a GH43 family member. For example, the enzyme is an Fv43D, a Pf43A, an Fv43E, an Fv43B, an Af43A, an Fo43A, a Gz43A, or a XynB3 polypeptide. Such polypeptides are described below.

6.4.1. Fv43D Polypeptides

In certain embodiments, the enzyme with inverting β-xylosidase activity is an Fv43D polypeptide. The amino acid sequence of Fv43D (SEQ ID NO:2) is shown in FIG. 19B and on the first line of FIG. 32. SEQ ID NO:2 is the sequence of the immature Fv43D. Fv43D has a predicted signal sequence corresponding to residues 1 to 20 of SEQ ID NO:2 (underlined in FIG. 19B); cleavage of the signal sequence is predicted to yield a mature protein having a sequence corresponding to residues 21 to 350 of SEQ ID NO:2. The predicted conserved domain residues are in boldface type in FIG. 19B. Fv43D was shown to have β-xylosidase activity in an assay using p-nitrophenyl-β-xylopyranoside, xylobiose, or mixed, linear xylo-oligomers as substrates. The predicted catalytic residues are: either D37 or D71; D155; and E251.

As used herein, "an Fv43D polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, or 320 contiguous amino acid residues among residues 21 to 350 of SEQ ID NO:2. An Fv43D polypeptide preferably is unaltered as compared to native Fv43D in residues D37 or D71; D155, and E251. An Fv43D polypeptide is preferably unaltered in at least 70%, 75%, 80%, 85%, 90%, 95%, 98%, or 99% of the amino acid residues that are conserved among two or more, three or more, four or more, five or more, six or more, seven or more, eight or more, or all nine of Fv43D, Fo43A, Gz43A, Pf43A, Fv43A, Fv43B, Af43A, Pf43B, and Fv43E, as shown in the alignment of FIG. 32. An Fv43D polypeptide suitably comprises the entire predicted conserved domain of native Fv43D as shown in FIG. 19B. An exemplary Fv43D polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Fv43D sequence as shown in FIG. 19B. The Fv43D polypeptide of the invention suitably has β-xylosidase activity. In certain embodiments, the Fv43D polypeptide of the invention has inverting β-xylosidase activity.

6.4.2. Pf43A Polypeptides

In certain embodiments, the enzyme with inverting β-xylosidase activity is a Pf43A polypeptide. The amino acid sequence of Pf43A (SEQ ID NO:8) is shown in FIG. 22B and on the fourth line of FIG. 32. SEQ ID NO:8 is the sequence of the immature Pf43A. Pf43A has a predicted signal sequence corresponding to residues 1 to 20 of SEQ ID NO:8 (underlined in FIG. 22B); cleavage of the signal sequence is predicted to yield a mature protein having a sequence corresponding to residues 21 to 445 of SEQ ID NO:8. The predicted catalytic domain residues are in boldface type, the predicted carbohydrate binding domain residues are in uppercase type, and the predicted linker residues separating the catalytic domain and carbohydrate binding domain are in italics in FIG. 22B. Pf43A was shown to have β-xylosidase activity in an assay using p-nitrophenyl-β-xylopyranoside, xylobiose or mixed, linear xylo-oligomers as substrates. The predicted catalytic residues are: either D32 or D60; D145; and E196.

As used herein, "a Pf43A polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, 350, or 400 contiguous amino acid residues among residues 21 to 445 of SEQ ID NO:8. A Pf43A polypeptide preferably is unaltered as compared to native Pf43A in residues D32 or D60; D145, and E196. A Pf43A polypeptide is preferably unaltered in at least 70%, 75%, 80%, 85%, 90%, 95%, 98%, or 99% of the amino acid residues that are conserved among two or more, three or more, four or more, five or more, six or more, seven or more, eight or more, or all nine of Fv43D, Fo43A, Gz43A, Pf43A, Fv43A, Fv43B, Af43A, Pf43B, and Fv43E, as shown in the alignment of FIG. 32. A Pf43A polypeptide suitably comprises the entire predicted conserved domain of native Pf43A as shown in FIG. 22B. An exemplary Pf43A polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Pf43A sequence as shown in FIG. 22B. The Pf43A polypeptide of the invention suitably has β-xylosidase activity. In certain embodiments, the Pf43A polypeptide of the invention has inverting β-xylosidase activity.

6.4.3. Fv43E Polypeptides

In certain embodiments, the enzyme with inverting β-xylosidase activity is an Fv43E polypeptide. The amino acid sequence of Fv43E (SEQ ID NO:10) is shown in FIG. 23B and on the ninth line of FIG. 32. SEQ ID NO:10 is the sequence of the immature Fv43E. Fv43E has a predicted signal sequence corresponding to residues 1 to 18 of SEQ ID NO:10 (underlined in FIG. 23B); cleavage of the signal sequence is predicted to yield a mature protein having a sequence corresponding to residues 19 to 530 of SEQ ID NO:10. The predicted catalytic domain residues are in boldface type in FIG. 23B. Fv43E was shown to have β-xylosidase activity in an assay using p-nitrophenyl-β-xylopyranoside, xylobiose and mixed, linear xylo-oligomers as substrates. The predicted catalytic residues are: either D40 or D71; D155; and E242.

As used herein, "an Fv43E polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, 350, 400, 450, or 500 contiguous amino acid residues among residues 19 to 530 of SEQ ID NO:10. An Fv43E polypeptide preferably is unaltered as compared to native Fv43E in residues D40 or D71; D155; and E242. An Fv43E polypeptide is preferably unaltered in at least 70%, 75%, 80%, 85%, 90%, 95%, 98%, or 99% of the amino acid residues that are conserved among two or more, three or more, four or more, five or more, six or more, seven or more, eight or more, or all nine of Fv43D, Fo43A, Gz43A, Pf43A, Fv43A, Fv43B, Af43A, Pf43B, and Fv43E, as shown in the alignment of FIG. 32. An Fv43E polypeptide suitably comprises the entire predicted conserved domain of native Fv43E as shown in FIG. 23B. An exemplary Fv43E polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Fv43E sequence as shown in FIG. 23B. The Fv43E polypeptide of the invention suitably has β-xylosidase activity. In certain embodiments, the Fv43E polypeptide of the invention has inverting β-xylosidase activity.

6.4.4. Fv43B Polypeptides

In certain embodiments, the enzyme with inverting β-xylosidase activity is an Fv43B polypeptide. The amino acid sequence of Fv43B (SEQ ID NO:12) is shown in FIG. 24B and on the sixth line of FIG. 32. SEQ ID NO:12 is the sequence of the immature Fv43B. Fv43B has a predicted signal sequence corresponding to residues 1 to 16 of SEQ ID NO:12 (underlined in FIG. 24B); cleavage of the signal sequence is predicted to yield a mature protein having a sequence corresponding to residues 17 to 574 of SEQ ID NO:12. The predicted catalytic domain residues are in boldface type in FIG. 24B. Fv43B was shown to have both β-xylosidase and L-α-arabinofuranosidase activity in assays using p-nitrophenyl-β-xylopyranoside and/or p-nitrophenyl-α-L-arabinofuranoside as substrates. It was shown to release arabinose from branched arabino-xylooligomers and to increase xylose release from oligomer mixtures in the presence of other xylosidase enzymes. The predicted catalytic residues are: either D38 or D68; D151; and E236.

As used herein, "an Fv43B polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, 350, 400, 450, 500, or 550 contiguous amino acid residues among residues 17 to 472 of SEQ ID NO:12. An Fv43B polypeptide preferably is unaltered as compared to native Fv43B in residues D38 or D68; D151; and E236. An Fv43B polypeptide is preferably unaltered in at least 70%, 75%, 80%, 85%, 90%, 95%, 98%, or 99% of the amino acid residues that are conserved among two or more, three or more, four or more, five or more, six or more, seven or more, eight or more, or all nine of Fv43D, Fo43A, Gz43A, Pf43A, Fv43A, Fv43B, Af43A, Pf43B, and Fv43E, as shown in the alignment of FIG. 32. An Fv43B polypeptide suitably comprises the entire predicted conserved domain of native Fv43B as shown in FIG. 24B. An exemplary Fv43B polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Fv43B sequence as shown in FIG. 24B. The Fv43B polypeptide of the invention suitably has β-xylosidase activity. In certain embodiments, the Fv43B polypeptide of the invention has inverting β-xylosidase activity.

6.4.5. Af43A Polypeptides

In certain embodiments, the enzyme with inverting β-xylosidase activity is an Af43A polypeptide. The amino acid sequence of Af43A (SEQ ID NO:14) is shown in FIG. 25B and on the seventh line of FIG. 32. SEQ ID NO:14 is the sequence of the immature Af43A. The predicted conserved domain residues are in boldface type in FIG. 25B. Af43A was shown to have L-α-arabinofuranosidase activity in an assay using p-nitrophenyl-α-L-arabinofuranoside and by the release of arabinose from converting the set of oligomers produced via the action of an endoxylanase. The predicted catalytic residues are: either D26 or D58; D139; and E227.

As used herein, "an Af43A polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, or 300 contiguous amino acid residues of SEQ ID NO:14. An Af43A polypeptide preferably is unaltered as compared to native Af43A in residues D26 or D58; D139; and E227. An Af43A polypeptide is preferably unaltered in at least 70%, 75%, 80%, 85%, 90%, 95%, 98%, or 99% of the amino acid residues that are conserved among two or more, three or more, four or more, five or more, six or more, seven or more, eight or more, or all nine of Fv43D, Fo43A, Gz43A, Pf43A, Fv43A, Fv43B, Af43A, Pf43B, and Fv43E, as shown in the alignment of FIG. 32. An Af43A polypeptide suitably comprises the entire predicted conserved domain of native Af43A as shown in FIG. 25B. An exemplary Fv43B polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Af43A sequence as shown in FIG. 25B. The Af43A polypeptide of the invention suitably has β-xylosidase activity. In certain embodiments, the Af43A polypeptide of the invention has inverting β-xylosidase activity.

6.4.6. Fo43A Polypeptides

In certain embodiments, the enzyme with inverting β-xylosidase activity is an Fo43A polypeptide. The amino acid sequence of Fo43A (SEQ ID NO:24) is shown in FIG. 31B and on the second line of FIG. 32. SEQ ID NO:24 is the sequence of the immature Fo43A. Fo43A has a predicted signal sequence corresponding to residues 1 to 17 of SEQ ID NO:24 (underlined in FIG. 31B); cleavage of the signal sequence is predicted to yield a mature protein having a sequence corresponding to residues 21 to 348 of SEQ ID NO:24. The predicted conserved domain residues are in boldface type in FIG. 31B. Fo43A was shown to have β-xylosidase activity in an assay using p-nitrophenyl-β-xylopyranoside, xylobiose or mixed, linear xylo-oligomers as substrates. The predicted catalytic residues are: either D37 or D72; D159; and E251.

As used herein, "an Fo43A polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, or 320 contiguous amino acid residues among residues 21 to 348 of SEQ ID NO:24. An Fo43A polypeptide preferably is unaltered as compared to native Fo43A in residues D37 or D72; D159; and E251. An Fo43A polypeptide is preferably unaltered in at least 70%, 75%, 80%, 85%, 90%, 95%, 98%, or 99% of the amino acid residues that are conserved among two or more, three or more, four or more, five or more, six or more, seven or more, eight or more, or all nine of Fv43D, Fo43A, Gz43A, Pf43A, Fv43A, Fv43B, Af43A, Pf43B, and Fv43E, as shown in the alignment of FIG. 32. An Fo43A polypeptide suitably comprises the entire predicted conserved domain of native Fo43A as shown in FIG. 31B. An exemplary Fo43A polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Fo43A sequence as shown in FIG. 31B. The Fo43A polypeptide of the invention suitably has β-xylosidase activity. In certain embodiments, the Fo43A polypeptide of the invention has inverting β-xylosidase activity.

6.4.7. Gz43A Polypeptides

In certain embodiments, the enzyme with inverting β-xylosidase activity is a Gz43A polypeptide. The amino acid sequence of Gz43A (SEQ ID NO:22) is shown in FIG. 30B and on the third line of FIG. 32. SEQ ID NO:22 is the sequence of the immature Gz43A. Gz43A has a predicted signal sequence corresponding to residues 1 to 18 of SEQ ID NO:22 (underlined in FIG. 30B); cleavage of the signal sequence is predicted to yield a mature protein having a sequence corresponding to residues 19 to 340 of SEQ ID NO:22. The predicted conserved domain residues are in boldface type in FIG. 30B. Gz43A was shown to have β-xylosidase activity in an assay using p-nitrophenyl-β-xylopyranoside, xylobiose or mixed, linear xylo-oligomers as substrates. The predicted catalytic residues are: either D33 or D68; D154; and E243.

As used herein, "a Gz43A polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, or 300 contiguous amino acid residues among residues 19 to 340 of SEQ ID NO:22. A Gz43A polypeptide preferably is unaltered as compared to native Gz43A in residues either D33 or D68; D154; and E243. A Gz43A polypeptide is preferably unaltered in at least 70%, 75%, 80%, 85%, 90%, 95%, 98%, or 99% of the amino acid residues that are conserved among two or more, three or more, four or more, five or more, six or more, seven or more, eight or more, or all nine of Fv43D, Fo43A, Gz43A, Pf43A, Fv43A, Fv43B, Af43A, Pf43B, and Fv43E, as shown in the alignment of FIG. 32. A Gz43A polypeptide suitably comprises the entire predicted conserved domain of native Gz43A as shown in FIG. 30B. An exemplary Gz43A polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Fo43A sequence as shown in FIG. 30B. The Gz43A polypeptide of the invention suitably has β-xylosidase activity. In certain embodiments, the Gz43A polypeptide of the invention has inverting β-xylosidase activity.

6.4.8. G. stearothermophilus XynB3 Polypeptides

In other aspects, the enzyme with inverting β-xylosidase activity is a G. stearothermophilus XynB3 polypeptide. The sequence of G. stearothermophilus XynB3 is presented as SEQ ID NO:25. G. stearothermophilus XynB3 is a 535-amino-acid GH43 family enzyme from Geobacillus stearothermophilus T-6. The enzyme cleaves single xylose units from the non-reducing end of xylooligomers; the three catalytic residues D15, D128, and E187 were found to be essential for its activity (Shallom et al., 2005, Biochemistry, 44:387-397).

As used herein, "a G. stearothermophilus XynB3 polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, 350, 400, 450, or 500 contiguous amino acid residues of SEQ ID NO:25. A G. stearothermophilus XynB3 polypeptide preferably is unaltered as compared to native XynB3 in residues D15, D128, and E187. The G. stearothermophilus XynB3 polypeptide of the invention suitably has β-xylosidase activity. In certain embodiments, the G. stearothermophilus XynB3 polypeptide of the invention has inverting β-xylosidase activity.

6.4.9. Vibrio sp. XloA Polypeptides

In certain embodiments, the enzyme with inverting β-xylosidase activity is a Vibrio sp. XloA polypeptide. Vibrio sp. XloA is a β-1,3-xylosidase from Vibrio sp. strain XY-214.

As used herein, "a Vibrio sp. XloA polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, 350, or 400 contiguous amino acid residues of β-1,3-Xylosidase from Vibrio sp. Strain XY-214 (Umemoto et al., 2008, Appl. Environ. Microbiol. 74(1): 305-308; Genbank Accession No. AB300564). The Vibrio sp. XloA polypeptide of the invention suitably has β-xylosidase activity. In certain embodiments, the Vibrio sp. XloA polypeptide of the invention has inverting β-xylosidase activity.

6.5 Enzymes with Retaining β-xylosidase Activity

According to the present disclosure, an enzyme with retaining β-xylosidase activity is used to improve or increase AXP (e.g., EXP) production in SSF reactions. Thus, the present disclosure pertains, in one aspect, to a composition comprising at least one retaining β-xylosidase polypeptide. In another aspect, the present disclosure pertains to a method of producing a desired AXP compound or an improved or increased amount of an AXP product in an SSF reaction comprising culturing a complete fermentation medium, said complete fermentation medium comprises at least one retaining β-xylosidase polypeptide.

Suitable inverting β-xylosidase polypeptides can be selected from those that are members of the glycoside hydrolase family 3 ("GH3"), GH30, GH31, GH39, GH52, GH54, or GH116 family enzymes.

As described in Section 6.3.1.5 above, retaining β-xylosidase activity can be determined by suitable assays.

Accordingly, in certain aspects, the enzyme with retaining β-xylosidase activity herein is a GH3, GH30, GH31, GH39, GH52, GH54, or GH116 family member. For example, the enzyme is an *Aspergillus japonicus* XlnD, a *Fusarium verticillioides* Fv30A, a *Fusarium verticillioides* Fv30B, a *Fusarium verticillioides* Fv39A, a *Fusarium verticillioides* Fv39B, a *Thermoanaerobacter saccharolyticum* XynB, a *Geobacillus stearothermophilus* XylA, or a *Trichoderma koningii* (*Hypocrea koningii*) Xyl1 polypeptide. Such polypeptides are described below.

6.5.1. *Aspergillus japonicus* XlnD Polypeptides

In certain embodiments, the enzyme with retaining β-xylosidase activity is a XlnD polypeptide. The amino acid sequence of XlnD (SEQ ID NO:40) is shown in FIG. 35B. SEQ ID NO:40 is the sequence of the immature XlnD. XlnD has a predicted signal sequence corresponding to residues 1 to 17 of SEQ ID NO:40 (underlined in FIG. 35B); cleavage of the signal sequence is predicted to yield a mature protein having a sequence corresponding to residues 18 to 804 of SEQ ID NO:40.

As used herein, "a XlnD polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, 350, 400, 450, 500, 550, 600, 650, 700, or 750 contiguous amino acid residues among residues 18-804 of SEQ ID NO:40. An exemplary XlnD polypeptide of the invention comprises a sequence having at least 85%, 86%, 87%, 88%, 89%, 90%, 91%, 92%, 93%, 94%, 95%, 96%, 97%, 98%, 99%, or 100% identity to the mature XlnD sequence as shown in FIG. 35B. The XlnB polypeptide of the invention suitably has β-xylosidase activity. In certain embodiments, the XlnB polypeptide of the invention has retaining β-xylosidase activity.

6.5.2. *Fusarium verticillioides* Fv30A Polypeptides

In certain embodiments, the enzyme with retaining β-xylosidase activity is an Fv30A polypeptide. The amino acid sequence of XlnD (SEQ ID NO:42) is shown in FIG. 36B. SEQ ID NO:42 is the sequence of the immature Fv30A. XlnD has a predicted signal sequence corresponding to residues 1 to 19 of SEQ ID NO:42 (underlined in FIG. 36B); cleavage of the signal sequence is predicted to yield a mature protein having a sequence corresponding to residues 20 to 537 of SEQ ID NO:42.

As used herein, "an Fv30A polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, 350, 400, 450, or 500 contiguous amino acid residues among residues 20 to 537 of SEQ ID NO:42. An exemplary Fv30A polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Fv30A sequence as shown in FIG. 36B. The Fv30A polypeptide of the invention suitably has β-xylosidase activity. In certain embodiments, the Fv30A polypeptide of the invention has retaining β-xylosidase activity.

6.5.3. *Fusarium verticillioides* Fv30B Polypeptides

In certain embodiments, the enzyme with retaining β-xylosidase activity is an Fv30B polypeptide. The amino acid sequence of Fv30B (SEQ ID NO:44) is shown in FIG. 37B. SEQ ID NO:44 is the sequence of the immature Fv30B. Fv30B has a predicted signal sequence corresponding to residues 1 to 24 of SEQ ID NO:44 (underlined in FIG. 37B); cleavage of the signal sequence is predicted to yield a mature protein having a sequence corresponding to residues 25 to 485 of SEQ ID NO:44.

As used herein, "an Fv30B polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, 350, 400, or 450 contiguous amino acid residues among residues 25-485 of SEQ ID NO:44. An exemplary Fv30B polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Fv30B sequence as shown in FIG. 37B. The Fv30B polypeptide of the invention suitably has β-xylosidase activity. In certain embodiments, the Fv30B polypeptide of the invention has retaining β-xylosidase activity.

6.5.4. *Fusarium verticillioides* Fv39A Polypeptides

In certain embodiments, the enzyme with retaining β-xylosidase activity is an Fv39A polypeptide. The amino acid sequence of Fv39A (SEQ ID NO:46) is shown in FIG. 38B. SEQ ID NO:46 is the sequence of the immature Fv39A. Fv39A has a predicted signal sequence corresponding to residues 1 to 19 of SEQ ID NO:46 (underlined in FIG. 38B); cleavage of the signal sequence is predicted to yield a mature protein having a sequence corresponding to residues 20 to 439 of SEQ ID NO:46.

As used herein, "an Fv39A polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, 350, or 400 contiguous amino acid residues among residues 20-439 of SEQ ID NO:46. An exemplary Fv39A polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Fv39A sequence as shown in FIG. 38B. The Fv39A polypeptide of the invention suitably has β-xylosidase activity. In certain embodiments, the Fv39A polypeptide of the invention has retaining β-xylosidase activity.

6.5.5. *Fusarium verticillioides* Fv39B Polypeptides

In certain embodiments, the enzyme with retaining β-xylosidase activity is an Fv39B polypeptide. The amino acid sequence of Fv39B (SEQ ID NO:48) is shown in FIG. 39B. SEQ ID NO:48 is the sequence of the immature Fv39B. Fv39B has a predicted signal sequence corresponding to residues 1 to 18 of SEQ ID NO:48 (underlined in FIG. 39B); cleavage of the signal sequence is predicted to yield a mature protein having a sequence corresponding to residues 19 to 456 of SEQ ID NO:48.

As used herein, "an Fv39B polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, or 350 contiguous amino acid residues among residues 19-456 of SEQ ID NO:48. An exemplary Fv39B polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Fv39B sequence as shown in FIG. 39B. The Fv39B polypeptide of the invention suitably has β-xylosidase activity. In certain embodiments, the Fv39B polypeptide of the invention has retaining β-xylosidase activity.

6.5.6. *Thermoanaerobacter saccharolyticum* XynB Polypeptides

In certain embodiments, the enzyme with retaining β-xylosidase activity is a XynB polypeptide. The amino acid sequence of XynB (SEQ ID NO:50) is shown in FIG. 40B. XynB does not have a predicted signal sequence from the SignalP algorithm (available at: http://www.cbs.dtu.dk).

As used herein, "a XynB polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, 350, 400, or 450 contiguous amino acid residues of SEQ ID NO:50. An exemplary XynB polypeptide of the invention comprises a sequence having at least 85%, 86%, 87%, 88%, 89%, 90%, 91%, 92%, 93%, 94%, 95%, 96%, 97%, 98%, 99%, or 100% identity to XynB sequence as shown in FIG. 40B. The XynB polypeptide of the invention suitably has β-xylosidase activity. In certain embodiments, the XynB polypeptide of the invention has retaining β-xylosidase activity.

6.5.7. *Geobacillus stearothermophilus* XylA Polypeptides

In certain embodiments, the enzyme with retaining β-xylosidase activity is a XylA polypeptide. The amino acid sequence of XylA (SEQ ID NO:52) is shown in FIG. 41B. XylA does not have a predicted signal sequence from the SignalP algorithm (available at: http://www.cbs.dtu.dk), but has a signal sequence predicted from the Uniprot algorithm (available at: http://www.uniprot.org/uniprot) that corresponds to residues 1 to 18 of SEQ ID NO:52 (underlined); cleavage of the signal sequence is predicted to yield a mature protein having a sequence corresponding to residues 19-705 of SEQ ID NO:52.

As used herein, "a XylA polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, 350, 400, 450, 500, 550, 600, or 650 contiguous amino acid residues of SEQ ID NO:52, or to residues 19-705 of SEQ ID NO:52. An exemplary XylA polypeptide of the invention comprises a sequence having at least 85%, 86%, 87%, 88%, 89%, 90%, 91%, 92%, 93%, 94%, 95%, 96%, 97%, 98%, 99%, or 100% identity to the mature XylA sequence as shown in FIG. 41B. The XylA polypeptide of the invention suitably has β-xylosidase activity. In certain embodiments, the XylA polypeptide of the invention has retaining β-xylosidase activity.

6.5.8. *Trichoderma koninqii* (*Hypocrea koningii*) Xyl1 Polypeptides

In certain embodiments, the enzyme with retaining β-xylosidase activity is a Xyl1 polypeptide. The amino acid sequence of Xyl1 (SEQ ID NO:54) is shown in FIG. 42B. SEQ ID NO:54 is the sequence of the immature Xyl1. Xyl1 has a predicted signal sequence corresponding to residues 1 to 21 of SEQ ID NO:54 (underlined in FIG. 42B); cleavage of the signal sequence is predicted to yield a mature protein having a sequence corresponding to residues 22 to 500 of SEQ ID NO:54.

As used herein, "a Xyl1 polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, 350, 400, or 450 contiguous amino acid residues among residues 22-500 of SEQ ID NO:54. An exemplary Xyl1 polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Xyl1 sequence as shown in FIG. 42B. The Xyl1 polypeptide of the invention suitably has β-xylosidase activity. In certain embodiments, the Xyl1 polypeptide of the invention has retaining β-xylosidase activity.

6.6 Recombinant Methods for Production of Enzymes for Use in SSF

6.6.1. Nucleic Acids and Expression Vectors

Natural or synthetic polynucleotide fragments encoding an enzyme for use in SSF ("SSF enzyme"), including an inverting β-xylosidase polypeptide or other saccharifying enzyme(s) (e.g., a cellulase or a hemicellulase), can be incorporated into heterologous nucleic acid constructs or vectors. Those vectors can then be introduced into, or replicated in a suitable host cell, including, for example, a filamentous fungal, yeast, or bacterial cell. The vectors and methods disclosed herein can be used to express one or more SSF enzyme(s). Any vector can be used as long as it is replicable and viable in the cells into which it is introduced. Many suitable vectors and promoters are known to those of skill in the art, among which a large number are commercially available. Cloning and expression vectors have been extensively described in the literature, for example, in Sambrook et al., 2001, Molecular Cloning: A Laboratory Manual (CSHL Press) and in Ausubel et al., 2002, Short Protocols in Molecular Biology (Current Protocols), the content of each concerning expression vectors is expressly incorporated by reference herein. Other exemplary expression vectors that are suitable for fungal host cellsare described in van den Hondel et al., 1991, Bennett and Lasure (eds.) More Gene Manipulations in Fungi. Academic Press, pp. 396-428.

It is known in the art that various DNA sequences of interest can be inserted into plasmids or vectors (collectively referred to herein as "vectors") using a number of standard procedures. Typically, for example, the DNA sequence of interest is inserted into an appropriate restriction endonuclease site using standard procedures and under standard conditions. Such procedures and related sub-cloning procedures are\within the scope of knowledge of those ordinarily skilled in the art.

Recombinant filamentous fungi comprising the coding sequence for an SSF enzyme can be produced by introducing a heterologous nucleic acid construct comprising the SSF enzyme coding DNA sequence into the genetic material of the filamentous fungi host cells.

Once the desired form of nucleic acid sequence encoding the SSF enzyme is obtained, it can optionally be modified in a variety of ways. Where the sequence involves non-coding flanking regions, the flanking regions can be subjected to resection, mutagenesis, etc. Thus, transitions, transversions, deletions, and/or insertions can be performed on the naturally occurring sequence.

A selected SSF enzyme coding sequence can be inserted into a suitable vector according to well-known recombinant techniques, which can then be used to transform a filamentous fungal host cell capable of expressing the SSF enzyme. Due to the inherent degeneracy of the genetic code, other DNA sequences that encode substantially the same or a functionally equivalent amino acid sequence can be used to clone and express the SSF enzyme.

The present disclosure also includes recombinant nucleic acid constructs comprising one or more of the SSF enzyme-encoding nucleic acid sequences as described above. The constructs each suitably comprises a vector, such as a plasmid or a viral vector, into which a sequence of the disclosure has been inserted, in a forward or reverse orientation.

A heterologous nucleic acid construct can suitably include the coding sequence of an SSF enzyme: (i) in isolation; (ii) in combination with additional coding sequences, such as, for example, fusion protein or signal peptide coding sequences, where the desired SSF enzyme coding sequence is the dominant coding sequence; (iii) in combination with one or more non-coding sequences, such as, for example, introns and control elements, such as, for example, promoter and terminator elements, or 5' and/or 3' untranslated regions, effective for expression of the coding sequence in a suitable host; and/or (iv) in a vector or host environment in which the SSF enzyme coding sequence is heterologous relative to the host cell.

In certain aspects, a heterologous nucleic acid construct is employed to transfer an SSF enzyme-encoding nucleic acid sequence into a cell in vitro, for example, a cell of an established filamentous fungal or yeast lines. For long-term production of an SSF enzyme, stable expression is preferred. It follows that any method effective to generate stable transformants can suitably be used to practice the invention disclosed herein. Appropriate vectors are typically equipped with a selectable marker-encoding nucleic acid sequence, insertion sites, and suitable control elements, such as, for example, promoter and termination sequences. The vectors may comprise regulatory sequences, including, for example, non-coding sequences, such as introns and control elements that are operably linked to the coding sequences, and that are effective for expression of the coding sequence in the host cells. Suitable control elements include, for example, promoter and terminator elements, or 5' and/or 3' untranslated regions. A number of vectors and promoters are known to those of skill in the art, and among which, many are commercially available. Suitable vectors and promoters are also described in the literature, for example, in Sambrook, et al., 2001, Molecular Cloning: A Laboratory Manual (CSHL Press).

Exemplary promoters include, for example, constitutive promoters and inducible promoters, such as, without limitation, a CMV promoter, an SV40 early promoter, an RSV promoter, an EF-1α promoter, a promoter containing the tet responsive element (TRE) in the tet-on or tet-off system (see, e.g., ClonTech's description of its Tet-On® and Tet-Off® Advanced Inducible Gene Expression System), or the β actin promoter and the metallothionine promoter that can upregulated by addition of certain metal salts. A promoter sequence is a DNA sequence which is recognized by the particular filamentous fungal host cell for expression purposes. It is operably linked to DNA sequence encoding the SSF enzyme of interest. Such a linkage positions the promoter with respect to the initiation codon of the DNA sequence encoding the SSF enzyme of interest in the expression vector. The promoter sequence contains transcription and/or translation control sequences, which mediate the expression of the SSF enzyme of interest. Examples include promoters from the *Aspergillus niger, A. awamori,* or *A. oryzae* glucoamylase, α-amylase, or α-glucosidase encoding genes; the *A. nidulans* gpdA or trpC genes; the *Neurospora crassa* cbh1 or trp1 genes; the *A. niger* or *Rhizomucor miehei* aspartic proteinase encoding genes; the *H. jecorina* cbh1, cbh2, egl1, egl2, or other cellulase encoding genes.

The choice of selectable marker will depend on the host cell, and appropriate selectable markers suitable for use in different host cells are known in the art. Exemplary selectable marker genes include argB from *A. nidulans* or *H. jecorina*, amdS from *A. nidulans*, pyr4 from *Neurospora crassa* or *H. jecorina*, pyrG from *Aspergillus niger* or *A. nidulans*. Other suitable selectable markers include, for example, trpc, trp1, oliC31, niaD or leu2, which are included in heterologous nucleic acid constructs used to transform a mutant strain such as a trp⁻, pyr⁻, or leu⁻ mutant strain, or the like.

Such selectable markers can confer, to the transformants, the ability to utilize a metabolite that is otherwise not metabolized by the host cell. For example, the amdS gene from *H. jecorina*, which encodes the enzyme acetamidase, allows the transformant cells to grow on acetamide as a nitrogen source. In a further example, selectable marker (e.g., pyrG) can restore the ability of an auxotrophic mutant strain to grow on a selective minimal medium. In yet another example, selectable marker (e.g., olic31) can confer, to the transformants, the ability to grow in the presence of an inhibitory drug or an antibiotic.

The selectable marker coding sequence is suitably cloned into a plasmid using methods and techniques known in the art. Exemplary plasmids include, without limitation, pUC18, pBR322, pRAX, and pUC100. For example, the pRAX plasmid contains AMAL sequences from *A. nidulans*, making it possible to replicate in *A. niger*.

The practice of the present disclosure will employ, unless otherwise specifically indicated, conventional techniques of molecular biology, microbiology, recombinant DNA, and immunology, which are within the ordinary skill in the art. Such techniques are described extensively in the literature. See, e.g., Sambrook et al., 2001, Molecular Cloning: A Laboratory Manual (CSHL Press); Ausubel et al., 2002, Short Protocols in Molecular Biology (Current Protocols); Freshney, 2005, Culture of Animal Cells: A Manual of Basic Technique (Wiley-Liss); and Dunn et al., 2003, Short Protocols in Protein Science (Wiley). All patents, patent applications, articles and publications mentioned herein, are hereby incorporated by reference.

6.6.2. Host Organisms and Protein Expression

Provided by this disclosure are host cells that are engineered to express an SSF protein of interest for use in the methods described herein. Suitable host cells include any microorganism (e.g., a bacterium, a protist, an alga, a fungus (e.g., a yeast, or a filamentous fungus), or any other microbe). Suitable host cell is preferably a bacterium, a yeast, or a filamentous fungus cell.

Suitable bacterial genera include, but are not limited to, *Escherichia, Bacillus, Lactobacillus, Pseudomonas* and *Streptomyces*. Suitable bacterial species include, but are not limited to, *Escherichia coli, Bacillus subtilis, Bacillus licheniformis, Lactobacillus brevis, Pseudomonas aeruginosa* and *Streptomyces lividans*.

Suitable genera of yeast include, but are not limited to, *Saccharomyces, Schizosaccharomyces, Candida, Hansenula, Pichia, Kluyveromyces,* and *Phaffia*. Suitable yeast species include, but are not limited to, *Saccharomyces cerevisiae, Schizosaccharomyces pombe, Candida albicans, Hansenula polymorpha, Pichia pastoris, P. canadensis, Kluyveromyces marxianus* and *Phaffia rhodozyma*.

Suitable filamentous fungi include all filamentous forms of the subdivision Eumycotina. Suitable filamentous fungal genera include, but are not limited to, *Acremonium, Aspergillus, Aureobasidium, Bjerkandera, Ceriporiopsis, Chrysoporium, Coprinus, Coriolus, Corynascus, Chaertomium,*

*Cryptococcus, Filobasidium, Fusarium, Gibberella, Humicola, Magnaporthe, Mucor, Myceliophthora, Mucor, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes*, and *Trichoderma*.

Suitable filamentous fungal species include, but are not limited to, *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarchroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum, Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei*, and *Trichoderma viride*.

Once a recombinant SSF enzyme expression construct has been generated, for example, in accordance with the methods described herein, the construct can be transformed into a suitable host cell using routine methodology.

6.6.3. Methods of Enzyme Isolation and/or Purification

In certain aspects, a recombinant SSF enzyme is engineered with a signal sequence such that the recombinant SSF enzyme is secreted into the culture medium of the host cell. In certain aspects, the SSF enzyme of interest is recovered in the form of fermentation broth. The term "fermentation broth," as used herein, refers to an enzyme preparation produced by fermentation that then undergoes no or minimal recovery and/or purification thereafter. For example, microbial cultures are grown to saturation, incubated under carbon-limiting conditions to allow protein synthesis (e.g., expression of enzymes), and once the enzyme is secreted into the cell culture medium, the fermentation broth is one from which an SSF enzyme of interest can be recovered. The fermentation broth can, for example, contain the unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In certain embodiments, the fermentation broth contains the spent cell culture medium, extracellular enzymes, and either live or killed microbial cells. In some embodiments, the fermentation broth is fractionated to remove the microbial cells, and as such comprises the spent cell culture medium and extracellular enzymes.

In some aspects, partial or complete purification of an SSF enzyme may be desirable. In certain embodiments, an SSF enzyme is purified to at least 40%, at least 50%, at least 60%, at least 70%, at least 80%, at least 95%, at least 98%, or at least 99% homogeneity.

However, in certain other aspects, an SSF enzyme of interest can be produced in a cellular form (i.e., partially or entirely not secreted), which then may require recovery from a cell lysate. In such cases, the SSF enzyme is purified from the cells in which it was produced using techniques routinely employed in the art. Examples of such techniques include, without limitation, affinity chromatography (see, e.g., van Tilbeurgh et al., 1984, FEBS Lett. 169:215-218), ion-exchange chromatographic methods (see, e.g., Goyal et al., 1991, Bioresource Technol. 36:37-50; Fliess et al., 1983, Eur. J. Appl. Microbiol. Biotechnol. 17:314-318; Bhikhabhai et al., 1984, J. Appl. Biochem. 6:336-345; Ellouz et al., 1987, J. Chromatography 396:307-317), ion-exchange chromatographic methods employing materials that have high resolution power (see, e.g., Medve et al., 1998, J. Chromatography A 808:153-165), hydrophobic interaction chromatography (see, e.g., Tomaz and Queiroz, 1999, J. Chromatography A 865:123-128), and two-phase partitioning (see, e.g., Brumbauer, et al., 1999, Bioseparation 7:287-295).

Suitably, the SSF enzyme is fractionated to segregate proteins having pre-identified properties, such as binding affinity to particular binding agents or media, e.g., antibodies or receptors; a certain molecular weight range; or a certain isolectric point range.

Once expression of a given SSF enzyme is achieved, the SSF enzyme thereby produced can be purified from the cells or from the cell culture. Exemplary procedures suitable for such purification include, without limitation, antibody-affinity column chromatography; ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. A number of methods of protein purification can be employed and these methods are known in the art and described extensively in the literature. For example, protein purification methods are described in Deutscher, 1990, Methods in Enzymology, 182(57):779; and Scopes, 1982, Methods in Enzymology 90: 479-91.

Often time, the selection of purification step(s) or methods depends, e.g., on the nature of the production process, and the particular proteins that are produced.

6.6.4. Fermenting Microorganisms

The SSF methods of the disclosure employ a "fermenting microorganism" to generate a fermentation product (e.g., ethanol) from the sugars produced in an attendant saccharification reaction and/or added to the system. Fermenting microorganisms capable of producing ethanol are sometimes referred to as ethanologens.

The term "fermenting microorganism," as used herein, refers to any microorganism suitable for use in a desired fermentation process. Suitable fermenting microorganisms according to the instant disclosure are able to ferment, i.e., convert, sugars, such as, for example, glucose, xylose, arabinose, mannose, galactose, or oligosaccharides, directly or indirectly into the desired fermentation product.

Examples of suitable fermenting microorganisms include, without limitation, fungal organisms, such as yeast. Specifically, a suitable yeast can be selected from strains of the *Saccharomyces* spp., and in particular, *Saccharomyces cerevisiae*. Various types of yeast are commercially available, among which, for example, ETHANOL RED™ yeast (available from Fermentis/Lesaffre, USA), FALI (available from Fleischmann's Yeast, USA), SUPERSTART™ and THERMOSACC® fresh yeast (available from Ethanol Technology, WI, USA), BIOFERM AFT and XR (available from NABC—North American Bioproducts Corporation, GA, USA), GERT STRAND (available from Gert Strand AB, Sweden), or FERMIOL (available from DSM Specialties) can be employed in performing the methods of the invention described herein.

In other aspects, the yeast is a *Saccharomyces distaticus* or a *Saccharomyces uvarum*. In yet other aspects, the yeast is a *Kluyveromyces*. Non-limiting examples of *Kluvermoyces* include *Kluyveromyces marxianus* or *Kluyveromyces fragilis*. In yet other aspects, the yeast is a *Candida*. Non-limiting examples of *Candida* include *Candida pseudotropicalis* and *Candida brassicae*. In yet other aspects, the yeast is a *Clavispora*. Non-limiting examples of *Clavispora* include *Clavispora lusitaniae* and *Clavispora opuntiae*. In another aspect, the yeast is a *Pachysolen*, e.g., a *Pachysolen tannophilus*. In another aspect, the yeast is a *Bretannomyces*, e.g., a *Bretanomyces clausenii*. Yeast fermentation has been described in the literature. See, e.g., Philippidis, 1996, Cellulose bioconversion technology, in Handbook on Bioethanol: Production and Utilization (Wyman, ed., Taylor & Francis, Washington, D.C., 179-212).

Bacteria that can efficiently ferment glucose to ethanol include, for example, *Zymomonas mobilis* and *Clostridium thermocellum* (see, e.g., Philippidis, 1996, supra).

The cloning of heterologous genes in a *Saccharomyces cerevisiae* (see, e.g., Chen and Ho, 1993, Appl. Biochem. Biotechnol. 39-40:135-147; Ho et al., 1998, Appl. Environ. Microbiol. 64:1852-1859), or in a bacterium such as an *Escherichia coli* (see, e.g., Beall et al., 1991, Biotech. Bioeng. 38: 296-303), a *Klebsiella oxytoca* (see, e.g., Ingram, et al., 1998, Biotechnol. Bioeng. 58:204-214), or a *Zymomonas mobilis* (see, e.g., Zhang et al., 1995, Science 267:240-243; Deanda et al., 1996, Appl. Environ. Microbiol. 62:4465-4470), has led to the construction of organisms capable of converting hexoses and pentoses to ethanol (cofermentation). Such microorganisms can advantageously be used in the methods of the present disclosure.

In certain embodiments, the fermenting microorganism is a *Zymomonas mobilis* with improved tolerance for acetate (see, e.g., U.S. Patent Publication US 2009/0221078).

In certain embodiments, the fermenting microorganism is a *Zymomonas mobilis* with improved utilization of xylose (see, e.g., U.S. Patent Publication US 2009/0246846).

In certain embodiment, the fermenting microorganism is a *Zymomonas mobilis* with the ability to ferment pentoses into ethanol (see, e.g., U.S. Patent Publication US 2003/0162271).

6.6.5. Fermentation Media

In some aspects, the SSF reactions or methods of the disclosure are performed in a fermentation medium or a complete fermentation medium. The term "fermentation medium," as used herein, refers to a medium before all of the components necessary for the SSF reaction to take place are present. A fermentation medium can thus be, for example, a medium resulting from a partial saccharification process. A fermentation medium can, in other embodiments, be a medium containing all the components necessary for the SSF reaction to take place. In that case, the fermentation medium is also termed "a complete fermentation medium." Moreover, a fermentation medium can, in yet other embodiments, be a medium wherein an SSF reaction is in progress or under way, and as such may contain certain products of saccharification.

A complete fermentation medium includes enzymes capable of hydrolyzing carbohydrate-based cellulosic or other substrates, a fermenting organism, and a carbohydrate-based cellulosic or other substrate (e.g., as described in Section 6.7.2 below). Over the course of culturing the complete fermentation medium, fermentable sugars are formed through enzymatic hydrolysis, which are in turn metabolized by the fermenting organism to produce a fermentation product.

6.7. Simultaneous Saccharification and Fermentation Processes

In certain aspects, an SSF reaction of the present disclosure is performed at a temperature of between 25° C. and 50° C. For example, the SSF reaction takes place at a temperature of 25° C. or above, 28° C. or above, 30° C. or above, 32° C. or above, 35° C. or above, or 38° C. or above. For example, the SSF reaction takes place at a temperature of 50° C. or below, 45° C. or below, 40° C. or below, 38° C. or below, 35° C. or below, or 30° C. or below. For example, the SSF reaction takes place in a temperature range of from 28° C. to 45° C., such as from 30° C. to 40° C., from 32° C. to 38° C. In an exemplary embodiment, the SSF reaction is carried out at a temperature of from 32° C. to 35° C. In another embodiment, the SSF reaction is carried out at a temperature of about 32° C. The temperature at which the SSF reaction is carried out can, for example, be adjusted up or down during the reaction.

In SSF, the enzymatic hydrolysis of cellulose and the fermentation of glucose to ethanol are combined in one step (see, e.g., Philippidis, 1996, Cellulose bioconversion technology, Handbook on Bioethanol: Production and Utilization, Wyman, ed., Taylor & Francis, Washington, D.C., pp. 179-212).

SSF processes are usually carried out as batch fermentation processes, wherein the fermentation is conducted from start to finish in a single tank. Alternatively, SSF processes can be carried out as continuous fermentation processes which are steady-state fermentation systems that operate without interruption, and wherein each stage of the fermentation occurs in a separate section of a given fermentation system, and flow rates are set to correspond to required residence times. In other words, the individual steps in a fermentation process of the disclosure can be performed batch-wise or continuously. Processes where all steps are performed batch-wise, or processes where all steps are performed continuously, or processes where one or more steps are performed batch-wise and one or more steps are performed continuously are contemplated herein.

In certain embodiments, a fed-batch SSF process may be desirable. A fed-batch process entails a batch phase and a feeding phase. The culture medium of the batch phase and the culture medium added during the feeding phase are chemically defined, and the culture medium of the feeding phase is added, at least for a fraction of the feeding phase, at a feeding rate that follows a pre-defined exponential function, thereby maintaining the specific growth rate at a pre-defined value.

An SSF reaction of the present disclosure can suitably proceed for a period of 3 to 7 d. For example, an SSF reaction of the disclosure can proceed for up 3 d, 4 d, 5 d, 6 d, or 7 d.

The SSF fermentation processes of the disclosure include, without limitation, fermentation processes used to produce fermentation products including alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5 diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, β-carotene); hormones, and other compounds.

In certain aspects, the present disclosure provides a set of SSF conditions that are specifically suitable for use with a recombinant fermenting bacteria such as a *Zymonmonas* (i.e., also termed "recombiant *Zymomonas* SSF conditions" herein). For example, these conditions include carrying out the SSF flask runs anaerobically under suitable recombinant *Zymomonas mobilis*, using pretreated substrates such as, for example, corn cob, bagasse, Kraft pulp substrate, and carrying out the reaction at about 33° C., pH 5.8, and about 10 wt. % to 25 wt. % solids loading, dependent upon the particular substrates and pretreatment. These conditions also include, for example, commencing the fermentation by the addition of 10% of a suitable *Zymomonas mobilis* strain, for example, strains ZW705 (recombinant) or ZW1 (wild-type) inoculum (5 g), into the reaction mixture without any additional nutrients.

In certain aspects, the present disclosure provides a set of SSF conditions that are specifically suitable for use with a fermenting microorganism that is a fungus, for example, a *S. cerevisiae* yeast (i.e., also termed "yeast SSF conditions" herein). For example, these conditions include carrying out the reaction with a suitable yeast strain, for example the THERMOSACC® DRY yeast, at 38° C. and pH 5.0, inoculation at 0.1 wt % without any additional nutrients, carrying out the SSF runs anaerobically by, for example $CO_2$ out-gassing, using a reaction mixture comprising pretreated substrate, water, sulfuric acid, saccharification enzyme(s) and the yeast strain, as well as agitating the reaction vessel at an appropriate speed, for example, at 100 RPM, for a suitable period of time, for example, 3 d.

6.7.1. Recovery of SSF Products

The fermentation product can be any substance that is produced by the fermenting organism. In a specific aspect, the substance is an alcohol. It will be understood that the term "alcohol" encompasses a substance that contains one or more hydroxyl moieties. In a specific aspect, the alcohol is arabinitol. In another aspect, the alcohol is butanol. In another aspect, the alcohol is ethanol. In another aspect, the alcohol is glycerol. In another aspect, the alcohol is methanol. In another aspect, the alcohol is 1,3-propanediol. In yet another aspect, the alcohol is sorbitol. In another more aspect, the alcohol is xylitol. See, e.g., Gong et al., 1999, Ethanol production from renewable resources, in Advances in Biochemical Engineering/Biotechnology, Scheper, ed., Springer-Verlag Berlin Heidelberg, Germany, 65: 207-241; Silveira and Jonas 2002, Appl. Microbiol. Biotechnol. 59: 400-408; Nigam, and Singh, 1995, Process Biochem. 30 (2): 117-124; Ezeji et al., 2003, World J. Microbiol. Biotechnol. 19 (6): 595-603.

Distillation can be performed on the fermentation broth from the fermentation step to recover the fermentation products such as, for example, ethanol. The fermentation and distillation steps can be carried out simultaneously or separately/sequentially. In some aspects, after distillation, two products are recovered: an alcohol, such as, for example, ethanol, and a fermentation rest or residual product (whole stillage). The alcohol, being an azeotropic mixture with water, is further purified in the separation step by a standard process such as, for example, molecular sieving. For example, ethanol with a purity of up to about 96 vol. % can be obtained, which can be used as, for example, fuel ethanol, drinking ethanol, i.e., potable neutral spirits, or industrial ethanol.

For other substances or fermentation products, any method known in the art can be used for recovery, including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, distillation, or extraction.

6.7.2. Sources of Carbohydrates or Feedstocks

Any suitable cellulosic substrates or raw materials can be used in practicing the SSF processes of the present disclosure. The substrate can be selected based on the desired fermentation product, i.e., the substance to be obtained from the fermentation, and the process employed, as is well known in the art.

Examples of substrates suitable for use in the methods of present disclosure, include cellulose-containing materials, such as wood or plant residues, or low molecular sugars DP1-3 obtained from processed cellulosic materials that can then be metabolized by the fermenting microorganism, and/or which can be supplied by direct addition to the fermentation medium.

The biomass can include any composition comprising cellulose and/or hemicellulose (lignocellulosic biomass can also comprise lignin), e.g., seeds, grains, tubers, plant waste or byproducts of food processing or industrial processing (e.g., stalks), corn (including cobs, stover, and the like), grasses (e.g., Indian grass, such as *Sorghastrum nutans*; or, switch grass, e.g., *Panicum* species, such as *Panicum virgatum*), wood (including wood chips, processing waste), paper, pulp, recycled paper (e.g., newspaper). Other biomass materials include, but are not limited to, potatoes, soybean (rapeseed), barley, rye, oats, wheat, beets or sugar cane bagasse.

6.8. Pretreatment of Biomass

Prior to an SSF reaction, biomass (e.g., lignocellulosic material) is preferably subject to a pretreatment step in order to render xylan, hemicellulose, cellulose and/or lignin material more accessible to enzymes, and thus more amenable to saccharification and fermentation by the methods of the disclosure.

In one aspect, the pretreatment entails subjecting dried biomass material in a suitable vessel, such as for example, a reactor, to a catalyst comprised of a dilute solution of a strong acid and a metal salt; this can lower the activation energy, or the temperature, of cellulose hydrolysis to obtain higher sugar yields; see, e.g., U.S. Pat. Nos. 6,660,506; 6,423,145.

Another exemplary pretreatment method entails hydrolyzing biomass by subjecting the material to a first stage hydrolysis step in an aqueous medium at a temperature and a pressure level chosen to effectuate primarily depolymerization of hemicellulose without major depolymerization of cellulose to glucose. This step results in a slurry, in which the liquid aqueous phase contains dissolved monosaccharides resulting from depolymerization of hemicellulose, and the solid phase contains cellulose and lignin. A second hydrolysis step can involve conditions under which at least a major portion of the cellulose is depolymerized, resulting in a liquid aqueous phase containing dissolved/soluble depolymerization products of cellulose. See, e.g., U.S. Pat. No. 5,536,325.

Another exemplary method comprises processing a biomass material by one or more stages of dilute acid hydrolysis using about 0.4% to 2% of a strong acid; and treating an unreacted solid lignocellulosic component of the acid-hydrolyzed biomass material by alkaline delignification. See, e.g., U.S. Pat. No. 6,409,841.

Another exemplary pretreatment method comprises prehydrolyzing biomass (e.g., lignocellulosic materials) in a prehydrolysis vessel, for example, a reactor; adding an acidic liquid to the solid lignocellulosic material to make a mixture; heating the mixture to a suitable reaction temperature; maintaining the reaction temperature for a time period sufficient to fractionate the lignocellulosic material into a solubilized portion containing at least about 20% of the lignin from the lignocellulosic material and a solid fraction containing cellulose; removing a solubilized portion from the solid fraction while maintaining the mixture at or near the reaction temperature, wherein the cellulose in the solid fraction is rendered more amenable to enzymatic digestion; and recovering a solubilized portion. See, e.g., U.S. Pat. No. 5,705,369.

In another exemplary method, the pretreatment method uses hydrogen peroxide $H_2O_2$. See, e.g., Gould, 1984, Biotech. Bioengr. 26:46-52.

In yet another exemplary method, pretreatment comprises contacting biomass with stoichiometric amounts of sodium hydroxide and ammonium hydroxide at very low biomass concentration. See, e.g., Teixeira et al., 1999, Appl. Biochem. Biotech. 77-79:19-34.

In another embodiment, pretreatment comprises contacting the lignocellulose with a chemical (e.g., a base, such as sodium carbonate or potassium hydroxide) at a pH of about 9 to about 14 at moderate temperature, pressure and pH. See, e.g., PCT patent application publication WO2004/081185.

In another exemplary method, the pretreatment uses ammonia. For example, the pretreatment method comprises subjecting the biomass to low ammonia concentration under conditions of high solids. See, e.g., U.S. Patent Publication No. 20070031918, PCT patent application publication WO 2006/11901.

The invention is further illustrated by the following examples. The examples are provided for illustrative purposes only. They are not to be construed as limiting the scope or content of the invention in any way.

7. EXAMPLE 1: ANALYSIS OF EXP FORMATION IN SSF REACTIONS

7.1. Materials & Methods
7.1.1. Substrates

Below is a list of substrates used in this work. The cellulose, xylan, and lignin compositions of the pretreated substrates are listed as well. Compositional analyses were performed using the standard assays detailed in the NREL protocols for Standard Biomass Analytical Procedures (available at: http://www.nrel.gov/biomass/pdfs/42618.pdf):

Dilute ammonia pretreated corn cob. Corn cob was pretreated prior to enzymatic hydrolysis according to the methods and processing ranges described in, for example, US Patent Application Publications 2007-0031918-A1, US-2007-0031919-A1, US-2007-0031953-A1, US-2007-0037259-A1, and PCT patent application publication WO06/110901 A2 (unless otherwise noted). The composition of the substrate comprises: 34.8% cellulose, 29.2% xylan, 12.8% lignin.

Dilute sulfuric acid pretreated sugar cane bagasse. This substrate was produced and provided by NREL, as detailed in Schell et al, 2003, (App. Biochem. Biotechnol. Vol. 105-108, 69-85). The bagasse was pretreated at a solids concentration of 20% (w/w), temperature of 165° C., 1.44% (w/w) acid and an approximate residence time of 8 min. The composition of the substrate comprises: 55.0% cellulose, 3.1% xylan, 31.2% lignin.

Mixed hardwood industrial unbleached pulp substrate. This substrate was produced using the Kraft process and oxygen delignification (Kappa Number=13). (Research funded by l'Agence Nationale de la Recherche (ANR-05-BIOE-007) through l'Agence de l'Environnement et de la Maitrise de l'Energie (ADEME 0501C0099). The composition of the substrate comprises: 74.6% cellulose, 20.7% xylan, 2.6% lignin.

Softwood industrial unbleached pulp substrate. This substrate was produced using the Kraft process and oxygen delignification (Kappa Number=14). (Research funded by l'Agence Nationale de la Recherche (ANR-05-BIOE-007) through l'Agence de l'Environnement et de la Maitrise de l'Energie (ADEME 0501C0099). The composition of the substrate comprises: 81.9% cellulose, 8.0% xylan, 1.9% lignin.

7.1.2. Enzymes

Below is a list of enzymes and enzyme mixtures used in this work.

Accellerase™ 1500 (Danisco U.S. Inc., Genencor) is a high β-glucosidase activity cellulase enzyme complex produced by a genetically modified *Trichoderma reesei*. It contains multiple enzyme activities a majority of which are exoglucanase, endoglucanase, β-glucosidase, and hemi-cellulase activities.

Multifect® Xylanase (Danisco U.S. Inc., Genencor), also produced by a *Trichoderma reesei*, is a hemicellulase enzyme complex designed to work as an accessory product to supplement whole cellulase with xylanase activity, and to work synergistically to enhance various polysaccharide conversions in the lignocellulosic biomass processing industry. The predominant xylanase activity in Multifect® Xylanase is that of *T. reesei* Xyn2 (see, LaGrange et al., 1996, Appl. Environ. Microbiol. 62:1036-1044).

Bxl1: is a β-xylosidase from *Trichoderma reesei*. The amino acid sequence of Bxl1 is provided herewith as SEQ ID NO:4. Bxl1 has been shown to have β-xylosidase activity in an assay using p-nitrophenyl-β-xylopyranoside, xylobiose or mixed, linear xylo-oligomers as substrates.

Xyn3: is a GH10 family xylanase from *Trichoderma reesei*. The amino acid sequence of Xyn3 is provided herewith as SEQ ID NO:18. Xyn3 was shown to have endoxylanase activity using birchwood azo-xylan (Megazyme, Wicklow, Ireland), and indirectly by its ability to increase xylose monomer production in the presence of xylobiosidase when Xyn3 in combination with xylobiosidase act on pretreated biomass or on isolated hemicellulose.

Fv3A: is a GH3 family enzyme from *Fusarium verticillioides*. The amino acid sequence of Fv3A is provided herewith as SEQ ID NO:6. Fv3A was shown to have β-xylosidase activity in an assay using p-nitrophenyl-β-xylopyranoside, xylobiose and mixed, linear xylo-oligomers (FIGS. 15 and 16) and branched arabinoxylan oligomers from hemicellulose as substrates.

Fv51A is a GH51 family enzyme from *Fusarium verticillioides*. The amino acid sequence of Fv51A is provided herein as SEQ ID NO:16. Fv51A was shown to have L-α-arabinofuranosidase activity in an assay using p-nitrophenyl-α-L-arabinofuranoside and by the release of arabinose from the set of oligomers released from hemicellulose by the action of endoxylanase.

Fv43D: is a GH43 family enzyme from *Fusarium verticillioides*. The amino acid sequence of Fv43D is provided herein as SEQ ID NO:2. Fv43D was shown to have β-xylosidase activity in an assay using p-nitrophenyl-β-xylopyranoside, xylobiose, or mixed, linear xylo-oligomers as substrates. (FIGS. 15 and 16).

Fv43B: is a GH43 family enzyme from *Fusarium verticillioides*. The amino acid sequence of Fv43B is provided herein as SEQ ID NO:12. Fv43E was shown to have β-xylosidase activity in an assay using p-nitrophenyl-β-xylopyranoside, xylobiose or mixed, linear xylo-oligomers as substrates.

Pf43A: is a GH43 family enzyme from *Penicillium funiculosum*. The amino acid sequence of Pf43A is provided herein as SEQ ID NO:8. Pf43A was shown to have β-xylosidase activity in an assay using p-nitrophenyl-β-xylopyranoside, xylobiose or mixed, linear xylo-oligomers as substrates.

Fv43E: is a GH43 family enzyme from *Fusarium verticillioides*. The amino acid sequence of Fv43E is provided herein as SEQ ID NO:10. Fv43E was shown to have β-xylosidase activity in an assay using p-nitrophenyl-β-xylopyranoside, xylobiose or mixed, linear xylo-oligomers as substrates.

Af43A: is a GH43 family enzyme from *Aspergillus fumigatus*. The amino acid sequence of Af43A is provided herein as SEQ ID NO:14. Af43A was shown to have L-α-arabinofuranosidase activity in an assay using p-nitrophenyl-α-L-arabinofuranoside and by the release of arabinose from the set of oligomers released from hemicellulose by the action of endoxylanase.

XlnA: XlnA is a xylanase from *Aspergillus tubengensis*. The amino acid sequence of XlnA is provided herein as SEQ ID NO:20. The XlnA protein used in the present examples was unpurified, in the form of an enzyme preparation whose main constituent was XlnA.

Bgl1: Bgl1 is *T. reesei* β-glucosidase 1 (SEQ ID NO:26). The Bgl1 gene has been described, for example, in Barnett et al., 1991, Bio-Technology 9(6):562-567.

7.1.3. Strains

Strain #229:

A *Trichoderma reesei* strain, derived from RL-P37 (Sheir-Neiss and Montenecourt, 1984, Appl. Microbiol. Biotechnol. 20:46-53) through mutagenesis and selection for high cellulase production titer, was co-transformed with the β-glucosidase expression cassette (which comprised a cbh1 promoter, *T. reesei* β-glucosidase 1 gene, a cbh1 terminator, and an amdS marker (*A. nidulans* acetamidase)), and the endoxylanase expression cassette (which comprised a cbh1 promoter, *T. reesei* xyn3, and a cbh1 terminator) using PEG mediated transformation (see, e.g., Penttila et al., 1987, Gene 61(2):155-64). Numerous transformants were isolated and examined for (3-glucosidase and endoxylanase production. One transformant, referred to as *T. reesei* strain #229, was used in certain studies described herein.

Strain H3A:

*T. reesei* strain #229 was co-transformed with the β-xylosidase Fv3A expression cassette (which comprised a cbh1 promoter, an fv3A gene, a cbh1 terminator, and an alsR marker (chlorimuron ethyl resistant mutant of the native *T. reesei* acetolactate synthase)), the β-xylosidase Fv43D expression cassette (which comprised an egl1 promoter, an fv43D gene, a native fv43D terminator), and the Fv51A α-arabinofuranosidase expression cassette (which comprised an egl1 promoter, an fv51A gene, a native fv51A terminator) using electroporation (see, e.g., PCT patent application publication WO2008/153712 A2). Transformants were selected on Vogels agar plates containing chlorimuron ethyl. Numerous transformants were isolated and examined for β-xylosidase and L-α-arabinofuranosidase production. *T. reesei* integrated expression strain H3A, which recombinantly expresses *T. reesei* β-glucosidase 1, *T. reesei* xyn3, Fv3A, Fv51A, and Fv43D, was isolated, and used in certain studies described herein.

7.1.4. Organisms and Inoculum Preparation 7.1.4.1. *Zymomonas mobilis*

Background:

*Zymomonas mobilis* strain ZW1 is a wild type strain similar to strain ZM4 from American Type Culture Collection (ATCC 31821, Manassas, Va.). Recombinant *Zymomonas mobilis* strain ZW705 was produced from strain ZW801-4 as summarized below. Cultures of *Z. mobilis* strain ZW801-4 were grown under conditions of stress as follows. ZW801-4 is a recombinant xylose-utilizing strain of *Z. mobilis* that was described in U.S. Patent Application Publication 2008/0286870. Strain ZW801-4 was derived from strain ZW800, which was, in turn, derived from strain ZW658, all as was described in U.S. Patent Application Publication 2008/0286870. ZW658 was constructed by integrating two operons, $P_{gap}$xylAB and $P_{gap}$taltkt, containing four xylose-utilizing genes encoding xylose isomerase, xylulokinase, transaldolase, and transketolase, into the genome of ZW1 (ATCC #31821) via sequential transposition events, and followed by adaptation steps conducted on selective media containing xylose. ZW658 was deposited as ATCC #PTA-7858. In ZW658, the gene encoding glucose-fructose oxidoreductase was insertionally-inactivated using host-mediated, double-crossover, homologous recombination and spectinomycin resistance as a selectable marker to create ZW800. The spectinomycin resistance marker, which was bounded by loxP sites, was removed by site specific recombination using Cre recombinase to create ZW801-4.

A continuous culture of ZW801-4 was grown in a 250 mL stirred, pH- and temperature-controlled fermentors (Sixfors; Bottmingen, Switzerland). The basal medium for fermentation was 5 g/L yeast extract, 15 mM ammonium phosphate, 1 g/L magnesium sulfate, 10 mM sorbitol, 50 g/L xylose, and 50 g/L glucose. Adaptation to growth in the presence of high concentrations of acetate and ammonia was achieved by gradually increasing the concentration of ammonium acetate in the above continuous culture media while maintaining an established growth rate as measured by the specific dilution rate over a period of 97 d to a concentration of 160 mM. Further increases in ammonium ion concentration were achieved by incremental additions of ammonium phosphate, to a final total ammonium ion concentration of 210 mM by the end of 139 d of continuous culture. Strain ZW705 was isolated from the adapted population by plating, PCR amplification, and/or other conventional well-known methods.

7.1.4.2. Growth of Seed Cultures for SSF

*Zymomonas mobilis* strains ZW705 and ZW1 were maintained as 20% glycerol stocks, frozen at −80° C. To make a seed culture, a 2 mL of this frozen stock was thawed and used to inoculate 45 mL of a medium containing 5 g/L of yeast extract, 4 g/L of potassium hydrogen phosphate, 1 g/L of magnesium sulfate, and 100 g/L of glucose at pH 5.8. The starting OD 600 nm was 0.4. The culture was grown at 32° C. in a capped 50 mL tube to an OD 600 nm of about 2.5, and it was then used to inoculate a final seed culture containing 200 g/L glucose, 4 g/L potassium hydrogen phosphate, 2 g/L magnesium sulfate, and 20 g/L yeast extract, at pH 5.8. That culture was grown at 32° C. in a pH-controlled and stirred fermenter to an OD 600 nm of about 10, and a remaining glucose concentration of about 80 g/L. A volume of this seed culture (having an OD 600 nm of about 10) equivalent to 10% of the SSF fermentation volume was used to start the SSF.

7.1.4.3. Yeast

The yeast ethanologen used was the THERMOSACC® DRY yeast (Ethanol Technology, Milwaukee, Wis.) which is only capable of fermenting C6 (i.e., glucose) carbon surgars into ethanol (EtOH). The dry yeast was hydrated with sterile deionized water for 2-3 hrs prior to inoculation.

7.1.5. Fermentation Using Sugars

*Zymomonas mobilis* fermentation using synthetic sugars was carried out for 3 d in the 500 mL Sixfors bioreactor, using a batch and fed-batch process. The synthetic sugars consisted of glucose and xylose. For the batch process, the sugars were initially loaded at a concentration of about 80 g/L glucose and 70 g/L xylose. For the fed-batch process, a concentrated stock sugar solution was prepared first, which was then fed into the bioreactor using a syringe pump (PHD2000, Harvard Apparatus, Holliston, Mass.). The flow rate was set and controlled such that it gave a final equivalent sugar loading of about 80 g/L glucose and 70 g/L xylose at day 3. For the batch or the fed-batch processes, the *Zymomonas* inoculum was loaded into the reaction mixture in the beginning at 10 wt. % and the fermentations were carried out anaerobically at 33° C. and pH 5.5.

7.1.6. Simultaneous Saccharification and Fermentation (SSF)

SSF flask runs were carried out anaerobically under suitable recombinant *Zymomonas mobilis* and yeast fermentation conditions. Unless otherwise stated, the recombinant *Zymomonas* SSF experiments using dilute ammonia pretreated corn cob, bagasse, or Kraft pulp substrate were carried out at 33° C., pH 5.8, and 25 wt. %, 20 wt. %, 10 wt. % solids loading, respectively. 25 wt. % solids (12.5 g dry weight), 20 wt. % solids (10.0 g dry weight), or 10 wt. % solids (5.0 g dry weight) of the respective substrates were each loaded first into a 125 mL Erlenmeyer flask, followed by the addition of deionized water pre-mixed with the required amount of 6N sulfuric acid, in order to titrate the substrate pH to 5.8. The cellulase and hemicellulase enzymes, described above, were added in an amount based on mg cellulase protein/g cellulose and mg hemicellulase protein/g xylan in the biomass substrate, respectively. Fermentation was initiated by the addition of 10 wt. % *Zymomonas mobilis* strains ZW705 (recombinant) or ZW1 (wild-type) inoculum (5 g) into the reaction mixture without any additional nutrients. For the THERMOSACC® DRY yeast SSF, the reactions were carried out at 38° C. and pH 5.0. The level of yeast inoculation was at 0.1% w/w without any additional nutrients. The anaerobic environment and $CO_2$ outgassing were maintained by a 23 Gauge needle protruding from a rubber stopper that was used to cap the flask. At the start of fermentation, all SSF runs had an initial 50 g total reaction weight in a flask and the reaction mixture consisted of pretreated substrate, water, sulfuric acid, enzyme, and either *Zymomonas* or yeast cells. The flasks were agitated inside a shaker incubator (New Brunswick Scientific, Innova 44, Edison, N.J.) at 100 RPM for 3 d.

7.1.7. Separate Hydrolysis and Fermentation (SHF)

The SHF runs involved a saccharification stage that was followed by a fermentation stage. The saccharification conditions were based on the NREL Laboratory Analytical Procedure (see, Selig et al., 2008, Enzymatic Saccharification of Lignocellulosic Biomass Laboratory Analytical Procedure (LAP), Technical Report NREL/TP-510-42629) except for certain modifications of the enzyme types and/or levels, cellulose loading, and pH. 25 wt. % solids (12.5 g dry weight) of dilute ammonia pretreated corn cob or 10 wt. % solids (5.0 g dry weight) of the mixed hardwood pulp was loaded into a 125 mL Erlenmeyer flask. This was then followed by the addition of deionized water pre-mixed with the required amount of 6N sulfuric acid so as to titrate the substrate pH to 5.3. The saccharification step was commenced by the addition of cellulase and hemicellulase enzymes in an amount based the total mg protein/g cellulose and the total mg protein/g xylan in the biomass substrate, respectively. For all *Zymomonas* SHF runs, a temperature of 50° C. and a pH of 5.30 were used for the saccharification at a duration of 3 d, followed by the fermentation step using similar conditions as those described in the SSF process (above). Sodium hydroxide was used to raise the pH from 5.3 to 5.8. This was followed by the addition of 10 wt. % of *Zymomonas* inoculum to commence fermentation.

7.1.8. Fed-Batch SSF

The fed-batch SSF studies were carried out under similar conditions as described in the SSF process (above) except that the dilute ammonia pretreated corn cob substrate (required to achieve a final 25 wt. % solids) was divided evenly into 8 batches, and fed batch-wise into the bioreactor, with the final batch loaded at the 30th hr.

7.1.9. HPLC Analysis and EXP Quantification

Fermentation samples were taken at timed intervals and analyzed for ethanol, residual sugars, ethyl-β-xylopyranoside (EXP), and other metabolic products, such as, for example, acetic acid and glycerol, using a Waters HPLC system (Alliance system, Waters Corp., Milford, Mass.). The HPLC column was purchased from BioRad (Aminex HPX-87H, BioRad Inc., Hercules, Calif.). The EXP quantification under refractive index detection followed a set of procedures that were similar to those described in by Zhang et al. (in 2009, Enzyme and Microbial Technology 44:196-202). Another metabolic co-product, succinic acid, was found to co-elute with the EXP and to have potentially inflated the EXP quantification. It was determined that, for the yeast and *Zymomonas* fermentations, the concentrations of succinic acid generated at the conditions tested were no more than 1-2 g/L, as measured using both an UV detector at 220 nm and an enzymatic assay kit (K-SUCC, Megazyme, Co. Wicklow, Ireland).

7.2. Results

7.2.1. EXP Formation and Identification

7.2.1.1. EXP Formation in SSF with Recombinant *Zymomonas mobilis*

Formation of a byproduct was observed under the SSF fermentation conditions described above, using a recombinant *Zymomonas mobilis* strain that is capable of co-fermenting glucose and xylose into ethanol. The substrate used in this study was dilute ammonia pretreated corn cob, which has a high xylan content, treated with commercial cellulase/hemi-cellulase enzyme preparations (Accellerase™ 1500 at 20 mg/g cellulose) and Multifect® Xylanase (5 mg/g xylan), both derived from *Trichoderma reesei* (*T. reesei*). Under the conditions tested, the highest amount of formation of the byproduct was found under fed-batch SSF, and the second highest in SSF (Table 1). SHF using dilute ammonia pretreated corn cob, batch, and fed-batch fermentation processes using sugars (80 g/L glucose+70 g/L xylose) formed little of this byproduct.

The byproduct generated under the SSF conditions, using dilute ammonia pretreated corn cob and the *Zymomonas mobilis* strain as described above had an elution time on an HPLC HPX-87H column of approximately 11.75 mins (at a flow rate of 0.6 mL/min), close to that of succinic acid. FIG. 1 panel 2 shows a peak eluting at 11.611 min, following incubation of xylose and Multifect® Xylanase with ethanol. That particular peak was absent when no alcohol was present in the incubation. It was observed that the position of the byproduct generated in the presence of alcohol during incubation shifted to an extent and in a direction that tracked the alcohol added. The elution times of the byproduct produced after incubation with methanol (MeOH) at19.46 min, and the byproduct produced after incubartion with n-PrOH at 27.65 min were shorter and longer, respectively, when compared to the byproduct produced after incubation with ethanol (EtOH), at 21.99 min. The elution times of the products produced by incubation of xylose with Multifect® Xylanase and 0.72 M alcohol shift, relative to the ethanol-induced product (at 11.61 min), to shorter elution times with MeOH (at 11.03 min) and longer elution times with n-PrOH (at 13.60 min). These results were consistent with the conclusion that the mobile peaks in question were xylose-alcohol adducts (alkyl-xylopyranosides) formed by reverse hydrolysis from xylose and alcohol, with the components eluting at 11.03, 11.61 and 13.60 corresponding to the methyl-, ethyl- and n-propyl-xylopyranosides, respectively.

7.2.1.2. Time Course

The time course for the appearance of the methyl-, ethyl- and n-propyl xylopyranosides is shown in FIG. 2. The relative amounts of the products formed after 100 hrs were as follows: methyl→ethyl→n-propyl-xyloside (FIG. 2), consistent with the order reported by Drouet et al. (in 1994, Biotech. & Bioeng. 43:1075-1080) for the formation of the alkyl-β-D-xylopyranosides by reverse hydrolysis in the presence of MeOH, EtOH, and n-PrOH. The coincidence of the elution times of the ethyl xylopyranoside (EXP) with those observed under the SSF conditions, the dependencies of the elution time on the presence and nature of the alcohol, and the relative reactivities of these alcohols, all suggested that the EXP was the byproduct generated under the SSF conditions.

7.2.1.3. Identification of ethyl-β-glycosides in an EXP Sample by $^1$H NMR Analysis Preparation of ethyl b-D-xylopyranoside Standard:

A sample of ethyl xylosides was prepared by dissolving 50 mg of D-xylose in 3 mL of ethanol and heating the resulting solution in the presence of Amberlyst 15 H$^+$ resin (100 mg) at 70° C. for 3 hrs. The resin was filtered and the ethanol solvent removed under reduced pressure, yielding a colorless oil. Analysis by $^1$H NMR revealed a mixture of ethyl xylosides, with α-D-xylopyranoside predominating, along with amounts of ethyl β-xylopyranoside and ethyl α/β-xylofuranoside.

$^1$H NMR of EXP Sample:

A lyophilized EXP sample purified and fractionated (using HPLC) from a dilute ammonia pretreated corn cob SSF fermentation broth sample was reconstituted into 750 μL of $D_2O$ and transferred to a PP-528 glass NMR tube. A proton NMR spectrum was acquired on a Varian 500 MHz VNMRS NMR system using a basic s2pul pulse sequence for over 8 pulses. The $^1$H NMR spectrum (500 MHz, $D_2O$), referenced to the HOD signal at d 4.80, indicated the presence of at least 4 distinct ethyl glycosides, based on the appearance of several triplet signals in the d 1.20-1.26 region. The spectrum also contained 5 distinct doublets at d 4.43, 4.49, 4.53, and 4.66 with coupling constants of 7.8 Hz indicative of b-glycosidic linkages. The signal at d 4.43 was the most intense and matches the chemical shift reported in the literature (Drouet et al., 1994, Biotech. & Bioeng. 43:1075-1080), Zhang et al. (2009, Enzyme and Microbial Technology 44:196-202) for ethyl-β-D-xylopyranoside. Overall the signals observed in the $^1$H NMR spectrum (FIG. 3) indicated the presence of the β-anomer, β-D-ethylxylopyranoside, along with 3-4 additional ethyl β-glycosides.

7.2.2. EXP Formation with Yeast and Wild-Type *Zymomonas mobilis*

Co-fermentation of C5/C6 sugars using the ethanologen *Zymomonas mobilis* under SSF and fed-batch SSF conditions with a dilute ammonia pretreated corn cob substrate resulted in high levels of EXP. A new experiment was designed to determine whether EXP is formed when SSF is performed using wild-type yeast and *Zymomonas mobilis*, which are organisms that are only capable of fermenting C6 sugars. The results (FIG. 4) indicated that the EXP was produced at high levels in the SSF reactions wherein the yeast (5.5 g/L) or wild-type *Zymomonas mobilis* (9.1 g/L) did the fermenting. Thus, the EXP formation is not specific to the recombinant *Zymomonas mobilis*, as it was also detected during SSF by a *Saccharomyces cerevisiae* yeast and a wild-type *Zymomonas mobilis*.

7.2.3. EXP Formation from Other Sources of Biomass

Additional experiments were designed to determine if EXP could be formed using substrates other than the dilute ammonia pretreated corn cob. From the results shown in Table 2, the formation of EXP appears to be linked to the fermentation of any high xylan-containing substrates under the SSF conditions with the *T. reesei* cellulase/hemicellulase preparations. For example, as much as 16.1 g/L EXP was formed under the recombinant *Zymomonas* SSF conditions using a mixed hardwood industrial Kraft pulp with high xylan content. On the other hand, the lower xylan-containing substrates, such as the pretreated bagasse and the softwood pulp, produced lower amounts of EXP (0.91 and 4.75 g/L, respectively) under similar conditions. Furthermore, it was again demonstrated that, only under the SSF processes as described herein would large amounts of EXP be generated. Formation of EXP was much decreased under the SHF process conditions, (3.52 g/L), even when a higher xylan-containing substrate was used.

7.2.4. EXP Formation with Different Permutations of Enzymes Used in SSF 7.2.4.1. EXP Formation with Bxl1

According to Drouet et al. (in 1994, Biotech. & Bioeng. 43:1075-1080), EXP formation was catalyzed by *T. reesei* Bxl1 via both a transxylosylation and a reverse hydrolysis reaction. FIG. 5 shows that the EXP formation under the yeast SSF conditions described above was enhanced in the presence of *T. reesei* Bxl1. With the addition of 5 mg/g Bxl1, the EXP production was increased from 5.5 g/L to 18.8 g/L.

EXP formation under recombinant *Zymomonas mobilis* SSF conditions with 25 wt. % solids of dilute ammonia pretreated corn cob substrate was also enhanced in the presence of *T. reesei* Bxl1, as shown in FIG. 6. EXP plateaued at a concentration of 25.6 g/L, with the addition of 6 mg/g *T. reesei* Bxl1. A cellulase/hemi-cellulase enzyme complex from *T. reesei* integrated strain #229 (which over-expresses xylanase, *T. reesei* Xyn3) was used in this experiment in place of Accellerase™ 1500+Multifect® Xylanase. The ability of *T. reesei* Bxl1 to catalyze EXP formation is surprisingly strong, because only 1 mg/g of it was added but an over 2-fold increase of EXP as compared to the control sample (enzyme complex from *T. reesei* integrated strain #229 alone) was clearly observed.

The effect of *Fusarium verticillioides* hemi-cellulase addition on EXP formation was investigated. Accellerase™ 1500+Multifect® Xylanase, Accellerase™ 1500+XlnA, and enzyme complex from the integrated *T. reesei* strain #229, with the addition of Bxl1, and *Fusarium verticillioides* hemi-cellulases (Fv3A, and Fv51A L-α-arabinofuranosidase were used. This study was conducted under recombinant *Zymomonas* SSF conditions. The substrate used was a 25 wt. % solids dilute ammonia pre-treated corn cob. Results were shown in FIG. 7, which indicated that the addition of XlnA and Accellerase™ 1500 produced more EXP (31.5 vs. 19.5) than the addition of Multifect® Xylanase and Accellerase™ 1500. The enzyme complex from the integrated *T. reesei* strain #229 alone produced the least amount of EXP (9.1 g/L) among all three enzyme configurations. This is possibly due to the fact that Bxl1 represented a smaller fraction of the total amount of proteins in the enzyme complex in the *T. reesei* strain #229 enzyme complex, which also produced a relatively large amount of accumulated xylobiose, as compared to other two enzyme configurations. For Accellerase™ 1500+Multifect® Xylanase and Accellerase™ 1500+XlnA, the addition of Fv3A or Fv51A did not result in substantial increases in EXP formation. With the enzyme complex from integrated *T. reesei* strain #229, however, the addition of Fv3A alone gave a 2-fold increase in EXP formation while the addition of Fv51A increased EXP formation by 1.4 fold, as compared to a 3-fold increase in EXP when *T. reesei* Bxl1 was added to the enzyme complex produced from the integrated *T. reesei* strain #229.

7.2.4.2. EXP Formation Using Purified Enzymes

The results discussed above indicated that the EXP formation was strongly affected and effectively catalyzed by *T. reesei* Bxl1 and that *T. reesei* Bxl1 is remarkably and particularly effective at making EXP under the SSF conditions using certain high xylan-containing biomass substrates. However, all of the enzymes tested so far (and discussed above) were not purified and might contain background enzyme activities similar to that of the *T. reesei* Bxl1, capable of making EXP. To investigate the effect of background enzyme activities, the effect of purified enzymes on EXP formation was also studied. A cellulase mixture of purified *T. reesei* cellobiohydrases, CBH1 and CBH2; *T. reesei* endoglucanase, EG2; and *T. reesei* β-glucosidase, Bgl1, was used as a substitute for Accellerase™ 1500, while purified *T. reesei* Xyn3 was used as a substitute for Multifect™ Xylanase. It is clear from the results depicted in FIG. 8 that the cellulase alone does not produce EXP. The addition of unpurified *T. reesei* Xyn3 produced large amounts of EXP, for example, about 13.1 g/L. This large increase is potentially due to a larger background *T. reesei* Bxl1 that exists within the unpurified *T. reesei* Xyn3 sample.

7.2.4.3. EXP Formation Using GH43 Class Bxl Enzymes

Bxl1, which is a GH3 family hydrolases, has being shown to be active and effective at catalyzing the formation of EXP under the SSF conditions (above). A question remains as to whether other GH family β-xylosidases can also catalyze the formation of EXP under similar conditions. A number of β-xylosidases from the GH43 family, including Fv43B, Pf43A, Fv43E, and Af43A, were tested under the recombinant *Zymomonas* SSF conditions using a 25 wt. % solids dilute ammonia pretreated corn cob substrate. Pf43A, Fv43E, and Af43A were found to increase EXP formation slightly, as compared to the control sample made from a protein preparation of strain #229. On the other hand, Fv43B gave a greater increase of EXP formation by 1.5-fold (FIG. 9). Because all of these GH43 family enzymes were expressed in *T. reesei*, and because they were all unpurified protein preparations in this study, it could be postulated that the increase in EXP formation may be attributed to the presence of native Bxl1 in the protein preparations.

8. EXAMPLE 2: REDUCTION IN EXP BY HEMICELLULASES

The following examples show that EXP is reduced by addition of certain hemicellulases to SSF reactions.

8.1. Reduction in EXP by Fv43D in SSF by *Zymomonas*

EXP formation typically consumes both xylose (directly, or from xylobiose or other xylo-oligomers) and ethanol on an equal molar basis. This consumption mechanism directly results in a substantial decrease in yield for ethanol, because many microorganisms, including *Zymomonas*, are incapable of degrading and fermenting, or otherwise utilizing EXP. One (1) g of EXP is calculated to be equivalent to a 0.688 g loss of ethanol that would have been produced (assuming xylose is fermented into ethanol at a rate of 0.51 g/g xylose). Thus preventing the formation of EXP can lead to an attendant increase in ethanol yield. It was found, as shown in FIG. 10, that the addition of the *Fusarium verticillioides* β-xylosidase, Fv43D, at only 1 mg/g xylan, greatly reduced (~4-fold) the amount of EXP formed under the recombinant *Zymomonas* SSF conditions.

8.2 Reduction in EXP by Fv43D in SSF by Yeast

Similar to the results obtained from the C5/C6-fermenting recombinant *Zymomonas*, the supplementation of Accellerase™ 1500+Multifect® Xylanase with Fv43D in an SSF reaction using yeast as a C6-fermenting microorganism also resulted in a reduction in EXP formation. Specifically the addition of Fv43D at 1 mg/g xylan resulted in a 2 to 3-fold reduction in EXP (FIG. 11).

8.3 Reduction in EXP by Fv43D in SSF with Multifect Xylanase, with XlnA and with Enzyme Complex from *T. reesei* Integrated Strain #229

The reduction in EXP by the addition of Fv43D to three enzyme configurations, Accellerase™ 1500+Multifect® Xylanase, Accellerase™ 1500+*A. niger* xylanase, and the enzyme complex produced from the integrated *T. reesei* strain #229, under the recombinant *Zymomonas* SSF conditions was investigated. The substrate used was a 25 wt. % solids dilute ammonia pretreated corn cob.

FIG. 12 shows that the addition of only 1 mg/g xylan of Fv43D to Accellerase™ 1500+Multifect® Xylanase, and to Accellerase™ 1500+XlnA, resulted in an over 4-fold reduction in EXP formation, and the same addition to the enzyme complex produced from the integrated *T. reesei* strain #229 resulted in a 1.36-fold reduction of EXP formation. At the same time, a corresponding increase in ethanol was observed with all three enzyme configurations, confirming the benefit of Fv43D in terms of reducing EXP formation and preventing ethanol yield loss.

8.4 Reduction in EXP Formation in SSF with Purified Enzymes

To insure that the reduction of EXP from Fv43D was not due to background enzyme activities, purified enzymes including a purified Fv43D were used to test for reductions of EXP formation. A *T. reesei* cellulase mixture of purified CBH1, CBH2, EG2 and Bgl1 was used to substitute for Accellerase™ 1500, and a purified *T. reesei* Xyn3 was used as a substitute for Multifect® Xylanase. The results as depicted in FIG. 13 showed a slight reduction in EXP formation and an attendant slight increase in ethanol titer, when purified and unpurified Fv43D were added. The relatively small reduction in EXP formation is likely due to the lack of background *T. reesei* Bxl1 in the purified enzymes (e.g., the cellulases and Xyn3). It is also noted that only a small amount of EXP (5.7 g/L) was formed by the control sample, due to the action of *T. reesei* Xyn3. Further addition of Fv43D thus does not substantially reduce EXP formation. To investigate this further, another study with results shown in FIG. 14A was performed to investigate the effect of EXP reduction by Fv43D addition in the presence of a large amount of Bxl1.

8.5 EXP Reduction Dose Response from the Addition of Fv43D to SSF

EXP formation in the presence of Bxl1 was substantial where more than 20 g/L of EXP was consistently detected, although the exact amount varies by the SSF conditions used. A dose response study was performed to assess reduction of EXP formation in relation to the amount of Fv43D added. FIG. 14A shows the results for EXP reduction from the addition of increasing amounts of Fv43D to the enzyme complex produced from the *T. reesei* integrated strain #229 and *T. reesei* Bxl1. Similar to the results shown previously, 1 mg/g of Fv43D was found to be effective at reducing EXP formation by nearly 3-fold and at the same time resulted in an increase in ethanol titer. However, addition of increasing amounts of Fv43D at 3, 6, and 9 mg/g did not greatly reduce EXP formation, although a significant increase in ethanol titer was observed. It appeared that even with addition of a large amount of Fv43D (at 9 mg/g), the EXP concentration could not be reduced to below 6.6 g/L, a level at which the amount of EXP may have reached equilibrium for the specific conditions that were used for testing. Under these particular experimental conditions, further additions of Fv43D beyond, for example, 1 mg/g xylan, no longer had an effect on reducing EXP formation.

These observations can potentially be explained by the mechanism of EXP formation and reduction under SSF conditions.

The proposed mechanism, which is based on the observations made from this work and is consistent with the data reported in the literature (see, e.g., Drouet et al., 1994, Biotech. & Bioeng. 43:1075-1080 and Zhang et al., 2009, Enzyme and Microbial Technology 44:196-202), is described in detail in Example 3 below.

8.6 EXP Reduction by the Addition of Fo43A and Gz43A to SSF

Fo43A and Gz43A, which are inverting GH43 family β-xylosidases, were also tested for efficacy in reducing EXP formation under the SSF conditions described herein. Based on the results shown in FIG. 14B, these two enzymes were each able to reduce EXP formation by nearly 4-fold, when they are added to a enzyme blend comprising a protein complex produced from the *T. reesei* integrated strain #229, *T. reesei* Bxl1, a dilute ammonia pretreated corn cob substrate, and a recombinant *Zymomonas*, and at 3 mg/g xylan. Similar to what was observed with the addition of Fv43D (above), a reduction in EXP formation and a corresponding increase (by about 10 g/L) in ethanol titer was observed.

9. EXAMPLE 3: MECHANISM OF EXP FORMATION

Observations that the yield of EXP was approximately four times higher under the SSF conditions (FIGS. 10 and 11) in the presence of *Fusarium verticillioides* β-xylosidase Fv3A as compared to the yield of EXP in the presence of *Fusarium verticillioides* β-xylosidase Fv43D led to an effort to understand the mechanism of EXP formation.

Potentially there are two possible routes for the formation of EXP: (1) by transglycosylation; or (2) by reverse hydrolysis. Each of these routes are depicted as follows:

Transglycosylation: X—O—X+EtOH→X—O-Et+X   1)

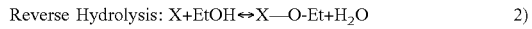

Reverse Hydrolysis: X+EtOH↔X—O-Et+H$_2$O   2)

According to Drouet et al. (in 1994, Biotech. & Bioeng. 43:1075-1080), the transglycosylation mechanism is the more rapid of the two. The fact that only the β anomer (see FIG. 29) is formed in a transglycosylation reaction implies that the reaction is catalyzed by enzymes that operate with retention of anomeric configuration on the substrates, wherein the sugars are linked by β-glycosyl linkages. On the other hand, formation of the β anomer of EXP by reverse hydrolysis would suggest that the starting substrate is either α- or β-xylose, depending on whether EXP is formed, respectively, by inversion or retention of anomeric configuration.

The β-xylosidases, Fv3A (a member of the GH3 family) and Fv43D (a member of the GH43 family), operate with retention and inversion of configuration, respectively. To distinguish and identify which of the two potential mechanisms described above is the true mechanism, an experiment was performed in which Multifect® Xylanase (which is an enzyme preparation characterized by the retaining activity of *T. reesei* Xyn2) and purified Fv43D and Fv3A were incubated at 46° C. with xylobiose and ethanol. The kinetics of EXP formation in these samples was examined by HPLC.

As shown in FIG. 15 and Table 3, after a short period of time Multifect® Xylanase with Fv3A produced a substantial amount of EXP, which appeared to correspond with xylose formation (e.g., having a constant ratio of EXP formation to xylose formation with time). When Fv43D was used with Multifect® Xylanase, on the other hand, EXP appeared with a substantial lag relative to xylose formation. It can be postulated that Multifect® Xylanase and Fv3A produced EXP rapidly through transglycosylation. A xylose-enzyme ester adduct would have been formed first with C1 anomeric inversion, followed by a second inversion by ethanol doing an S$_N$2 displacement, at the C1 carbon of the attached xylose, of the active site carboxyl group. The double inversion gives retention of configuration in the product. On the other hand, Fv43D did not appear to catalyze a transglycosylation reaction; instead it produced EXP much more slowly though reverse hydrolysis. As Fv43D operates with inversion of anomeric configuration, EXP was likely formed from α-D-xylose, which in turn was formed from xylobiose by Fv43D, but also by inversion at C1 of β-D-xylose in an aqueous solution. FIG. 15 indicates that EXP can also be formed by reverse hydrolysis from xylose, catalyzed by Multifect® Xylanase. Because the β-xylosidase mechanism in this case was retaining, the likely substrate of this reaction was β-D-xylose.

9.1 Equilibrium Equation for EXP Formation

Under the SSF conditions, Multifect® Xylanase and Fv3A would encounter not only xylobiose but larger xylose oligomers as well. Hydrolysis of such oligomers could result in an increased formation of EXP, if upon scission, one of the oligomer products is transglycosylated to produce an ethyl glycosyl adduct. Further scission, by transglycosylation, could then form an additional ethyl adduct such that the ratio of EXP formation to xylose formation would be greater than that observed when only xylobiose is transglycosylated. For example:

X4+EtOH→X2-Et+X2   3)

X2-Et+EtOH→2EXP   4)

X2+EtOH→EXP+X   5)

It is noted that if only xylobiose is transglycosylated, the only EXP formation is from the reaction of line 5).

These possibilities were examined by comparing hydrolysis of xylose oligomers (average molecular weight=539) with that of xylobiose using each of the same three enzymes: Fv3A, Fv43D, and Multifect® Xylanase. The results are depicted in FIG. 16.

Plotted in FIG. 16 (left panel) and FIG. 16 (right panel) are the ratios of EXP to Xylose RI peak areas generated following incubation of xylobiose (20 mg/mL) (FIG. 16 (left)) or xylose oligomer (20 mg/mL) (FIG. 16 (right)) in the presence of 0.9 M EtOH at 46° C. in the presence of Multifect® Xylanase (560 μg/mL), Fv43D (36 μg/mL), or Fv3A (54 μg/mL), at concentrations that would give rates of xylose formation that were within a factor of two of each other. The EXP formation rates were nearly the same for xylobiose and xylose oligomers in the presence of Multifect® Xylanase and Fv43D. However, in the case of Fv3A, the EXP yield was about ⅓ higher in the presence of the xylose oligomers as compared to in the presence of xylobiose. As outlined above, this observation suggests that, at least for Fv3A, transglycosylation can occur with ethanol upon scission of oligomers larger than a xylobiose. Such transglycosylation of ≥dp3 oligomers does not appear to occur as prevalently in the cases of Multifect® Xylanase, although the EXP yield did appear to be higher than that was observed for Fv3A in both the xylobiose and xylose oligomer cases. This higher yield is likely an indication of a higher rate of transglycosylation with ethanol for Multifect® Xylanase than for Fv3A. The fact that for both Multifect® Xylanase and Fv3A, EXP is formed for every 2.5 to 3.5 scission reactions is remarkable, considering that the molarity of ethanol is 0.9 M as compared to 55 M for $H_2O$. The selectivity for ethanol likely indicates a greater affinity for ethanol over water at or near the active site of the particular enzyme, with that affinity being higher for Multifect® Xylanase relative to that for Fv3A. The ratio of EXP to xylose is the same for Fv43D with xylobiose or xylose oligomer as substrate, which can be explained by the fact that, in this the case of Fv43D, EXP is formed by reverse hydrolysis from xylose, which was the product of hydrolysis from both xylobiose and xylose oligomer substrates.

In the case of Multifect® Xylanase and Fv3A, the maximum yield of EXP is attained after 3.5 hrs of incubation. The EXP yield at this point of incubation using Multifect® Xylanase was about 7 to 8 times that of the EXP yield obtained using Fv43D. After 3.5 hours the yield of EXP decreased in the Multifect® Xylanase reaction and the Fv3A reaction with a $t_{1/2}$ of 40-60 h. The reaction involving Fv3A was likely the enzyme-catalyzed hydrolysis of EXP from the high value formed in the transglycosylation reaction toward the equilibrium value of EXP/xylose formed upon reverse hydrolysis. In SSF reactions, the speediness of EXP formation and the sluggishness of the subsequent EXP hydrolysis in the presence of β-xylosidases having retaining activities suggests that the concentration of EXP is likely to remain substantially higher throughout the duration of an SSF reaction when a retaining β-xylosidase is present than when an inverting β-xylosidase is present. This further suggests that replacing retaining β-xylosidases with inverting β-xylosidases in SSF reactions would be beneficial for product yield. It is noted that all of the above mentioned reactions are enzyme catalyzed. Control samples/reactions, in the absence of enzyme, showed no formation of EXP upon incubation of xylobiose, of xylose oligomer, or of xylose in the presence of 0.9M ethanol at 46° C.

9.2 Calculation of Equilibrium Constant

It has been suggested by Drouet et al. (in 1994, Biotech. & Bioeng. 43:1075-1080) that the extent of formation of the alkyl-xylopyranoside (AXP), for example, EXP, upon reverse hydrolysis can be determined by the equilibrium established between the alcohol, xylose and the alkyl-xylopyranoside product.

The dissociation constant for ethyl-xylopyranoside (EXP) would be:

$$Kd = \frac{[\text{xylose}][\text{EtOH}]}{[\text{EXP}]}$$

Using this formula, a Kd of 27 M can be calculated from the data of FIG. 2 as the equilibrium constant when Multifect® Xylanase was present in the SSF reaction. Also using this formula, a Kd of about 9.4 M can be calculated from the data of FIG. 16 as the equilibrium constant when Fv43D was present in the SSF reaction. From Drouet et al. (1994, Biotech. Bioeng. 43:1075-1080), used *T. reesei* β-xylosidase and calculated a Kd of 40 M, although it did not appear that the EXP concentration had reached the equilibrium constant even after 160 hrs of incubation. The equilibrium constant calculations above were all made from SSF reactions started with xylose and ethanol, with the exception of the results depicted in FIG. 16 of the disclosure, where the xylobiose and xylose oligomers were completely hydrolyzed by Fv43D in 20 hrs but the SSF reaction was allowed to proceed for a total of 145 hrs. Thus it is postulated that the Kd falls in the range of between about 10 and about 40M and is probably closer to the lower value, because the inverting β-xylosidase Fv43D produces a significant amount of EXP by the reverse reaction at equilibrium.

10. EXAMPLE 4: DELETION OF BXL1 GENE FROM *T. REESEI*

10.1 Construction of the Bxl1 Deletion Cassette

To construct the bxl1 deletion cassette, 5' and 3' flanking sequences of the bxl1 gene (Margolles-Clark et al., 1996, App. Environ. Microbiol. 62(10):3840-6) from *Trichoderma reesei* genomic-DNA were amplified by PCR with primer pairs MH375/MH376 and MH377/MH378 respectively (shown in Table 4), using PfuUltra II Fusion HS DNA Polymerase (Stratagene). The 3'-flanking sequence contained part of the Bxl1 coding sequence to avoid the nearby bgl1 gene. Primer MH376 was phosphorylated at the 5'-end. One (1) μL of T4 DNA Ligase at a concentration of 5 U/μL (Roche Applied Bioscience), 1 μL of 10× ligation buffer (Roche) and approximately 20 ng of the PCR fragments were incubated for 10 mins at room temperature in a total volume of 10 μL. The ligation reaction mixture was used as a template for a PCR reaction with primer pair MH379/MH380 and PfuUltra II Fusion HS DNA Polymerase (Stratagene).

The resulting 4.0 kb fragment was cloned into pCR-Blunt II-TOPO according to manufacturer's specifications (Invitrogen). The plasmid was transformed into *E. coli* One Shot® TOP10 Chemically Competent cells (Invitrogen). A colony, which contained the 4.0 kb bxl1 5'+3' PCR fusion product cloned into the TOPO vector, was isolated. The plasmid was extracted by QiaPrep plasmid purification (Qiagen) and its sequence confirmed (Sequetech, Mountain View, Calif.). The resulting plasmid was digested with AclI and AscI (NEB) to allow for subsequent cloning with the fragment containing the hygromycin-resistance gene.

The hygromycin resistance gene was amplified with primers MH292/MH290 from a vector containing the *Aspergillus nidulans* oliC promoter, the hygromycin resistance gene (*E. coli*, hygromycin phosphotransferase, hph), and the *Aspergillus nidulans* trpC terminator, using PfuUltra II Fusion HS DNA Polymerase (Stratagene). The PCR-amplified fragment was cloned into pCR-blunt II-TOPO (Invitrogen) and transformed into E. coli One Shot® TOP10 Chemically Competent cells (Invitrogen). A colony was isolated and sequencing confirmed that the extracted plasmid displayed a mutated 5' AscI restriction site, which was replaced with a NarI site (GGCGCGCC→GGCGCCC). The construct was then digested with NarI (Roche), AscI (NEB) and DraI (Roche), and the resulting 2.5 kb fragment was isolated using the QiaQuick Gel Extraction kit in accordance with the manufacturer's protocol (Qiagen) in preparation for cloning subsequently into the Bxl1-deletion plasmid.

Ligation of the two isolated fragments as described above was performed with 1 μL 10× Ligation Buffer (Roche), 1 μL 5 U/ml T4 DNA Ligase (Roche), and 50 ng of each fragment in a reaction volume of 10 μL. The ligation mixture was cloned into E. coli One Shot® TOP10 Chemically Competent cells and a single colony was isolated. The bxl1-deletion vector (FIG. 17, pCR-BluntII-TOPO, bxl1 deletion, hph-loxP) containing the loxP-flanked hygromycin resistance gene was extracted from the E. coli and the appropriate ligations were verified by restriction digest using Bmt1, resulting in 4 fragments of 4754, 2195, 1899, and 1182 base pairs.

The bxl1-deletion cassette was generated by amplifying the fragment from plasmid pCR-BluntII-TOPO, bxl1 deletion, hph-loxP using primers MH379/MH380 in a total volume of 10 mL and PfuUltra II Fusion HS DNA Polymerase (Stratagene). The PCR product was cleaned and concentrated using a QiaexII kit (Qiagen). The DNA was further concentrated by SpeedVac to a concentration of about 1.5 mg/mL.

10.2 Transformation of Bxl1 Deletion Plasmid into T. reesei

The DNA from the bxl1-deletion cassette was transformed into T. reesei strain #229, which overexpressed T. reesei Bgl1 and T. reesei Xyn3 as previously described herein. Transformants were selected on a medium containing 100 ppm Hygromycin B (Invitrogen). A transformant containing the bxl1 deletion was selected by PCR. A bxl1-deficient T. reesei strain is referred to herein as a "bxl1⁻" strain.

11. EXAMPLE 5: EXPRESSION OF FV43D BY T. REESEI STRAIN

The following example shows how Trichoderma reesei was engineered to express Fv43D. A T. reesei strain engineered to express Fv43D is referred to herein as a "Fv43D⁺" strain 11.1 Construction of Expression Cassette A F. verticillioides β-xylosidase Fv43D expression cassette was constructed by PCR amplification of the Fv43D gene from F. verticillioides genomic DNA sample using the primers SK1322/SK1297 (Table 5). A region of the promoter of the endoglucanase gene egl1 was amplified by PCR from a T. reesei genomic DNA sample extracted from an engineered T. reesei strain RL-P37 (see, e.g., Sheir-Neiss G. and B. S. Montenecourt, Appl. Microbiol. Biotechnology, 20 (1984) pp. 46-53), using the primers SK1236/SK1321. These two amplified fragments were subsequently fused together in a fusion PCR reaction using the primers SK1236/SK1297. The resulting fusion PCR fragment was cloned into pCR-Blunt II-TOPO vector (Invitrogen) to yield plasmid TOPO Blunt/Pegl1-Fv43D (FIG. 18), which was in turn used to transform E. coli One Shot® TOP10 chemically competent cells (Invitrogen). Plasmid DNA was extracted from several E. coli clones and confirmed by restriction digests.

The expression cassette from TOPO Blunt/Pegl1-Fv43D was amplified by PCR using primers SK1236/SK1297 (Table 5) to generate a DNA product for transformation of T. reesei. The expression cassette was co-transformed with an existing selection marker cassette containing the als gene (acetolactate synthase).

11.2 Transformation of bxl1-Deficient T. reesei with Fv43D Expression Cassette

The bxl1-deletion T. reesei host strain is transformed with the Fv43D expression cassette (comprising an egl1 promoter, an Fv43D open reading frame, and a native terminator of Fv43D) and an existing selection marker cassette containing the native als gene, using a standard transformation method such as, for example, electroporation (see, e.g., PCT patent application publication WO 08/153,712). Transformants are selected on minimal media agar plates containing chlorimuron ethyl. These transformants are bxl1⁻Fv43D⁺ T. reesei.

11.3 Transformation of bxl1-Expressing T. reesei with Fv43D Expression Cassette

A T. reesei host strain having a wild type bxl1 gene (see, PCT patent application publication WO 2005/001036 A2) was transformed with the Fv43D expression cassette (comprising an egl1 promoter, an Fv43D open reading frame, and a native Fv43D terminator) and an existing selection marker cassette containing the native als gene, using standard transformation methods such as, for example, electroporation (see, e.g., PCT patent application publication WO 08/153, 712). Transformants were selected on minimal media agar plates containing chlorimuron ethyl. These transformants are Fv43D⁺ T. reesei.

12. EXAMPLE 6: USE OF CELLULASE PRODUCED ENGINEERED T. REESEI STRAINS IN SSF

The transformants bxl1⁻Fv43D⁺ T. reesei, and Fv43D⁺ T. reesei are used to produce cellulase-containing culture broths. These culture broths are then used in SSf reactions in continuous, batch, or fed-batch configurations, as described herein to reduce the production of AXP and reduce the sugar yield loss by the production of a trans-xylosication of reverse hydrolysis product.

In a particular example, the transformant of a bxl1⁻ T. reesei strain #229 ("229 Bxl del") was cultured to produce a cellulase-containing culture broth, which was then supplemented with either a purified T. reesei Bxl1 (at 0.5 mg/g or 1 mg/g of xylan) or a purified FV43D, at 1 mg/g of xylan. The concentration of the EXP and ethanol at days 1 and 3 were plotted in FIGS. 43A (Day 1) and 43B (Day 3), respectively. The reactions were carried out under the recombinant Zymomonas SSF conditions using a 25 wt. % solids loading of dilute ammonia pretreated corn cob substrate.

What is claimed is:

1. A method for simultaneous saccharification and fermentation (SSF) comprising culturing a complete fermentation medium, said complete fermentation medium comprising at least one fermenting microorganism, at least one xylan-containing biomass, at least one cellulase, at least one hemicellulase, at least one retaining β-xylosidase, and at least one inverting β-xylosidase, for a period and under conditions suitable for producing a fermentation product, which is an alcohol, wherein the at least one inverting β-xylosidase comprises an Fv43D polypeptide having at least 90% sequence identity to SEQ ID NO:2, or to residues 21 to 350 of SEQ ID NO:2, and the complete fermentation medium comprises a greater amount of the at least one inverting β-xylosidase than that of the at least one retaining β-xylosidase on a mole basis.

2. The method of claim 1, wherein the complete fermentation medium comprises an effective amount of the at least one inverting β-xylosidase such that the complete fermentation medium produces less short chain alkyl-β-xylopyranoside ("AXP") than does a control fermentation medium cultured for the period and under the conditions of the complete fermentation medium, wherein the control fermentation medium comprises the at least one fermenting microorganism, the at least one xylan-containing biomass, the at least one cellulase, the at least one hemicellulase, and the at least one retaining β-xylosidase, and lacks the at least one inverting β-xylosidase.

3. The method of claim 2, wherein the complete fermentation medium comprises an effective amount of the at least one inverting β-xylosidase such that the complete fermentation medium produces at least 50% less AXP than does the control fermentation medium.

4. The method of claim 3, wherein the complete fermentation medium comprises an effective amount of the at least one inverting β-xylosidase such that the complete fermentation medium produces at least 60% less AXP than does the control fermentation medium.

5. The method of claim 4, wherein the complete fermentation medium comprises an effective amount of the at least one inverting β-xylosidase such that the complete fermentation medium produces at least 70% less AXP than does the control fermentation medium.

6. The method of claim 2, wherein the AXP is a methyl-β-xylopyranoside (MXP), an ethyl-β-xylopyranoside (EXP), a propyl-β-xylopyranoside (PXP), or a butyl-β-xylopyranoside (BXP).

7. The method of claim 2, wherein the complete fermentation medium comprises an effective amount of the at least one inverting β-xylosidase such that the complete fermentation medium produces at least 40% less AXP than does the control fermentation medium.

8. The method of claim 1 wherein the at least one inverting β-xylosidase comprises residues 21 to 350 of SEQ ID NO:2.

9. The method of claim 1, wherein the complete fermentation medium comprises an effective amount of the at least one inverting β-xylosidase to increase the yield of the fermentation product, as compared to the yield of the fermentation product from a control fermentation medium cultured for the period and the under conditions of the complete fermentation medium, wherein the control fermentation medium comprises the at least one fermenting microorganism, the at least one xylan-containing biomass, the at least one cellulase, the at least one hemicellulase, and the at least one retaining β-xylosidase, and lacks the at least one inverting β-xylosidase, wherein the yield of the fermentation product is increased by at least 1%.

10. The method of claim 9, wherein the yield of the fermentation product is increased by at least 2%.

11. The method of claim 10, wherein the yield of the fermentation product is increased by at least 5%.

12. The method of claim 11, wherein the yield of the fermentation product is increased by at least 10%.

13. The method of claim 9, wherein the alcohol is methanol, ethanol, propanol, propane-1,3-diol, or butanol.

14. The method of claim 1, further comprising a Pf43A polypeptide wherein the Pf43A polypeptide has at least 90% sequence identity to SEQ ID NO:8, or to residues 21 to 445 of SEQ ID NO:8.

15. The method of claim 1, further comprising a Fv43E polypeptide wherein the Fv43E polypeptide has at least 90% sequence identity to SEQ ID NO:10, or to residues 19 to 530 of SEQ ID NO:10.

16. The method of claim 1, further comprising a Fv43B polypeptide wherein the Fv43B polypeptide has at least 90% sequence identity to to SEQ ID NO:12, or to residues 17 to 574 of SEQ ID NO:12.

17. The method of claim 1, further comprising a Af43A polypeptide wherein the Af43A polypeptide has at least 90% sequence identity to SEQ ID NO:14, or to residues 15-558 of SEQ ID NO:14.

18. The method of claim 1, further comprising a Fo43A polypeptide wherein the Fo43A polypeptide has at least 90% sequence identity to SEQ ID NO:24, or to residues 21-348 of SEQ ID NO:24.

19. The method of claim 1, further comprising a Gz43A polypeptide wherein the Gz43A polypeptide has at least 90% sequence identity to SEQ ID NO:22, or to residues 19-340 of SEQ ID NO:22.

20. The method of claim 1, further comprising a XynB3 polypeptide wherein the XynB3 polypeptide has at least 90% sequence identity to SEQ ID NO:25.

21. The method of claim 1, wherein the at least one inverting β-xylosidase is present in the complete fermentation medium at a concentration of 0.3 mg to 10 mg per gram of xylan in the xylan-containing biomass.

22. The method of claim 21, wherein the at least one inverting β-xylosidase is present at a concentration of 0.4 mg to 10 mg per gram of xylan in the xylan-containing biomass.

23. The method of claim 21, wherein the at least one inverting β-xylosidase is present at a concentration of 0.3 mg to 3 mg per gram of xylan in the xylan-containing biomass.

24. The method of claim 1, wherein the SSF is performed as a continuous, a batch, or a fed-batch process.

25. The method of claim 1, further comprising a step of forming the complete fermentation medium.

26. The method of claim 25, wherein the step of forming the complete fermentation medium comprises combining (a) the fermenting microorganism, (b) the xylan-containing biomass, (c) the cellulase, (d) the hemicellulase, (e) the at least one inverting β-xylosidase, and (f) a medium lacking one or more or all of (a)-(e).

27. The method of claim 26, wherein the cellulase is present in the form of a whole cellulase preparation.

28. The method of claim 27, wherein the whole cellulase preparation comprises a hemicellulase.

29. The method of claim 27, wherein the whole cellulase preparation is a culture broth obtained from culturing a filamentous fungus.

30. The method of claim 29, wherein the filamentous fungus is a *T. reesei*.

31. The method of claim 1, wherein the fermenting microorganism is a fungus.

32. The method of claim 31, wherein the fungus is a *Saccharomyces cerevisiae* yeast.

33. The method of claim 1, wherein the fermenting microorganism is a bacterium.

34. The method of claim 33, wherein the bacterium is a *Zymomonas mobilis*.

35. The method of claim 1, wherein the xylan-containing biomass is corn stover, bagasses, sorghum, giant reed, elephant grass, miscanthus, Japanese cedar, wheat straw, switchgrass, hardwood pulp, or softwood pulp.

36. The method of claim 35, wherein the xylan-containing biomass is in a slurry.

37. The method of claim 35, wherein the xylan-containing biomass has been pretreated.

38. The method of claim 1, further comprising the step of recovering the fermentation product.

39. The method of claim 1, wherein the ratio of the at least one inverting β-xylosidase to the at least one retaining β-xylosidase in the complete fermentation medium is at least 2:1, on a mole basis.

* * * * *